(12) United States Patent
Biediger et al.

(10) Patent No.: US 10,875,875 B2
(45) Date of Patent: Dec. 29, 2020

(54) PROPIONIC ACID DERIVATIVES AND METHODS OF USE THEREOF

(71) Applicants: Ronald J. Biediger, Houston, TX (US); Michele A. Benish, The Woodlands, TX (US); Lindsay Bonner Hardy, Lexington, MA (US); Vincent A. Boyd, Tyler, TX (US); Robert V. Market, Pearland, TX (US); Thomas P. Thrash, Houston, TX (US); Brandon M. Young, Germantown, TN (US)

(72) Inventors: Ronald J. Biediger, Houston, TX (US); Michele A. Benish, The Woodlands, TX (US); Lindsay Bonner Hardy, Lexington, MA (US); Vincent A. Boyd, Tyler, TX (US); Robert V. Market, Pearland, TX (US); Thomas P. Thrash, Houston, TX (US); Brandon M. Young, Germantown, TN (US)

(73) Assignee: Aviara Pharmaceuticals, Inc., Houston, TX (US)

( * ) Notice: Subject to any disclaimer, the term of this patent is extended or adjusted under 35 U.S.C. 154(b) by 175 days.

(21) Appl. No.: 15/497,414

(22) Filed: Apr. 26, 2017

(65) Prior Publication Data
US 2018/0312523 A1 Nov. 1, 2018

(51) Int. Cl.

| | | |
|---|---|---|
| *C07D 498/04* | (2006.01) | |
| *C07D 213/75* | (2006.01) | |
| *C07D 213/64* | (2006.01) | |
| *C07D 207/327* | (2006.01) | |
| *C07D 307/54* | (2006.01) | |
| *C07D 401/12* | (2006.01) | |
| *C07D 221/18* | (2006.01) | |
| *C07D 207/333* | (2006.01) | |
| *C07D 333/22* | (2006.01) | |
| *C07D 231/16* | (2006.01) | |
| *C07D 471/04* | (2006.01) | |
| *C07D 261/08* | (2006.01) | |
| *C07D 213/55* | (2006.01) | |
| *C07D 213/48* | (2006.01) | |
| *C07D 213/69* | (2006.01) | |
| *C07D 209/08* | (2006.01) | |
| *C07D 237/14* | (2006.01) | |
| *A61P 35/00* | (2006.01) | |
| *C07D 237/22* | (2006.01) | |
| *C07D 513/04* | (2006.01) | |
| *C07D 221/04* | (2006.01) | |

(52) U.S. Cl.
CPC ............ *C07D 498/04* (2013.01); *A61P 35/00* (2018.01); *C07D 207/327* (2013.01); *C07D 207/333* (2013.01); *C07D 209/08* (2013.01); *C07D 213/48* (2013.01); *C07D 213/55* (2013.01); *C07D 213/64* (2013.01); *C07D 213/69* (2013.01); *C07D 213/75* (2013.01); *C07D 221/04* (2013.01); *C07D 221/18* (2013.01); *C07D 231/16* (2013.01); *C07D 237/14* (2013.01); *C07D 237/22* (2013.01); *C07D 261/08* (2013.01); *C07D 307/54* (2013.01); *C07D 333/22* (2013.01); *C07D 401/12* (2013.01); *C07D 471/04* (2013.01); *C07D 513/04* (2013.01)

(58) Field of Classification Search
CPC ..................................... C07D 498/04
See application file for complete search history.

(56) References Cited

U.S. PATENT DOCUMENTS 6,972,296 B2 * 12/2005 Biediger .............. C07D 213/75
  514/349
7,812,038 B2 * 10/2010 Biediger .............. C07D 213/75
  514/345

* cited by examiner

*Primary Examiner* — David K O'Dell
(74) *Attorney, Agent, or Firm* — Benjamin Aaron Adler

(57) ABSTRACT

Provided herein are compounds and pharmaceutical compositions of formula I

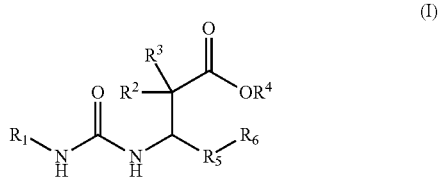

where $R^1$, $R^2$, $R^3$, $R^4$, $R^5$ and $R^6$ are as described herein. Also provided pharmaceutically acceptable salts or stereoisomers of these compounds. In addition methods are provided for inhibiting the binding of an integrin to treat various pathophysiological conditions.

17 Claims, No Drawings

PROPIONIC ACID DERIVATIVES AND METHODS OF USE THEREOF

BACKGROUND OF THE INVENTION

Field of the Invention

The present invention relates generally to field of medicinal chemistry and therapeutic compounds. More specifically, the present invention relates to derivatives of propionic acid as integrin inhibitors.

Description of the Related Art

Integrins are a large family of cell adhesion protein molecules that are expressed on numerous cells and which mediate a variety of cell-cell and cell-matrix interactions. Accordingly, the regulation of a number of physiological processes, such as, and including, cell adhesion, migration, signaling, survival and differentiation are known to involve these molecules. Each Integrin consists of a non-covalently associated alpha and beta transmembrane heterodimer subunit, with 18 different alpha and 8 different beta units being identified to date. Integrins function as conduits for signaling that occurs between the inside of cells and their external environment. Through ligand interactions, Integrins sense the extracellular environment, activate, and then relay this information to the inside of the cell. This process is fundamental to the functional interaction of cells to various tissues such as and including the vascular endothelium, bone marrow stromal cells, some tumor cells and the gastrointestinal mucosal. Additionally, as Integrins are widely expressed on leukocytes, especially T-cells, and thus are critical players in the regulation of the pathophysiologic processes of inflammation and autoimmune disease.

To date, approximately 24 different integrin molecules have been identified. Of these, the integrins derived from the alpha 4 subunit are associated with disease states of current unmet medical need. Two such integrins are alpha 4 beta 1 (also called VLA-4 for very late antigen-4) and alpha 4 beta 7 (also known as mucosal vascular addressin cell adhesion molecule 1 (MAdCAM-1)). These two integrins are the primary pathogenic targets of this patent application.

There are three main types of white blood cells: granulocytes, monocytes and lymphocytes. The alpha 4 integrins are expressed on the surface of monocytes, lymphocytes and two subclasses of granulocytes: eosinophils and basophils. These proteins play a key role in cell adhesion through their ability to recognize and bind to other cell surface portions of other proteins such as vascular cell adhesion molecule 1 (VCAM-I), fibronectin, or other proteins associated with the endothelial cells that line the interior wall of capillaries. For example, following infection or damage of tissue surrounding a capillary, endothelial cells express a series of adhesion molecules, including VCAM-I, that are critical for binding the white blood cells that are necessary for fighting infection. In a similar fashion, alpha 4 beta 7, critical for homing to intestinal mucosa, is induced during T cell activation in Peyer's patches or mesenteric lymph nodes.

Some of the disease conditions that currently are, and in the future might be, treated by the inhibition of the alpha 4 integrins include, but is not limited to, hematopoietic stem cell transplant therapy, sickle cell disease, dry eye, atherosclerosis, rheumatoid arthritis, asthma, allergy, multiple sclerosis, lupus, inflammatory bowel disease, graft rejection, contact hypersensitivity, stroke, pulmonary arterial hypertension and diabetes. It has been suggested that cell adhesion involving alpha4 beta1 may be involved in the metastasis and survival of certain cancer cells. Inhibitors of alpha4 beta1 binding may, therefore, also be useful in the treatment of some forms of cancer.

The isolation and purification of a peptide which inhibits the binding of alpha 4 beta 1 to a protein is disclosed in U.S. Pat. No. 5,510,332. Peptides which inhibit binding are disclosed in WO 95/15973, EP 0 341915, EP 0 422 938 A1, U.S. Pat. No. 5,192,746 and WO 96/06108. Novel small molecule compounds which are useful for inhibition and prevention of cell adhesion and cell adhesion-mediated pathologies are disclosed in WO 96/22966, WO 98/04247 and US 2004/0234624 A1 (WO 98/04913), WO2005014534 A1, U.S. Pat. Nos. 7,812,03, 6,972,296, 6,723,711, 6,262, 084.

It is the objective of this invention to provide novel small molecule compounds which are antagonists of the action of alpha 4 beta 1 and alpha 4 beta 7 binding and their corresponding pharmaceutical compositions which include such novel compounds.

SUMMARY OF THE INVENTION

The present invention is directed to a compound of formula I having a chemical structure of

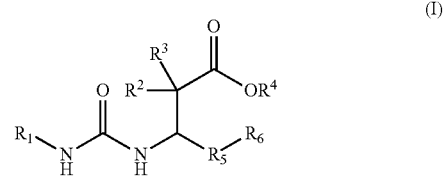

(I)

In these compounds $R^1$ may be

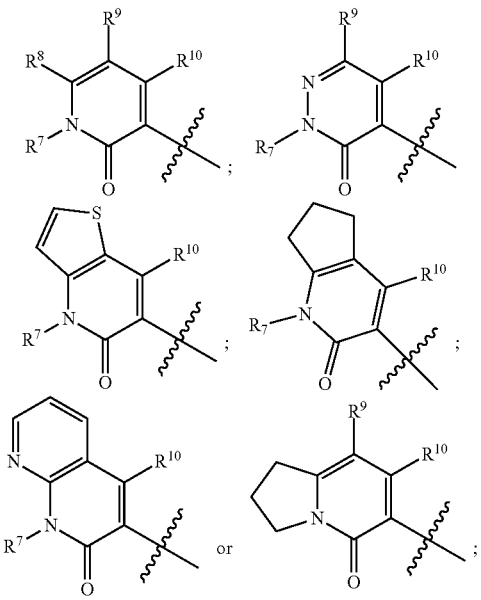

$R^2$ and $R^3$ may be independently hydrogen or $C_{1-4}$ alkyl; $R^4$ may be H or $C_{1-4}$ alkyl; $R^5$ may be phenyl, aryl, heterocyclyl or aralkyl which is substituted with one or more of hydrogen, $C_{1-4}$ alkyl, alkoxy, aryloxy, oxo, halogen, haloalkoxy, —$CF_3$, hydroxyl, —$OCF_3$, aryl, —$OCF_2H$, —OCF$_2$CF$_2$H, —O(C$_{3-6}$ cycloalkyl), —OCH$_2$CF$_3$, thioalkoxy, dialkylamino, C$_{3-6}$ cycloalkyl or haloalkyl; R$^6$ may be C$_{1-4}$ alkyl, halogen, phenyl, aryl or heterocyclyl which is substituted with one or more of hydrogen, C$_{1-4}$ alkyl, alkoxy, aryl, aryloxy, halogen, oxo, acetyl, haloalkoxy, —CF$_3$, hydroxyl, —OCF$_3$, aryl, —OCF$_2$H, —OCF$_2$CF$_2$H, —O(C$_{3-6}$ cycloalkyl), —OCH$_2$CF$_3$, thioalkoxy, dialkylamino, cycloalkyl or haloalkyl; R$^7$ may be H or C$_{1-4}$ alkyl; R$^8$, R$^9$ and R$^{10}$ may be independently hydrogen, halogen, C$_{1-4}$ alkyl, C$_{3-6}$ cycloalkyl, or hydroxyl. The compounds encompass pharmaceutically acceptable salt or stereoisomers thereof.

The present invention is directed to a related compound of formula I having a chemical structure of

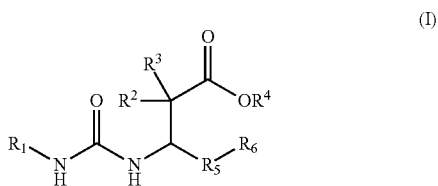

In these compounds, R$^1$ may be

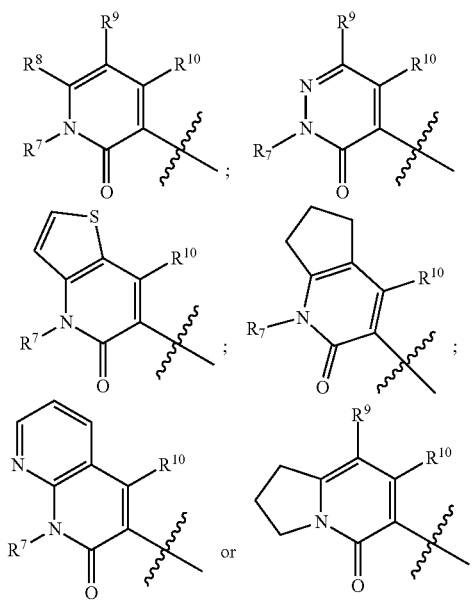

R$^2$ and R$^3$ may be independently hydrogen or methyl; R$^4$ may be hydrogen; methyl, ethyl or t-butyl; R$^5$ may be phenyl, aryl, heterocyclyl or aralkyl which is substituted with one or more of hydrogen, C$_{1-4}$ alkyl, alkoxy, aryloxy, oxo, halogen, haloalkoxy, —CF$_3$, hydroxyl, —OCF$_3$, aryl, —OCF$_2$H, —OCF$_2$CF$_2$H, —O(C$_{3-6}$ cycloalkyl), —OCH$_2$CF$_3$, thioalkoxy, dialkylamino, C$_{3-6}$ cycloalkyl or haloalkyl; R$^6$ may be C$_{1-4}$ alkyl, halogen, phenyl, aryl, or heterocyclyl which is substituted with one or more of hydrogen, C$_{1-4}$ alkyl, alkoxy, aryl, aryloxy, halogen, oxo, acetyl, haloalkoxy, —CF$_3$, hydroxyl, —OCF$_3$, aryl, —OCF$_2$H, —OCF$_2$CF$_2$H, —O(C$_{3-6}$ cycloalkyl), —OCH$_2$CF$_3$, thioalkoxy, dialkylamino, C$_{3-6}$ cycloalkyl or haloalkyl; R$^7$ may be H; methyl or ethyl; R$^8$ and R$^9$ may independently hydrogen or methyl and R$^{10}$ may be hydroxyl. The compounds encompass pharmaceutically acceptable salt or stereoisomers thereof.

The present invention also is directed to pharmaceutical composition, comprising at least one compound as described herein and one or more pharmaceutically acceptable carriers.

The present invention is directed further to a method for treating a pathophysiological condition mediated by α4 integrins i.e. α4β1, α4β7 or mixed α4β1 and α4β7 integrins in a subject in need of such treatment. The method comprises administering a pharmacologically effective amount of the pharmaceutical composition as described herein.

The present invention also is directed to a method for inhibiting integrin binding in a cell associated with a pathophysiological condition. The method comprises contacting the cell with one or more compounds as described herein.

Other and further aspects, features, benefits, and advantages of the present invention will be apparent from the following description of the presently preferred embodiments of the invention given for the purpose of disclosure.

DETAILED DESCRIPTION OF THE INVENTION

As used herein in the specification, "a" or "an" may mean one or more. As used herein in the claim(s), when used in conjunction with the word "comprising", the words "a" or "an" may mean one or more than one.

As used herein "another" or "other" may mean at least a second or more of the same or different claim element or components thereof. Similarly, the word "or" is intended to include "and" unless the context clearly indicates otherwise. "Comprise" means "include."

As used herein, the term "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

The term "nd" is intended to mean not yet determined

The term alpha 4 integrin(s) (aka α4-integrin(s)) refers to the class of integrin dimer molecules composed of the alpha 4 subunit coupled with another subunit normally referred to as a beta (b) subunit. Typical, but not exclusive, examples are α4β1 and α4β7.

The term "alkyl" as used herein, alone or in combination, refers to C$_1$-C$_{12}$ straight or branched, substituted or unsubstituted saturated chain radicals derived from saturated hydrocarbons by the removal of one hydrogen atom, unless the term alkyl is preceded by a C$_x$-C$_y$ designation. Representative examples of alkyl groups include methyl, ethyl, n-propyl, iso-propyl, n-butyl, sec-butyl, iso-butyl, and tert-butyl among others.

The term "alkenyl" as used herein, alone or in combination, refers to a substituted or unsubstituted straight-chain or substituted or unsubstituted branched-chain alkenyl radical containing from 2 to 10 carbon atoms. Examples of such radicals include, but are not limited to, ethenyl, E- and Z-pentenyl, decenyl and the like.

The term "alkynyl" as used herein, alone or in combination, refers to a substituted or unsubstituted straight or substituted or unsubstituted branched chain alkynyl radical containing from 2 to 10 carbon atoms. Examples of such radicals include, but are not limited to ethynyl, propynyl, propargyl, butynyl, hexynyl, decynyl and the like.

The term "cycloalkyl" as used herein refers to an aliphatic ring system having 3 to 10 carbon atoms and 1 to 3 rings, including, but not limited to cyclopropyl, cyclopentyl, cyclohexyl, norbornyl, and adamantyl among others. Cycloalkyl groups can be unsubstituted or substituted with one, two or three substituents independently selected from lower alkyl, haloalkyl, alkoxy, thioalkoxy, amino, alkylamino, dialkylamino, hydroxy, halo, mercapto, nitro, carboxaldehyde, carboxy, alkoxycarbonyl and carboxamide.

"Cycloalkyl" includes cis or trans forms. Furthermore, the substituents may either be in endo or exo positions in the bridged bicyclic systems.

The term "halo" or "halogen" as used herein refers to I, Br, Cl or F.

The term "haloalkyl" as used herein refers to $C_1$-$C_4$ alkyl radical, to which is appended at least one halogen substituent, for example chloromethyl, fluoroethyl, difluoromethyl, trifluoromethyl and pentafluoroethyl among others.

The term "alkoxy" as used herein, alone or in combination, refers to an alkyl ether radical, wherein the term "alkyl" is as defined above. Examples of suitable alkyl ether radicals include, but are not limited to, methoxy, ethoxy, n-propoxy, iso-propoxy, n-butoxy, iso-butoxy, sec-butoxy, tert-butoxy and the like.

The term "haloalkoxy" as used herein, alone or in combination, refers to an haloalkyl ether radical, wherein the term "haloalkyl" is as defined above. Examples of suitable haloalkyl ether radicals include, but are not limited to, chloromethoxy, trifluoromethoxy, difluoromethoxy, trifluoroethoxy and the like The term "thioalkoxy" refers to a thioether radical of formula alkyl —S—, wherein "alkyl" is as defined above.

The term "dialkylamino" as used herein refers to $R_fR_gN$— wherein $R_f$ and $R_g$ are independently selected from $C_1$-$C_4$ alkyl, for example diethylamino, and methyl propylamino, among others.

The term "aryl" or "aromatic" as used herein alone or in combination refers to a substituted or unsubstituted carbocyclic aromatic group having about 6 to 12 carbon atoms such as phenyl, naphthyl, indenyl, indanyl, azulenyl, fluorenyl and anthracenyl; or a heterocyclic aromatic group containing at least one endocyclic N, O or S atom such as furyl, thienyl, pyridyl, dihydropyridyl, pyrrolyl, oxazolyl, thiazolyl, imidazolyl, pyrazolyl, 2-pyrazolinyl, pyrazolidinyl, isoxazolyl, isothiazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, 2,3-dihydrobenzofuranyl, benzo[b]thiophenyl, benzodioxolyl, 1H-indazolyl, benzimidazolyl, benzthiazolyl, purinyl, 4H-quinolizinyl, isoquinolinyl, cinnolinyl, phthalazinyl, quinazolinyl, quinoxalinyl, 1,8-naphthridinyl, pteridinyl, carbazolyl, acridinyl, phenazinyl, phenothiazinyl, phenoxyazinyl, pyrazolo[I,5-c]triazinyl and the like. "Aralkyl" and "alkylaryl" employ the term "alkyl" as defined above. Rings may be multiply substituted.

The term "biaryl" as used herein, alone or in combination, refers to a radical of formula aryl-aryl, wherein the term "aryl" is as defined above.

The term "aralkyl" as used herein, alone or in combination, refers to an aryl substituted alkyl radical, wherein the terms "alkyl" and "aryl" are as defined above. Examples of suitable aralkyl radicals include, but are not limited to, phenylmethyl, phenethyl, phenylhexyl, diphenylmethyl, pyridylmethyl, tetrazolyl methyl, furylmethyl, imidazolyl methyl, indolylmethyl, thienylpropyl and the like.

The term "aryloxy" as used herein, alone or in combination, refers to an aryl ether radical, wherein the term "aryl" is as defined above.

The term "benzyl" as used herein refers to $C_6H_5CH_2$—.

The term "heterocyclyl" as used herein, alone or in combination, refers to a non-aromatic 3- to 10-membered ring containing at least one endocyclic N, O, or S atom. The heterocycle may be optionally aryl-fused. The heterocycle may also optionally be substituted with at least one substituent which is independently selected from the group consisting of hydrogen, halogen, hydroxyl, amino, nitro, trifluoromethyl, trifluoromethoxy, trifluoroethoxy, alkyl, alkoxy, aralkyl, alkenyl, alkynyl, aryl, cyano, carboxy, carboalkoxy, carboxyalkyl, oxo, acetyl, arylsulfonyl and aralkylaminocarbonyl among others.

The term "heteroaryl" as used herein refers to aromatic moieties containing one or more heteroatoms (e.g., N, O, S, or the like) as part of the ring structure and having in the range of 5 up to 14 total atoms in the ring structure (i.e., carbon atoms and heteroatoms). "Substituted heteroaryl" refers to heteroaryl groups further bearing one or more substituents.

The term "stereoisomer" as used herein refers to a compound made up of the same atoms bonded by the same bonds but having different three-dimensional structures which are not interchangeable. The three-dimensional structures are called configurations The term "pharmaceutically acceptable salts" as used herein of a compound is meant salts which are pharmaceutically acceptable as defined herein and which have the desired pharmacological action of the parent compound. Such salts comprise the addition salts of pharmaceutically acceptable bases formed when an acid proton contained in the parent compound is either replaced by a metal ion e.g. an alkaline metal ion, an alkaline-earth metal ion or aluminium ion; or coordinated with a pharmaceutically acceptable organic or inorganic base. Acceptable organic bases include diethanolamine, ethanolamine, N-methylglucamine, triethanolamine, tromethamine and the like. Acceptable inorganic bases include aluminium hydroxide, calcium hydroxide, potassium hydroxide, sodium carbonate and sodium hydroxide. Especially, sodium is preferred and it can be either the mono sodium or di-sodium form or a mixture thereof.

The term "effective amount" as used herein refers to generally an amount effective to accomplish the intended purpose, e.g., a pharmacologically effective amount. However, the amount can be less than that amount when a plurality of the compositions are to be administered, i.e., the total effective amount can be administered in cumulative dosage units. The amount of active agent can also be more than the effective amount when the composition provides sustained release of the pharmacologically active agent. The total amount of a pharmacologically active agent to be used can be determined by methods known to those skilled in the art. However, because the compositions may deliver the pharmacologically active agent more efficiently than prior compositions, less amounts of active agent than those used in prior dosage unit forms or delivery systems can be administered to a subject while still achieving the same blood levels and/or therapeutic effects.

As used herein, the term "sodium" means the sodium salt of the disclosed compounds and includes the monosodium salt, the disodium salt and mixtures thereof.

As used herein, the term "contacting" refers to any suitable method of bringing a compound or a pharmaceutical composition into contact with a cell in vivo, in vitro or ex vivo. For in vivo applications, any known method of administration is suitable as described herein.

As used herein, the term "subject" refers to any recipient, for example a human or non-human mammal, of the compounds and/or pharmaceutical compositions described herein.

Use of the above terms is meant to encompass substituted and unsubstituted moieties. Substitution may be by one or more groups such as alcohols, ethers, esters, amides, sulfones, sulfides, hydroxyl, nitro, cyano, carboxy, amines, heteroatoms, lower alkyl, lower alkoxy, lower alkoxycarbonyl, alkoxyalkoxy, acyloxy, halogens, trifluoromethoxy, trifluoromethyl, alkyl, aralkyl, alkenyl, alkynyl, aryl, cyano, carboxy, carboalkoxy, carboxyalkyl, cycloalkyl, cycloalkylalkyl, heterocyclyl, alkylheterocyclyl, heterocyclylalkyl, oxo, arylsulfonyl and aralkylaminocarbonyl or any of the substituents of the preceding paragraphs or any of those substituents either attached directly or by suitable linkers. The linkers are typically short chains of 1-3 atoms containing any combination of —C—, —C(O)—, —NH—, —S—, —S(O)—, —O—, —C(O)O— or —S(O)O—. Rings may be substituted multiple times.

In one embodiment of the invention there is provided a compound of formula I having a chemical structure of

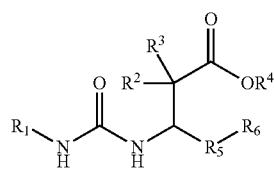

(I)

where R¹ is

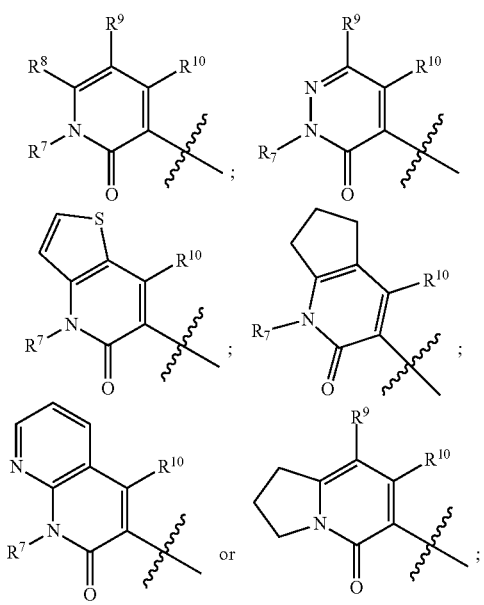

$R^2$ and $R^3$ are independently hydrogen or $C_{1-4}$ alkyl; $R^4$ is H or $C_{1-4}$ alkyl; $R^5$ is phenyl, aryl, heterocyclyl or aralkyl which is substituted with one or more of hydrogen, $C_{1-4}$ alkyl, alkoxy, aryloxy, oxo, halogen, haloalkoxy, —$CF_3$, hydroxyl, —$OCF_3$, aryl, —$OCF_2H$, —$OCF_2CF_2H$, —$O(C_{3-6}$ cycloalkyl), —$OCH_2CF_3$, thioalkoxy, dialkylamino, $C_{3-6}$ cycloalkyl or haloalkyl; $R^6$ is $C_{1-4}$ alkyl, halogen, phenyl, aryl or heterocyclyl which is substituted with one or more of hydrogen, $C_{1-4}$ alkyl, alkoxy, aryl, aryloxy, halogen, oxo, acetyl, haloalkoxy, —$CF_3$, hydroxyl, —$OCF_3$, aryl, —$OCF_2H$, —$OCF_2CF_2H$, —$O(C_{3-6}$ cycloalkyl), —$OCH_2CF_3$, thioalkoxy, dialkylamino, $C_{3-6}$ cycloalkyl or haloalkyl; $R^7$ is H or $C_{1-4}$ alkyl; $R^8$, $R^9$ and $R^{10}$ are independently hydrogen, halogen, $C_{1-4}$ alkyl, $C_{3-6}$ cycloalkyl, or hydroxyl; or a pharmaceutically acceptable salt or stereoisomers thereof.

In this embodiment $R_2$ and $R_3$ are each hydrogen and $R^4$ is hydrogen, methyl, ethyl or t-butyl. Also in this embodiment $R^7$ is hydrogen, methyl or ethyl. Also in this embodiment $R^8$ and $R^9$ are independently hydrogen or methyl. Also in this embodiment $R^{10}$ is hydroxyl. Also in this embodiment and all aspects thereof as described the pharmaceutically acceptable salt is a mono or a disodium salt and the stereoisomer is of the (S)-configuration.

In one aspect of this embodiment, the provided compound of formula I is the compound of formula I A having a chemical structure of

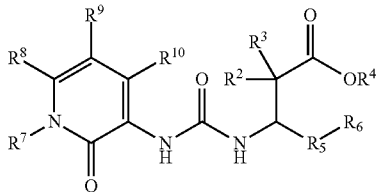

(IA)

where, $R^2$, $R^3$, $R^4$, $R^5$, $R^6$, $R^7$, $R^8$, $R^9$ and $R^{10}$ are as described supra or a pharmaceutically acceptable salt or stereoisomers thereof.

In another aspect of this embodiment, the provided compound of formula I is the compound of formula I B having a chemical structure of

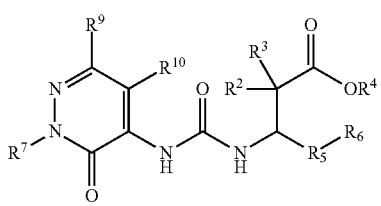

(IB)

where, $R^2$, $R^3$, $R^4$, $R^5$, $R^6$, $R^7$, $R^9$ and $R^{10}$ are as described supra or a pharmaceutically acceptable salt or stereoisomers thereof.

In yet another aspect of this embodiment, the provided compound of formula I is the compound of formula I C having a chemical structure of

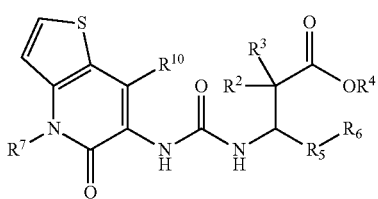
(IC)

where, $R^2$, $R^3$, $R^4$, $R^5$, $R^6$, $R^7$ and $R^{10}$ are as described supra or a pharmaceutically acceptable salt or stereoisomers thereof.

In yet another aspect of this embodiment, the provided compound of formula I is the compound of formula I is a compound of formula I D having a chemical structure of

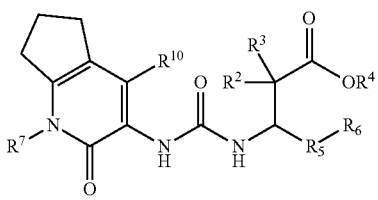
(ID)

where, $R^2$, $R^3$, $R^4$, $R^5$, $R^6$, $R^7$ and $R^{10}$ are as described supra or a pharmaceutically acceptable salt or stereoisomers thereof.

In yet another aspect of this embodiment, the provided compound of formula I is the compound of formula IE having a chemical structure of

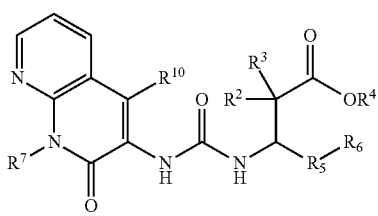
(IE)

where, $R^2$, $R^3$, $R^4$, $R^5$, $R^6$, $R^7$ and $R^{10}$ are as described supra or a pharmaceutically acceptable salt or stereoisomers thereof.

In yet another aspect of this embodiment, the provided compound of formula I is the compound of formula IF having a chemical structure of

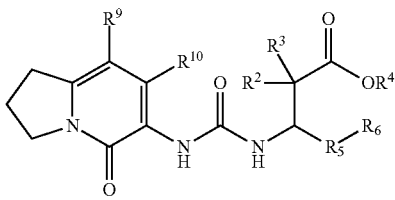
(IF)

where, $R^2$, $R^3$, $R^4$, $R^5$, $R^6$, $R^9$ and $R^{10}$ are as described supra or a pharmaceutically acceptable salt or stereoisomers thereof.

In another embodiment of the invention, there is provided pharmaceutical compositions comprising at least one compound as described supra and one or more pharmaceutically acceptable carriers.

In yet another embodiment of the invention, there is provided a method for treating a pathophysiological condition mediated by α4 integrins, e.g. α4β1, α4β7 or mixed α4β1 and α4β7 integrins, in a subject in need of such treatment comprising administering to the subject a pharmacologically effective amount of the pharmaceutical composition as described supra. In this embodiment the pathophysiological condition is hematopoietic stem cell transplant therapy, sickle cell disease, dry eye, atherosclerosis, rheumatoid arthritis, asthma, allergy, multiple sclerosis, lupus, inflammatory bowel disease, graft rejection, contact hypersensitivity, stroke, pulmonary arterial hypertension, diabetes or cancer.

In yet another embodiment of the invention, there is a method for inhibiting integrin binding in a cell associated with a pathophysiological condition, comprising: contacting the cell with one or more compounds as described supra. In this embodiment the integrin is $α_4β_1$ and/or $α_4β_7$ integrin. Also in this embodiment the pathophysiological condition is a cancer.

In yet another embodiment of the invention, there is provided a compound of formula II having a chemical structure of

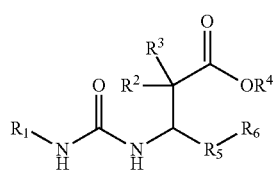
(I)

where $R^1$ is

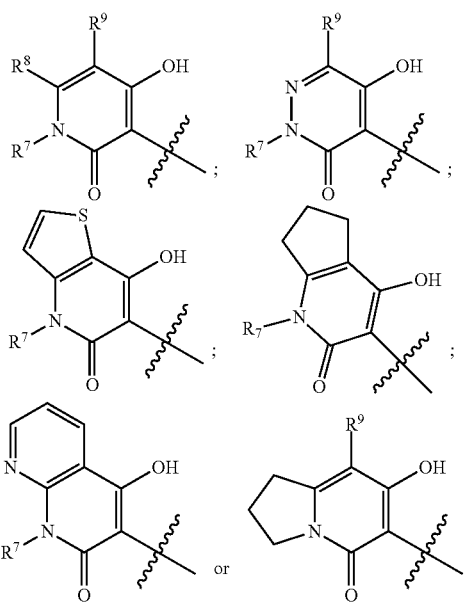

$R^2$ and $R^3$ are independently hydrogen; $R^4$ is hydrogen; methyl, ethyl or t-butyl; $R^5$ is phenyl, aryl, heterocyclyl or aralkyl which is substituted with one or more of hydrogen, $C_{1-4}$ alkyl, alkoxy, aryloxy, oxo, halogen, haloalkoxy, —$CF_3$, hydroxyl, —$OCF_3$, aryl, —$OCF_2H$, —$OCF_2CF_2H$, —$O(C_{3-6}$ cycloalkyl), —$OCH_2CF_3$, thioalkoxy, dialkylamino, $C_{3-6}$ cycloalkyl or haloalkyl; $R^6$ is $C_{1-4}$ alkyl, halogen, phenyl, aryl, heteroaryl which is substituted with one or more of hydrogen, $C_{1-4}$ alkyl, alkoxy, aryl, aryloxy, halogen, oxo, acetyl, haloalkoxy, —$CF_3$, hydroxyl, —$OCF_3$, aryl, —$OCF_2H$, —$OCF_2CF_2H$, —$O(C_{3-6}$ cycloalkyl), —$OCH_2CF_3$, thioalkoxy, dialkylamino, $C_{3-6}$ cycloalkyl or haloalkyl; $R^7$ is hydrogen, methyl or ethyl; $R^8$ and $R^9$ independently hydrogen or methyl; or a pharmaceutically acceptable salt or stereoisomers thereof.

In yet another embodiment of the invention, there are provided the compounds:

ethyl (S)-3-(biphenyl-3-yl)-3-(3-(4-hydroxy-1,5-dimethyl-2-oxo-1,2-dihydropyridin-3-yl)ureido)propanoate 1-9;

ethyl (S)-3-(biphenyl-3-yl)-3-(3-(1-ethyl-4-hydroxy-5-methyl-2-oxo-1,2-dihydropyridin-3-yl)ureido)propanoate 1-10;

ethyl 3-(3-(1-ethyl-4-hydroxy-5-methyl-2-oxo-1,2-dihydropyridin-3-yl)ureido)-3-(3-(2-oxo-3-phenylpyridin-1(2H)-yl)phenyl)propanoate 1-11;

ethyl (S)-3-(3-(4-hydroxy-1,5-dimethyl-2-oxo-1,2-dihydropyridin-3-yl)ureido)-3-(2'-methylbiphenyl-3-yl)propanoate 1-12;

ethyl (S)-3-(2'-fluorobiphenyl-3-yl)-3-(3-(4-hydroxy-1,5-dimethyl-2-oxo-1,2-dihydro pyridin-3-yl)ureido)propanoate 1-13;

ethyl (S)-3-(6-fluorobiphenyl-3-yl)-3-(3-(4-hydroxy-1,5-dimethyl-2-oxo-1,2-dihydro pyridin-3-yl)ureido)propanoate 1-14;

ethyl (S)-3-(3-(1-ethyl-4-hydroxy-5-methyl-2-oxo-1,2-dihydropyridin-3-yl)ureido)-3-(2'-methylbiphenyl-3-yl)propanoate;

ethyl (S)-3-(3-(1-ethyl-4-hydroxy-5-methyl-2-oxo-1,2-dihydropyridin-3-yl)ureido)-3-(4'-methylbiphenyl-3-yl)propanoate 1-15;

ethyl 3-(3-(1H-pyrrol-1-yl)phenyl)-3-(3-(4-hydroxy-1,5-dimethyl-2-oxo-1,2-dihydro pyridin-3-yl)ureido)propanoate 1-16;

ethyl (S)-3-(2',4'-difluorobiphenyl-3-yl)-3-(3-(4-hydroxy-1,5-dimethyl-2-oxo-1,2-di hydropyridin-3-yl)ureido)propanoate 1-17;

ethyl (S)-3-(2',5'-difluorobiphenyl-3-yl)-3-(3-(4-hydroxy-1,5-dimethyl-2-oxo-1,2-di hydropyridin-3-yl)ureido)propanoate 1-18;

ethyl (S)-3-(3-(4-hydroxy-1,5-dimethyl-2-oxo-1,2-dihydropyridin-3-yl)ureido)-3-(6-methylbiphenyl-3-yl)propanoate 1-19;

ethyl (S)-3-(3-(4-hydroxy-1,5-dimethyl-2-oxo-1,2-dihydropyridin-3-yl)ureido)-3-(6-methoxybiphenyl-3-yl)propanoate 1-20;

ethyl (S)-3-(3-(4-hydroxy-1,5-dimethyl-2-oxo-1,2-dihydropyridin-3-yl)ureido)-3-(4'-methylbiphenyl-3-yl)propanoate 1-21;

ethyl (S)-3-(3-(4-hydroxy-1,5-dimethyl-2-oxo-1,2-dihydropyridin-3-yl)ureido)-3-(3'-methylbiphenyl-3-yl)propanoate 1-22;

ethyl (S)-3-(3-(4-hydroxy-1,5-dimethyl-2-oxo-1,2-dihydropyridin-3-yl)ureido)-3-(3-(pyridin-3-yl)phenyl)propanoate 1-23;

ethyl (S)-3-(3',5'-difluorobiphenyl-3-yl)-3-(3-(4-hydroxy-1,5-dimethyl-2-oxo-1,2-dihydropyridin-3-yl)ureido)propanoate 1-24;

ethyl (S)-3-(3',5'-dimethylbiphenyl-3-yl)-3-(3-(4-hydroxy-1,5-dimethyl-2-oxo-1,2-di hydropyridin-3-yl)ureido)propanoate 1-25;

ethyl (S)-3-(3-(4-hydroxy-1,5-dimethyl-2-oxo-1,2-dihydropyridin-3-yl)ureido)-3-(4'-methoxybiphenyl-3-yl)propanoate 1-26;

ethyl (S)-3-(3-(4-hydroxy-1,5-dimethyl-2-oxo-1,2-dihydropyridin-3-yl)ureido)-3-(2'-methoxybiphenyl-3-yl)propanoate 1-27;

ethyl (S)-3-(3-(4-hydroxy-1-methyl-2-oxo-1,2-dihydropyridin-3-yl)ureido)-3-(3-(pyrazin-2-yl)phenyl)propanoate 1-28, ethyl (S)-3-(3-(4-hydroxy-1,5-dimethyl-2-oxo-1,2-dihydropyridin-3-yl)ureido)-3-(4'-(trifluoromethoxy)biphenyl-3-yl)propanoate 1-29;

ethyl (S)-3-(3',4'-difluorobiphenyl-3-yl)-3-(3-(4-hydroxy-1,5-dimethyl-2-oxo-1,2-dihydropyridin-3-yl)ureido)propanoate 1-30;

ethyl (S)-3-(2',5'-dimethylbiphenyl-3-yl)-3-(3-(4-hydroxy-1,5-dimethyl-2-oxo-1,2-dihydropyridin-3-yl)ureido)propanoate 1-31;

ethyl (S)-3-(3-(4-hydroxy-1,5-dimethyl-2-oxo-1,2-dihydropyridin-3-yl)ureido)-3-(3'-methoxybiphenyl-3-yl)propanoate 1-32;

ethyl (S)-3-(3-(4-hydroxy-1,5-dimethyl-2-oxo-1,2-dihydropyridin-3-yl)ureido)-3-(3'-(trifluoromethoxy)biphenyl-3-yl)propanoate 1-33;

ethyl (S)-3-(2',3'-dimethylbiphenyl-3-yl)-3-(3-(4-hydroxy-1,5-dimethyl-2-oxo-1,2-dihydropyridin-3-yl)ureido)propanoate 1-34;

ethyl 3-(3-(4-hydroxy-1,5-dimethyl-2-oxo-1,2-dihydropyridin-3-yl)ureido)-3-(6-oxo-1-phenyl-1,6-dihydropyridin-3-yl)propanoate 1-35;

ethyl (S)-3-(2',6'-difluorobiphenyl-3-yl)-3-(3-(4-hydroxy-1,5-dimethyl-2-oxo-1,2-di hydropyridin-3-yl)ureido)propanoate 1-36;

ethyl (S)-3-(3'-fluorobiphenyl-3-yl)-3-(3-(4-hydroxy-1,5-dimethyl-2-oxo-1,2-di hydropyridin-3-yl)ureido)propanoate 1-37;

ethyl (S)-3-(4'-fluorobiphenyl-3-yl)-3-(3-(4-hydroxy-1,5-dimethyl-2-oxo-1,2-dihydro pyridin-3-yl)ureido)propanoate 1-38;

ethyl (S)-3-(3-(4-hydroxy-1,5-dimethyl-2-oxo-1,2-dihydropyridin-3-yl)ureido)-3-(2'-(trifluoromethoxy)biphenyl-3-yl)propanoate 1-39;

ethyl (S)-3-(2',4'-dimethoxybiphenyl-3-yl)-3-(3-(4-hydroxy-1,5-dimethyl-2-oxo-1,2-dihydropyridin-3-yl)ureido)propanoate 1-40;

ethyl (S)-3-(3',4'-dimethoxybiphenyl-3-yl)-3-(3-(4-hydroxy-1,5-dimethyl-2-oxo-1,2-dihydropyridin-3-yl)ureido)propanoate 1-41;

ethyl (S)-3-(2',6'-dimethylbiphenyl-3-yl)-3-(3-(4-hydroxy-1,5-dimethyl-2-oxo-1,2-di hydropyridin-3-yl)ureido)propanoate 1-42;

ethyl 3-(4'-chlorobiphenyl-3-yl)-3-(3-(4-hydroxy-1,5-dimethyl-2-oxo-1,2-dihydropyridin-3-yl)ureido)propanoate 1-43;

ethyl (S)-3-(3'-chlorobiphenyl-3-yl)-3-(3-(4-hydroxy-1,5-dimethyl-2-oxo-1,2-dihydropyridin-3-yl)ureido)propanoate 1-44;

ethyl 3-(2'-chlorobiphenyl-3-yl)-3-(3-(4-hydroxy-1,5-dimethyl-2-oxo-1,2-dihydropyridin-3-yl)ureido) propanoate 1-45;

ethyl (S)-3-(3-(4-hydroxy-1,5-dimethyl-2-oxo-1,2-dihydropyridin-3-yl)ureido)-3-(2'-(trifluoromethyl)biphenyl-3-yl)propanoate 1-46;

ethyl (S)-3-(5,6-dimethoxybiphenyl-3-yl)-3-(3-(4-hydroxy-1,5-dimethyl-2-oxo-1,2-dihydropyridin-3-yl)ureido)propanoate 1-47;

ethyl (S)-3-(3-(4-hydroxy-1,5-dimethyl-2-oxo-1,2-dihydropyridin-3-yl)ureido)-3-(3-(6-methoxypyridin-3-yl)phenyl)propanoate 1-48;

ethyl (S)-3-(2',5'-dimethoxybiphenyl-3-yl)-3-(3-(4-hydroxy-1,5-dimethyl-2-oxo-1,2-dihydropyridin-3-yl)ureido)propanoate 1-49;

ethyl 3-(3-(4-hydroxy-1,5-dimethyl-2-oxo-1,2-dihydropyridin-3-yl)ureido)-3-(3-(pyrimidin-5-yl)phenyl)propanoate 1-50;

ethyl (S)-3-(2',6'-dimethoxybiphenyl-3-yl)-3-(3-(4-hydroxy-1,5-dimethyl-2-oxo-1,2-dihydropyridin-3-yl)ureido)propanoate 1-51;

ethyl 3-(3',4'-dichlorobiphenyl-3-yl)-3-(3-(1-ethyl-4-hydroxy-5-methyl-2-oxo-1,2-dihydro pyridin-3-yl)ureido)propanoate 1-52;

ethyl 3-(3',4'-dichlorobiphenyl-3-yl)-3-(3-(4-hydroxy-1,5-dimethyl-2-oxo-1,2-dihydropyridin-3-yl)ureido)propanoate 1-53;

ethyl (S)-3-(3-(4-hydroxy-1,5-dimethyl-2-oxo-1,2-dihydropyridin-3-yl)ureido)-3-(5-phenylfuran-2-yl)propanoate 1-54;

ethyl (S)-3-(3-(2,5-dimethyl-1H-pyrrol-1-yl)phenyl)-3-(3-(4-hydroxy-1,5-dimethyl-2-oxo-1,2-dihydropyridin-3-yl)ureido)-propanoate 1-55;

ethyl 3-(3'-chloro-4'-fluorobiphenyl-3-yl)-3-(3-(4-hydroxy-1,5-dimethyl-2-oxo-1,2-dihydropyridin-3-yl)ureido) propanoate 1-56;

ethyl 3-(2',3'-dichlorobiphenyl-3-yl)-3-(3-(4-hydroxy-1,5-dimethyl-2-oxo-1,2-dihydropyridin-3-yl)ureido)propanoate 1-57;

ethyl 3-(3',5'-dichlorobiphenyl-3-yl)-3-(3-(4-hydroxy-1,5-dimethyl-2-oxo-1,2-dihydropyridin-3-yl)ureido)propanoate 1-58;

ethyl (S)-3-(2',4'-difluorobiphenyl-3-yl)-3-(3-(4-hydroxy-1,6-dimethyl-2-oxo-1,2-dihydropyridin-3-yl)ureido)propanoate 1-59;

ethyl (S)-3-(2',4'-difluorobiphenyl-3-yl)-3-(3-(4-hydroxy-1-methyl-2-oxo-1,2-dihydropyridin-3-yl)ureido)propanoate 1-60;

ethyl (S)-3-(3-(4-hydroxy-1,5-dimethyl-2-oxo-1,2-dihydropyridin-3-yl)ureido)-3-(3'-methoxy-2'-methylbiphenyl-3-yl)propanoate 1-61;

ethyl (S)-3-(3-(4-hydroxy-1,5-dimethyl-2-oxo-1,2-dihydropyridin-3-yl)ureido)-3-(5'-methoxy-2'-methylbiphenyl-3-yl)propanoate 1-62;

ethyl 3-(3-(4-hydroxy-1,5-dimethyl-2-oxo-1,2-dihydropyridin-3-yl)ureido)-3-(6-(2,2,2-trifluoroethoxy)biphenyl-3-yl)propanoate 1-63;

ethyl (S)-3-(2'-ethylbiphenyl-3-yl)-3-(3-(4-hydroxy-1,5-dimethyl-2-oxo-1,2-dihydro pyridin-3-yl)ureido)propanoate 1-64;

ethyl (S)-3-(4-fluorobiphenyl-3-yl)-3-(3-(4-hydroxy-1,5-dimethyl-2-oxo-1,2-dihydro pyridin-3-yl)ureido)propanoate 1-65;

ethyl (S)-3-(2',4'-difluorobiphenyl-3-yl)-3-(3-(4-hydroxy-2-oxo-1,2-dihydropyridin-3-yl)ureido)propanoate 1-66;

ethyl (S)-3-(3',4'-dimethylbiphenyl-3-yl)-3-(3-(4-hydroxy-1,5-dimethyl-2-oxo-1,2-di hydropyridin-3-yl)ureido)propanoate 1-67;

ethyl (S)-3-(2',3'-difluorobiphenyl-3-yl)-3-(3-(4-hydroxy-1,5-dimethyl-2-oxo-1,2-di hydropyridin-3-yl)ureido)propanoate 1-68;

ethyl (S)-3-(4'-fluoro-3'-methylbiphenyl-3-yl)-3-(3-(4-hydroxy-1,5-dimethyl-2-oxo-1,2-dihydropyridin-3-yl)ureido)propanoate 1-69;

ethyl (S)-3-(3-(4-hydroxy-1,5-dimethyl-2-oxo-1,2-dihydropyridin-3-yl)ureido)-3-(1-phenyl-1H-pyrrol-2-yl)propanoate 1-70;

ethyl (S)-3-(3'-chlorobiphenyl-3-yl)-3-(3-(4-hydroxy-1,5-dimethyl-2-oxo-1,2-dihydropyridin-3-yl)ureido)propanoate 1-71;

ethyl (S)-3-(3-(4-hydroxy-1,5-dimethyl-2-oxo-1,2-dihydropyridin-3-yl)ureido)-3-(2-methylbiphenyl-3-yl)propanoate 1-72;

ethyl (S)-3-(3-(4-hydroxy-1-methyl-2-oxo-1,2-dihydropyridin-3-yl)ureido)-3-(3'-methoxybiphenyl-3-yl)propanoate 1-73;

ethyl (S)-3-(2',6'-dimethylbiphenyl-3-yl)-3-(3-(4-hydroxy-1-methyl-2-oxo-1,2-dihydropyridin-3-yl)ureido)propanoate 1-74;

ethyl 3-(5'-chloro-2',4'-difluorobiphenyl-3-yl)-3-(3-(4-hydroxy-1,5-dimethyl-2-oxo-1,2-dihydropyridin-3-yl)ureido)propanoate 1-75;

ethyl (S)-3-(2',3'-dimethoxybiphenyl-3-yl)-3-(3-(4-hydroxy-1,5-dimethyl-2-oxo-1,2-dihydropyridin-3-yl)ureido)propanoate 1-76;

ethyl (S)-3-(biphenyl-3-yl)-3-(3-(4-hydroxy-1-methyl-2-oxo-1,2-dihydropyridin-3-yl)ureido) propanoate 1-77;

ethyl (S)-3-(3'-chlorobiphenyl-3-yl)-3-(3-(4-hydroxy-1-methyl-2-oxo-1,2-dihydropyridin-3-yl)ureido)propanoate 1-78;

ethyl (S)-3-(3-(1H-pyrrol-1-yl)phenyl)-3-(3-(4-hydroxy-1-methyl-2-oxo-1,2-dihydropyridin-3-yl)ureido)propanoate 1-79;

ethyl (S)-3-(3-(4-hydroxy-1-methyl-2-oxo-1,2-dihydropyridin-3-yl)ureido)-3-(3-(6-methoxypyridin-3-yl)phenyl) propanoate 1-80;

ethyl (S)-3-(2'-fluoro-3'-methoxybiphenyl-3-yl)-3-(3-(4-hydroxy-1-methyl-2-oxo-1,2-dihydropyridin-3-yl)ureido) propanoate 1-81;

ethyl (S)-3-(3-(4-hydroxy-1-methyl-2-oxo-1,2-dihydropyridin-3-yl)ureido)-3-(4'-(trifluoromethoxy)biphenyl-3-yl) propanoate 1-82;

ethyl 3-(2',4'-dichlorobiphenyl-3-yl)-3-(3-(4-hydroxy-1,5-dimethyl-2-oxo-1,2-dihydropyridin-3-yl)ureido)propanoate 1-83;

ethyl (S)-3-(3-(4-hydroxy-1-methyl-2-oxo-1,2-dihydropyridin-3-yl)ureido)-3-(2'-(trifluoromethoxy)biphenyl-3-yl) propanoate 1-84;

ethyl (S)-3-(2',4'-difluorobiphenyl-3-yl)-3-(3-(4-hydroxy-1-methyl-2-oxo-2,5,6,7-tetrahydro-1H-cyclopenta[b]pyridin-3-yl)ureido)propanoate 1-85;

ethyl (S)-3-(3-(4-hydroxy-1-methyl-2-oxo-1,2-dihydropyridin-3-yl)ureido)-3-(3'-(trifluoromethoxy)biphenyl-3-yl) propanoate 1-86;

ethyl (S)-3-(2',4'-difluorobiphenyl-3-yl)-3-(3-(7-hydroxy-4-methyl-5-oxo-4,5-dihydrothieno[3,2-b]pyridin-6-yl)ureido)propanoate 1-87;

ethyl (S)-3-(3-(benzo[d][1,3]dioxol-5-yl)phenyl)-3-(3-(4-hydroxy-1-methyl-2-oxo-1,2-dihydropyridin-3-yl)ureido)propanoate 1-88;

ethyl (S)-3-(3-(benzo[d][1,3]dioxol-5-yl)phenyl)-3-(3-(4-hydroxy-1,5-dimethyl-2-oxo-1,2-dihydropyridin-3-yl)ureido)propanoate 1-89;

ethyl (S)-3-(3-(1H-indazol-1-yl)phenyl)-3-(3-(4-hydroxy-1-methyl-2-oxo-1,2-dihydropyridin-3-yl)ureido)propanoate 1-90;

ethyl (S)-3-(2',4'-difluoro-6-methoxybiphenyl-3-yl)-3-(3-(4-hydroxy-1-methyl-2-oxo-1,2-dihydropyridin-3-yl)ureido)propanoate 1-91;

ethyl (S)-3-(3-(4-hydroxy-1-methyl-2-oxo-1,2-dihydropyridin-3-yl)ureido)-3-(4-phenylthiophen-2-yl)propanoate 1-92;

ethyl (S)-3-(3-(1-ethyl-1H-indol-6-yl)phenyl)-3-(3-(4-hydroxy-1-methyl-2-oxo-1,2-dihydropyridin-3-yl)ureido)propanoate 1-93;

ethyl (S)-3-(3-(1H-pyrazol-1-yl)phenyl)-3-(3-(4-hydroxy-1-methyl-2-oxo-1,2-dihydropyridin-3-yl)ureido)propanoate 1-94;

ethyl (S)-3-(4-(2,4-difluorophenyl)thiophen-2-yl)-3-(3-(4-hydroxy-1-methyl-2-oxo-1,2-dihydropyridin-3-yl)ureido)propanoate 1-95;

ethyl (S)-3-(3',6-dimethoxybiphenyl-3-yl)-3-(3-(4-hydroxy-1-methyl-2-oxo-1,2-dihydropyridin-3-yl)ureido)propanoate 1-96;

ethyl 3-(2',5'-dichlorobiphenyl-3-yl)-3-(3-(4-hydroxy-1,5-dimethyl-2-oxo-1,2-dihydropyridin-3-yl)ureido)propanoate 1-97;

ethyl (S)-3-(2',4'-difluorobiphenyl-3-yl)-3-(3-(4-hydroxy-1-methyl-2-oxo-1,2-dihydro-1,8-naphthyridin-3-yl)ureido)propanoate 1-98;

ethyl (S)-3-(3',6-dimethoxybiphenyl-3-yl)-3-(3-(4-hydroxy-1,5-dimethyl-2-oxo-1,2-dihydropyridin-3-yl)ureido)propanoate 1-99;

ethyl (S)-3-(3-(4-hydroxy-1-methyl-2-oxo-1,2-dihydropyridin-3-yl)ureido)-3-(4-(3-methoxyphenyl)thiophen-2-yl)propanoate 1-100;

ethyl (S)-3-(3-(4-hydroxy-1-methyl-2-oxo-1,2-dihydropyridin-3-yl)ureido)-3-(6-methoxybiphenyl-3-yl)propanoate 1-101;

ethyl (S)-3-(4-(3-chlorophenyl)thiophen-2-yl)-3-(3-(4-hydroxy-1-methyl-2-oxo-1,2-dihydropyridin-3-yl)ureido)propanoate 1-102;

ethyl (S)-3-(2',4'-difluorobiphenyl-3-yl)-3-(3-(1-ethyl-4-hydroxy-2-oxo-1,2-dihydropyridin-3-yl)ureido)propanoate 1-103;

ethyl (S)-3-(3-(4-hydroxy-1-methyl-2-oxo-1,2-dihydropyridin-3-yl)ureido)-3-(3-(thiophen-2-yl)phenyl)propanoate 1-104;

ethyl (S)-3-(3-(4-hydroxy-1-methyl-2-oxo-1,2-dihydropyridin-3-yl)ureido)-3-(6-methoxy-2',6'-dimethylbiphenyl-3-yl)propanoate 1-105;

ethyl (S)-3-(3'-chloro-6-methoxybiphenyl-3-yl)-3-(3-(4-hydroxy-1-methyl-2-oxo-1,2-dihydropyridin-3-yl)ureido)propanoate 1-106;

ethyl (S)-3-(3-(4-hydroxy-1-methyl-2-oxo-1,2-dihydropyridin-3-yl)ureido)-3-(6-methoxy-3'-(trifluoromethoxy)biphenyl-3-yl)propanoate 1-107;

ethyl (S)-3-(3-(4-hydroxy-1-methyl-2-oxo-1,2-dihydropyridin-3-yl)ureido)-3-(6-methoxy-4'-(trifluoromethoxy)biphenyl-3-yl)propanoate 1-108;

ethyl (S)-3-(2',6'-dichlorobiphenyl-3-yl)-3-(3-(4-hydroxy-1-methyl-2-oxo-1,2-dihydropyridin-3-yl)ureido)propanoate 1-109;

ethyl (S)-3-(3-(5-chlorothiophen-2-yl)phenyl)-3-(3-(4-hydroxy-1-methyl-2-oxo-1,2-dihydropyridin-3-yl)ureido)propanoate 1-110;

ethyl (S)-3-(3-(1H-imidazol-1-yl)phenyl)-3-(3-(4-hydroxy-1-methyl-2-oxo-1,2-dihydropyridin-3-yl)ureido)propanoate 1-111;

ethyl (S)-3-(3-(4-hydroxy-1-methyl-2-oxo-1,2-dihydropyridin-3-yl)ureido)-3-(3-(4-methylthiophen-3-yl)phenyl)propanoate 1-112;

ethyl (S)-3-(2',4'-difluoro-6-methylbiphenyl-3-yl)-3-(3-(4-hydroxy-1-methyl-2-oxo-1,2-dihydropyridin-3-yl)ureido)propanoate 1-113;

ethyl (S)-3-(3-(4-hydroxy-1-methyl-2-oxo-1,2-dihydropyridin-3-yl)ureido)-3-(3'-methoxy-6-methylbiphenyl-3-yl)propanoate 1-114;

ethyl (S)-3-(4-(2,6-dimethylphenyl)thiophen-2-yl)-3-(3-(4-hydroxy-1-methyl-2-oxo-1,2-dihydropyridin-3-yl)ureido)propanoate 1-115;

ethyl (S)-3-(3-(1H-pyrrol-3-yl)phenyl)-3-(3-(4-hydroxy-1-methyl-2-oxo-1,2-dihydropyridin-3-yl)ureido)propanoate 1-116;

ethyl (S)-3-(3-(4-hydroxy-1-methyl-2-oxo-1,2-dihydropyridin-3-yl)ureido)-3-(2',6,6'-trimethylbiphenyl-3-yl)propanoate 1-117;

ethyl (S)-3-(3-(4-hydroxy-1-methyl-2-oxo-1,2-dihydropyridin-3-yl)ureido)-3-(2',6,6'-trifluorobiphenyl-3-yl)propanoate 1-118;

ethyl (S)-3-(6-fluoro-3'-methoxybiphenyl-3-yl)-3-(3-(4-hydroxy-1-methyl-2-oxo-1,2-dihydropyridin-3-yl)ureido)propanoate 1-119;

ethyl (S)-3-(3-(4-hydroxy-1-methyl-2-oxo-1,2-dihydropyridin-3-yl)ureido)-3-(3-(1-methyl-1H-pyrazol-4-yl)phenyl)propanoate 1-120;

ethyl (S)-3-(2',4'-difluorobiphenyl-3-yl)-3-(3-(5-hydroxy-2-methyl-3-oxo-2,3-dihydropyridazin-4-yl)ureido)propanoate 1-121;

ethyl (S)-3-(2',6'-dimethylbiphenyl-3-yl)-3-(3-(4-hydroxy-1,6-dimethyl-2-oxo-1,2-dihydropyridin-3-yl)ureido)propanoate 1-122;

ethyl (S)-3-(3',6-dimethoxybiphenyl-3-yl)-3-(3-(4-hydroxy-1,6-dimethyl-2-oxo-1,2-dihydropyridin-3-yl)ureido)propanoate 1-123;

ethyl (S)-3-(4-(2,4-difluorophenyl)thiophen-2-yl)-3-(3-(4-hydroxy-1,6-dimethyl-2-oxo-1,2-dihydropyridin-3-yl)ureido)propanoate 1-124;

ethyl (S)-3-(3-(4-hydroxy-1,6-dimethyl-2-oxo-1,2-dihydropyridin-3-yl)ureido)-3-(3'-methoxybiphenyl-3-yl)propanoate 1-125;

ethyl (S)-3-(3-(4-hydroxy-1,6-dimethyl-2-oxo-1,2-dihydropyridin-3-yl)ureido)-3-(6-methoxy-3'-(trifluoromethoxy)biphenyl-3-yl)propanoate 1-126;

ethyl (S)-3-(3'-chloro-6-methylbiphenyl-3-yl)-3-(3-(4-hydroxy-1-methyl-2-oxo-1,2-dihydropyridin-3-yl)ureido)propanoate 1-127;

ethyl (S)-3-(3'-chlorobiphenyl-3-yl)-3-(3-(4-hydroxy-1,6-dimethyl-2-oxo-1,2-dihydropyridin-3-yl)ureido)propanoate 1-128;

ethyl (S)-3-(2',4'-difluorobiphenyl-3-yl)-3-(3-(4-hydroxy-6-methyl-2-oxo-1,2-dihydropyridin-3-yl)ureido)propanoate 1-129;

ethyl (S)-3-(3-(4-hydroxy-1-methyl-2-oxo-1,2-dihydropyridin-3-yl)ureido)-3-(5-methoxybiphenyl-3-yl)propanoate 1-130;

ethyl (S)-3-(3-(furan-3-yl)phenyl)-3-(3-(4-hydroxy-1-methyl-2-oxo-1,2-dihydropyridin-3-yl)ureido)propanoate 1-131;

ethyl (S)-3-(3-(3,5-dimethylisoxazol-4-yl)phenyl)-3-(3-(4-hydroxy-1-methyl-2-oxo-1,2-dihydropyridin-3-yl)ureido)propanoate 1-132;

ethyl (S)-3-(6-fluoro-2',6'-dimethylbiphenyl-3-yl)-3-(3-(4-hydroxy-1-methyl-2-oxo-1,2-dihydropyridin-3-yl)ureido)propanoate 1-133;

ethyl (S)-3-(5-(2,4-difluorophenyl)thiophen-2-yl)-3-(3-(4-hydroxy-1-methyl-2-oxo-1,2-dihydropyridin-3-yl)ureido)propanoate 1-134;

ethyl (S)-3-(3-(4-hydroxy-1-methyl-2-oxo-1,2-dihydropyridin-3-yl)ureido)-3-(5-(3-methoxyphenyl)thiophen-2-yl)propanoate 1-135;
ethyl (S)-3-(3',5-dimethoxybiphenyl-3-yl)-3-(3-(4-hydroxy-1-methyl-2-oxo-1,2-dihydropyridin-3-yl)ureido)propanoate 1-136;
ethyl (S)-3-(3-(4-hydroxy-1-methyl-2-oxo-1,2-dihydropyridin-3-yl)ureido)-3-(5-methoxy-3'-(trifluoromethoxy)biphenyl-3-yl)propanoate 1-137;
ethyl (S)-3-(2',4'-difluoro-5-methoxybiphenyl-3-yl)-3-(3-(4-hydroxy-1-methyl-2-oxo-1,2-dihydropyridin-3-yl)ureido)propanoate 1-138;
ethyl (S)-3-(3',5-dimethoxybiphenyl-3-yl)-3-(3-(4-hydroxy-1,6-dimethyl-2-oxo-1,2-dihydropyridin-3-yl)ureido)propanoate 1-139;
ethyl (S)-3-(3-(4-hydroxy-1,6-dimethyl-2-oxo-1,2-dihydropyridin-3-yl)ureido)-3-(5-methoxy-3'-(trifluoromethoxy)biphenyl-3-yl)propanoate 1-140;
ethyl (S)-3-(3-(4-hydroxy-1,6-dimethyl-2-oxo-1,2-dihydropyridin-3-yl)ureido)-3-(3'-methoxy-6-methylbiphenyl-3-yl)propanoate 1-141;
ethyl (S)-3-(4-fluorobiphenyl-3-yl)-3-(3-(4-hydroxy-1-methyl-2-oxo-1,2-dihydro pyridin-3-yl)ureido)propanoate 1-142;
ethyl (S)-3-(3-(4-hydroxy-1-methyl-2-oxo-1,2-dihydropyridin-3-yl)ureido)-3-(6-phenylpyridin-2-yl)propanoate 1-143;
ethyl (S)-3-(3-(4-hydroxy-1-methyl-2-oxo-1,2-dihydropyridin-3-yl)ureido)-3-(5-methyl-3'-(trifluoromethoxy)biphenyl-3-yl)propanoate 1-144;
ethyl (S)-3-(3-(4-hydroxy-1-methyl-2-oxo-1,2-dihydropyridin-3-yl)ureido)-3-(2',5,6'-trimethylbiphenyl-3-yl)propanoate 1-145;
ethyl (S)-3-(2',4'-difluoro-5-methylbiphenyl-3-yl)-3-(3-(4-hydroxy-1-methyl-2-oxo-1,2-dihydropyridin-3-yl)ureido)propanoate 1-146;
ethyl (S)-3-(2',4'-difluoro-5-methylbiphenyl-3-yl)-3-(3-(4-hydroxy-1,6-dimethyl-2-oxo-1,2-dihydropyridin-3-yl)ureido)propanoate 1-147;
ethyl (S)-3-(3-(4-hydroxy-1-methyl-2-oxo-1,2-dihydropyridin-3-yl)ureido)-3-(6-methyl-3'-(trifluoromethoxy)biphenyl-3-yl)propanoate 1-148;
ethyl (S)-3-(3-(4-hydroxy-1,6-dimethyl-2-oxo-1,2-dihydropyridin-3-yl)ureido)-3-(6-methyl-3'-(trifluoromethoxy)biphenyl-3-yl)propanoate 1-149;
ethyl (S)-3-(6-fluoro-2',6'-dimethylbiphenyl-3-yl)-3-(3-(4-hydroxy-1,6-dimethyl-2-oxo-1,2-dihydropyridin-3-yl)ureido)propanoate 1-150;
ethyl (S)-3-(3-(4-hydroxy-1-methyl-2-oxo-1,2-dihydropyridin-3-yl)ureido)-3-(5-methoxy-2',6'-dimethylbiphenyl-3-yl)propanoate 1-151;
ethyl (S)-3-(3-(4-hydroxy-1,6-dimethyl-2-oxo-1,2-dihydropyridin-3-yl)ureido)-3-(5-methoxy-2',6'-dimethylbiphenyl-3-yl)propanoate 1-152;
ethyl (S)-3-(2',4'-difluoro-5-methoxybiphenyl-3-yl)-3-(3-(4-hydroxy-1,6-dimethyl-2-oxo-1,2-dihydropyridin-3-yl)ureido)propanoate 1-153;
ethyl (S)-3-(3-(4-hydroxy-1-methyl-2-oxo-1,2-dihydropyridin-3-yl)ureido)-3-(3'-methoxy-5-methylbiphenyl-3-yl)propanoate 1-154;
ethyl (S)-3-(2',6'-dimethylbiphenyl-3-yl)-3-(3-(7-hydroxy-5-oxo-1,2,3,5-tetrahydro indolizin-6-yl)ureido)propanoate 1-155;
ethyl (S)-3-(3-(4-hydroxy-1-methyl-2-oxo-1,2-dihydropyridin-3-yl)ureido)-3-(4'-methyl-[2,3'-bithiophen]-5-yl)propanoate 1-156;
ethyl (S)-3-(3-(4-hydroxy-1,6-dimethyl-2-oxo-1,2-dihydropyridin-3-yl)ureido)-3-(4'-methyl-[2,3'-bithiophen]-5-yl)propanoate 1-157;
ethyl (S)-3-(3-(4-hydroxy-1,6-dimethyl-2-oxo-1,2-dihydropyridin-3-yl)ureido)-3-(3'-methoxy-5-methylbiphenyl-3-yl)propanoate 1-158;
ethyl (S)-3-(5-(2,6-dimethylphenyl)thiophen-2-yl)-3-(3-(4-hydroxy-1-methyl-2-oxo-1,2-dihydropyridin-3-yl)ureido)propanoate 1-159;
ethyl (S)-3-(5-(2,6-dimethylphenyl)thiophen-2-yl)-3-(3-(4-hydroxy-1,6-dimethyl-2-oxo-1,2-dihydropyridin-3-yl)ureido)propanoate 1-160;
ethyl (S)-3-(4-fluoro-2',6'-dimethylbiphenyl-3-yl)-3-(3-(4-hydroxy-1,6-dimethyl-2-oxo-1,2-dihydropyridin-3-yl)ureido)propanoate 1-161;
ethyl (S)-3-(4-fluoro-2',6'-dimethylbiphenyl-3-yl)-3-(3-(4-hydroxy-1-methyl-2-oxo-1,2-dihydropyridin-3-yl)ureido)propanoate 1-162;
ethyl (S)-3-(3-(4-hydroxy-1-methyl-2-oxo-1,2-dihydropyridin-3-yl)ureido)-3-(2',4,4'-trifluorobiphenyl-3-yl)propanoate 1-163;
ethyl (S)-3-(3-(4-hydroxy-1,6-dimethyl-2-oxo-1,2-dihydropyridin-3-yl)ureido)-3-(2',4,4'-trifluorobiphenyl-3-yl)propanoate 1-164;
ethyl (S)-3-(4-fluoro-3'-methoxybiphenyl-3-yl)-3-(3-(4-hydroxy-1-methyl-2-oxo-1,2-dihydropyridin-3-yl)ureido)propanoate 1-165;
ethyl (S)-3-(4-fluoro-3'-(trifluoromethoxy)biphenyl-3-yl)-3-(3-(4-hydroxy-1-methyl-2-oxo-1,2-dihydropyridin-3-yl)ureido)propanoate 1-166;
ethyl (S)-3-(4-fluoro-3'-(trifluoromethoxy)biphenyl-3-yl)-3-(3-(4-hydroxy-1,6-dimethyl-2-oxo-1,2-dihydropyridin-3-yl)ureido)propanoate 1-167;
ethyl (S)-3-(3-(4-hydroxy-1-methyl-2-oxo-1,2-dihydropyridin-3-yl)ureido)-3-(4-methoxybiphenyl-3-yl)propanoate 1-168;
ethyl (S)-3-(3-(4-hydroxy-1,6-dimethyl-2-oxo-1,2-dihydropyridin-3-yl)ureido)-3-(2',5,6'-trimethylbiphenyl-3-yl)propanoate 1-169;
ethyl (S)-3-(3-(4-hydroxy-1-methyl-2-oxo-1,2-dihydropyridin-3-yl)ureido)-3-(2'-methylbiphenyl-3-yl)propanoate 1-170;
ethyl (S)-3-(3-(4-hydroxy-1,6-dimethyl-2-oxo-1,2-dihydropyridin-3-yl)ureido)-3-(2'-methylbiphenyl-3-yl)propanoate 1-171;
ethyl (S)-3-(5-fluoro-2',6'-dimethylbiphenyl-3-yl)-3-(3-(4-hydroxy-1-methyl-2-oxo-1,2-dihydropyridin-3-yl)ureido)propanoate 1-172;
ethyl (S)-3-(3-(4-hydroxy-1-methyl-2-oxo-1,2-dihydropyridin-3-yl)ureido)-3-(5-(3-(trifluoromethoxy)phenyl)thiophen-2-yl)propanoate 1-173;
ethyl (S)-3-(3-(4-hydroxy-1-methyl-2-oxo-1,2-dihydropyridin-3-yl)ureido)-3-(4-methoxy-2',6'-dimethylbiphenyl-3-yl)propanoate 1-174;
ethyl (S)-3-(4-fluoro-3'-methoxybiphenyl-3-yl)-3-(3-(4-hydroxy-1,6-dimethyl-2-oxo-1,2-dihydropyridin-3-yl)ureido)propanoate 1-175;
ethyl (S)-3-(5-fluoro-3'-methoxybiphenyl-3-yl)-3-(3-(4-hydroxy-1-methyl-2-oxo-1,2-dihydropyridin-3-yl)ureido)propanoate 1-176;
ethyl (S)-3-(5-fluoro-3'-methoxybiphenyl-3-yl)-3-(3-(4-hydroxy-1,6-dimethyl-2-oxo-1,2-dihydropyridin-3-yl)ureido)propanoate 1-177;
ethyl (S)-3-(5-fluoro-3'-(trifluoromethoxy)biphenyl-3-yl)-3-(3-(4-hydroxy-1,6-dimethyl-2-oxo-1,2-dihydropyridin-3-yl)ureido)propanoate 1-178;

ethyl (S)-3-(5-fluoro-3'-(trifluoromethoxy)biphenyl-3-yl)-3-(3-(4-hydroxy-1-methyl-2-oxo-1,2-dihydropyridin-3-yl)ureido)propanoate 1-179;

ethyl (S)-3-(5-(3,5-dimethylisoxazol-4-yl)thiophen-2-yl)-3-(3-(4-hydroxy-1-methyl-2-oxo-1,2-dihydropyridin-3-yl)ureido)propanoate 1-180;

ethyl (S)-3-(3-(3,5-dimethylisoxazol-4-yl)phenyl)-3-(3-(4-hydroxy-1,6-dimethyl-2-oxo-1,2-dihydropyridin-3-yl)ureido)propanoate 1-181;

ethyl (S)-3-(2-fluorobiphenyl-3-yl)-3-(3-(4-hydroxy-1,6-dimethyl-2-oxo-1,2-dihydro pyridin-3-yl)ureido)propanoate 1-182;

ethyl (S)-3-(6-fluoro-2'-methylbiphenyl-3-yl)-3-(3-(4-hydroxy-1,6-dimethyl-2-oxo-1,2-dihydropyridin-3-yl)ureido)propanoate 1-183;

ethyl (S)-3-(6-fluoro-2'-methylbiphenyl-3-yl)-3-(3-(4-hydroxy-1-methyl-2-oxo-1,2-dihydropyridin-3-yl)ureido)propanoate 1-184;

ethyl (S)-3-(3-(4-hydroxy-1-methyl-2-oxo-1,2-dihydropyridin-3-yl)ureido)-3-(5-phenylthiophen-2-yl)propanoate 1-185;

ethyl (S)-3-(5-(2,5-difluorophenyl)thiophen-2-yl)-3-(3-(4-hydroxy-1-methyl-2-oxo-1,2-dihydropyridin-3-yl)ureido)propanoate 1-186;

ethyl (S)-3-(3-(4-hydroxy-1-methyl-2-oxo-1,2-dihydropyridin-3-yl)ureido)-3-(5-(tri fluoromethoxy)biphenyl-3-yl)propanoate 1-187;

ethyl (S)-3-(3-(4-hydroxy-1-methyl-2-oxo-1,2-dihydropyridin-3-yl)ureido)-3-(2'-methylbiphenyl-4-yl)propanoate 1-188;

ethyl (S)-3-(3-(7-hydroxy-5-oxo-1,2,3,5-tetrahydroindolizin-6-yl)ureido)-3-(5-methoxybiphenyl-3-yl)propanoate 1-189;

ethyl (S)-3-(3-(4-hydroxy-1-methyl-2-oxo-1,2-dihydropyridin-3-yl)ureido)-3-(5-(tri fluoromethyl)biphenyl-3-yl)propanoate 1-190;

ethyl (S)-3-(5-(3-chlorophenyl)thiophen-2-yl)-3-(3-(4-hydroxy-1-methyl-2-oxo-1,2-dihydropyridin-3-yl)ureido)propanoate 1-191;

ethyl (S)-3-(5-(3-fluorophenyl)thiophen-2-yl)-3-(3-(4-hydroxy-1-methyl-2-oxo-1,2-dihydropyridin-3-yl)ureido)propanoate 1-192;

tert-butyl (S)-3-(2',4'-difluorobiphenyl-4-yl)-3-(3-(4-hydroxy-1-methyl-2-oxo-1,2-dihydropyridin-3-yl)ureido)propanoate 1-193;

tert-butyl (S)-3-(2',4'-difluorobiphenyl-4-yl)-3-(3-(4-hydroxy-1,6-dimethyl-2-oxo-1,2-dihydropyridin-3-yl)ureido)propanoate 1-194;

tert-butyl (S)-3-(2',4'-difluorobiphenyl-4-yl)-3-(3-(4-hydroxy-1,5-dimethyl-2-oxo-1,2-dihydropyridin-3-yl)ureido)propanoate 1-195;

ethyl (S)-3-(3-(4-hydroxy-1-methyl-2-oxo-1,2-dihydropyridin-3-yl)ureido)-3-(2'-methyl-6-(trifluoromethoxy)biphenyl-3-yl)propanoate 1-196;

ethyl (S)-3-(3-(4-hydroxy-1-methyl-2-oxo-1,2-dihydropyridin-3-yl)ureido)-3-(6-(trifluoromethoxy)biphenyl-3-yl)propanoate 1-197;

ethyl 3-(3'-acetylbiphenyl-3-yl)-3-(3-(4-hydroxy-1,5-dimethyl-2-oxo-1,2-dihydropyridin-3-yl)ureido)propanoate 1-198;

ethyl 3-(4'-acetylbiphenyl-3-yl)-3-(3-(4-hydroxy-1,5-dimethyl-2-oxo-1,2-dihydropyridin-3-yl)ureido)propanoate 1-199;

ethyl (S)-3-(3-(4-hydroxy-1,5-dimethyl-2-oxo-1,2-dihydropyridin-3-yl)ureido)-3-(4-phenylthiophen-2-yl)propanoate 1-200;

ethyl (S)-3-(3-(4-hydroxy-1,5-dimethyl-2-oxo-1,2-dihydropyridin-3-yl)ureido)-3-(5-phenylthiophen-2-yl)propanoate 1-201;

ethyl (S)-3-(2',4'-difluorobiphenyl-3-yl)-3-(3-(7-hydroxy-5-oxo-1,2,3,5-tetrahydroindolizin-6-yl)ureido)propanoate 1-202;

ethyl (S)-3-(3-(4-hydroxy-1-methyl-2-oxo-1,2-dihydropyridin-3-yl)ureido)-3-(3-(thiazol-2-yl)phenyl)propanoate 1-203;

ethyl (S)-3-(3-(4-hydroxy-1,6-dimethyl-2-oxo-1,2-dihydropyridin-3-yl)ureido)-3-(5-methyl-3'-(trifluoromethoxy)biphenyl-3-yl)propanoate 1-204;

ethyl (S)-3-(3-(4-hydroxy-1,6-dimethyl-2-oxo-1,2-dihydropyridin-3-yl)ureido)-3-(2',4',5-trifluorobiphenyl-3-yl)propanoate 1-205;

ethyl (S)-3-(3-(4-hydroxy-1-methyl-2-oxo-1,2-dihydropyridin-3-yl)ureido)-3-(2',4',5-trifluorobiphenyl-3-yl)propanoate 1-206;

ethyl (S)-3-(3-(4-hydroxy-1-methyl-2-oxo-1,2-dihydropyridin-3-yl)ureido)-3-(3'-methoxy-6-(trifluoromethoxy)biphenyl-3-yl)propanoate 1-207;

ethyl (S)-3-(3-(4-hydroxy-1,6-dimethyl-2-oxo-1,2-dihydropyridin-3-yl)ureido)-3-(3'-methoxy-6-(trifluoromethoxy)biphenyl-3-yl)propanoate 1-208;

ethyl (S)-3-(2',6'-dimethylbiphenyl-4-yl)-3-(3-(4-hydroxy-1-methyl-2-oxo-1,2-dihydropyridin-3-yl)ureido)propanoate 1-209;

ethyl (S)-3-(3-(4-hydroxy-1,6-dimethyl-2-oxo-1,2-dihydropyridin-3-yl)ureido)-3-(2'-methylbiphenyl-4-yl)propanoate 1-210;

ethyl (S)-3-(2',6'-dimethylbiphenyl-4-yl)-3-(3-(4-hydroxy-1,6-dimethyl-2-oxo-1,2-dihydropyridin-3-yl)ureido)propanoate 1-211;

ethyl (S)-3-(3-(4-hydroxy-1-methyl-2-oxo-1,2-dihydropyridin-3-yl)ureido)-3-(3-(pyridin-2-yl)phenyl)propanoate 1-212;

ethyl (S)-3-(3-(4-hydroxy-1-methyl-2-oxo-1,2-dihydropyridin-3-yl)ureido)-3-(3-(6-methoxypyridazin-3-yl)phenyl)propanoate 1-213;

ethyl (S)-3-(3-(4-hydroxy-1-methyl-2-oxo-1,2-dihydropyridin-3-yl)ureido)-3-(5-phenylpyridin-3-yl)propanoate 1-214;

(S)-ethyl 3-(5-fluoro-2',6'-dimethylbiphenyl-3-yl)-3-(3-(4-hydroxy-1,6-dimethyl-2-oxo-1,2-dihydropyridin-3-yl)ureido)propanoate 1-215;

tert-butyl (S)-3-(biphenyl-4-yl)-3-(3-(1,5-dimethyl-4-oxido-2-oxo-1,2-dihydropyridin-3-yl)ureido)propanoate 1-216;

ethyl (S)-3-(3-(4-hydroxy-1-methyl-2-oxo-1,2-dihydropyridin-3-yl)ureido)-3-(3-(6'-methoxypyridin-2-yl)phenyl)propanoate 1-217;

ethyl (S)-3-(3-(4-hydroxy-1,5-dimethyl-2-oxo-1,2-dihydropyridin-3-yl)ureido)-3-(4'-methoxybiphenyl-3-yl)propanoate 1-218;

ethyl (S)-3-(3-(1H-imidazol-1-yl)phenyl)-3-(3-(4-hydroxy-1-methyl-2-oxo-1,2-dihydropyridin-3-yl)ureido)propanoate 1-219;

ethyl 3-(3-bromophenyl)-3-(3-(4-hydroxy-1,5-dimethyl-2-oxo-1,2-dihydropyridin-3-yl)ureido)propanoate 1-220, ethyl 3-(3-bromophenyl)-3-(3-(1-ethyl-4-hydroxy-5-methyl-2-oxo-1,2-dihydro pyridin-3-yl)ureido)propanoate 1-221 ethyl (S)-3-(2',4'-difluorobiphenyl-4-yl)-3-(3-(4-hydroxy-1-methyl-2-oxo-1,2-di hydropyridin-3-yl)ureido)propanoate 1-222;

ethyl (S)-3-(2',4'-difluorobiphenyl-4-yl)-3-(3-(4-hydroxy-1,6-dimethyl-2-oxo-1,2-di hydropyridin-3-yl)ureido)propanoate 1-223, (S)-3-(biphenyl-3-yl)-3-(3-(4-hydroxy-1,5-dimethyl-2-oxo-1,2-dihydropyridin-3-yl)ureido)propanoic acid 1-224;
(S)-3-(biphenyl-3-yl)-3-(3-(1-ethyl-4-hydroxy-5-methyl-2-oxo-1,2-dihydropyridin-3-yl)ureido)propanoic acid 1-225;
3-(3-(1-ethyl-4-hydroxy-5-methyl-2-oxo-1,2-dihydropyridin-3-yl)ureido)-3-(3-(2-oxo-3-phenylpyridin-1(2H)-yl)phenyl)propanoic acid 1-226;
(S)-3-(3-(4-hydroxy-1,5-dimethyl-2-oxo-1,2-dihydropyridin-3-yl)ureido)-3-(2'-methylbiphenyl-3-yl)propanoic acid 1-227;
(S)-3-(2'-fluorobiphenyl-3-yl)-3-(3-(4-hydroxy-1,5-dimethyl-2-oxo-1,2-dihydropyridin-3-yl)ureido)propanoic acid 1-228;
(S)-3-(6-fluorobiphenyl-3-yl)-3-(3-(4-hydroxy-1,5-dimethyl-2-oxo-1,2-dihydropyridin-3-yl)ureido)propanoic acid 1-229;
(S)-3-(3-(1-ethyl-4-hydroxy-5-methyl-2-oxo-1,2-dihydropyridin-3-yl)ureido)-3-(2'-methylbiphenyl-3-yl)propanoic acid 1-230;
(S)-3-(3-(1-ethyl-4-hydroxy-5-methyl-2-oxo-1,2-dihydropyridin-3-yl)ureido)-3-(4'-methylbiphenyl-3-yl)propanoic acid 1-231;
3-(3-(1H-pyrrol-1-yl)phenyl)-3-(3-(4-hydroxy-1,5-dimethyl-2-oxo-1,2-dihydropyridin-3-yl)ureido)propanoic acid 1-232;
(S)-3-(2',4'-difluorobiphenyl-3-yl)-3-(3-(4-hydroxy-1,5-dimethyl-2-oxo-1,2-dihydropyridin-3-yl)ureido)propanoic acid 1-233;
(S)-3-(2',5'-difluorobiphenyl-3-yl)-3-(3-(4-hydroxy-1,5-dimethyl-2-oxo-1,2-dihydropyridin-3-yl)ureido)propanoic acid 1-234;
(S)-3-(3-(4-hydroxy-1,5-dimethyl-2-oxo-1,2-dihydropyridin-3-yl)ureido)-3-(6-methylbiphenyl-3-yl)propanoic acid 1-235;
(S)-3-(3-(4-hydroxy-1,5-dimethyl-2-oxo-1,2-dihydropyridin-3-yl)ureido)-3-(6-methoxybiphenyl-3-yl)propanoic acid 1-236;
(S)-3-(3-(4-hydroxy-1,5-dimethyl-2-oxo-1,2-dihydropyridin-3-yl)ureido)-3-(4'-methylbiphenyl-3-yl)propanoic acid 1-237;
(S)-3-(3-(4-hydroxy-1,5-dimethyl-2-oxo-1,2-dihydropyridin-3-yl)ureido)-3-(3'-methylbiphenyl-3-yl)propanoic acid 1-238;
(S)-3-(3-(4-hydroxy-1,5-dimethyl-2-oxo-1,2-dihydropyridin-3-yl)ureido)-3-(3-(pyridin-3-yl)phenyl)propanoic acid 1-239;
(S)-3-(3',5'-difluorobiphenyl-3-yl)-3-(3-(4-hydroxy-1,5-dimethyl-2-oxo-1,2-dihydropyridin-3-yl)ureido)propanoic acid 1-240;
(S)-3-(3',5'-dimethylbiphenyl-3-yl)-3-(3-(4-hydroxy-1,5-dimethyl-2-oxo-1,2-dihydropyridin-3-yl)ureido)propanoic acid 1-241;
(S)-3-(3-(4-hydroxy-1,5-dimethyl-2-oxo-1,2-dihydropyridin-3-yl)ureido)-3-(4'-methoxybiphenyl-3-yl)propanoic acid 1-242;
(S)-3-(3-(4-hydroxy-1,5-dimethyl-2-oxo-1,2-dihydropyridin-3-yl)ureido)-3-(2'-methoxybiphenyl-3-yl)propanoic acid 1-243;
(S)-3-(3-(4-hydroxy-1,5-dimethyl-2-oxo-1,2-dihydropyridin-3-yl)ureido)-3-(4'-(trifluoromethyl)biphenyl-3-yl)propanoic acid 1-244;
(S)-3-(3-(4-hydroxy-1,5-dimethyl-2-oxo-1,2-dihydropyridin-3-yl)ureido)-3-(3'-methoxybiphenyl-3-yl)propanoic acid 1-245;
(S)-3-(3-(4-hydroxy-1,5-dimethyl-2-oxo-1,2-dihydropyridin-3-yl)ureido)-3-(3'-(trifluoromethoxy)biphenyl-3-yl)propanoic acid 1-246;
(S)-3-(3',4'-difluorobiphenyl-3-yl)-3-(3-(4-hydroxy-1,5-dimethyl-2-oxo-1,2-dihydropyridin-3-yl)ureido)propanoic acid 1-247;
(S)-3-(2',5'-dimethylbiphenyl-3-yl)-3-(3-(4-hydroxy-1,5-dimethyl-2-oxo-1,2-dihydropyridin-3-yl)ureido)propanoic acid 1-248;
(S)-3-(2',3'-dimethylbiphenyl-3-yl)-3-(3-(4-hydroxy-1,5-dimethyl-2-oxo-1,2-dihydropyridin-3-yl)ureido)propanoic acid 1-249;
3-(3-(4-hydroxy-1,5-dimethyl-2-oxo-1,2-dihydropyridin-3-yl)ureido)-3-(6-oxo-1-phenyl-1,6-dihydropyridin-3-yl)propanoic acid 1-250;
(S)-3-(2',6'-difluorobiphenyl-3-yl)-3-(3-(4-hydroxy-1,5-dimethyl-2-oxo-1,2-dihydropyridin-3-yl)ureido)propanoic acid 1-251;
(S)-3-(3'-fluorobiphenyl-3-yl)-3-(3-(4-hydroxy-1,5-dimethyl-2-oxo-1,2-dihydropyridin-3-yl)ureido)propanoic acid 1-252;
(S)-3-(4'-fluorobiphenyl-3-yl)-3-(3-(4-hydroxy-1,5-dimethyl-2-oxo-1,2-dihydropyridin-3-yl)ureido)propanoic acid 1-253;
(S)-3-(3-(4-hydroxy-1,5-dimethyl-2-oxo-1,2-dihydropyridin-3-yl)ureido)-3-(2'-(trifluoromethoxy)biphenyl-3-yl)propanoic acid 1-254;
(S)-3-(2',4'-dimethoxybiphenyl-3-yl)-3-(3-(4-hydroxy-1,5-dimethyl-2-oxo-1,2-dihydropyridin-3-yl)ureido)propanoic acid 1-255;
(S)-3-(3',4'-dimethoxybiphenyl-3-yl)-3-(3-(4-hydroxy-1,5-dimethyl-2-oxo-1,2-dihydropyridin-3-yl)ureido)propanoic acid 1-256;
(S)-3-(2',6'-dimethylbiphenyl-3-yl)-3-(3-(4-hydroxy-1,5-dimethyl-2-oxo-1,2-dihydropyridin-3-yl)ureido)propanoic acid 1-257;
3-(4'-chlorobiphenyl-3-yl)-3-(3-(4-hydroxy-1,5-dimethyl-2-oxo-1,2-dihydropyridin-3-yl)ureido)propanoic acid 1-258;
3-(3'-chlorobiphenyl-3-yl)-3-(3-(4-hydroxy-1,5-dimethyl-2-oxo-1,2-dihydropyridin-3-yl)ureido)propanoic acid 1-259;
3-(2'-chlorobiphenyl-3-yl)-3-(3-(4-hydroxy-1,5-dimethyl-2-oxo-1,2-dihydropyridin-3-yl)ureido)propanoic acid 1-260;
(S)-3-(3-(4-hydroxy-1,5-dimethyl-2-oxo-1,2-dihydropyridin-3-yl)ureido)-3-(2'-(trifluoromethyl)biphenyl-3-yl)propanoic acid 1-261;
(S)-3-(5,6-dimethoxybiphenyl-3-yl)-3-(3-(4-hydroxy-1,5-dimethyl-2-oxo-1,2-dihydropyridin-3-yl)ureido)propanoic acid 1-262;
(S)-3-(3-(4-hydroxy-1,5-dimethyl-2-oxo-1,2-dihydropyridin-3-yl)ureido)-3-(3-(6-methoxypyridin-3-yl)phenyl)propanoic acid 1-263;
(S)-3-(2',5'-dimethoxybiphenyl-3-yl)-3-(3-(4-hydroxy-1,5-dimethyl-2-oxo-1,2-dihydropyridin-3-yl)ureido)propanoic acid 1-264;
3-(3-(4-hydroxy-1,5-dimethyl-2-oxo-1,2-dihydropyridin-3-yl)ureido)-3-(3-(pyrimidin-5-yl)phenyl)propanoic acid 1-265;
(S)-3-(2',6'-dimethoxybiphenyl-3-yl)-3-(3-(4-hydroxy-1,5-dimethyl-2-oxo-1,2-dihydropyridin-3-yl)ureido)propanoic acid 1-266;
3-(3',4'-dichlorobiphenyl-3-yl)-3-(3-(1-ethyl-4-hydroxy-5-methyl-2-oxo-1,2-dihydropyridin-3-yl)ureido)propanoic acid 1-267;

3-(3',4'-dichlorobiphenyl-3-yl)-3-(3-(4-hydroxy-1,5-dimethyl-2-oxo-1,2-dihydropyridin-3-yl)ureido)propanoic acid 1-268;
(S)-3-(3-(4-hydroxy-1,5-dimethyl-2-oxo-1,2-dihydropyridin-3-yl)ureido)-3-(5-phenylfuran-2-yl)propanoic acid 1-269;
(S)-3-(3-(2,5-dimethyl-1H-pyrrol-1-yl)phenyl)-3-(3-(4-hydroxy-1,5-dimethyl-2-oxo-1,2-dihydropyridin-3-yl)ureido)propanoic acid 1-270;
3-(3'-chloro-4'-fluorobiphenyl-3-yl)-3-(3-(4-hydroxy-1,5-dimethyl-2-oxo-1,2-dihydropyridin-3-yl)ureido)propanoic acid 1-271;
3-(2',3'-dichlorobiphenyl-3-yl)-3-(3-(4-hydroxy-1,5-dimethyl-2-oxo-1,2-dihydropyridin-3-yl)ureido)propanoic acid 1-272;
3-(3',5'-dichlorobiphenyl-3-yl)-3-(3-(4-hydroxy-1,5-dimethyl-2-oxo-1,2-dihydropyridin-3-yl)ureido)propanoic acid 1-273;
(S)-3-(2',4'-difluorobiphenyl-3-yl)-3-(3-(4-hydroxy-1,6-dimethyl-2-oxo-1,2-dihydropyridin-3-yl)ureido)propanoic acid 1-274;
(S)-3-(2',4'-difluorobiphenyl-3-yl)-3-(3-(4-hydroxy-1-methyl-2-oxo-1,2-dihydropyridin-3-yl)ureido)propanoic acid 1-275;
(S)-3-(3-(4-hydroxy-1,5-dimethyl-2-oxo-1,2-dihydropyridin-3-yl)ureido)-3-(3'-methoxy-2'-methylbiphenyl-3-yl)propanoic acid 1-276;
(S)-3-(3-(4-hydroxy-1,5-dimethyl-2-oxo-1,2-dihydropyridin-3-yl)ureido)-3-(5'-methoxy-2'-methylbiphenyl-3-yl)propanoic acid 1-277;
3-(3-(4-hydroxy-1,5-dimethyl-2-oxo-1,2-dihydropyridin-3-yl)ureido)-3-(6-(2,2,2-trifluoroethoxy)biphenyl-3-yl)propanoic acid 1-278;
(S)-3-(2'-ethylbiphenyl-3-yl)-3-(3-(4-hydroxy-1,5-dimethyl-2-oxo-1,2-dihydropyridin-3-yl)ureido)propanoic acid 1-279;
(S)-3-(4-fluorobiphenyl-3-yl)-3-(3-(4-hydroxy-1,5-dimethyl-2-oxo-1,2-dihydropyridin-3-yl)ureido)propanoic acid 1-280;
(S)-3-(2',4'-difluorobiphenyl-3-yl)-3-(3-(4-hydroxy-2-oxo-1,2-dihydropyridin-3-yl)ureido)propanoic acid 1-281;
(S)-3-(3',4'-dimethylbiphenyl-3-yl)-3-(3-(4-hydroxy-1,5-dimethyl-2-oxo-1,2-dihydropyridin-3-yl)ureido)propanoic acid 1-282;
(S)-3-(2',3'-difluorobiphenyl-3-yl)-3-(3-(4-hydroxy-1,5-dimethyl-2-oxo-1,2-dihydropyridin-3-yl)ureido)propanoic acid 1-283;
(S)-3-(4'-fluoro-3'-methylbiphenyl-3-yl)-3-(3-(4-hydroxy-1,5-dimethyl-2-oxo-1,2-dihydropyridin-3-yl)ureido)propanoic acid 1-284;
(S)-3-(3-(4-hydroxy-1,5-dimethyl-2-oxo-1,2-dihydropyridin-3-yl)ureido)-3-(1-phenyl-1H-pyrrol-2-yl)propanoic acid 1-285;
(S)-3-(3'-chlorobiphenyl-3-yl)-3-(3-(4-hydroxy-1,5-dimethyl-2-oxo-1,2-dihydropyridin-3-yl)ureido)propanoic acid 1-286;
(S)-3-(3-(4-hydroxy-1,5-dimethyl-2-oxo-1,2-dihydropyridin-3-yl)ureido)-3-(2-methylbiphenyl-3-yl)propanoic acid 1-287;
(S)-3-(3-(4-hydroxy-1-methyl-2-oxo-1,2-dihydropyridin-3-yl)ureido)-3-(3'-methoxybiphenyl-3-yl)propanoic acid 1-288;
(S)-3-(2',6'-dimethylbiphenyl-3-yl)-3-(3-(4-hydroxy-1-methyl-2-oxo-1,2-dihydropyridin-3-yl)ureido)propanoic acid 1-289;
3-(5'-chloro-2',4'-difluorobiphenyl-3-yl)-3-(3-(4-hydroxy-1,5-dimethyl-2-oxo-1,2-dihydropyridin-3-yl)ureido)propanoic acid 1-290;
(S)-3-(2',3'-dimethoxybiphenyl-3-yl)-3-(3-(4-hydroxy-1,5-dimethyl-2-oxo-1,2-dihydropyridin-3-yl)ureido)propanoic acid 1-291;
(S)-3-(biphenyl-3-yl)-3-(3-(4-hydroxy-1-methyl-2-oxo-1,2-dihydropyridin-3-yl)ureido)propanoic acid 1-292;
(S)-3-(3'-chlorobiphenyl-3-yl)-3-(3-(4-hydroxy-1-methyl-2-oxo-1,2-dihydropyridin-3-yl)ureido)propanoic acid 1-293;
(S)-3-(3-(1H-pyrrol-1-yl)phenyl)-3-(3-(4-hydroxy-1-methyl-2-oxo-1,2-dihydropyridin-3-yl)ureido)propanoic acid 1-294;
(S)-3-(3-(4-hydroxy-1-methyl-2-oxo-1,2-dihydropyridin-3-yl)ureido)-3-(3-(6-methoxypyridin-3-yl)phenyl)propanoic acid 1-295;
(S)-3-(2'-fluoro-3'-methoxybiphenyl-3-yl)-3-(3-(4-hydroxy-1-methyl-2-oxo-1,2-dihydropyridin-3-yl)ureido)propanoic acid 1-296;
(S)-3-(3-(4-hydroxy-1-methyl-2-oxo-1,2-dihydropyridin-3-yl)ureido)-3-(4'-(trifluoromethoxy)biphenyl-3-yl)propanoic acid 1-297;
3-(2',4'-dichlorobiphenyl-3-yl)-3-(3-(4-hydroxy-1,5-dimethyl-2-oxo-1,2-dihydropyridin-3-yl)ureido)propanoic acid 1-298;
(S)-3-(3-(4-hydroxy-1-methyl-2-oxo-1,2-dihydropyridin-3-yl)ureido)-3-(2'-(trifluoromethoxy)biphenyl-3-yl)propanoic acid 1-299;
(S)-3-(2',4'-difluorobiphenyl-3-yl)-3-(3-(4-hydroxy-1-methyl-2-oxo-2,5,6,7-tetrahydro-1H-cyclopenta[b]pyridin-3-yl)ureido)propanoic acid 1-300;
(S)-3-(3-(4-hydroxy-1-methyl-2-oxo-1,2-dihydropyridin-3-yl)ureido)-3-(3'-(trifluoromethoxy)biphenyl-3-yl)propanoic acid 1-301;
(S)-3-(2',4'-difluorobiphenyl-3-yl)-3-(3-(7-hydroxy-4-methyl-5-oxo-4,5-dihydrothieno[3,2-b]pyridin-6-yl)ureido)propanoic acid 1-302;
(S)-3-(3-(benzo[d][1,3]dioxol-5-yl)phenyl)-3-(3-(4-hydroxy-1-methyl-2-oxo-1,2-dihydropyridin-3-yl)ureido)propanoic acid 1-303;
(S)-3-(3-(benzo[d][1,3]dioxol-5-yl)phenyl)-3-(3-(4-hydroxy-1,5-dimethyl-2-oxo-1,2-dihydropyridin-3-yl)ureido)propanoic acid 1-304;
(S)-3-(3-(1H-indazol-1-yl)phenyl)-3-(3-(4-hydroxy-1-methyl-2-oxo-1,2-dihydropyridin-3-yl)ureido)propanoic acid 1-305;
(S)-3-(2',4'-difluoro-6-methoxybiphenyl-3-yl)-3-(3-(4-hydroxy-1-methyl-2-oxo-1,2-dihydropyridin-3-yl)ureido)propanoic acid 1-306;
(S)-3-(3-(4-hydroxy-1-methyl-2-oxo-1,2-dihydropyridin-3-yl)ureido)-3-(4-phenylthiophen-2-yl)propanoic acid 1-307;
(S)-3-(3-(1-ethyl-1H-indol-6-yl)phenyl)-3-(3-(4-hydroxy-1-methyl-2-oxo-1,2-dihydropyridin-3-yl)ureido)propanoic acid 1-308;
(S)-3-(3-(1H-pyrazol-1-yl)phenyl)-3-(3-(4-hydroxy-1-methyl-2-oxo-1,2-dihydropyridin-3-yl)ureido)propanoic acid 1-309;
(S)-3-(4-(2,4-difluorophenyl)thiophen-2-yl)-3-(3-(4-hydroxy-1-methyl-2-oxo-1,2-dihydropyridin-3-yl)ureido)propanoic acid 1-310;
(S)-3-(3',6-dimethoxybiphenyl-3-yl)-3-(3-(4-hydroxy-1-methyl-2-oxo-1,2-dihydropyridin-3-yl)ureido)propanoic acid 1-311;

3-(2',5'-dichlorobiphenyl-3-yl)-3-(3-(4-hydroxy-1,5-dimethyl-2-oxo-1,2-dihydropyridin-3-yl)ureido)propanoic acid 1-312;

(S)-3-(2',4'-difluorobiphenyl-3-yl)-3-(3-(4-hydroxy-1-methyl-2-oxo-1,2-dihydro-1,8-naphthyridin-3-yl)ureido) propanoic acid 1-313;

(S)-3-(3',6-dimethoxybiphenyl-3-yl)-3-(3-(4-hydroxy-1,5-dimethyl-2-oxo-1,2-dihydropyridin-3-yl)ureido)propanoic acid 1-314;

(S)-3-(3-(4-hydroxy-1-methyl-2-oxo-1,2-dihydropyridin-3-yl)ureido)-3-(4-(3-methoxyphenyl)thiophen-2-yl)propanoic acid 1-315;

(S)-3-(3-(4-hydroxy-1-methyl-2-oxo-1,2-dihydropyridin-3-yl)ureido)-3-(6-methoxybiphenyl-3-yl)propanoic acid 1-316;

(S)-3-(4-(3-chlorophenyl)thiophen-2-yl)-3-(3-(4-hydroxy-1-methyl-2-oxo-1,2-dihydropyridin-3-yl)ureido)propanoic acid 1-317;

(S)-3-(2',4'-difluorobiphenyl-3-yl)-3-(3-(1-ethyl-4-hydroxy-2-oxo-1,2-dihydropyridin-3-yl)ureido)propanoic acid 1-318;

(S)-3-(3-(4-hydroxy-1-methyl-2-oxo-1,2-dihydropyridin-3-yl)ureido)-3-(3-(thiophen-2-yl)phenyl)propanoic acid 1-319;

(S)-3-(3-(4-hydroxy-1-methyl-2-oxo-1,2-dihydropyridin-3-yl)ureido)-3-(6-methoxy-2',6'-dimethylbiphenyl-3-yl) propanoic acid 1-320;

(S)-3-(3'-chloro-6-methoxybiphenyl-3-yl)-3-(3-(4-hydroxy-1-methyl-2-oxo-1,2-dihydropyridin-3-yl)ureido)propanoic acid 1-321;

(S)-3-(3-(4-hydroxy-1-methyl-2-oxo-1,2-dihydropyridin-3-yl)ureido)-3-(6-methoxy-3'-(trifluoromethoxy)biphenyl-3-yl)propanoic acid 1-322;

(S)-3-(3-(4-hydroxy-1-methyl-2-oxo-1,2-dihydropyridin-3-yl)ureido)-3-(6-methoxy-4'-(trifluoromethoxy)biphenyl-3-yl)propanoic acid 1-323;

(S)-3-(2',6'-dichlorobiphenyl-3-yl)-3-(3-(4-hydroxy-1-methyl-2-oxo-1,2-dihydropyridin-3-yl)ureido)propanoic acid 1-324;

(S)-3-(3-(5-chlorothiophen-2-yl)phenyl)-3-(3-(4-hydroxy-1-methyl-2-oxo-1,2-dihydropyridin-3-yl)ureido)propanoic acid 1-325;

(S)-3-(3-(1H-imidazol-1-yl)phenyl)-3-(3-(4-hydroxy-1-methyl-2-oxo-1,2-dihydropyridin-3-yl)ureido)propanoic acid 1-326;

(S)-3-(3-(4-hydroxy-1-methyl-2-oxo-1,2-dihydropyridin-3-yl)ureido)-3-(3-(4-methylthiophen-3-yl)phenyl)propanoic acid 1-327;

(S)-3-(2',4'-difluoro-6-methylbiphenyl-3-yl)-3-(3-(4-hydroxy-1-methyl-2-oxo-1,2-dihydropyridin-3-yl)ureido) propanoic acid 1-328;

(S)-3-(3-(4-hydroxy-1-methyl-2-oxo-1,2-dihydropyridin-3-yl)ureido)-3-(3'-methoxy-6-methylbiphenyl-3-yl)propanoic acid 1-329;

(S)-3-(4-(2,6-dimethylphenyl)thiophen-2-yl)-3-(3-(4-hydroxy-1-methyl-2-oxo-1,2-dihydropyridin-3-yl)ureido) propanoic acid 1-330;

(S)-3-(3-(1H-pyrrol-3-yl)phenyl)-3-(3-(4-hydroxy-1-methyl-2-oxo-1,2-dihydropyridin-3-yl)ureido)propanoic acid 1-331;

(S)-3-(3-(4-hydroxy-1-methyl-2-oxo-1,2-dihydropyridin-3-yl)ureido)-3-(2',6,6'-trimethylbiphenyl-3-yl)propanoic acid 1-332;

(S)-3-(3-(4-hydroxy-1-methyl-2-oxo-1,2-dihydropyridin-3-yl)ureido)-3-(2',6,6'-trifluorobiphenyl-3-yl)propanoic acid 1-333;

(S)-3-(6-fluoro-3'-methoxybiphenyl-3-yl)-3-(3-(4-hydroxy-1-methyl-2-oxo-1,2-dihydropyridin-3-yl)ureido)propanoic acid 1-334;

(S)-3-(3-(4-hydroxy-1-methyl-2-oxo-1,2-dihydropyridin-3-yl)ureido)-3-(3-(1-methyl-1H-pyrazol-4-yl)phenyl)propanoic acid 1-335;

(S)-3-(2',4'-difluorobiphenyl-3-yl)-3-(3-(5-hydroxy-2-methyl-3-oxo-2,3-dihydropyridazin-4-yl)ureido)propanoic acid 1-336;

(S)-3-(2',6'-dimethylbiphenyl-3-yl)-3-(3-(4-hydroxy-1,6-dimethyl-2-oxo-1,2-dihydropyridin-3-yl)ureido)propanoic acid 1-337;

(S)-3-(3',6-dimethoxybiphenyl-3-yl)-3-(3-(4-hydroxy-1,6-dimethyl-2-oxo-1,2-dihydropyridin-3-yl)ureido)propanoic acid 1-338;

(S)-3-(4-(2,4-difluorophenyl)thiophen-2-yl)-3-(3-(4-hydroxy-1,6-dimethyl-2-oxo-1,2-dihydropyridin-3-yl) ureido)propanoic acid 1-339;

(S)-3-(3-(4-hydroxy-1,6-dimethyl-2-oxo-1,2-dihydropyridin-3-yl)ureido)-3-(3'-methoxybiphenyl-3-yl)propanoic acid 1-340;

(S)-3-(3-(4-hydroxy-1,6-dimethyl-2-oxo-1,2-dihydropyridin-3-yl)ureido)-3-(6-methoxy-3'-(trifluoromethoxy)biphenyl-3-yl)propanoic acid 1-341;

(S)-3-(3'-chloro-6-methylbiphenyl-3-yl)-3-(3-(4-hydroxy-1-methyl-2-oxo-1,2-dihydropyridin-3-yl)ureido)propanoic acid 1-342;

(S)-3-(3'-chlorobiphenyl-3-yl)-3-(3-(4-hydroxy-1,6-dimethyl-2-oxo-1,2-dihydropyridin-3-yl)ureido)propanoic acid 1-343;

(S)-3-(2',4'-difluorobiphenyl-3-yl)-3-(3-(4-hydroxy-6-methyl-2-oxo-1,2-dihydropyridin-3-yl)ureido)propanoic acid 1-344;

(S)-3-(3-(4-hydroxy-1-methyl-2-oxo-1,2-dihydropyridin-3-yl)ureido)-3-(5-methoxybiphenyl-3-yl)propanoic acid 1-345;

(S)-3-(3-(furan-3-yl)phenyl)-3-(3-(4-hydroxy-1-methyl-2-oxo-1,2-dihydropyridin-3-yl)ureido)propanoic acid 1-346;

(S)-3-(3-(3,5-dimethylisoxazol-4-yl)phenyl)-3-(3-(4-hydroxy-1-methyl-2-oxo-1,2-dihydropyridin-3-yl)ureido) propanoic acid 1-347;

(S)-3-(6-fluoro-2',6'-dimethylbiphenyl-3-yl)-3-(3-(4-hydroxy-1-methyl-2-oxo-1,2-dihydropyridin-3-yl)ureido) propanoic acid 1-348;

(S)-3-(5-(2,4-difluorophenyl)thiophen-2-yl)-3-(3-(4-hydroxy-1-methyl-2-oxo-1,2-dihydropyridin-3-yl)ureido) propanoic acid 1-349;

(S)-3-(3-(4-hydroxy-1-methyl-2-oxo-1,2-dihydropyridin-3-yl)ureido)-3-(5-(3-methoxyphenyl)thiophen-2-yl)propanoic acid 1-350;

(S)-3-(3',5-dimethoxybiphenyl-3-yl)-3-(3-(4-hydroxy-1-methyl-2-oxo-1,2-dihydropyridin-3-yl)ureido)propanoic acid 1-351;

(S)-3-(3-(4-hydroxy-1-methyl-2-oxo-1,2-dihydropyridin-3-yl)ureido)-3-(5-methoxy-3'-(trifluoromethoxy)biphenyl-3-yl)propanoic acid 1-352;

(S)-3-(2',4'-difluoro-5-methoxybiphenyl-3-yl)-3-(3-(4-hydroxy-1-methyl-2-oxo-1,2-dihydropyridin-3-yl)ureido) propanoic acid 1-353;

(S)-3-(3',5-dimethoxybiphenyl-3-yl)-3-(3-(4-hydroxy-1,6-dimethyl-2-oxo-1,2-dihydropyridin-3-yl)ureido)propanoic acid 1-354;

(S)-3-(3-(4-hydroxy-1,6-dimethyl-2-oxo-1,2-dihydropyridin-3-yl)ureido)-3-(5-methoxy-3'-(trifluoromethoxy)biphenyl-3-yl)propanoic acid 1-355;

(S)-3-(3-(4-hydroxy-1,6-dimethyl-2-oxo-1,2-dihydropyridin-3-yl)ureido)-3-(3'-methoxy-6-methylbiphenyl-3-yl)propanoic acid 1-356;

(S)-3-(4-fluorobiphenyl-3-yl)-3-(3-(4-hydroxy-1-methyl-2-oxo-1,2-dihydropyridin-3-yl)ureido)propanoic acid 1-357;

(S)-3-(3-(4-hydroxy-1-methyl-2-oxo-1,2-dihydropyridin-3-yl)ureido)-3-(6-phenylpyridin-2-yl)propanoic acid 1-358;

(S)-3-(3-(4-hydroxy-1-methyl-2-oxo-1,2-dihydropyridin-3-yl)ureido)-3-(5-methyl-3'-(trifluoromethoxy)biphenyl-3-yl)propanoic acid 1-359;

(S)-3-(3-(4-hydroxy-1-methyl-2-oxo-1,2-dihydropyridin-3-yl)ureido)-3-(2',5,6'-trimethylbiphenyl-3-yl)propanoic acid 1-360;

(S)-3-(2',4'-difluoro-5-methylbiphenyl-3-yl)-3-(3-(4-hydroxy-1-methyl-2-oxo-1,2-dihydropyridin-3-yl)ureido)propanoic acid 1-361;

(S)-3-(2',4'-difluoro-5-methylbiphenyl-3-yl)-3-(3-(4-hydroxy-1,6-dimethyl-2-oxo-1,2-dihydropyridin-3-yl)ureido)propanoic acid 1-362;

(S)-3-(3-(4-hydroxy-1-methyl-2-oxo-1,2-dihydropyridin-3-yl)ureido)-3-(6-methyl-3'-(trifluoromethoxy)biphenyl-3-yl)propanoic acid 1-363;

(S)-3-(3-(4-hydroxy-1,6-dimethyl-2-oxo-1,2-dihydropyridin-3-yl)ureido)-3-(6-methyl-3'-(trifluoromethoxy)biphenyl-3-yl)propanoic acid 1-364;

(S)-3-(6-fluoro-2',6'-dimethylbiphenyl-3-yl)-3-(3-(4-hydroxy-1,6-dimethyl-2-oxo-1,2-dihydropyridin-3-yl)ureido)propanoic acid 1-365;

(S)-3-(3-(4-hydroxy-1-methyl-2-oxo-1,2-dihydropyridin-3-yl)ureido)-3-(5-methoxy-2',6'-dimethylbiphenyl-3-yl)propanoic acid 1-366;

(S)-3-(3-(4-hydroxy-1,6-dimethyl-2-oxo-1,2-dihydropyridin-3-yl)ureido)-3-(5-methoxy-2',6'-dimethylbiphenyl-3-yl)propanoic acid 1-367;

(S)-3-(2',4'-difluoro-5-methoxybiphenyl-3-yl)-3-(3-(4-hydroxy-1,6-dimethyl-2-oxo-1,2-dihydropyridin-3-yl)ureido)propanoic acid 1-368;

(S)-3-(3-(4-hydroxy-1-methyl-2-oxo-1,2-dihydropyridin-3-yl)ureido)-3-(3'-methoxy-5-methylbiphenyl-3-yl)propanoic acid 1-369;

(S)-3-(2',6'-dimethylbiphenyl-3-yl)-3-(3-(7-hydroxy-5-oxo-1,2,3,5-tetrahydroindolizin-6-yl)ureido)propanoic acid 1-370;

(S)-3-(3-(4-hydroxy-1-methyl-2-oxo-1,2-dihydropyridin-3-yl)ureido)-3-(4'-methyl-[2,3'-bithiophen]-5-yl)propanoic acid 1-371;

(S)-3-(3-(4-hydroxy-1,6-dimethyl-2-oxo-1,2-dihydropyridin-3-yl)ureido)-3-(4'-methyl-[2,3'-bithiophen]-5-yl)propanoic acid 1-372;

(S)-3-(3-(4-hydroxy-1,6-dimethyl-2-oxo-1,2-dihydropyridin-3-yl)ureido)-3-(3'-methoxy-5-methylbiphenyl-3-yl)propanoic acid 1-373;

(S)-3-(5-(2,6-dimethylphenyl)thiophen-2-yl)-3-(3-(4-hydroxy-1-methyl-2-oxo-1,2-dihydropyridin-3-yl)ureido)propanoic acid 1-374;

(S)-3-(5-(2,6-dimethylphenyl)thiophen-2-yl)-3-(3-(4-hydroxy-1,6-dimethyl-2-oxo-1,2-dihydropyridin-3-yl)ureido)propanoic acid 1-375;

(S)-3-(4-fluoro-2',6'-dimethylbiphenyl-3-yl)-3-(3-(4-hydroxy-1,6-dimethyl-2-oxo-1,2-dihydropyridin-3-yl)ureido)propanoic acid 1-376;

(S)-3-(4-fluoro-2',6'-dimethylbiphenyl-3-yl)-3-(3-(4-hydroxy-1-methyl-2-oxo-1,2-dihydropyridin-3-yl)ureido)propanoic acid 1-377;

(S)-3-(3-(4-hydroxy-1-methyl-2-oxo-1,2-dihydropyridin-3-yl)ureido)-3-(2',4,4'-trifluorobiphenyl-3-yl)propanoic acid 1-378;

(S)-3-(3-(4-hydroxy-1,6-dimethyl-2-oxo-1,2-dihydropyridin-3-yl)ureido)-3-(2',4,4'-trifluorobiphenyl-3-yl)propanoic acid 1-379;

(S)-3-(4-fluoro-3'-methoxybiphenyl-3-yl)-3-(3-(4-hydroxy-1-methyl-2-oxo-1,2-dihydropyridin-3-yl)ureido)propanoic acid 1-380;

(S)-3-(4-fluoro-3'-(trifluoromethoxy)biphenyl-3-yl)-3-(3-(4-hydroxy-1-methyl-2-oxo-1,2-dihydropyridin-3-yl)ureido)propanoic acid 1-381;

(S)-3-(4-fluoro-3'-(trifluoromethoxy)biphenyl-3-yl)-3-(3-(4-hydroxy-1,6-dimethyl-2-oxo-1,2-dihydropyridin-3-yl)ureido)propanoic acid 1-382;

(S)-3-(3-(4-hydroxy-1-methyl-2-oxo-1,2-dihydropyridin-3-yl)ureido)-3-(4-methoxybiphenyl-3-yl)propanoic acid 1-383;

(S)-3-(3-(4-hydroxy-1,6-dimethyl-2-oxo-1,2-dihydropyridin-3-yl)ureido)-3-(2',5,6'-trimethylbiphenyl-3-yl)propanoic acid 1-384;

(S)-3-(3-(4-hydroxy-1-methyl-2-oxo-1,2-dihydropyridin-3-yl)ureido)-3-(2'-methylbiphenyl-3-yl)propanoic acid 1-385;

(S)-3-(3-(4-hydroxy-1,6-dimethyl-2-oxo-1,2-dihydropyridin-3-yl)ureido)-3-(2'-methylbiphenyl-3-yl)propanoic acid 1-386;

(S)-3-(5-fluoro-2',6'-dimethylbiphenyl-3-yl)-3-(3-(4-hydroxy-1-methyl-2-oxo-1,2-dihydropyridin-3-yl)ureido)propanoic acid 1-387;

(S)-3-(3-(4-hydroxy-1-methyl-2-oxo-1,2-dihydropyridin-3-yl)ureido)-3-(5-(3-(trifluoromethoxy)phenyl)thiophen-2-yl)propanoic acid 1-388;

(S)-3-(3-(4-hydroxy-1-methyl-2-oxo-1,2-dihydropyridin-3-yl)ureido)-3-(4-methoxy-2',6'-dimethylbiphenyl-3-yl)propanoic acid 1-389;

(S)-3-(4-fluoro-3'-methoxybiphenyl-3-yl)-3-(3-(4-hydroxy-1,6-dimethyl-2-oxo-1,2-dihydropyridin-3-yl)ureido)propanoic acid 1-390;

(S)-3-(5-fluoro-3'-methoxybiphenyl-3-yl)-3-(3-(4-hydroxy-1-methyl-2-oxo-1,2-dihydropyridin-3-yl)ureido)propanoic acid 1-391;

(S)-3-(5-fluoro-3'-methoxybiphenyl-3-yl)-3-(3-(4-hydroxy-1,6-dimethyl-2-oxo-1,2-dihydropyridin-3-yl)ureido)propanoic acid 1-392;

(S)-3-(5-fluoro-3'-(trifluoromethoxy)biphenyl-3-yl)-3-(3-(4-hydroxy-1,6-dimethyl-2-oxo-1,2-dihydropyridin-3-yl)ureido)propanoic acid 1-393;

(S)-3-(5-fluoro-3'-(trifluoromethoxy)biphenyl-3-yl)-3-(3-(4-hydroxy-1-methyl-2-oxo-1,2-dihydropyridin-3-yl)ureido)propanoic acid 1-394;

(S)-3-(5-(3,5-dimethylisoxazol-4-yl)thiophen-2-yl)-3-(3-(4-hydroxy-1-methyl-2-oxo-1,2-dihydropyridin-3-yl)ureido)propanoic acid 1-395;

(S)-3-(3-(3,5-dimethylisoxazol-4-yl)phenyl)-3-(3-(4-hydroxy-1,6-dimethyl-2-oxo-1,2-dihydropyridin-3-yl)ureido)propanoic acid 1-396;

(S)-3-(2-fluorobiphenyl-3-yl)-3-(3-(4-hydroxy-1,6-dimethyl-2-oxo-1,2-dihydropyridin-3-yl)ureido)propanoic acid 1-397;

(S)-3-(6-fluoro-2'-methylbiphenyl-3-yl)-3-(3-(4-hydroxy-1,6-dimethyl-2-oxo-1,2-dihydropyridin-3-yl)ureido)propanoic acid 1-398;

(S)-3-(6-fluoro-2'-methylbiphenyl-3-yl)-3-(3-(4-hydroxy-1-methyl-2-oxo-1,2-dihydropyridin-3-yl)ureido)propanoic acid 1-399;

(S)-3-(3-(4-hydroxy-1-methyl-2-oxo-1,2-dihydropyridin-3-yl)ureido)-3-(5-phenylthiophen-2-yl)propanoic acid 1-400;

(S)-3-(5-(2,5-difluorophenyl)thiophen-2-yl)-3-(3-(4-hydroxy-1-methyl-2-oxo-1,2-dihydropyridin-3-yl)ureido)propanoic acid 1-401;

(S)-3-(3-(4-hydroxy-1-methyl-2-oxo-1,2-dihydropyridin-3-yl)ureido)-3-(5-(trifluoromethoxy)biphenyl-3-yl)propanoic acid 1-402;

(S)-3-(3-(4-hydroxy-1-methyl-2-oxo-1,2-dihydropyridin-3-yl)ureido)-3-(2'-methylbiphenyl-4-yl)propanoic acid 1-403;

(S)-3-(3-(7-hydroxy-5-oxo-1,2,3,5-tetrahydroindolizin-6-yl)ureido)-3-(5-methoxybiphenyl-3-yl)propanoic acid 1-404;

(S)-3-(3-(4-hydroxy-1-methyl-2-oxo-1,2-dihydropyridin-3-yl)ureido)-3-(5-(trifluoromethyl)biphenyl-3-yl)propanoic acid 1-405;

(S)-3-(5-(3-chlorophenyl)thiophen-2-yl)-3-(3-(4-hydroxy-1-methyl-2-oxo-1,2-dihydropyridin-3-yl)ureido)propanoic acid 1-406;

(S)-3-(5-(3-fluorophenyl)thiophen-2-yl)-3-(3-(4-hydroxy-1-methyl-2-oxo-1,2-dihydropyridin-3-yl)ureido)propanoic acid 1-407;

(S)-3-(2',4'-difluorobiphenyl-4-yl)-3-(3-(4-hydroxy-1-methyl-2-oxo-1,2-dihydropyridin-3-yl)ureido)propanoic acid 1-408;

(S)-3-(2',4'-difluorobiphenyl-4-yl)-3-(3-(4-hydroxy-1,6-dimethyl-2-oxo-1,2-dihydropyridin-3-yl)ureido)propanoic acid 1-409;

(S)-3-(2',4'-difluorobiphenyl-4-yl)-3-(3-(4-hydroxy-1,5-dimethyl-2-oxo-1,2-dihydropyridin-3-yl)ureido)propanoic acid 1-410;

(S)-3-(3-(4-hydroxy-1-methyl-2-oxo-1,2-dihydropyridin-3-yl)ureido)-3-(2'-methyl-6-(trifluoromethoxy)biphenyl-3-yl)propanoic acid 1-411;

(S)-3-(3-(4-hydroxy-1-methyl-2-oxo-1,2-dihydropyridin-3-yl)ureido)-3-(6-(trifluoromethoxy)biphenyl-3-yl)propanoic acid 1-412;

3-(3'-acetylbiphenyl-3-yl)-3-(3-(4-hydroxy-1,5-dimethyl-2-oxo-1,2-dihydropyridin-3-yl)ureido)propanoic acid 1-413;

3-(4'-acetylbiphenyl-3-yl)-3-(3-(4-hydroxy-1,5-dimethyl-2-oxo-1,2-dihydropyridin-3-yl)ureido)propanoic acid 1-414;

(S)-3-(3-(4-hydroxy-1,5-dimethyl-2-oxo-1,2-dihydropyridin-3-yl)ureido)-3-(4-phenylthiophen-2-yl)propanoic acid 1-415;

(S)-3-(3-(4-hydroxy-1,5-dimethyl-2-oxo-1,2-dihydropyridin-3-yl)ureido)-3-(5-phenylthiophen-2-yl)propanoic acid 1-416;

(S)-3-(2',4'-difluorobiphenyl-3-yl)-3-(3-(7-hydroxy-5-oxo-1,2,3,5-tetrahydroindolizin-6-yl)ureido)propanoic acid 1-417;

(S)-3-(3-(4-hydroxy-1-methyl-2-oxo-1,2-dihydropyridin-3-yl)ureido)-3-(3-(thiazol-2-yl)phenyl)propanoic acid 1-418;

(S)-3-(3-(4-hydroxy-1,6-dimethyl-2-oxo-1,2-dihydropyridin-3-yl)ureido)-3-(5-methyl-3'-(trifluoromethoxy)biphenyl-3-yl)propanoic acid 1-419;

(S)-3-(3-(4-hydroxy-1,6-dimethyl-2-oxo-1,2-dihydropyridin-3-yl)ureido)-3-(2',4',5-trifluorobiphenyl-3-yl)propanoic acid 1-420;

(S)-3-(3-(4-hydroxy-1-methyl-2-oxo-1,2-dihydropyridin-3-yl)ureido)-3-(2',4',5-trifluorobiphenyl-3-yl)propanoic acid 1-421;

(S)-3-(3-(4-hydroxy-1-methyl-2-oxo-1,2-dihydropyridin-3-yl)ureido)-3-(3'-methoxy-6-(trifluoromethoxy)biphenyl-3-yl)propanoic acid 1-422;

(S)-3-(3-(4-hydroxy-1,6-dimethyl-2-oxo-1,2-dihydropyridin-3-yl)ureido)-3-(3'-methoxy-6-(trifluoromethoxy)biphenyl-3-yl)propanoic acid 1-423;

(S)-3-(2',6'-dimethylbiphenyl-4-yl)-3-(3-(4-hydroxy-1-methyl-2-oxo-1,2-dihydropyridin-3-yl)ureido)propanoic acid 1-424;

(S)-3-(3-(4-hydroxy-1,6-dimethyl-2-oxo-1,2-dihydropyridin-3-yl)ureido)-3-(2'-methylbiphenyl-4-yl)propanoic acid 1-425;

(S)-3-(2',6'-dimethylbiphenyl-4-yl)-3-(3-(4-hydroxy-1,6-dimethyl-2-oxo-1,2-dihydropyridin-3-yl)ureido)propanoic acid 1-426;

(S)-3-(3-(4-hydroxy-1-methyl-2-oxo-1,2-dihydropyridin-3-yl)ureido)-3-(3-(pyridin-2-yl)phenyl)propanoic acid 1-427;

(S)-3-(3-(4-hydroxy-1-methyl-2-oxo-1,2-dihydropyridin-3-yl)ureido)-3-(3-(6-methoxypyridazin-3-yl)phenyl)propanoic acid 1-428;

(S)-3-(3-(4-hydroxy-1-methyl-2-oxo-1,2-dihydropyridin-3-yl)ureido)-3-(5-phenylpyridin-3-yl)propanoic acid 1-429;

(S)-3-(5-fluoro-2',6'-dimethylbiphenyl-3-yl)-3-(3-(4-hydroxy-1,6-dimethyl-2-oxo-1,2-dihydropyridin-3-yl)ureido)propanoic acid;

(S)-3-(biphenyl-4-yl)-3-(3-(1,5-dimethyl-4-oxido-2-oxo-1,2-dihydropyridin-3-yl)ureido) propanoic acid 1-430;

(S)-3-(3-(4-hydroxy-1-methyl-2-oxo-1,2-dihydropyridin-3-yl)ureido)-3-(3-(6'-methoxypyridin-2-yl)phenyl)propanoic acid 1-431;

(S)-3-(3-(4-hydroxy-1,5-dimethyl-2-oxo-1,2-dihydropyridin-3-yl)ureido)-3-(4'-methoxybiphenyl-3-yl) propanoic acid 1-432;

(S)-3-(3-(1H-imidazol-1-yl)phenyl)-3-(3-(4-hydroxy-1-methyl-2-oxo-1,2-dihydropyridin-3-yl)ureido)propanoic acid 1-433;

(S)-3-(3-(4-hydroxy-1-methyl-2-oxo-1,2-dihydropyridin-3-yl)ureido)-3-(3-(pyrazin-2-yl)phenyl)propanoic acid 1-434, 3-(3-bromophenyl)-3-(3-(4-hydroxy-1,5-dimethyl-2-oxo-1,2-dihydropyridin-3-yl)ureido) propanoic acid 1-435, 3-(3-bromophenyl)-3-(3-(1-ethyl-4-hydroxy-5-methyl-2-oxo-1,2-dihydropyridin-3-yl)ureido) propanoic acid 1-436, sodium (S)-3-(biphenyl-3-yl)-3-(3-(1,5-dimethyl-4-oxido-2-oxo-1,2-dihydropyridin-3-yl) ureido)propanoate 1-437;

sodium (S)-3-(biphenyl-3-yl)-3-(3-(1-ethyl-5-methyl-4-oxido-2-oxo-1,2-dihydropyridin-3-yl)ureido)propanoate 1-438;

sodium 3-(3-(1-ethyl-5-methyl-4-oxido-2-oxo-1,2-dihydropyridin-3-yl)ureido)-3-(3-(2-oxo-3-phenylpyridin-1(2H)-yl)phenyl)propanoate 1-439;

sodium (S)-3-(3-(1,5-dimethyl-4-oxido-2-oxo-1,2-dihydropyridin-3-yl)ureido)-3-(2'-methylbiphenyl-3-yl)propanoate 1-440;

sodium (S)-3-(3-(1,5-dimethyl-4-oxido-2-oxo-1,2-dihydropyridin-3-yl)ureido)-3-(2'-fluorobiphenyl-3-yl)propanoate 1-441;

sodium (S)-3-(3-(1,5-dimethyl-4-oxido-2-oxo-1,2-dihydropyridin-3-yl)ureido)-3-(6-fluorobiphenyl-3-yl)propanoate 1-442;

sodium (S)-3-(3-(1-ethyl-5-methyl-4-oxido-2-oxo-1,2-dihydropyridin-3-yl)ureido)-3-(2'-methylbiphenyl-3-yl)propanoate 1-443;

sodium (S)-3-(3-(1-ethyl-5-methyl-4-oxido-2-oxo-1,2-dihydropyridin-3-yl)ureido)-3-(4'-methylbiphenyl-3-yl)propanoate 1-444;

sodium 3-(3-(1H-pyrrol-1-yl)phenyl)-3-(3-(1,5-dimethyl-4-oxido-2-oxo-1,2-dihydro pyridin-3-yl)ureido)propanoate 1-445;

sodium (S)-3-(2',4'-difluorobiphenyl-3-yl)-3-(3-(1,5-dimethyl-4-oxido-2-oxo-1,2-dihydropyridin-3-yl)ureido)propanoate 1-446;

sodium (S)-3-(2',5'-difluorobiphenyl-3-yl)-3-(3-(1,5-dimethyl-4-oxido-2-oxo-1,2-di hydropyridin-3-yl)ureido) propanoate 1-447;

sodium (S)-3-(3-(1,5-dimethyl-4-oxido-2-oxo-1,2-dihydropyridin-3-yl)ureido)-3-(6-methylbiphenyl-3-yl)propanoate 1-448;

sodium (S)-3-(3-(1,5-dimethyl-4-oxido-2-oxo-1,2-dihydropyridin-3-yl)ureido)-3-(6-methoxybiphenyl-3-yl)propanoate 1-449;

sodium (S)-3-(3-(1,5-dimethyl-4-oxido-2-oxo-1,2-dihydropyridin-3-yl)ureido)-3-(4'-methylbiphenyl-3-yl)propanoate 1-450;

sodium (S)-3-(3-(1,5-dimethyl-4-oxido-2-oxo-1,2-dihydropyridin-3-yl)ureido)-3-(3'-methylbiphenyl-3-yl)propanoate 1-451;

sodium (S)-3-(3-(1,5-dimethyl-4-oxido-2-oxo-1,2-dihydropyridin-3-yl)ureido)-3-(3-(pyridin-3-yl)phenyl)propanoate 1-452;

sodium (S)-3-(3',5'-difluorobiphenyl-3-yl)-3-(3-(1,5-dimethyl-4-oxido-2-oxo-1,2-di hydropyridin-3-yl)ureido) propanoate 1-453;

sodium (S)-3-(3-(1,5-dimethyl-4-oxido-2-oxo-1,2-dihydropyridin-3-yl)ureido)-3-(3',5'-dimethylbiphenyl-3-yl)propanoate 1-454;

sodium (S)-3-(3-(1,5-dimethyl-4-oxido-2-oxo-1,2-dihydropyridin-3-yl)ureido)-3-(4'-methoxybiphenyl-3-yl)propanoate 1-455;

sodium (S)-3-(3-(1,5-dimethyl-4-oxido-2-oxo-1,2-dihydropyridin-3-yl)ureido)-3-(2'-methoxybiphenyl-3-yl)propanoate 1-456;

sodium (S)-3-(3-(1,5-dimethyl-4-oxido-2-oxo-1,2-dihydropyridin-3-yl)ureido)-3-(4'-(trifluoromethyl)biphenyl-3-yl)propanoate 1-457;

sodium (S)-3-(3',4'-difluorobiphenyl-3-yl)-3-(3-(1,5-dimethyl-4-oxido-2-oxo-1,2-di hydropyridin-3-yl)ureido) propanoate 1-458;

sodium (S)-3-(3-(1,5-dimethyl-4-oxido-2-oxo-1,2-dihydropyridin-3-yl)ureido)-3-(2',5'-dimethylbiphenyl-3-yl)propanoate 1-459;

sodium (S)-3-(3-(1,5-dimethyl-4-oxido-2-oxo-1,2-dihydropyridin-3-yl)ureido)-3-(3'-methoxybiphenyl-3-yl)propanoate 1-460;

sodium (S)-3-(3-(1,5-dimethyl-4-oxido-2-oxo-1,2-dihydropyridin-3-yl)ureido)-3-(3'-(trifluoromethoxy)biphenyl-3-yl)propanoate 1-461;

sodium (S)-3-(3-(1,5-dimethyl-4-oxido-2-oxo-1,2-dihydropyridin-3-yl)ureido)-3-(2',3'-dimethylbiphenyl-3-yl)propanoate 1-462;

sodium 3-(3-(1,5-dimethyl-4-oxido-2-oxo-1,2-dihydropyridin-3-yl)ureido)-3-(6-oxo-1-phenyl-1,6-dihydropyridin-3-yl)propanoate 1-463;

sodium (S)-3-(2',6'-difluorobiphenyl-3-yl)-3-(3-(1,5-dimethyl-4-oxido-2-oxo-1,2-di hydropyridin-3-yl)ureido) propanoate 1-464;

sodium (S)-3-(3-(1,5-dimethyl-4-oxido-2-oxo-1,2-dihydropyridin-3-yl)ureido)-3-(3'-fluorobiphenyl-3-yl)propanoate 1-465;

sodium (S)-3-(3-(1,5-dimethyl-4-oxido-2-oxo-1,2-dihydropyridin-3-yl)ureido)-3-(4'-fluorobiphenyl-3-yl)propanoate 1-466;

sodium (S)-3-(3-(1,5-dimethyl-4-oxido-2-oxo-1,2-dihydropyridin-3-yl)ureido)-3-(2'-(trifluoromethoxy)biphenyl-3-yl)propanoate 1-467;

sodium (S)-3-(2',4'-dimethoxybiphenyl-3-yl)-3-(3-(1,5-dimethyl-4-oxido-2-oxo-1,2-dihydropyridin-3-yl)ureido)propanoate 1-468;

sodium (S)-3-(3',4'-dimethoxybiphenyl-3-yl)-3-(3-(1,5-dimethyl-4-oxido-2-oxo-1,2-dihydropyridin-3-yl)ureido)propanoate 1-469;

sodium (S)-3-(3-(1,5-dimethyl-4-oxido-2-oxo-1,2-dihydropyridin-3-yl)ureido)-3-(2',6'-dimethylbiphenyl-3-yl)propanoate 1-470;

sodium 3-(4'-chlorobiphenyl-3-yl)-3-(3-(1,5-dimethyl-4-oxido-2-oxo-1,2-dihydropyridin-3-yl)ureido)propanoate 1-471;

sodium 3-(3'-chlorobiphenyl-3-yl)-3-(3-(1,5-dimethyl-4-oxido-2-oxo-1,2-dihydropyridin-3-yl)ureido)propanoate 1-472;

sodium 3-(2'-chlorobiphenyl-3-yl)-3-(3-(1,5-dimethyl-4-oxido-2-oxo-1,2-dihydropyridin-3-yl)ureido)propanoate 1-473;

sodium (S)-3-(3-(1,5-dimethyl-4-oxido-2-oxo-1,2-dihydropyridin-3-yl)ureido)-3-(2'-(trifluoromethyl)biphenyl-3-yl)propanoate 1-474;

sodium (S)-3-(5,6-dimethoxybiphenyl-3-yl)-3-(3-(1,5-dimethyl-4-oxido-2-oxo-1,2-dihydropyridin-3-yl)ureido)propanoate 1-475;

sodium (S)-3-(3-(1,5-dimethyl-4-oxido-2-oxo-1,2-dihydropyridin-3-yl)ureido)-3-(3-(6-methoxypyridin-3-yl)phenyl)propanoate 1-476;

sodium (S)-3-(2',5'-dimethoxybiphenyl-3-yl)-3-(3-(1,5-dimethyl-4-oxido-2-oxo-1,2-dihydropyridin-3-yl)ureido)propanoate 1-477;

sodium 3-(3-(1,5-dimethyl-4-oxido-2-oxo-1,2-dihydropyridin-3-yl)ureido)-3-(3-(pyrimidin-5-yl)phenyl)propanoate 1-478;

sodium (S)-3-(2',6'-dimethoxybiphenyl-3-yl)-3-(3-(1,5-dimethyl-4-oxido-2-oxo-1,2-dihydropyridin-3-yl)ureido)propanoate 1-479;

sodium 3-(3',4'-dichlorobiphenyl-3-yl)-3-(3-(1-ethyl-5-methyl-4-oxido-2-oxo-1,2-dihydropyridin-3-yl)ureido) propanoate 1-480;

sodium 3-(3',4'-dichlorobiphenyl-3-yl)-3-(3-(1,5-dimethyl-4-oxido-2-oxo-1,2-dihydropyridin-3-yl)ureido)propanoate 1-481;

sodium (S)-3-(3-(1,5-dimethyl-4-oxido-2-oxo-1,2-dihydropyridin-3-yl)ureido)-3-(5-phenylfuran-2-yl)propanoate 1-482;

sodium (S)-3-(3-(2,5-dimethyl-1H-pyrrol-1-yl)phenyl)-3-(3-(1,5-dimethyl-4-oxido-2-oxo-1,2-dihydropyridin-3-yl)ureido)propanoate 1-483;

sodium 3-(3'-chloro-4'-fluorobiphenyl-3-yl)-3-(3-(1,5-dimethyl-4-oxido-2-oxo-1,2-dihydropyridin-3-yl)ureido)propanoate 1-484;

sodium 3-(2',3'-dichlorobiphenyl-3-yl)-3-(3-(1,5-dimethyl-4-oxido-2-oxo-1,2-dihydropyridin-3-yl)ureido)propanoate 1-485;

sodium 3-(3',5'-dichlorobiphenyl-3-yl)-3-(3-(1,5-dimethyl-4-oxido-2-oxo-1,2-dihydropyridin-3-yl)ureido)propanoate 1-486;

sodium (S)-3-(2',4'-difluorobiphenyl-3-yl)-3-(3-(1,6-dimethyl-4-oxido-2-oxo-1,2-dihydropyridin-3-yl)ureido)propanoate 1-487;

sodium (S)-3-(2',4'-difluorobiphenyl-3-yl)-3-(3-(1-methyl-4-oxido-2-oxo-1,2-dihydropyridin-3-yl)ureido)propanoate 1-488;
sodium (S)-3-(3-(1,5-dimethyl-4-oxido-2-oxo-1,2-dihydropyridin-3-yl)ureido)-3-(3'-methoxy-2'-methylbiphenyl-3-yl)propanoate 1-489;
sodium (S)-3-(3-(1,5-dimethyl-4-oxido-2-oxo-1,2-dihydropyridin-3-yl)ureido)-3-(5'-methoxy-2'-methylbiphenyl-3-yl)propanoate 1-490;
sodium 3-(3-(1,5-dimethyl-4-oxido-2-oxo-1,2-dihydropyridin-3-yl)ureido)-3-(6-(2,2,2-trifluoroethoxy)biphenyl-3-yl)propanoate 1-491;
sodium (S)-3-(3-(1,5-dimethyl-4-oxido-2-oxo-1,2-dihydropyridin-3-yl)ureido)-3-(2'-ethylbiphenyl-3-yl)propanoate 1-492;
sodium (S)-3-(3-(1,5-dimethyl-4-oxido-2-oxo-1,2-dihydropyridin-3-yl)ureido)-3-(4-fluorobiphenyl-3-yl)propanoate 1-493;
sodium (S)-3-(2',4'-difluorobiphenyl-3-yl)-3-(3-(4-oxido-2-oxo-1,2-dihydropyridin-3-yl)ureido)propanoate 1-494;
sodium (S)-3-(3-(1,5-dimethyl-4-oxido-2-oxo-1,2-dihydropyridin-3-yl)ureido)-3-(3',4'-dimethylbiphenyl-3-yl)propanoate 1-495;
sodium (S)-3-(2',3'-difluorobiphenyl-3-yl)-3-(3-(1,5-dimethyl-4-oxido-2-oxo-1,2-dihydropyridin-3-yl)ureido)propanoate 1-496;
sodium (S)-3-(3-(1,5-dimethyl-4-oxido-2-oxo-1,2-dihydropyridin-3-yl)ureido)-3-(4'-fluoro-3'-methylbiphenyl-3-yl)propanoate 1-497;
sodium (S)-3-(3-(1,5-dimethyl-4-oxido-2-oxo-1,2-dihydropyridin-3-yl)ureido)-3-(1-phenyl-1H-pyrrol-2-yl)propanoate 1-498;
sodium (S)-3-(3'-chlorobiphenyl-3-yl)-3-(3-(1,5-dimethyl-4-oxido-2-oxo-1,2-dihydropyridin-3-yl)ureido)propanoate 1-499;
sodium (S)-3-(3-(1,5-dimethyl-4-oxido-2-oxo-1,2-dihydropyridin-3-yl)ureido)-3-(2-methylbiphenyl-3-yl)propanoate 1-500;
sodium (S)-3-(3'-methoxybiphenyl-3-yl)-3-(3-(1-methyl-4-oxido-2-oxo-1,2-dihydro pyridin-3-yl)ureido)propanoate 1-501;
sodium (S)-3-(2',6'-dimethylbiphenyl-3-yl)-3-(3-(1-methyl-4-oxido-2-oxo-1,2-dihydropyridin-3-yl)ureido)propanoate 1-502;
sodium 3-(5'-chloro-2',4'-difluorobiphenyl-3-yl)-3-(3-(1,5-dimethyl-4-oxido-2-oxo-1,2-dihydropyridin-3-yl)ureido)propanoate 1-503;
sodium (S)-3-(2',3'-dimethoxybiphenyl-3-yl)-3-(3-(1,5-dimethyl-4-oxido-2-oxo-1,2-dihydropyridin-3-yl)ureido)propanoate 1-504;
sodium (S)-3-(biphenyl-3-yl)-3-(3-(1-methyl-4-oxido-2-oxo-1,2-dihydropyridin-3-yl)ureido)propanoate 1-505;
sodium (S)-3-(3'-chlorobiphenyl-3-yl)-3-(3-(1-methyl-4-oxido-2-oxo-1,2-dihydro pyridin-3-yl)ureido)propanoate 1-506;
sodium (S)-3-(3-(1H-pyrrol-1-yl)phenyl)-3-(3-(1-methyl-4-oxido-2-oxo-1,2-dihydro pyridin-3-yl)ureido)propanoate 1-507;
sodium (S)-3-(3-(6-methoxypyridin-3-yl)phenyl)-3-(3-(1-methyl-4-oxido-2-oxo-1,2-dihydropyridin-3-yl)ureido)propanoate 1-508;
sodium (S)-3-(2'-fluoro-3'-methoxybiphenyl-3-yl)-3-(3-(1-methyl-4-oxido-2-oxo-1,2-dihydropyridin-3-yl)ureido)propanoate 1-509;
sodium (S)-3-(3-(1-methyl-4-oxido-2-oxo-1,2-dihydropyridin-3-yl)ureido)-3-(4'-(trifluoromethoxy)biphenyl-3-yl)propanoate 1-510;
sodium 3-(2',4'-dichlorobiphenyl-3-yl)-3-(3-(1,5-dimethyl-4-oxido-2-oxo-1,2-dihydropyridin-3-yl)ureido)propanoate 1-511;
sodium (S)-3-(3-(1-methyl-4-oxido-2-oxo-1,2-dihydropyridin-3-yl)ureido)-3-(2'-(trifluoromethoxy)biphenyl-3-yl)propanoate 1-512;
sodium (S)-3-(2',4'-difluorobiphenyl-3-yl)-3-(3-(1-methyl-4-oxido-2-oxo-2,5,6,7-tetrahydro-1H-cyclopenta[b]pyridin-3-yl)ureido)propanoate 1-513;
sodium (S)-3-(3-(1-methyl-4-oxido-2-oxo-1,2-dihydropyridin-3-yl)ureido)-3-(3'-(trifluoromethoxy)biphenyl-3-yl)propanoate 1-514;
sodium (S)-3-(2',4'-difluorobiphenyl-3-yl)-3-(3-(4-methyl-7-oxido-5-oxo-4,5-dihydrothieno[3,2-b]pyridin-6-yl)ureido)propanoate 1-515;
sodium (S)-3-(3-(benzo[d][1,3]dioxol-5-yl)phenyl)-3-(3-(1-methyl-4-oxido-2-oxo-1,2-dihydropyridin-3-yl)ureido)propanoate 1-516;
sodium (S)-3-(3-(benzo[d][1,3]dioxol-5-yl)phenyl)-3-(3-(1,5-dimethyl-4-oxido-2-oxo-1,2-dihydropyridin-3-yl)ureido)propanoate 1-517;
sodium (S)-3-(3-(1H-indazol-1-yl)phenyl)-3-(3-(1-methyl-4-oxido-2-oxo-1,2-dihydro pyridin-3-yl)ureido)propanoate 1-518;
sodium (S)-3-(2',4'-difluoro-6-methoxybiphenyl-3-yl)-3-(3-(1-methyl-4-oxido-2-oxo-1,2-dihydropyridin-3-yl)ureido)propanoate 1-519;
sodium (S)-3-(3-(4-hydroxy-1-methyl-2-oxo-1,2-dihydropyridin-3-yl)ureido)-3-(4-phenyl thiophen-2-yl)propanoate 1-520;
sodium (S)-3-(3-(1-ethyl-1H-indol-6-yl)phenyl)-3-(3-(1-methyl-4-oxido-2-oxo-1,2-dihydro pyridin-3-yl)ureido)propanoate 1-521;
sodium (S)-3-(3-(1H-pyrazol-1-yl)phenyl)-3-(3-(1-methyl-4-oxido-2-oxo-1,2-dihydro pyridin-3-yl)ureido)propanoate 1-522;
sodium (S)-3-(4-(2,4-difluorophenyl)thiophen-2-yl)-3-(3-(1-methyl-4-oxido-2-oxo-1,2-dihydropyridin-3-yl)ureido)propanoate 1-523;
sodium (S)-3-(3',6-dimethoxybiphenyl-3-yl)-3-(3-(1-methyl-4-oxido-2-oxo-1,2-dihydro pyridin-3-yl)ureido)propanoate 1-524;
sodium 3-(2',5'-dichlorobiphenyl-3-yl)-3-(3-(4-hydroxy-1,5-dimethyl-2-oxo-1,2-dihydro pyridin-3-yl)ureido)propanoate 1-525;
sodium (S)-3-(2',4'-difluorobiphenyl-3-yl)-3-(3-(1-methyl-4-oxido-2-oxo-1,2-dihydro-1,8-naphthyridin-3-yl)ureido)propanoate 1-526;
sodium (S)-3-(3',6-dimethoxybiphenyl-3-yl)-3-(3-(1,5-dimethyl-4-oxido-2-oxo-1,2-dihydropyridin-3-yl)ureido)propanoate 1-527;
sodium (S)-3-(4-(3-methoxyphenyl)thiophen-2-yl)-3-(3-(1-methyl-4-oxido-2-oxo-1,2-dihydro pyridin-3-yl)ureido)propanoate 1-528;
sodium (S)-3-(6-methoxybiphenyl-3-yl)-3-(3-(1-methyl-4-oxido-2-oxo-1,2-dihydro pyridin-3-yl)ureido)propanoate 1-529;
sodium (S)-3-(4-(3-chlorophenyl)thiophen-2-yl)-3-(3-(1-methyl-4-oxido-2-oxo-1,2-dihydro pyridin-3-yl)ureido)propanoate 1-530;
sodium (S)-3-(2',4'-difluorobiphenyl-3-yl)-3-(3-(1-ethyl-4-oxido-2-oxo-1,2-dihydropyridin-3-yl)ureido)propanoate 1-531;
sodium (S)-3-(3-(1-methyl-4-oxido-2-oxo-1,2-dihydropyridin-3-yl)ureido)-3-(3-(thiophen-2-yl)phenyl)propanoate 1-532;

sodium (S)-3-(6-methoxy-2',6'-dimethylbiphenyl-3-yl)-3-(3-(1-methyl-4-oxido-2-oxo-1,2-dihydropyridin-3-yl)ureido)propanoate 1-533;

sodium (S)-3-(3'-chloro-6-methoxybiphenyl-3-yl)-3-(3-(1-methyl-4-oxido-2-oxo-1,2-dihydropyridin-3-yl)ureido)propanoate 1-534;

sodium (S)-3-(6-methoxy-3'-(trifluoromethoxy)biphenyl-3-yl)-3-(3-(1-methyl-4-oxido-2-oxo-1,2-dihydropyridin-3-yl)ureido)propanoate 1-535;

sodium (S)-3-(6-methoxy-4'-(trifluoromethoxy)biphenyl-3-yl)-3-(3-(1-methyl-4-oxido-2-oxo-1,2-dihydropyridin-3-yl)ureido)propanoate 1-536;

sodium (S)-3-(2',6'-dichlorobiphenyl-3-yl)-3-(3-(1-methyl-4-oxido-2-oxo-1,2-dihydropyridin-3-yl)ureido)propanoate 1-537;

sodium (S)-3-(3-(5-chlorothiophen-2-yl)phenyl)-3-(3-(1-methyl-4-oxido-2-oxo-1,2-dihydropyridin-3-yl)ureido)propanoate 1-538;

sodium (S)-3-(3-(1H-imidazol-1-yl)phenyl)-3-(3-(1-methyl-4-oxido-2-oxo-1,2-dihydropyridin-3-yl)ureido)propanoate 1-539;

sodium (S)-3-(3-(1-methyl-4-oxido-2-oxo-1,2-dihydropyridin-3-yl)ureido)-3-(3-(4-methylthiophen-3-yl)phenyl)propanoate 1-540;

sodium (S)-3-(2',4'-difluoro-6-methylbiphenyl-3-yl)-3-(3-(1-methyl-4-oxido-2-oxo-1,2-dihydropyridin-3-yl)ureido)propanoate 1-541;

sodium (S)-3-(3'-methoxy-6-methylbiphenyl-3-yl)-3-(3-(1-methyl-4-oxido-2-oxo-1,2-dihydropyridin-3-yl)ureido)propanoate 1-542;

sodium (S)-3-(3-(1,5-dimethyl-4-oxido-2-oxo-1,2-dihydropyridin-3-yl)ureido)-3-(4-(2,6-dimethylphenyl)thiophen-2-yl)propanoate 1-543;

sodium (S)-3-(3-(1H-pyrrol-3-yl)phenyl)-3-(3-(1-methyl-4-oxido-2-oxo-1,2-dihydro pyridin-3-yl)ureido)propanoate 1-544;

sodium (S)-3-(3-(1-methyl-4-oxido-2-oxo-1,2-dihydropyridin-3-yl)ureido)-3-(2',6,6'-trimethylbiphenyl-3-yl)propanoate 1-545;

sodium (S)-3-(3-(1-methyl-4-oxido-2-oxo-1,2-dihydropyridin-3-yl)ureido)-3-(2',6,6'-trifluorobiphenyl-3-yl)propanoate 1-546;

sodium (S)-3-(6-fluoro-3'-methoxybiphenyl-3-yl)-3-(3-(1-methyl-4-oxido-2-oxo-1,2-dihydropyridin-3-yl)ureido)propanoate 1-547;

sodium (S)-3-(3-(1-methyl-1H-pyrazol-4-yl)phenyl)-3-(3-(1-methyl-4-oxido-2-oxo-1,2-dihydropyridin-3-yl)ureido)propanoate 1-548;

sodium (S)-3-(2',4'-difluorobiphenyl-3-yl)-3-(3-(2-methyl-5-oxido-3-oxo-2,3-dihydropyridazin-4-yl)ureido)propanoate 1-549;

sodium (S)-3-(3-(1,6-dimethyl-4-oxido-2-oxo-1,2-dihydropyridin-3-yl)ureido)-3-(2',6'-dimethylbiphenyl-3-yl)propanoate 1-550;

sodium (S)-3-(3',6-dimethoxybiphenyl-3-yl)-3-(3-(1,6-dimethyl-4-oxido-2-oxo-1,2-dihydropyridin-3-yl)ureido)propanoate 1-551;

sodium (S)-3-(4-(2,4-difluorophenyl)thiophen-2-yl)-3-(3-(1,6-dimethyl-4-oxido-2-oxo-1,2-dihydropyridin-3-yl)ureido)propanoate 1-552;

sodium (S)-3-(3-(1,6-dimethyl-4-oxido-2-oxo-1,2-dihydropyridin-3-yl)ureido)-3-(3'-methoxybiphenyl-3-yl)propanoate 1-553;

sodium (S)-3-(3-(1,6-dimethyl-4-oxido-2-oxo-1,2-dihydropyridin-3-yl)ureido)-3-(6-methoxy-3'-(trifluoromethoxy)biphenyl-3-yl)propanoate 1-554;

sodium (S)-3-(3'-chloro-6-methylbiphenyl-3-yl)-3-(3-(1-methyl-4-oxido-2-oxo-1,2-dihydropyridin-3-yl)ureido)propanoate 1-555;

sodium (S)-3-(3'-chlorobiphenyl-3-yl)-3-(3-(1,6-dimethyl-4-oxido-2-oxo-1,2-dihydropyridin-3-yl)ureido)propanoate 1-556;

sodium (S)-3-(2',4'-difluorobiphenyl-3-yl)-3-(3-(6-methyl-4-oxido-2-oxo-1,2-dihydropyridin-3-yl)ureido)propanoate 1-557;

sodium (S)-3-(5-methoxybiphenyl-3-yl)-3-(3-(1-methyl-4-oxido-2-oxo-1,2-dihydropyridin-3-yl)ureido)propanoate 1-558;

sodium (S)-3-(3-(furan-3-yl)phenyl)-3-(3-(1-methyl-4-oxido-2-oxo-1,2-dihydropyridin-3-yl)ureido)propanoate 1-559;

sodium (S)-3-(3-(3,5-dimethylisoxazol-4-yl)phenyl)-3-(3-(1-methyl-4-oxido-2-oxo-1,2-dihydropyridin-3-yl)ureido)propanoate 1-560;

sodium (S)-3-(6-fluoro-2',6'-dimethylbiphenyl-3-yl)-3-(3-(1-methyl-4-oxido-2-oxo-1,2-dihydropyridin-3-yl)ureido)propanoate 1-561;

sodium (S)-3-(5-(2,4-difluorophenyl)thiophen-2-yl)-3-(3-(1-methyl-4-oxido-2-oxo-1,2-dihydropyridin-3-yl)ureido)propanoate 1-562;

sodium (S)-3-(5-(3-methoxyphenyl)thiophen-2-yl)-3-(3-(1-methyl-4-oxido-2-oxo-1,2-dihydropyridin-3-yl)ureido)propanoate 1-563;

sodium (S)-3-(3',5-dimethoxybiphenyl-3-yl)-3-(3-(1-methyl-4-oxido-2-oxo-1,2-dihydropyridin-3-yl)ureido)propanoate 1-564;

sodium (S)-3-(5-methoxy-3'-(trifluoromethoxy)biphenyl-3-yl)-3-(3-(1-methyl-4-oxido-2-oxo-1,2-dihydropyridin-3-yl)ureido)propanoate 1-565;

sodium (S)-3-(2',4'-difluoro-5-methoxybiphenyl-3-yl)-3-(3-(1-methyl-4-oxido-2-oxo-1,2-dihydropyridin-3-yl)ureido)propanoate 1-566;

sodium (S)-3-(3',5-dimethoxybiphenyl-3-yl)-3-(3-(1,6-dimethyl-4-oxido-2-oxo-1,2-dihydropyridin-3-yl)ureido)propanoate 1-567;

sodium (S)-3-(3-(1,6-dimethyl-4-oxido-2-oxo-1,2-dihydropyridin-3-yl)ureido)-3-(5-methoxy-3'-(trifluoromethoxy)biphenyl-3-yl)propanoate 1-568;

sodium (S)-3-(3-(1,6-dimethyl-4-oxido-2-oxo-1,2-dihydropyridin-3-yl)ureido)-3-(3'-methoxy-6-methylbiphenyl-3-yl)propanoate 1-569;

sodium (S)-3-(4-fluorobiphenyl-3-yl)-3-(3-(1-methyl-4-oxido-2-oxo-1,2-dihydropyridin-3-yl)ureido)propanoate 1-570;

sodium (S)-3-(3-(1-methyl-4-oxido-2-oxo-1,2-dihydropyridin-3-yl)ureido)-3-(6-phenylpyridin-2-yl)propanoate 1-571;

sodium (S)-3-(5-methyl-3'-(trifluoromethoxy)biphenyl-3-yl)-3-(3-(1-methyl-4-oxido-2-oxo-1,2-dihydropyridin-3-yl)ureido)propanoate 1-572;

sodium (S)-3-(3-(1-methyl-4-oxido-2-oxo-1,2-dihydropyridin-3-yl)ureido)-3-(2',5,6'-trimethylbiphenyl-3-yl)propanoate 1-573;

sodium (S)-3-(2',4'-difluoro-5-methylbiphenyl-3-yl)-3-(3-(1-methyl-4-oxido-2-oxo-1,2-dihydropyridin-3-yl)ureido)propanoate 1-574;

sodium (S)-3-(2',4'-difluoro-5-methylbiphenyl-3-yl)-3-(3-(1,6-dimethyl-4-oxido-2-oxo-1,2-dihydropyridin-3-yl)ureido)propanoate 1-575;

sodium (S)-3-(6-methyl-3'-(trifluoromethoxy)biphenyl-3-yl)-3-(3-(1-methyl-4-oxido-2-oxo-1,2-dihydropyridin-3-yl)ureido)propanoate 1-576;

sodium (S)-3-(3-(1,6-dimethyl-4-oxido-2-oxo-1,2-dihydropyridin-3-yl)ureido)-3-(6-methyl-3'-(trifluoromethoxy)biphenyl-3-yl)propanoate 1-577;
sodium (S)-3-(3-(1,6-dimethyl-4-oxido-2-oxo-1,2-dihydropyridin-3-yl)ureido)-3-(6-fluoro-2',6'-dimethylbiphenyl-3-yl)propanoate 1-578;
sodium (S)-3-(5-methoxy-2',6'-dimethylbiphenyl-3-yl)-3-(3-(1-methyl-4-oxido-2-oxo-1,2-dihydropyridin-3-yl)ureido)propanoate 1-579;
sodium (S)-3-(3-(1,6-dimethyl-4-oxido-2-oxo-1,2-dihydropyridin-3-yl)ureido)-3-(5-methoxy-2',6'-dimethylbiphenyl-3-yl)propanoate 1-580;
sodium (S)-3-(2',4'-difluoro-5-methoxybiphenyl-3-yl)-3-(3-(1,6-dimethyl-4-oxido-2-oxo-1,2-dihydropyridin-3-yl)ureido)propanoate 1-581;
sodium (S)-3-(3'-methoxy-5-methylbiphenyl-3-yl)-3-(3-(1-methyl-4-oxido-2-oxo-1,2-dihydropyridin-3-yl)ureido)propanoate 1-582;
sodium (S)-3-(2',6'-dimethylbiphenyl-3-yl)-3-(3-(7-oxido-5-oxo-1,2,3,5-tetrahydro indolizin-6-yl)ureido)propanoate 1-583;
sodium (S)-3-(4'-methyl-2,3'-bithiophen-5-yl)-3-(3-(1-methyl-4-oxido-2-oxo-1,2-di hydropyridin-3-yl)ureido)propanoate 1-584;
sodium (S)-3-(3-(1,6-dimethyl-4-oxido-2-oxo-1,2-dihydropyridin-3-yl)ureido)-3-(4'-methyl-2,3'-bithiophen-5-yl)propanoate 1-585;
sodium (S)-3-(3-(1,6-dimethyl-4-oxido-2-oxo-1,2-dihydropyridin-3-yl)ureido)-3-(3'-methoxy-5-methylbiphenyl-3-yl)propanoate 1-586;
sodium (S)-3-(5-(2,6-dimethylphenyl)thiophen-2-yl)-3-(3-(1-methyl-4-oxido-2-oxo-1,2-dihydropyridin-3-yl)ureido)propanoate 1-587;
sodium (S)-3-(3-(1,6-dimethyl-4-oxido-2-oxo-1,2-dihydropyridin-3-yl)ureido)-3-(5-(2,6-dimethylphenyl)thiophen-2-yl)propanoate 1-588;
sodium (S)-3-(3-(1,6-dimethyl-4-oxido-2-oxo-1,2-dihydropyridin-3-yl)ureido)-3-(4-fluoro-2',6'-dimethylbiphenyl-3-yl)propanoate 1-589;
sodium (S)-3-(4-fluoro-2',6'-dimethylbiphenyl-3-yl)-3-(3-(1-methyl-4-oxido-2-oxo-1,2-dihydropyridin-3-yl)ureido)propanoate 1-590;
sodium (S)-3-(3-(1-methyl-4-oxido-2-oxo-1,2-dihydropyridin-3-yl)ureido)-3-(2',4,4'-trifluorobiphenyl-3-yl)propanoate 1-591;
sodium (S)-3-(3-(1,6-dimethyl-4-oxido-2-oxo-1,2-dihydropyridin-3-yl)ureido)-3-(2',4,4'-trifluorobiphenyl-3-yl)propanoate 1-592;
sodium (S)-3-(4-fluoro-3'-methoxybiphenyl-3-yl)-3-(3-(1-methyl-4-oxido-2-oxo-1,2-dihydropyridin-3-yl)ureido)propanoate 1-593;
sodium (S)-3-(4-fluoro-3'-(trifluoromethoxy)biphenyl-3-yl)-3-(3-(1-methyl-4-oxido-2-oxo-1,2-dihydropyridin-3-yl)ureido)propanoate 1-594;
sodium (S)-3-(3-(1,6-dimethyl-4-oxido-2-oxo-1,2-dihydropyridin-3-yl)ureido)-3-(4-fluoro-3'-(trifluoromethoxy)biphenyl-3-yl)propanoate 1-595;
sodium (S)-3-(4-methoxybiphenyl-3-yl)-3-(3-(1-methyl-4-oxido-2-oxo-1,2-dihydro pyridin-3-yl)ureido)propanoate 1-596;
sodium (S)-3-(3-(1,6-dimethyl-4-oxido-2-oxo-1,2-dihydropyridin-3-yl)ureido)-3-(2',5,6'-trimethylbiphenyl-3-yl)propanoate 1-597;
sodium (S)-3-(3-(1-methyl-4-oxido-2-oxo-1,2-dihydropyridin-3-yl)ureido)-3-(2'-methylbiphenyl-3-yl)propanoate 1-598;
sodium (S)-3-(3-(1,6-dimethyl-4-oxido-2-oxo-1,2-dihydropyridin-3-yl)ureido)-3-(2'-methylbiphenyl-3-yl)propanoate 1-599;
sodium (S)-3-(5-fluoro-2',6'-dimethylbiphenyl-3-yl)-3-(3-(1-methyl-4-oxido-2-oxo-1,2-dihydropyridin-3-yl)ureido)propanoate 1-600;
sodium (S)-3-(3-(1-methyl-4-oxido-2-oxo-1,2-dihydropyridin-3-yl)ureido)-3-(5-(3-(trifluoromethoxy)phenyl)thiophen-2-yl)propanoate 1-601;
sodium (S)-3-(4-methoxy-2',6'-dimethylbiphenyl-3-yl)-3-(3-(1-methyl-4-oxido-2-oxo-1,2-dihydropyridin-3-yl)ureido)propanoate 1-602;
sodium (S)-3-(3-(1,6-dimethyl-4-oxido-2-oxo-1,2-dihydropyridin-3-yl)ureido)-3-(4-fluoro-3'-methoxybiphenyl-3-yl)propanoate 1-603;
sodium (S)-3-(5-fluoro-3'-methoxybiphenyl-3-yl)-3-(3-(1-methyl-4-oxido-2-oxo-1,2-dihydropyridin-3-yl)ureido)propanoate 1-604;
sodium (S)-3-(5-fluoro-3'-methoxybiphenyl-3-yl)-3-(3-(4-hydroxy-1,6-dimethyl-2-oxo-1,2-dihydropyridin-3-yl)ureido)propanoate 1-605;
sodium (S)-3-(3-(1,6-dimethyl-4-oxido-2-oxo-1,2-dihydropyridin-3-yl)ureido)-3-(5-fluoro-3'-trifluoromethoxybiphenyl-3-yl)propanoate 1-606;
sodium (S)-3-(5-fluoro-3'-(trifluoromethoxy)biphenyl-3-yl)-3-(3-(1-methyl-4-oxido-2-oxo-1,2-dihydropyridin-3-yl)ureido)propanoate 1-607;
sodium (S)-3-(5-(3,5-dimethylisoxazol-4-yl)thiophen-2-yl)-3-(3-(1-methyl-4-oxido-2-oxo-1,2-dihydropyridin-3-yl)ureido)propanoate 1-608;
sodium (S)-3-(3-(1,6-dimethyl-4-oxido-2-oxo-1,2-dihydropyridin-3-yl)ureido)-3-(3-(3,5-dimethylisoxazol-4-yl)phenyl)propanoate 1-609;
sodium (S)-3-(3-(1,6-dimethyl-4-oxido-2-oxo-1,2-dihydropyridin-3-yl)ureido)-3-(2-fluorobiphenyl-3-yl)propanoate 1-610;
sodium (S)-3-(3-(1,6-dimethyl-4-oxido-2-oxo-1,2-dihydropyridin-3-yl)ureido)-3-(6-fluoro-2'-methylbiphenyl-3-yl)propanoate 1-611;
sodium (S)-3-(6-fluoro-2'-methylbiphenyl-3-yl)-3-(3-(1-methyl-4-oxido-2-oxo-1,2-dihydropyridin-3-yl)ureido)propanoate 1-612;
sodium (S)-3-(3-(1-methyl-4-oxido-2-oxo-1,2-dihydropyridin-3-yl)ureido)-3-(5-phenylthiophen-2-yl)propanoate 1-613;
sodium (S)-3-(5-(2,5-difluorophenyl)thiophen-2-yl)-3-(3-(1-methyl-4-oxido-2-oxo-1,2-dihydropyridin-3-yl)ureido)propanoate 1-614;
sodium (S)-3-(3-(1-methyl-4-oxido-2-oxo-1,2-dihydropyridin-3-yl)ureido)-3-(5-(trifluoro methoxy)biphenyl-3-yl)propanoate 1-615;
sodium (S)-3-(3-(1-methyl-4-oxido-2-oxo-1,2-dihydropyridin-3-yl)ureido)-3-(2'-methylbiphenyl-4-yl)propanoate 1-616;
sodium (S)-3-(5-methoxybiphenyl-3-yl)-3-(3-(7-oxido-5-oxo-1,2,3,5-tetrahydroindolizin-6-yl)ureido)propanoate 1-617;
sodium (S)-3-(3-(1-methyl-4-oxido-2-oxo-1,2-dihydropyridin-3-yl)ureido)-3-(5-(trifluoro methyl)biphenyl-3-yl)propanoate 1-618;
sodium (S)-3-(5-(3-chlorophenyl)thiophen-2-yl)-3-(3-(1-methyl-4-oxido-2-oxo-1,2-dihydropyridin-3-yl)ureido)propanoate 1-619;
sodium (S)-3-(5-(3-fluorophenyl)thiophen-2-yl)-3-(3-(1-methyl-4-oxido-2-oxo-1,2-dihydropyridin-3-yl)ureido)propanoate 1-620;

sodium (S)-3-(2',4'-difluorobiphenyl-4-yl)-3-(3-(1-methyl-4-oxido-2-oxo-1,2-dihydropyridin-3-yl)ureido)propanoate 1-621;

sodium (S)-3-(2',4'-difluorobiphenyl-4-yl)-3-(3-(1,6-dimethyl-4-oxido-2-oxo-1,2-dihydropyridin-3-yl)ureido)propanoate 1-622;

sodium (S)-3-(2',4'-difluorobiphenyl-4-yl)-3-(3-(1,5-dimethyl-4-oxido-2-oxo-1,2-di hydropyridin-3-yl)ureido) propanoate 1-623;

sodium (S)-3-(3-(1-methyl-4-oxido-2-oxo-1,2-dihydropyridin-3-yl)ureido)-3-(2'-methyl-6-(trifluoromethoxy)biphenyl-3-yl)propanoate 1-624;

sodium (S)-3-(3-(1-methyl-4-oxido-2-oxo-1,2-dihydropyridin-3-yl)ureido)-3-(6-(trifluoromethoxy)biphenyl-3-yl) propanoate 1-625;

sodium 3-(3'-acetylbiphenyl-3-yl)-3-(3-(1,5-dimethyl-4-oxido-2-oxo-1,2-dihydro pyridin-3-yl)ureido)propanoate 1-626;

sodium 3-(4'-acetylbiphenyl-3-yl)-3-(3-(1,5-dimethyl-4-oxido-2-oxo-1,2-dihydro pyridin-3-yl)ureido)propanoate 1-627;

sodium (S)-3-(3-(1,5-dimethyl-4-oxido-2-oxo-1,2-dihydropyridin-3-yl)ureido)-3-(4-phenyl thiophen-2-yl)propanoate 1-627;

sodium (S)-3-(3-(1,5-dimethyl-4-oxido-2-oxo-1,2-dihydropyridin-3-yl)ureido)-3-(5-phenyl thiophen-2-yl)propanoate 1-628;

sodium (S)-3-(2',4'-difluorobiphenyl-3-yl)-3-(3-(7-oxido-5-oxo-1,2,3,5-tetrahydroindolizin-6-yl)ureido)propanoate 1-629;

sodium (S)-3-(3-(1-methyl-4-oxido-2-oxo-1,2-dihydropyridin-3-yl)ureido)-3-(3-(thiazol-2-yl)phenyl)propanoate 1-630;

sodium (S)-3-(3-(1,6-dimethyl-4-oxido-2-oxo-1,2-dihydropyridin-3-yl)ureido)-3-(5-methyl-3'-(trifluoromethoxy)biphenyl-3-yl)propanoate 1-631;

sodium (S)-3-(3-(1,6-dimethyl-4-oxido-2-oxo-1,2-dihydropyridin-3-yl)ureido)-3-(2',4',5-trifluorobiphenyl-3-yl) propanoate 1-632;

sodium (S)-3-(3-(1-methyl-4-oxido-2-oxo-1,2-dihydropyridin-3-yl)ureido)-3-(2',4',5-trifluorobiphenyl-3-yl)propanoate 1-633;

sodium (S)-3-(3'-methoxy-6-(trifluoromethoxy)biphenyl-3-yl)-3-(3-(1-methyl-4-oxido-2-oxo-1,2-dihydropyridin-3-yl)ureido)propanoate 1-634;

sodium (S)-3-(3-(1,6-dimethyl-4-oxido-2-oxo-1,2-dihydropyridin-3-yl)ureido)-3-(3'-methoxy-6-(trifluoromethoxy)biphenyl-3-yl)propanoate 1-635;

sodium (S)-3-(2',6'-dimethylbiphenyl-4-yl)-3-(3-(1-methyl-4-oxido-2-oxo-1,2-dihydropyridin-3-yl)ureido)propanoate 1-636;

sodium (S)-3-(3-(1,6-dimethyl-4-oxido-2-oxo-1,2-dihydropyridin-3-yl)ureido)-3-(2'-methylbiphenyl-4-yl)propanoate 1-637;

sodium (S)-3-(3-(1,6-dimethyl-4-oxido-2-oxo-1,2-dihydropyridin-3-yl)ureido)-3-(2',6'-dimethylbiphenyl-4-yl)propanoate 1-638;

sodium (S)-3-(3-(1-methyl-4-oxido-2-oxo-1,2-dihydropyridin-3-yl)ureido)-3-(3-(pyridin-2-yl)phenyl)propanoate 1-639;

sodium (S)-3-(3-(6-methoxypyridazin-3-yl)phenyl)-3-(3-(1-methyl-4-oxido-2-oxo-1,2-dihydropyridin-3-yl)ureido) propanoate 1-640;

sodium (S)-3-(3-(1-methyl-4-oxido-2-oxo-1,2-dihydropyridin-3-yl)ureido)-3-(5-phenylpyridin-3-yl)propanoate 1-641;

sodium (S)-3-(3-(1,6-dimethyl-4-oxido-2-oxo-1,2-dihydropyridin-3-yl)ureido)-3-(5-fluoro-2',6'-dimethylbiphenyl-3-yl)propanoate 1-642;

sodium (S)-3-(biphenyl-4-yl)-3-(3-(1,5-dimethyl-4-oxido-2-oxo-1,2-dihydropyridin-3-yl)ureido)propanoate 1-643;

sodium (S)-3-(3-(1-methyl-4-oxido-2-oxo-1,2-dihydropyridin-3-yl)ureido)-3-(3-(6'-methoxypyridin-2-yl)phenyl) propanoate 1-644;

sodium (S)-3-(3-(1,5-dimethyl-4-oxido-2-oxo-1,2-dihydropyridin-3-yl)ureido)-3-(4'-methoxybiphenyl-3-yl)propanoate 1-645;

sodium (S)-3-(3-(1H-imidazol-1-yl)phenyl)-3-(3-(1-methyl-4-oxido-2-oxo-1,2-dihydropyridin-3-yl)ureido) propanoate 1-646.

sodium (S)-3-(3-(4-hydroxy-1-methyl-2-oxo-1,2-dihydropyridin-3-yl)ureido)-3-(3-(pyrazin-2-yl)phenyl) propanoate 1-647, sodium 3-(3-bromophenyl)-3-(3-(4-hydroxy-1,5-dimethyl-2-oxo-1,2-dihydro pyridin-3-yl) ureido) propanoate 1-648, or sodium 3-(3-bromophenyl)-3-(3-(1-ethyl-4-hydroxy-5-methyl-2-oxo-1,2-dihydropyridin-3-yl)ureido) propanoate 1-649.

Provided herein are compounds and pharmaceutical compositions thereof that are derivatives of propanoic acid. Particularly, these compounds may comprise derivatives of biphenyl and biaryl propanoates such as, but not limited to, those compounds described in the Examples. These compounds encompass their pharmaceutically acceptable salts and/or their stereoisomers.

As is known in the art, pharmaceutical compositions may comprise known carriers, excipients, diluents, etc, for example, saline, a buffer, an oil, or a powder. The pharmaceutical compositions may delivered in a vehicle such as, but not limited to, a spray, a liposome, a nanoparticle, a microparticle, a microcapsule, a nanosuspension, a microsuspension, or a hydrogel.

The compounds and pharmaceutical compositions disclosed herein are useful as therapeutics and prophylactics against pathophysiological conditions in a subject in need of such treatment. The compounds and pharmaceutical composition may be administered one or more times to achieve a therapeutic effect. The compounds and pharmaceutical composition may be administered with other therapeutics for a particular pathophysiological condition. As is known in the art, the skilled person is well-able to determine dose, dosage regimens and routes of administration depending on the condition to be treated and the subject requiring treatment.

For example, treatment may be associated with inhibiting the binding of $\alpha_4$-integrin such as $\alpha_4\beta_1$ or $\alpha_4\beta_7$. Representative examples of a pathophysiological condition that might be treated by the inhibition of $\alpha_4\beta_1$ and/or $\alpha_4\beta_7$ binding include, but are not limited to, hematopoietic stem cell transplant therapy, sickle cell disease, dry eye, atherosclerosis, rheumatoid arthritis, asthma, allergy, multiple sclerosis, lupus, inflammatory bowel disease, graft rejection, contact hypersensitivity, stroke, pulmonary arterial hypertension and diabetes or cancer. In addition to being found on some white blood cells, $\alpha_4\beta_1$ is also found on various cancer cells, including leukemia, melanoma, lymphoma and sarcoma cells. It has been suggested that cell adhesion involving $\alpha_4\beta_1$ may be involved in the metastasis of certain cancers. Inhibitors of $\alpha_4\beta_1$ binding may, therefore, also be useful in the treatment of some forms of cancer.

The following examples are given for the purpose of illustrating various embodiments of the invention and are not meant to limit the present invention in any fashion.

Example 1

Synthesis of sodium (S)-3-(biphenyl-3-yl)-3-(3-(1,5-dimethyl-4-oxido-2-oxo-1,2-dihydro pyridin-3-yl)ureido)propanoate (1-11)

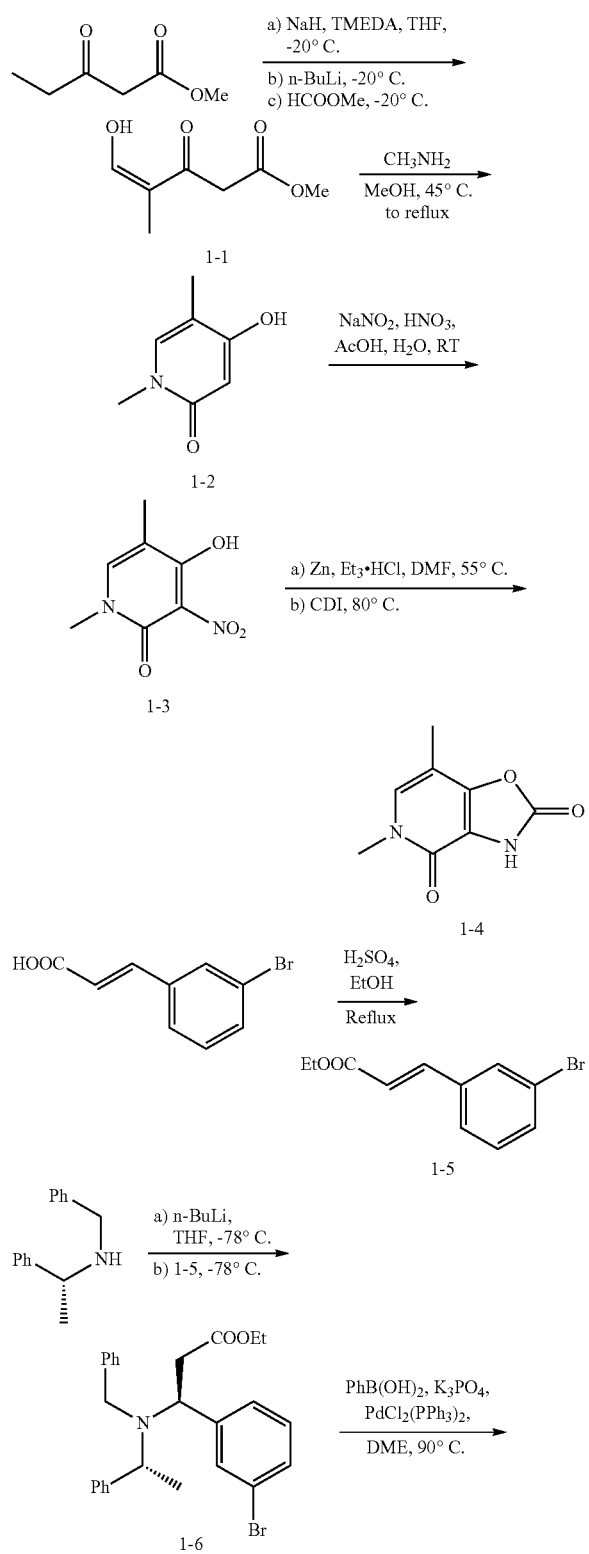

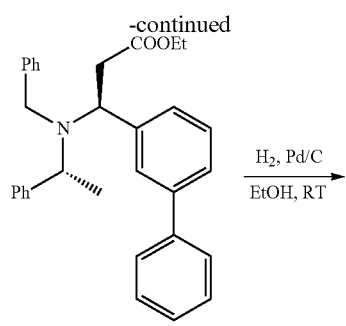

Step One: To a suspension of sodium hydride (6.4 g of 60% dispersion in mineral oil, 160 mmol) in THF (400 mL) under a dry nitrogen atmosphere, TMEDA (23.4 mL, 155 mmol) and methyl propionylacetate (18.1 mL, 144 mmol) were added and the mixture was cooled to −45° C. A solution of n-butyllithium (90 mL, 1.6M in hexanes, 274 mmol) was added dropwise and the resulting mixture was stirred at −45° C. for 1 hour. Methyl formate (6.0 mL, 97 mmol) was then added rapidly and the mixture was allowed to stir for 30 minutes before quenching with HCl (6 N, 250 mL). The reaction was diluted with diethyl ether (150 mL) and the organic layer was washed twice more with water. The aqueous layers were combined and sodium chloride was added until saturated. This mixture was extracted with ethyl acetate (3 times). The original ether layer was washed with saturated sodium bicarbonate solution and water. The combined aqueous washes were acidified with excess HCl (2 N), saturated with sodium chloride and extracted with ethyl acetate (3 times). All of the ethyl acetate extracts were combined and dried over MgSO$_4$. The resulting mixture was vacuum filtered through coarse silica gel and the filtrate was concentrated under reduced pressure to give methyl 5-hydroxy-4-methyl-3-oxopent-4-enoate (1-1, 13.49 g) as a light yellow oil. This material was used without further purification.

Step Two: To a solution of 1-1 (13.49 g, 85.3 mmol) in anhydrous methanol (250 mL) at room temperature, a solution of methylamine anhydrous methanol (2.0 M, 46.9 mL, 93.8 mmol) was added slowly. The solution was heated at 55° C. two hours then refluxed overnight. The reaction mixture was cooled to room temperature and concentrated to dryness. The residue was brought up in dichloromethane and filtered. The solid was collected and dried under vacuum to give 4-hydroxy-1,5-dimethylpyridin-2(1H)-one (1-2, 4.056 g) as a light yellow solid. The filtrate was concentrated, taken up in acetone and filtered to yield and additional portion (1.636 g).

This procedure was also used to prepare 1-ethyl-4-hydroxy-5-methylpyridin-2(1H)-one.

Step Three: To a suspension of 1-2 (1.636 g, 11.8 mmol) in glacial acetic acid (40 mL) at room temperature, NaNO$_2$ (41 mg, 0.59 mmol), water (3.36 mL) and HNO$_3$ (70%, 2.27 mL, 35.3 mmol) were added sequentially. The resulting bright yellow solution was stirred at room temperature overnight, was diluted with water, and extracted with ethyl acetate three times. The organic layers were combined and washed with brine, dried over MgSO$_4$ and filtered. This reaction was repeated on the remainder of the material from the previous step (4.047 g 1-2, 97 mL acetic acid; 100 mg NaNO$_2$, 8.3 mL water and 5.6 mL nitric acid). The filtrates from the two reactions were combined and concentrated under reduced pressure to give 4-hydroxy-1,5-dimethyl-3-nitropyridin-2(1H)-one (1-3, 6.47 g) as an yellow-orange solid.

This procedure was also used to prepare
1-ethyl-4-hydroxy-5-methyl-3-nitropyridin-2(1H)-one;
4-hydroxy-1-methyl-3-nitro-6,7-dihydro-1H-cyclopenta[b]pyridin-2(5H)-one;
7-hydroxy-4-methyl-6-nitrothieno[3,2-b]pyridin-5(4H)-one;
7-hydroxy-6-nitro-2,3-dihydroindolizin-5(1H)-one;
4-hydroxy-1-methyl-3-nitro-1,8-naphthyridin-2(1H)-one;
In the preparation of 5-hydroxy-2-methyl-4-nitropyridazin-3(2H)-one, this reaction was started at 0° C. and was allowed to warm to room temperature.

Step Four: To a solution of 1-3 (6.45 g, 35.0 mmol) in DMF (117 mL) at room temperature under a dry nitrogen atmosphere, Zn powder (10.3 g, 158 mmol) and triethylamine hydrochloride (26.5 g, 193 mmol) were added. The resulting mixture was heated to 70° C. for 1 hour, and was cooled to room temperature. To the resulting mixture, CDI (11.36 g, 70.1 mmol) was added as a solid. Upon addition, gas evolution occurred. The mixture was then heated to 85° C. for 2 hours, cooled to room temperature, and filtered through a Buchner funnel into HCl (2 N). The suspension was stirred for 15 minutes, and filtered. The solid was resuspended in HCl (1 N), stirred for 15 minutes, and was filtered again, washing with water. The solid was dried under vacuum to give 5,7-dimethyloxazolo[4,5-c]pyridine-2,4(3H,5H)-dione (1-4, 3.981 g) as an off-white solid.

This procedure was also used to prepare 5-ethyl-7-methyloxazolo[4,5-c]pyridine-2,4(3H,5H)-dione, and 7,8-dihydrooxazolo[4,5-f]indolizine-2,4(3H,6H)-dione. This procedure was modified by using hydrogen chloride in dioxane (4.0 M, 5.5 equivalents) in place of triethylamine hydrochloride at 15° C., warming to room temperature after adding CDI, to prepare 5-methyl-5,6,7,8-tetrahydro-2H-cyclopenta[b]oxazolo[5,4-d]pyridine-2,4(3H)-dione,
5-methyloxazolo[5,4-d]thieno[3,2-b]pyridine-2,4(3H,5H)-dione;
5-methyloxazolo[4,5-c][1,8]naphthyridine-2,4(3H,5H)-dione;
and 5-methyloxazolo[4,5-d]pyridazine-2,4(3H,5H)-dione.

Step Five: To a solution of 3-bromocinnamic acid (29.0 g, 127.7 mmol) in ethanol (450 mL), catalytic concentrated sulfuric (about 10 drops) was added. The reaction was heated to reflux overnight, concentrated under reduced pressure (to approximately 0.1 L), diluted with hot ethyl acetate, and washed with water (3 times) and saturated brine. The organic layer was dried over magnesium sulfate, filtered, and concentrated under reduced pressure to give (E)-ethyl 3-(3-bromophenyl)acrylate (1-5, 32.5 g).

This procedure was also used to prepare ethyl (E)-3-(3-bromo-4-fluorophenyl)acrylate and ethyl (E)-3-(3-nitrophenyl)acrylate.

Step Six: To a solution of (R)-(+)-N-benzyl-α-methylbenzylamine (20.3 g, 96 mmol) in tetrahydrofuran (150 mL) cooled to −78° C. under a nitrogen atmosphere, s-butyllithium (1.3 M in cyclohexane, 77 mL, 100 mmol) was added dropwise over 30 minutes. The mixture was stirred for 30 minutes, and a solution of 1-5 (20.4 g, 80 mmol) in tetrahydrofuran (100 mL) was added dropwise over 30 minutes. The resulting solution was stirred at −78° C. for 3 hours, ethanol (8 mL) was added and the mixture was poured onto saturated aqueous ammonium chloride. The resulting mixture was extracted with ethyl acetate (3 times), and the organic layers were combined, washed with brine, dried over magnesium sulfate (anhydrous), filtered and concentrated under reduced pressure. The residue was purified by chromatography on silica gel, eluting with hexanes increasing to hexanes:acetate (9:1) to give ethyl (S)-3-(benzyl((R)-1-phenylethyl) amino)-3-(3-bromophenyl)propanoate; (1-6, 27.19 g).

This procedure was also accomplished using n-butyllithium in hexanes instead of s-butyllithium in cyclohexane without affecting the outcome. This procedure was also used to prepare
ethyl (S)-3-(benzyl((R)-1-phenylethyl)amino)-3-(3-bromo-4-fluorophenyl)propanoate;
ethyl (S)-3-(benzyl((R)-1-phenylethyl)amino)-3-(3-bromo-4-methylphenyl)propanoate;
ethyl (S)-3-(benzyl((R)-1-phenylethyl)amino)-3-(3-bromo-4-methoxyphenyl)propanoate;
tert-butyl (S)-3-(benzyl((R)-1-phenylethyl)amino)-3-(4-bromophenyl)propanoate;
ethyl (S)-3-(benzyl((R)-1-phenylethyl)amino)-3-(5,6-dimethoxybiphenyl-3-yl)propanoate;
ethyl (S)-3-(benzyl((R)-1-phenylethyl)amino)-3-(3-nitrophenyl)propanoate (7-1);
ethyl (S)-3-(benzyl((R)-1-phenylethyl)amino)-3-(5-bromo-2-fluorophenyl)propanoate;
ethyl (S)-3-(benzyl((R)-1-phenylethyl)amino)-3-(2-methylbiphenyl-3-yl)propanoate;
ethyl (S)-3-(benzyl((R)-1-phenylethyl)amino)-3-(3-iodophenyl)propanoate;
ethyl (S)-3-(benzyl((R)-1-phenylethyl)amino)-3-(3-(1-ethyl-1H-indol-6-yl)phenyl)propanoate;
ethyl (S)-3-(benzyl((R)-1-phenylethyl)amino)-3-(6-methoxy-2',6'-dimethylbiphenyl-3-yl)propanoate;
ethyl (S)-3-(benzyl((R)-1-phenylethyl)amino)-3-(3-bromo-5-methoxyphenyl)propanoate;
ethyl (S)-3-(benzyl((R)-1-phenylethyl)amino)-3-(3-bromo-5-methylphenyl)propanoate;

ethyl (S)-3-(benzyl((R)-1-phenylethyl)amino)-3-(3-bromo-5-fluorophenyl)propanoate;
ethyl (S)-3-(benzyl((R)-1-phenylethyl)amino)-3-(2',4',5-trifluorobiphenyl-3-yl)propanoate;
ethyl (S)-3-(benzyl((R)-1-phenylethyl)amino)-3-(5-bromo-2-methoxyphenyl)propanoate;
ethyl (S)-3-(benzyl((R)-1-phenylethyl)amino)-3-(3-iodo-4-(trifluoromethoxy)phenyl)propanoate;
ethyl (S)-3-(benzyl((R)-1-phenylethyl)amino)-3-(5-fluoro-3'-methoxybiphenyl-3-yl) propanoate;
ethyl (S)-3-(benzyl((R)-1-phenylethyl)amino)-3-(5-fluoro-3'-(trifluoromethoxy)biphenyl-3-yl)propanoate;
ethyl (S)-3-(benzyl((R)-1-phenylethyl)amino)-3-(2-fluoro-3-iodophenyl)propanoate;
ethyl (S)-3-(benzyl((R)-1-phenylethyl)amino)-3-(3-bromo-5-(trifluoromethoxy)phenyl)propanoate; and
ethyl (S)-3-(benzyl((R)-1-phenylethyl)amino)-3-(2'-methyl-6-(trifluoromethoxy)bi-phenyl-3-yl)propanoate (from ethyl (E)-3-(2'-methyl-6-(trifluoromethoxy)biphenyl-3-yl)acrylate).

Step Seven: To a mixture of 1-6 (6.96 g, 14.9 mmol) and phenylboronic acid (2.00 g, 16.4 mmol) in dimethoxyethane (50 mL) at room temperature under nitrogen, tribasic potassium phosphate (7.91 g, 37.3 mmol) and bis(triphenylphoshine)palladium(II) dichloride (523 mg, 0.75 mmol) were added. The mixture was deoxygenated (toggle between vacuum and nitrogen gas 5 times) and heated to 85° C. overnight. The mixture was cooled, diluted with ethyl acetate, and washed with water and brine. The organic layer was dried, filtered and concentrated. The residue was purified by column chromatography on silica gel, eluting with hexanes and ethyl acetate to give ethyl (S)-3-(benzyl((R)-1-phenylethyl)amino)-3-(biphenyl-3-yl)propanoate (1-7, 5.49 g).

This procedure was also used to prepare ethyl (S)-3-(benzyl((R)-1-phenylethyl)amino)-3-(2'-methylbiphenyl-3-yl)propanoate;
ethyl (S)-3-(benzyl((R)-1-phenylethyl)amino)-3-(2'-methylbiphenyl-3-yl)propanoate;
ethyl (S)-3-(benzyl((R)-1-phenylethyl)amino)-3-(4'-methylbiphenyl-3-yl)propanoate;
ethyl (S)-3-(benzyl((R)-1-phenylethyl)amino)-3-(3'-methylbiphenyl-3-yl)propanoate;
ethyl (S)-3-(benzyl((R)-1-phenylethyl)amino)-3-(4'-methoxybiphenyl-3-yl)propanoate;
ethyl (S)-3-(benzyl((R)-1-phenylethyl)amino)-3-(2'-methoxybiphenyl-3-yl)propanoate;
ethyl (S)-3-(benzyl((R)-1-phenylethyl)amino)-3-(3'-methoxybiphenyl-3-yl)propanoate;
ethyl 3-(3'-chloro-4'-fluorobiphenyl-3-yl)-3-(3-(4-hydroxy-1,5-dimethyl-2-oxo-1,2-dihydropyridin-3-yl)ureido)propanoate (from ethyl 3-(3-bromophenyl)-3-(3-(4-hydroxy-1,5-dimethyl-2-oxo-1,2-dihydropyridin-3-yl)ureido) propanoate);
ethyl 3-(2',3'-dichlorobiphenyl-3-yl)-3-(3-(4-hydroxy-1,5-dimethyl-2-oxo-1,2-dihydropyridin-3-yl)ureido)propanoate;
ethyl (S)-3-(benzyl((R)-1-phenylethyl)amino)-3-(5-methoxybiphenyl-3-yl)propanoate;
ethyl 3-(1-ethyl-1H-indol-6-yl)benzoate (28-1, from 6-bromo-1-ethyl-1H-indole and 3-ethoxycarbonylphenylboronic acid).

This reaction could also be performed with the addition of 2-5 fold excess equivalents of triethylamine. This modification was used to prepare
ethyl 3-(3',4'-dichlorobiphenyl-3-yl)-3-(3-(4-hydroxy-1,5-dimethyl-2-oxo-1,2-dihydropyridin-3-yl)ureido)propanoate (from ethyl 3-(3-bromophenyl)-3-(3-(4-hydroxy-1,5-dimethyl-2-oxo-1,2-dihydropyridin-3-yl)ureido) propanoate); and
ethyl 3-(3',4'-dichloro biphenyl-3-yl)-3-(3-(1-ethyl-4-hydroxy-5-methyl-2-oxo-1,2-dihydro pyridin-3-yl)ureido) propanoate.

In another modification of this procedure, water was added as co-solvent. This modification was used to prepare 5-(2,4-difluorophenyl)thiophene-2-carbaldehyde (from 5-bromothiophene-2-carboxaldehyde) and 5-(3-methoxyphenyl)thiophene-2-carbaldehyde.

This procedure was further modified by using sodium bicarbonate as the base instead of potassium phosphate with DME and water as solvents. This modification was used to prepare 4'-methyl-[2,3'-bithiophene]-5-carbaldehyde [from 3-bromo-4-methylthiophene and (5-formylthiophen-2-yl)boronic acid]; 5-(3-(trifluoromethoxy)phenyl)thiophene-2-carbaldehyde (from 5-bromothiophene-2-carbaldehyde), and 5-(2,6-dimethylphenyl)thiophene-2-carbaldehyde.

This procedure was also be carried out in DMF instead of DME with water as co-solvent with the temperature between 80 and 90° C. to prepare ethyl (S)-3-(benzyl((R)-1-phenylethyl)amino)-3-(6-fluorobiphenyl-3-yl)propanoate;
ethyl (S)-3-(benzyl((R)-1-phenylethyl)amino)-3-(6-methylbiphenyl-3-yl) propanoate;
ethyl (S)-3-(benzyl((R)-1-phenylethyl)amino)-3-(6-methoxybiphenyl-3-yl) propanoate;
ethyl (S)-3-(benzyl((R)-1-phenylethyl)amino)-3-(3',5'-difluorobiphenyl-3-yl) propanoate;
ethyl (S)-3-(benzyl((R)-1-phenylethyl)amino)-3-(3',5'-dimethylbiphenyl-3-yl) propanoate;
ethyl (S)-3-(benzyl((R)-1-phenylethyl)amino)-3-(4'-(trifluoromethyl)biphenyl-3-yl) propanoate;
ethyl (S)-3-(benzyl((R)-1-phenylethyl)amino)-3-(3'-(trifluoromethoxy)biphenyl-3-yl) propanoate;
ethyl (S)-3-(benzyl((R)-1-phenylethyl)amino)-3-(4'-(trifluoromethoxy)biphenyl-3-yl) propanoate;
ethyl (S)-3-(benzyl((R)-1-phenylethyl)amino)-3-(3',4'-difluorobiphenyl-3-yl) propanoate;
ethyl (S)-3-(benzyl((R)-1-phenylethyl)amino)-3-(3'-(trifluoromethyl)biphenyl-3-yl) propanoate;
ethyl (S)-3-(benzyl((R)-1-phenylethyl)amino)-3-(2',6'-difluorobiphenyl-3-yl) propanoate;
ethyl (S)-3-(benzyl((R)-1-phenylethyl)amino)-3-(3'-fluorobiphenyl-3-yl)propanoate;
ethyl (S)-3-(benzyl((R)-1-phenylethyl)amino)-3-(4'-fluorobiphenyl-3-yl)propanoate;
ethyl (S)-3-(benzyl((R)-1-phenylethyl)amino)-3-(2'-(trifluoromethoxy)biphenyl-3-yl) propanoate;
ethyl (S)-3-(benzyl((R)-1-phenylethyl)amino)-3-(2',4'-dimethoxybiphenyl-3-yl) propanoate;
ethyl (S)-3-(benzyl((R)-1-phenylethyl)amino)-3-(3',4'-dimethoxybiphenyl-3-yl) propanoate;
ethyl (S)-3-(benzyl((R)-1-phenylethyl)amino)-3-(2',6'-dimethylbiphenyl-3-yl) propanoate;
ethyl (S)-3-(benzyl((R)-1-phenylethyl)amino)-3-(2'-(trifluoromethyl)biphenyl-3-yl) propanoate;
tert-butyl (S)-3-(benzyl((R)-1-phenylethyl)amino)-3-(biphenyl-4-yl)propanoate;
ethyl (S)-3-(benzyl((R)-1-phenylethyl)amino)-3-(3-(6-methoxypyridin-3-yl)phenyl) propanoate;
ethyl (S)-3-(benzyl((R)-1-phenylethyl)amino)-3-(2',5'-dimethoxybiphenyl-3-yl) propanoate;
ethyl (S)-3-(benzyl((R)-1-phenylethyl)amino)-3-(2',6'-dimethoxybiphenyl-3-yl) propanoate;
ethyl (S)-3-(benzyl((R)-1-phenylethyl)amino)-3-(4-fluorobiphenyl-3-yl)propanoate;

ethyl (S)-3-(benzyl((R)-1-phenylethyl)amino)-3-(3',4'-dimethylbiphenyl-3-yl) propanoate;
ethyl (S)-3-(benzyl((R)-1-phenylethyl)amino)-3-(2',3'-difluorobiphenyl-3-yl) propanoate;
ethyl (S)-3-(benzyl((R)-1-phenylethyl)amino)-3-(4'-fluoro-3'-methylbiphenyl-3-yl) propanoate;
ethyl (S)-3-(benzyl((R)-1-phenylethyl)amino)-3-(2',3'-dimethoxybiphenyl-3-yl) propanoate;
ethyl (S)-3-(3-(benzo[d][1,3]dioxol-5-yl)phenyl)-3-(benzyl((R)-1-phenylethyl) amino)propanoate;
ethyl (S)-3-(benzyl((R)-1-phenylethyl)amino)-3-(2',4'-difluoro-6-methoxybiphenyl-3-yl)propanoate;
ethyl (S)-3-(benzyl((R)-1-phenylethyl)amino)-3-(3',6-dimethoxybiphenyl-3-yl) propanoate;
ethyl (S)-3-(benzyl((R)-1-phenylethyl)amino)-3-(6-methoxy-3'-(trifluoromethoxy) biphenyl-3-yl)propanoate;
ethyl (S)-3-(benzyl((R)-1-phenylethyl)amino)-3-(6-methoxy-4'-(trifluoromethoxy) biphenyl-3-yl)propanoate;
ethyl (S)-3-(benzyl((R)-1-phenylethyl)amino)-3-(2',4'-difluoro-6-methylbiphenyl-3-yl)propanoate;
ethyl (S)-3-(benzyl((R)-1-phenylethyl)amino)-3-(3'-methoxy-6-methylbiphenyl-3-yl)propanoate;
ethyl (S)-3-(benzyl((R)-1-phenylethyl)amino)-3-(2',6,6'-trimethylbiphenyl-3-yl) propanoate;
ethyl (S)-3-(benzyl((R)-1-phenylethyl)amino)-3-(2',6,6'-trifluorobiphenyl-3-yl) propanoate;
ethyl (S)-3-(benzyl((R)-1-phenylethyl)amino)-3-(6-fluoro-3'-methoxybiphenyl-3-yl) propanoate;
ethyl (S)-3-(benzyl((R)-1-phenylethyl)amino)-3-(6-fluoro-2',6'-dimethylbiphenyl-3-yl)propanoate;
ethyl (S)-3-(benzyl((R)-1-phenylethyl)amino)-3-(3',5-dimethoxybiphenyl-3-yl) propanoate;
ethyl (S)-3-(benzyl((R)-1-phenylethyl)amino)-3-(5-methoxy-3'-(trifluoromethoxy) biphenyl-3-yl)propanoate;
ethyl (S)-3-(benzyl((R)-1-phenylethyl)amino)-3-(2',4'-difluoro-5-methoxybiphenyl-3-yl)propanoate;
ethyl (S)-3-(benzyl((R)-1-phenylethyl)amino)-3-(5-methyl-3'-(trifluoromethoxy) biphenyl-3-yl)propanoate;
ethyl (S)-3-(benzyl((R)-1-phenylethyl)amino)-3-(2',5,6'-trimethylbiphenyl-3-yl) propanoate;
ethyl (S)-3-(benzyl((R)-1-phenylethyl)amino)-3-(2',4'-difluoro-5-methylbiphenyl-3-yl)propanoate;
ethyl (S)-3-(benzyl((R)-1-phenylethyl)amino)-3-(6-methyl-3'-(trifluoromethoxy) biphenyl-3-yl)propanoate;
ethyl (S)-3-(benzyl((R)-1-phenylethyl)amino)-3-(5-methoxy-2',6'-dimethylbiphenyl-3-yl)propanoate;
ethyl (S)-3-(benzyl((R)-1-phenylethyl)amino)-3-(3'-methoxy-5-methylbiphenyl-3-yl)propanoate;
ethyl (S)-3-(benzyl((R)-1-phenylethyl)amino)-3-(5-fluoro-2',6'-dimethylbiphenyl-3-yl)propanoate;
ethyl (S)-3-(benzyl((R)-1-phenylethyl)amino)-3-(4-fluoro-2',6'-dimethylbiphenyl-3-yl)propanoate;
ethyl (S)-3-(benzyl((R)-1-phenylethyl)amino)-3-(2',4,4'-trifluorobiphenyl-3-yl) propanoate;
ethyl (S)-3-(benzyl((R)-1-phenylethyl)amino)-3-(4-fluoro-3'-methoxybiphenyl-3-yl) propanoate;
ethyl (S)-3-(benzyl((R)-1-phenylethyl)amino)-3-(4-fluoro-3'-(trifluoromethoxy) biphenyl-3-yl)propanoate;
ethyl (S)-3-(benzyl((R)-1-phenylethyl)amino)-3-(4-methoxybiphenyl-3-yl) propanoate;
ethyl (S)-3-(benzyl((R)-1-phenylethyl)amino)-3-(4-methoxy-2',6'-dimethylbiphenyl-3-yl)propanoate;
ethyl (S)-3-(benzyl((R)-1-phenylethyl)amino)-3-(3'-methoxy-6-(trifluoromethoxy) biphenyl-3-yl)propanoate;
ethyl (S)-3-(benzyl((R)-1-phenylethyl)amino)-3-(2-fluorobiphenyl-3-yl)propanoate;
ethyl (S)-3-(benzyl((R)-1-phenylethyl)amino)-3-(6-fluoro-2'-methylbiphenyl-3-yl) propanoate;
ethyl (S)-3-(benzyl((R)-1-phenylethyl)amino)-3-(2',6'-dimethylbiphenyl-4-yl) propanoate;
ethyl (S)-3-(benzyl((R)-1-phenylethyl)amino)-3-(2'-methylbiphenyl-4-yl) propanoate;
ethyl (S)-3-(benzyl((R)-1-phenylethyl)amino)-3-(5-(trifluoromethoxy)biphenyl-3-yl) propanoate;
ethyl (S)-3-(benzyl((R)-1-phenylethyl)amino)-3-(4-fluorobiphenyl-3-yl)propanoate;
ethyl 3-(3'-acetylbiphenyl-3-yl)-3-(tritylamino)propanoate (from 2-3);
ethyl 3-(4'-acetylbiphenyl-3-yl)-3-(tritylamino)propanoate;
2'-methyl-6-(trifluoromethoxy)biphenyl-3-carbaldehyde (from 24-1);
6-(trifluoromethoxy)biphenyl-3-carbaldehyde (from 3-bromo-2-methyl benzaldehyde);
2-methylbiphenyl-3-carbaldehyde (from 3-bromo-4-methoxybenzaldehyde);
6-methoxy-2',6'-dimethylbiphenyl-3-carbaldehyde (from 3-bromo-4-methoxy benzaldehyde);
3'-chloro-6-methoxybiphenyl-3-carbaldehyde;
3'-chloro-6-methylbiphenyl-3-carbaldehyde (from 3-bromo-4-methylbenzaldehyde);
5,6-dimethoxybiphenyl-3-carbaldehyde (from 3-bromo-5,6-dimethoxybenzal dehyde);
3-(1-(triisopropylsilyl)-1H-pyrrol-3-yl)benzaldehyde (from 3-bromobenzaldehyde and 1-(triisopropylsilyl)-1H-pyrrole-3-boronic acid);
3-(pyrazin-2-yl)benzaldehyde (from 3-formylphenyl boronic acid and iodopyrazine);
3-(6-methoxypyridin-2-yl)benzaldehyde (from 3-formylphenyl boronic acid and 2-bromo-6-methoxypyridine);
3-(1-methyl-1H-pyrazol-4-yl)benzaldehyde (from 3-formylphenyl boronic acid and 16-1);
3-(thiazol-2-yl)benzaldehyde (from 3-formylphenyl boronic acid and 2-bromothiazole);
3-(3,5-dimethylisoxazol-4-yl)benzaldehyde (from 3-formylphenyl boronic acid and 3,5-dimethyl-4-iodoisoxazole);
4-(2,4-difluorophenyl)thiophene-2-carbaldehyde (from 4-bromothiophene-2-carboxaldehyde);
4-(3-methoxyphenyl)thiophene-2-carbaldehyde;
4-(2,6-dimethylphenyl)thiophene-2-carbaldehyde;
5-(2,5-difluorophenyl)thiophene-2-carbaldehyde (from 5-bromothiophene-2-carboxaldehyde);
5-(3-chlorophenyl)thiophene-2-carbaldehyde;
5-(3-fluorophenyl)thiophene-2-carbaldehyde;
5-(3,5-dimethylisoxazol-4-yl)thiophene-2-carbaldehyde (from 5-formyl-2-thiopheneboronic acid and 3,5-dimethyl-4-iodoisoxazole);
ethyl 3-(6-(2,2,2-trifluoroethoxy)biphenyl-3-yl)-3-(tritylamino)propanoate (from ethyl 3-(3-bromo-4-(2,2,2-trifluoroethoxy)phenyl)-3-(tritylamino)propanoate);
ethyl 3-(4'-chlorobiphenyl-3-yl)-3-(3-(4-hydroxy-1,5-dimethyl-2-oxo-1,2-dihydro pyridin-3-yl)ureido)propanoate (from ethyl 3-(3-bromophenyl)-3-(3-(4-hydroxy-1,5-dimethyl-2-oxo-1,2-dihydropyridin-3-yl)ureido)propanoate);
ethyl 3-(3'-chlorobiphenyl-3-yl)-3-(3-(4-hydroxy-1,5-dimethyl-2-oxo-1,2-dihydro pyridin-3-yl)ureido)propanoate;
ethyl 3-(2'-chlorobiphenyl-3-yl)-3-(3-(4-hydroxy-1,5-dimethyl-2-oxo-1,2-dihydropyridin-3-yl)ureido)propanoate;
ethyl 3-(3-(4-hydroxy-1,5-dimethyl-2-oxo-1,2-dihydropyridin-3-yl)ureido)-3-(3-(pyrimidin-5-yl)phenyl)propanoate;
ethyl 3-(3',5'-dichlorobiphenyl-3-yl)-3-(3-(4-hydroxy-1,5-dimethyl-2-oxo-1,2-dihydropyridin-3-yl)ureido)propanoate;

ethyl 3-(2',5'-dichlorobiphenyl-3-yl)-3-(3-(4-hydroxy-1,5-dimethyl-2-oxo-1,2-dihydropyridin-3-yl)ureido)propanoate; and ethyl 3-(5'-chloro-2',4'-difluorobiphenyl-3-yl)-3-(tritylamino)propanoate (from 3-1).

Potassium carbonate could also be used as base instead of tribasic potassium phosphate with DMF and water as solvents. This modification was used to prepare ethyl (S)-3-(benzyl((R)-1-phenylethyl)amino)-3-(2'-fluoro-3'-methoxybiphenyl-3-yl)propanoate; and ethyl 3-(2',4'-dichlorobiphenyl-3-yl)-3-(3-(4-hydroxy-1,5-dimethyl-2-oxo-1,2-dihydropyridin-3-yl)ureido)propanoate (from ethyl 3-(3-bromophenyl)-3-(3-(4-hydroxy-1,5-dimethyl-2-oxo-1,2-dihydropyridin-3-yl)ureido)propanoate).

Finally, the procedure was accomplished using a heterogeneous mixture of toluene and water as co-solvents to prepare ethyl (S)-3-(benzyl((R)-1-phenylethyl)amino)-3-(2',4'-difluorobiphenyl-3-yl)propanoate; ethyl (S)-3-(benzyl((R)-1-phenylethyl)amino)-3-(2',5'-difluorobiphenyl-3-yl)propanoate; and ethyl (S)-3-(benzyl((R)-1-phenylethyl)amino)-3-(3-(pyridin-3-yl)phenyl)propanoate (from 1-6 and 3-pyridineboronic acid 1,3-propanediol ester).

Step Eight: To a solution of 1-7 (5.49 g, 11.3 mmol) in ethanol (75 mL), glacial acetic acid (0.4 mL), palladium metal on carbon (Degussa type E101 NE/W, 50% $H_2O$, 10% Pd dry weight basis, 1.8 g, 0.83 mmol Pd). The atmosphere was replaced with hydrogen (toggling between vacuum and hydrogen from a balloon several times) and the reaction was stirred overnight. The mixture was filtered through Celite® and the filtrate was concentrated under reduced pressure. The residue was brought up in ethyl acetate, washed with saturated aqueous sodium carbonate, and the organic layer was dried over magnesium sulfate, filtered, and concentrated under reduced pressure. The residue was purified by column chromatography on silica gel, eluting with 15% then 40% ethyl acetate in hexanes, followed by 10% methanol in chloroform to give ethyl (S)-3-amino-3-(biphenyl-3-yl)propanoate; (1-8, 1.89 g).

This procedure was also used to prepare ethyl (S)-3-amino-3-(2'-methylbiphenyl-3-yl)propanoate;
ethyl (S)-3-amino-3-(2'-fluorobiphenyl-3-yl)propanoate;
ethyl (S)-3-amino-3-(6-fluorobiphenyl-3-yl)propanoate;
ethyl (S)-3-amino-3-(2',4'-difluorobiphenyl-3-yl)propanoate;
ethyl (S)-3-amino-3-(2',5'-difluorobiphenyl-3-yl)propanoate;
ethyl (S)-3-amino-3-(6-methylbiphenyl-3-yl)propanoate;
ethyl (S)-3-amino-3-(6-methoxybiphenyl-3-yl)propanoate;
ethyl (S)-3-amino-3-(4'-methylbiphenyl-3-yl)propanoate;
ethyl (S)-3-amino-3-(3'-methylbiphenyl-3-yl)propanoate;
ethyl (S)-3-amino-3-(3-(pyridin-3-yl)phenyl)propanoate;
ethyl (S)-3-amino-3-(3',5'-difluorobiphenyl-3-yl)propanoate;
ethyl (S)-3-amino-3-(3',5'-dimethylbiphenyl-3-yl)propanoate;
ethyl (S)-3-amino-3-(4'-methoxybiphenyl-3-yl)propanoate;
ethyl (S)-3-amino-3-(2'-methoxybiphenyl-3-yl)propanoate;
ethyl (S)-3-amino-3-(4'-(trifluoromethyl)biphenyl-3-yl)propanoate;
ethyl (S)-3-amino-3-(3'-methoxybiphenyl-3-yl)propanoate;
ethyl (S)-3-amino-3-(3'-(trifluoromethoxy)biphenyl-3-yl)propanoate;
ethyl (S)-3-amino-3-(4'-(trifluoromethoxy)biphenyl-3-yl)propanoate;
ethyl (S)-3-amino-3-(3',4'-difluorobiphenyl-3-yl)propanoate;
ethyl (S)-3-amino-3-(2',6'-difluorobiphenyl-3-yl)propanoate;
ethyl (S)-3-amino-3-(3'-fluorobiphenyl-3-yl)propanoate;
ethyl (S)-3-amino-3-(4'-fluorobiphenyl-3-yl)propanoate;
ethyl (S)-3-amino-3-(2'-(trifluoromethoxy)biphenyl-3-yl)propanoate;
ethyl (S)-3-amino-3-(2',4'-dimethoxybiphenyl-3-yl)propanoate;
ethyl (S)-3-amino-3-(3',4'-dimethoxybiphenyl-3-yl)propanoate;
ethyl (S)-3-amino-3-(2',6'-dimethylbiphenyl-3-yl)propanoate;
ethyl (S)-3-amino-3-(2'-(trifluoromethyl)biphenyl-3-yl)propanoate;
tert-butyl (S)-3-amino-3-(biphenyl-4-yl)propanoate;
ethyl (S)-3-amino-3-(5,6-dimethoxybiphenyl-3-yl)propanoate;
ethyl (S)-3-amino-3-(3-(6-methoxypyridin-3-yl)phenyl)propanoate;
ethyl (S)-3-amino-3-(2',5'-dimethoxybiphenyl-3-yl)propanoate;
ethyl (S)-3-amino-3-(2',6'-dimethoxybiphenyl-3-yl)propanoate;
ethyl (S)-3-amino-3-(3'-methoxy-2'-methylbiphenyl-3-yl)propanoate;
ethyl (S)-3-amino-3-(5'-methoxy-2'-methylbiphenyl-3-yl)propanoate;
ethyl (S)-3-amino-3-(2'-ethylbiphenyl-3-yl)propanoate;
ethyl (S)-3-amino-3-(4-fluorobiphenyl-3-yl)propanoate;
ethyl (S)-3-amino-3-(3',4'-dimethylbiphenyl-3-yl)propanoate;
ethyl (S)-3-amino-3-(2',3'-difluorobiphenyl-3-yl)propanoate;
ethyl (S)-3-amino-3-(4'-fluoro-3'-methylbiphenyl-3-yl)propanoate;
ethyl (S)-3-amino-3-(2-methylbiphenyl-3-yl)propanoate;
ethyl (S)-3-amino-3-(2',3'-dimethoxybiphenyl-3-yl)propanoate;
ethyl (S)-3-amino-3-(2'-fluoro-3'-methoxybiphenyl-3-yl)propanoate;
ethyl (S)-3-amino-3-(3-(benzo[d][1,3]dioxol-5-yl)phenyl)propanoate;
ethyl (S)-3-(3-(1H-indazol-1-yl)phenyl)-3-aminopropanoate;
ethyl (S)-3-amino-3-(2',4'-difluoro-6-methoxybiphenyl-3-yl)propanoate;
ethyl (S)-3-amino-3-(3-(1-ethyl-1H-indol-6-yl)phenyl)propanoate;
ethyl (S)-3-(3-(1H-pyrazol-1-yl)phenyl)-3-aminopropanoate;
ethyl (S)-3-amino-3-(3',6-dimethoxybiphenyl-3-yl)propanoate;
ethyl (S)-3-amino-3-(6-methoxy-2',6'-dimethylbiphenyl-3-yl)propanoate;
ethyl (S)-3-amino-3-(6-trifluoromethoxy)biphenyl-3-yl)propanoate;
ethyl (S)-3-amino-3-(6-methoxy-3'-(trifluoromethoxy)biphenyl-3-yl)propanoate;
ethyl (S)-3-amino-3-(6-methoxy-4'-(trifluoromethoxy)biphenyl-3-yl)propanoate;
ethyl (S)-3-(3-(1H-imidazol-1-yl)phenyl)-3-aminopropanoate;
ethyl (S)-3-amino-3-(2',4'-difluoro-6-methyl-3-yl)propanoate;
ethyl (S)-3-amino-3-(3'-methoxy-6-methylbiphenyl-3-yl)propanoate;

ethyl (S)-3-amino-3-(2',6,6'-trimethylbiphenyl-3-yl)propanoate;
ethyl (S)-3-amino-3-(2',6,6'-trifluorobiphenyl-3-yl)propanoate;
ethyl (S)-3-amino-3-(6-fluoro-3'-methoxybiphenyl-3-yl)propanoate;
ethyl (S)-3-amino-3-(5-methoxybiphenyl-3-yl)propanoate;
ethyl (S)-3-amino-3-(6-fluoro-2',6'-dimethylbiphenyl-3-yl)propanoate;
ethyl (S)-3-amino-3-(3',5-dimethoxybiphenyl-3-yl)propanoate;
ethyl (S)-3-amino-3-(5-methoxy-3'-(trifluoromethoxy)biphenyl-3-yl)propanoate;
ethyl (S)-3-amino-3-(2',4'-difluoro-5-methoxybiphenyl-3-yl)propanoate;
ethyl (S)-3-amino-3-(5-methyl-3'-(trifluoromethoxy)biphenyl-3-yl)propanoate;
ethyl (S)-3-amino-3-(6-methyl-3'-(trifluoromethoxy)biphenyl-3-yl)propanoate;
ethyl (S)-3-amino-3-(5-methoxy-2',6'-dimethylbiphenyl-3-yl)propanoate;
ethyl (S)-3-amino-3-(3'-methoxy-5-methylbiphenyl-3-yl)propanoate;
ethyl (S)-3-amino-3-(4-fluoro-2',6'-dimethylbiphenyl-3-yl)propanoate;
ethyl (S)-3-amino-3-(2',4,4'-trifluorobiphenyl-3-yl)propanoate;
ethyl (S)-3-amino-3-(4-fluoro-3'-methoxybiphenyl-3-yl)propanoate;
ethyl (S)-3-amino-3-(4-fluoro-3'-(trifluoromethoxy)biphenyl-3-yl)propanoate;
ethyl (S)-3-amino-3-(3'-methoxy-6-(trifluoromethoxy)biphenyl-3-yl)propanoate;
ethyl (S)-3-amino-3-(2'-methyl-6-(trifluoromethoxy)biphenyl-3-yl)propanoate;
ethyl (S)-3-amino-3-(5-fluoro-3'-methoxybiphenyl-3-yl)propanoate;
ethyl (S)-3-amino-3-(5-fluoro-3'-(trifluoromethoxy)biphenyl-3-yl)propanoate;
ethyl (S)-3-amino-3-(2-fluorobiphenyl-3-yl)propanoate;
ethyl (S)-3-amino-3-(6-fluoro-2'-methylbiphenyl-3-yl)propanoate;
ethyl (S)-3-amino-3-(2',6'-dimethylbiphenyl-4-yl)propanoate;
ethyl (S)-3-amino-3-(2'-methylbiphenyl-4-yl)propanoate; and
ethyl (S)-3-amino-3-(5-(trifluoromethoxy)biphenyl-3-yl)propanoate.

This procedure was also performed at 50° C. to prepare
ethyl (S)-3-amino-3-(2',4',5-trifluorobiphenyl-3-yl)propanoate;
ethyl (S)-3-amino-3-(4-methoxybiphenyl-3-yl)propanoate; and
ethyl (S)-3-amino-3-(5-fluoro-2',6'-dimethylbiphenyl-3-yl)propanoate.

This procedure was also modified by pre-treating a solution of the starting material and acetic acid in ethanol with activated charcoal. The mixture was stirred for 30 min to 1 hour at 40-50° C. then was cooled before adding the palladium catalyst, exchanging the atmosphere with hydrogen gas, and completing the procedure at room temperature as described above to prepare
ethyl (S)-3-amino-3-(2',5-dimethylbiphenyl-3-yl)propanoate;
ethyl (S)-3-amino-3-(2',3'-dimethylbiphenyl-3-yl)propanoate;
and ethyl (S)-3-amino-3-(3'-(trifluoromethyl)biphenyl-3-yl)propanoate.

The hydrogenation was also carried out at 50° C. after pretreating with activated charcoal to prepare
ethyl (S)-3-amino-3-(2',5,6'-trimethylbiphenyl-3-yl)propanoate; and
ethyl (S)-3-amino-3-(2',4'-difluoro-5-methylbiphenyl-3-yl)propanoate; and ethyl (S)-3-amino-3-(4-methoxy-2',6'-dimethylbiphenyl-3-yl)propanoate.

The original procedure could also be modified to isolate the product as an acetic acid salt by concentrating the filtrate of the crude reaction mixture after filtering through Celite®. This modification gave ethyl (S)-3-amino-3-(5-fluoro-2',6'-dimethylbiphenyl-3-yl)propanoate acetic acid salt; and tert-butyl (S)-3-amino-3-(2',4'-difluorobiphenyl-4-yl)propanoate acetic acid salt.

Step Nine: A suspension of 1-5 (121 mg, 0.67 mmol) and 1-8 (800 mg, 3.86 mmol) in DMF (1.3 mL) under a dry nitrogen atmosphere was heated to 70° C. overnight, cooled to room temperature and then diluted with water. The resulting mixture was extracted with dichloromethane three times and the combined organic layers were dried over $MgSO_4$ and filtered. The filtrate was concentrated under reduced pressure and the resulting residue was purified by silica gel chromatography, eluting with a gradient of 5 to 75% ethyl acetate in hexanes to give ethyl (S)-3-(biphenyl-3-yl)-3-(3-(4-hydroxy-1,5-dimethyl-2-oxo-1,2-dihydropyridin-3-yl)ureido)propanoate (1-9, 120 mg).

For this transformation and the modifications described below, the temperature was varied from 50 to 90° C. without a significant difference in the outcome. The progress of the reaction was monitored by TLC to ensure completion and the time and temperature was adjusted as needed. This procedure was also used to prepare
ethyl (S)-3-(biphenyl-3-yl)-3-(3-(1-ethyl-4-hydroxy-5-methyl-2-oxo-1,2-dihydropyridin-3-yl)ureido)propanoate 1-10;
ethyl 3-(3-(1-ethyl-4-hydroxy-5-methyl-2-oxo-1,2-dihydropyridin-3-yl)ureido)-3-(3-(2-oxo-3-phenylpyridin-1(2H)-yl)phenyl)propanoate 1-11;
ethyl (S)-3-(3-(4-hydroxy-1,5-dimethyl-2-oxo-1,2-dihydropyridin-3-yl)ureido)-3-(2'-methylbiphenyl-3-yl)propanoate 1-12;
ethyl (S)-3-(2'-fluorobiphenyl-3-yl)-3-(3-(4-hydroxy-1,5-dimethyl-2-oxo-1,2-dihydro pyridin-3-yl)ureido)propanoate 1-13;
ethyl (S)-3-(6-fluorobiphenyl-3-yl)-3-(3-(4-hydroxy-1,5-dimethyl-2-oxo-1,2-dihydro pyridin-3-yl)ureido)propanoate 1-14;
ethyl (S)-3-(3-(1-ethyl-4-hydroxy-5-methyl-2-oxo-1,2-dihydropyridin-3-yl)ureido)-3-(2'-methylbiphenyl-3-yl)propanoate;
ethyl (S)-3-(3-(1-ethyl-4-hydroxy-5-methyl-2-oxo-1,2-dihydropyridin-3-yl)ureido)-3-(4'-methylbiphenyl-3-yl)propanoate 1-15;
ethyl 3-(3-(1H-pyrrol-1-yl)phenyl)-3-(3-(4-hydroxy-1,5-dimethyl-2-oxo-1,2-dihydro pyridin-3-yl)ureido)propanoate 1-16;
ethyl (S)-3-(2',4'-difluorobiphenyl-3-yl)-3-(3-(4-hydroxy-1,5-dimethyl-2-oxo-1,2-di hydropyridin-3-yl)ureido)propanoate 1-17;
ethyl (S)-3-(2',5'-difluorobiphenyl-3-yl)-3-(3-(4-hydroxy-1,5-dimethyl-2-oxo-1,2-di hydropyridin-3-yl)ureido)propanoate 1-18;
ethyl (S)-3-(3-(4-hydroxy-1,5-dimethyl-2-oxo-1,2-dihydropyridin-3-yl)ureido)-3-(6-methylbiphenyl-3-yl)propanoate 1-19;

ethyl (S)-3-(3-(4-hydroxy-1,5-dimethyl-2-oxo-1,2-dihydropyridin-3-yl)ureido)-3-(6-methoxybiphenyl-3-yl)propanoate 1-20;

ethyl (S)-3-(3-(4-hydroxy-1,5-dimethyl-2-oxo-1,2-dihydropyridin-3-yl)ureido)-3-(4'-methylbiphenyl-3-yl)propanoate 1-21;

ethyl (S)-3-(3-(4-hydroxy-1,5-dimethyl-2-oxo-1,2-dihydropyridin-3-yl)ureido)-3-(3'-methylbiphenyl-3-yl)propanoate 1-22;

ethyl (S)-3-(3-(4-hydroxy-1,5-dimethyl-2-oxo-1,2-dihydropyridin-3-yl)ureido)-3-(3-(pyridin-3-yl)phenyl)propanoate 1-23;

ethyl (S)-3-(3',5'-difluorobiphenyl-3-yl)-3-(3-(4-hydroxy-1,5-dimethyl-2-oxo-1,2-dihydropyridin-3-yl)ureido)propanoate 1-24;

ethyl (S)-3-(3',5'-dimethylbiphenyl-3-yl)-3-(3-(4-hydroxy-1,5-dimethyl-2-oxo-1,2-dihydropyridin-3-yl)ureido)propanoate 1-25;

ethyl (S)-3-(3-(4-hydroxy-1,5-dimethyl-2-oxo-1,2-dihydropyridin-3-yl)ureido)-3-(4'-methoxybiphenyl-3-yl)propanoate 1-26;

ethyl (S)-3-(3-(4-hydroxy-1-methyl-2-oxo-1,2-dihydropyridin-3-yl)ureido)-3-(3-(pyrazin-2-yl)phenyl)propanoate 1-28;

ethyl (S)-3-(3-(4-hydroxy-1,5-dimethyl-2-oxo-1,2-dihydropyridin-3-yl)ureido)-3-(4'-(trifluoromethoxy)biphenyl-3-yl)propanoate 1-29;

ethyl (S)-3-(3',4'-difluorobiphenyl-3-yl)-3-(3-(4-hydroxy-1,5-dimethyl-2-oxo-1,2-dihydropyridin-3-yl)ureido)propanoate 1-30;

ethyl (S)-3-(2',5'-dimethylbiphenyl-3-yl)-3-(3-(4-hydroxy-1,5-dimethyl-2-oxo-1,2-dihydropyridin-3-yl)ureido)propanoate 1-31;

ethyl (S)-3-(3-(4-hydroxy-1,5-dimethyl-2-oxo-1,2-dihydropyridin-3-yl)ureido)-3-(3'-(trifluoromethoxy)biphenyl-3-yl)propanoate 1-33;

ethyl (S)-3-(2',3'-dimethylbiphenyl-3-yl)-3-(3-(4-hydroxy-1,5-dimethyl-2-oxo-1,2-dihydropyridin-3-yl)ureido)propanoate 1-34;

ethyl 3-(3-(4-hydroxy-1,5-dimethyl-2-oxo-1,2-dihydropyridin-3-yl)ureido)-3-(6-oxo-1-phenyl-1,6-dihydropyridin-3-yl)propanoate 1-35;

ethyl (S)-3-(2',6'-difluorobiphenyl-3-yl)-3-(3-(4-hydroxy-1,5-dimethyl-2-oxo-1,2-dihydropyridin-3-yl)ureido)propanoate 1-36;

ethyl (S)-3-(3'-fluorobiphenyl-3-yl)-3-(3-(4-hydroxy-1,5-dimethyl-2-oxo-1,2-dihydropyridin-3-yl)ureido)propanoate 1-37;

ethyl (S)-3-(4'-fluorobiphenyl-3-yl)-3-(3-(4-hydroxy-1,5-dimethyl-2-oxo-1,2-dihydro pyridin-3-yl)ureido)propanoate 1-38;

ethyl (S)-3-(3-(4-hydroxy-1,5-dimethyl-2-oxo-1,2-dihydropyridin-3-yl)ureido)-3-(2'-(trifluoromethoxy)biphenyl-3-yl)propanoate 1-39;

ethyl (S)-3-(2',4'-dimethoxybiphenyl-3-yl)-3-(3-(4-hydroxy-1,5-dimethyl-2-oxo-1,2-dihydropyridin-3-yl)ureido)propanoate 1-40;

ethyl (S)-3-(3',4'-dimethoxybiphenyl-3-yl)-3-(3-(4-hydroxy-1,5-dimethyl-2-oxo-1,2-dihydropyridin-3-yl)ureido)propanoate 1-41;

ethyl (S)-3-(2',6'-dimethylbiphenyl-3-yl)-3-(3-(4-hydroxy-1,5-dimethyl-2-oxo-1,2-dihydropyridin-3-yl)ureido)propanoate 1-42;

ethyl 3-(4'-chlorobiphenyl-3-yl)-3-(3-(4-hydroxy-1,5-dimethyl-2-oxo-1,2-dihydropyridin-3-yl)ureido)propanoate 1-43;

ethyl (S)-3-(3'-chlorobiphenyl-3-yl)-3-(3-(4-hydroxy-1,5-dimethyl-2-oxo-1,2-dihydropyridin-3-yl)ureido)propanoate 1-44;

ethyl 3-(2'-chlorobiphenyl-3-yl)-3-(3-(4-hydroxy-1,5-dimethyl-2-oxo-1,2-dihydropyridin-3-yl)ureido)propanoate 1-45;

ethyl (S)-3-(3-(4-hydroxy-1,5-dimethyl-2-oxo-1,2-dihydropyridin-3-yl)ureido)-3-(2'-(trifluoromethyl)biphenyl-3-yl)propanoate 1-46;

ethyl (S)-3-(5,6-dimethoxybiphenyl-3-yl)-3-(3-(4-hydroxy-1,5-dimethyl-2-oxo-1,2-dihydropyridin-3-yl)ureido)propanoate 1-47;

ethyl (S)-3-(3-(4-hydroxy-1,5-dimethyl-2-oxo-1,2-dihydropyridin-3-yl)ureido)-3-(3-(6-methoxypyridin-3-yl)phenyl)propanoate 1-48;

ethyl (S)-3-(2',5'-dimethoxybiphenyl-3-yl)-3-(3-(4-hydroxy-1,5-dimethyl-2-oxo-1,2-dihydropyridin-3-yl)ureido)propanoate 1-49;

ethyl 3-(3-(4-hydroxy-1,5-dimethyl-2-oxo-1,2-dihydropyridin-3-yl)ureido)-3-(3-(pyrimidin-5-yl)phenyl)propanoate 1-50;

ethyl (S)-3-(2',6'-dimethoxybiphenyl-3-yl)-3-(3-(4-hydroxy-1,5-dimethyl-2-oxo-1,2-dihydropyridin-3-yl)ureido)propanoate 1-51;

ethyl 3-(3',4'-dichlorobiphenyl-3-yl)-3-(3-(1-ethyl-4-hydroxy-5-methyl-2-oxo-1,2-dihydro pyridin-3-yl)ureido)propanoate 1-52;

ethyl 3-(3',4'-dichlorobiphenyl-3-yl)-3-(3-(4-hydroxy-1,5-dimethyl-2-oxo-1,2-dihydropyridin-3-yl)ureido)propanoate 1-53;

ethyl (S)-3-(3-(4-hydroxy-1,5-dimethyl-2-oxo-1,2-dihydropyridin-3-yl)ureido)-3-(5-phenylfuran-2-yl)propanoate 1-54;

ethyl (S)-3-(3-(2,5-dimethyl-1H-pyrrol-1-yl)phenyl)-3-(3-(4-hydroxy-1,5-dimethyl-2-oxo-1,2-dihydropyridin-3-yl)ureido)propanoate 1-55;

ethyl 3-(3'-chloro-4-fluorobiphenyl-3-yl)-3-(3-(4-hydroxy-1,5-dimethyl-2-oxo-1,2-dihydropyridin-3-yl)ureido)propanoate 1-56;

ethyl 3-(2',3'-dichlorobiphenyl-3-yl)-3-(3-(4-hydroxy-1,5-dimethyl-2-oxo-1,2-dihydropyridin-3-yl)ureido)propanoate 1-57;

ethyl 3-(3',5'-dichlorobiphenyl-3-yl)-3-(3-(4-hydroxy-1,5-dimethyl-2-oxo-1,2-dihydropyridin-3-yl)ureido)propanoate 1-58;

ethyl (S)-3-(2',4'-difluorobiphenyl-3-yl)-3-(3-(4-hydroxy-1,6-dimethyl-2-oxo-1,2-dihydropyridin-3-yl)ureido)propanoate 1-59;

ethyl (S)-3-(2',4'-difluorobiphenyl-3-yl)-3-(3-(4-hydroxy-1-methyl-2-oxo-1,2-dihydropyridin-3-yl)ureido)propanoate 1-60;

ethyl (S)-3-(3-(4-hydroxy-1,5-dimethyl-2-oxo-1,2-dihydropyridin-3-yl)ureido)-3-(3'-methoxy-2'-methylbiphenyl-3-yl)propanoate 1-61;

ethyl (S)-3-(3-(4-hydroxy-1,5-dimethyl-2-oxo-1,2-dihydropyridin-3-yl)ureido)-3-(5'-methoxy-2'-methylbiphenyl-3-yl)propanoate 1-62;

ethyl 3-(3-(4-hydroxy-1,5-dimethyl-2-oxo-1,2-dihydropyridin-3-yl)ureido)-3-(6-(2,2,2-trifluoroethoxy)biphenyl-3-yl)propanoate 1-63;

ethyl (S)-3-(2'-ethylbiphenyl-3-yl)-3-(3-(4-hydroxy-1,5-dimethyl-2-oxo-1,2-dihydro pyridin-3-yl)ureido)propanoate 1-64;

ethyl 3-(4-fluorobiphenyl-3-yl)-3-(3-(4-hydroxy-1,5-dimethyl-2-oxo-1,2-dihydro pyridin-3-yl)ureido)propanoate 1-65;

ethyl (S)-3-(2',4'-difluorobiphenyl-3-yl)-3-(3-(4-hydroxy-2-oxo-1,2-dihydropyridin-3-yl)ureido)propanoate 1-66;

ethyl (S)-3-(3',4'-dimethylbiphenyl-3-yl)-3-(3-(4-hydroxy-1,5-dimethyl-2-oxo-1,2-di hydropyridin-3-yl)ureido)propanoate 1-67;

ethyl (S)-3-(2',3'-difluorobiphenyl-3-yl)-3-(3-(4-hydroxy-1,5-dimethyl-2-oxo-1,2-di hydropyridin-3-yl)ureido)propanoate 1-68;

ethyl (S)-3-(4'-fluoro-3'-methylbiphenyl-3-yl)-3-(3-(4-hydroxy-1,5-dimethyl-2-oxo-1,2-dihydropyridin-3-yl)ureido)propanoate 1-69;

ethyl (S)-3-(3-(4-hydroxy-1,5-dimethyl-2-oxo-1,2-dihydropyridin-3-yl)ureido)-3-(1-phenyl-1H-pyrrol-2-yl)propanoate 1-70;

ethyl (S)-3-(3'-chlorobiphenyl-3-yl)-3-(3-(4-hydroxy-1,5-dimethyl-2-oxo-1,2-dihydropyridin-3-yl)ureido)propanoate 1-71;

ethyl (S)-3-(3-(4-hydroxy-1,5-dimethyl-2-oxo-1,2-dihydropyridin-3-yl)ureido)-3-(2-methylbiphenyl-3-yl)propanoate 1-72;

ethyl (S)-3-(3-(4-hydroxy-1-methyl-2-oxo-1,2-dihydropyridin-3-yl)ureido)-3-(3'-methoxybiphenyl-3-yl)propanoate 1-73;

ethyl (S)-3-(2',6'-dimethylbiphenyl-3-yl)-3-(3-(4-hydroxy-1-methyl-2-oxo-1,2-dihydropyridin-3-yl)ureido)propanoate 1-74;

ethyl 3-(5'-chloro-2',4'-difluorobiphenyl-3-yl)-3-(3-(4-hydroxy-1,5-dimethyl-2-oxo-1,2-dihydropyridin-3-yl)ureido)propanoate 1-75;

ethyl (S)-3-(2',3'-dimethoxybiphenyl-3-yl)-3-(3-(4-hydroxy-1,5-dimethyl-2-oxo-1,2-dihydropyridin-3-yl)ureido)propanoate 1-76;

ethyl (S)-3-(biphenyl-3-yl)-3-(3-(4-hydroxy-1-methyl-2-oxo-1,2-dihydropyridin-3-yl)ureido) propanoate 1-77;

ethyl (S)-3-(3'-chlorobiphenyl-3-yl)-3-(3-(4-hydroxy-1-methyl-2-oxo-1,2-dihydropyridin-3-yl)ureido)propanoate 1-78;

ethyl (S)-3-(3-(1H-pyrrol-1-yl)phenyl)-3-(3-(4-hydroxy-1-methyl-2-oxo-1,2-dihydropyridin-3-yl)ureido)propanoate 1-79;

ethyl (S)-3-(3-(4-hydroxy-1-methyl-2-oxo-1,2-dihydropyridin-3-yl)ureido)-3-(3-(6-methoxypyridin-3-yl)phenyl)propanoate 1-80;

ethyl (S)-3-(2'-fluoro-3'-methoxybiphenyl-3-yl)-3-(3-(4-hydroxy-1-methyl-2-oxo-1,2-dihydropyridin-3-yl)ureido) propanoate 1-81;

ethyl (S)-3-(3-(4-hydroxy-1-methyl-2-oxo-1,2-dihydropyridin-3-yl)ureido)-3-(4'-(trifluoromethoxy)biphenyl-3-yl) propanoate 1-82;

ethyl 3-(2',4'-dichlorobiphenyl-3-yl)-3-(3-(4-hydroxy-1,5-dimethyl-2-oxo-1,2-dihydropyridin-3-yl)ureido)propanoate 1-83;

ethyl (S)-3-(3-(4-hydroxy-1-methyl-2-oxo-1,2-dihydropyridin-3-yl)ureido)-3-(2'-(trifluoromethoxy)biphenyl-3-yl) propanoate 1-84;

ethyl (S)-3-(2',4'-difluorobiphenyl-3-yl)-3-(3-(4-hydroxy-1-methyl-2-oxo-2,5,6,7-tetrahydro-1H-cyclopenta[b]pyridin-3-yl)ureido)propanoate 1-85;

ethyl (S)-3-(3-(4-hydroxy-1-methyl-2-oxo-1,2-dihydropyridin-3-yl)ureido)-3-(3'-(trifluoromethoxy)biphenyl-3-yl) propanoate 1-86;

ethyl (S)-3-(2',4'-difluorobiphenyl-3-yl)-3-(3-(7-hydroxy-4-methyl-5-oxo-4,5-dihydrothieno[3,2-b]pyridin-6-yl)ureido)propanoate 1-87;

ethyl (S)-3-(3-(benzo[d][1,3]dioxol-5-yl)phenyl)-3-(3-(4-hydroxy-1-methyl-2-oxo-1,2-dihydropyridin-3-yl)ureido)propanoate 1-88;

ethyl (S)-3-(3-(benzo[d][1,3]dioxol-5-yl)phenyl)-3-(3-(4-hydroxy-1,5-dimethyl-2-oxo-1,2-dihydropyridin-3-yl)ureido)propanoate 1-89;

ethyl (S)-3-(2',4'-difluoro-6-methoxybiphenyl-3-yl)-3-(3-(4-hydroxy-1-methyl-2-oxo-1,2-dihydropyridin-3-yl)ureido)propanoate 1-91;

ethyl (S)-3-(3-(4-hydroxy-1-methyl-2-oxo-1,2-dihydropyridin-3-yl)ureido)-3-(4-phenylthiophen-2-yl)propanoate 1-92;

ethyl (S)-3-(3-(1-ethyl-1H-indol-6-yl)phenyl)-3-(3-(4-hydroxy-1-methyl-2-oxo-1,2-dihydropyridin-3-yl)ureido)propanoate 1-93;

ethyl (S)-3-(3-(1H-pyrazol-1-yl)phenyl)-3-(3-(4-hydroxy-1-methyl-2-oxo-1,2-dihydropyridin-3-yl)ureido)propanoate 1-94;

ethyl (S)-3-(4-(2,4-difluorophenyl)thiophen-2-yl)-3-(3-(4-hydroxy-1-methyl-2-oxo-1,2-dihydropyridin-3-yl)ureido)propanoate 1-95;

ethyl (S)-3-(3',6-dimethoxybiphenyl-3-yl)-3-(3-(4-hydroxy-1-methyl-2-oxo-1,2-dihydropyridin-3-yl)ureido)propanoate 1-96;

ethyl 3-(2',5'-dichlorobiphenyl-3-yl)-3-(3-(4-hydroxy-1,5-dimethyl-2-oxo-1,2-dihydropyridin-3-yl)ureido)propanoate 1-97;

ethyl (S)-3-(3',6-dimethoxybiphenyl-3-yl)-3-(3-(4-hydroxy-1,5-dimethyl-2-oxo-1,2-dihydropyridin-3-yl)ureido)propanoate 1-99;

ethyl (S)-3-(3-(4-hydroxy-1-methyl-2-oxo-1,2-dihydropyridin-3-yl)ureido)-3-(4-(3-methoxyphenyl)thiophen-2-yl)propanoate 1-100;

ethyl (S)-3-(3-(4-hydroxy-1-methyl-2-oxo-1,2-dihydropyridin-3-yl)ureido)-3-(6-methoxybiphenyl-3-yl)propanoate 1-101;

ethyl (S)-3-(4-(3-chlorophenyl)thiophen-2-yl)-3-(3-(4-hydroxy-1-methyl-2-oxo-1,2-dihydropyridin-3-yl)ureido) propanoate 1-102;

ethyl (S)-3-(2',4'-difluorobiphenyl-3-yl)-3-(3-(1-ethyl-4-hydroxy-2-oxo-1,2-dihydro pyridin-3-yl)ureido)propanoate 1-103;

ethyl (S)-3-(3-(4-hydroxy-1-methyl-2-oxo-1,2-dihydropyridin-3-yl)ureido)-3-(3-(thiophen-2-yl)phenyl)propanoate 1-104;

ethyl (S)-3-(3-(4-hydroxy-1-methyl-2-oxo-1,2-dihydropyridin-3-yl)ureido)-3-(6-methoxy-2',6'-dimethylbiphenyl-3-yl)propanoate 1-105;

ethyl (S)-3-(3'-chloro-6-methoxybiphenyl-3-yl)-3-(3-(4-hydroxy-1-methyl-2-oxo-1,2-dihydropyridin-3-yl)ureido) propanoate 1-106;

ethyl (S)-3-(3-(4-hydroxy-1-methyl-2-oxo-1,2-dihydropyridin-3-yl)ureido)-3-(6-methoxy-3'-(trifluoromethoxy)biphenyl-3-yl)propanoate 1-107;

ethyl (S)-3-(3-(4-hydroxy-1-methyl-2-oxo-1,2-dihydropyridin-3-yl)ureido)-3-(6-methoxy-4'-(trifluoromethoxy)biphenyl-3-yl)propanoate 1-108;

ethyl (S)-3-(2',6'-dichlorobiphenyl-3-yl)-3-(3-(4-hydroxy-1-methyl-2-oxo-1,2-dihydropyridin-3-yl)ureido)propanoate 1-109;

ethyl (S)-3-(3-(5-chlorothiophen-2-yl)phenyl)-3-(3-(4-hydroxy-1-methyl-2-oxo-1,2-dihydropyridin-3-yl)ureido) propanoate 1-110;

ethyl (S)-3-(3-(1H-imidazol-1-yl)phenyl)-3-(3-(4-hydroxy-1-methyl-2-oxo-1,2-dihydropyridin-3-yl)ureido)propanoate 1-111;

ethyl (S)-3-(3-(4-hydroxy-1-methyl-2-oxo-1,2-dihydropyridin-3-yl)ureido)-3-(3-(4-methylthiophen-3-yl)phenyl)propanoate 1-112;

ethyl (S)-3-(2',4'-difluoro-6-methylbiphenyl-3-yl)-3-(3-(4-hydroxy-1-methyl-2-oxo-1,2-dihydropyridin-3-yl)ureido)propanoate 1-113;

ethyl (S)-3-(3-(4-hydroxy-1-methyl-2-oxo-1,2-dihydropyridin-3-yl)ureido)-3-(3'-methoxy-6-methylbiphenyl-3-yl)propanoate 1-114;

ethyl (S)-3-(4-(2,6-dimethylphenyl)thiophen-2-yl)-3-(3-(4-hydroxy-1-methyl-2-oxo-1,2-dihydropyridin-3-yl)ureido)propanoate 1-115;

ethyl (S)-3-(3-(1H-pyrrol-3-yl)phenyl)-3-(3-(4-hydroxy-1-methyl-2-oxo-1,2-dihydro pyridin-3-yl)ureido)propanoate 1-116;

ethyl (S)-3-(3-(4-hydroxy-1-methyl-2-oxo-1,2-dihydropyridin-3-yl)ureido)-3-(2',6,6'-trimethylbiphenyl-3-yl)propanoate 1-117;

ethyl (S)-3-(3-(4-hydroxy-1-methyl-2-oxo-1,2-dihydropyridin-3-yl)ureido)-3-(2',6,6'-trifluorobiphenyl-3-yl)propanoate 1-118;

ethyl (S)-3-(6-fluoro-3'-methoxybiphenyl-3-yl)-3-(3-(4-hydroxy-1-methyl-2-oxo-1,2-dihydropyridin-3-yl)ureido)propanoate 1-119;

ethyl (S)-3-(3-(4-hydroxy-1-methyl-2-oxo-1,2-dihydropyridin-3-yl)ureido)-3-(3-(1-methyl-1H-pyrazol-4-yl)phenyl)propanoate 1-120;

ethyl (S)-3-(2',4'-difluorobiphenyl-3-yl)-3-(3-(5-hydroxy-2-methyl-3-oxo-2,3-dihydropyridazin-4-yl)ureido)propanoate 1-121;

ethyl (S)-3-(2',6'-dimethylbiphenyl-3-yl)-3-(3-(4-hydroxy-1,6-dimethyl-2-oxo-1,2-dihydropyridin-3-yl)ureido)propanoate 1-122;

ethyl (S)-3-(3',6-dimethoxybiphenyl-3-yl)-3-(3-(4-hydroxy-1,6-dimethyl-2-oxo-1,2-dihydropyridin-3-yl)ureido)propanoate 1-123;

ethyl (S)-3-(4-(2,4-difluorophenyl)thiophen-2-yl)-3-(3-(4-hydroxy-1,6-dimethyl-2-oxo-1,2-dihydropyridin-3-yl)ureido)propanoate 1-124;

ethyl (S)-3-(3-(4-hydroxy-1,6-dimethyl-2-oxo-1,2-dihydropyridin-3-yl)ureido)-3-(3'-methoxybiphenyl-3-yl)propanoate 1-125;

ethyl (S)-3-(3-(4-hydroxy-1,6-dimethyl-2-oxo-1,2-dihydropyridin-3-yl)ureido)-3-(6-methoxy-3'-(trifluoromethoxy)biphenyl-3-yl)propanoate 1-126;

ethyl (S)-3-(3'-chloro-6-methylbiphenyl-3-yl)-3-(3-(4-hydroxy-1-methyl-2-oxo-1,2-dihydropyridin-3-yl)ureido)propanoate 1-127;

ethyl (S)-3-(3'-chlorobiphenyl-3-yl)-3-(3-(4-hydroxy-1,6-dimethyl-2-oxo-1,2-dihydropyridin-3-yl)ureido)propanoate 1-128;

ethyl (S)-3-(2',4'-difluorobiphenyl-3-yl)-3-(3-(4-hydroxy-6-methyl-2-oxo-1,2-dihydropyridin-3-yl)ureido)propanoate 1-129;

ethyl (S)-3-(3-(4-hydroxy-1-methyl-2-oxo-1,2-dihydropyridin-3-yl)ureido)-3-(5-methoxybiphenyl-3-yl)propanoate 1-130;

ethyl (S)-3-(3-(furan-3-yl)phenyl)-3-(3-(4-hydroxy-1-methyl-2-oxo-1,2-dihydro pyridin-3-yl)ureido)propanoate 1-131;

ethyl (S)-3-(3-(3,5-dimethylisoxazol-4-yl)phenyl)-3-(3-(4-hydroxy-1-methyl-2-oxo-1,2-dihydropyridin-3-yl)ureido)propanoate 1-132;

ethyl (S)-3-(6-fluoro-2',6'-dimethylbiphenyl-3-yl)-3-(3-(4-hydroxy-1-methyl-2-oxo-1,2-dihydropyridin-3-yl)ureido)propanoate 1-133;

ethyl (S)-3-(5-(2,4-difluorophenyl)thiophen-2-yl)-3-(3-(4-hydroxy-1-methyl-2-oxo-1,2-dihydropyridin-3-yl)ureido)propanoate 1-134;

ethyl (S)-3-(3-(4-hydroxy-1-methyl-2-oxo-1,2-dihydropyridin-3-yl)ureido)-3-(5-(3-methoxyphenyl)thiophen-2-yl)propanoate 1-135;

ethyl (S)-3-(3',5-dimethoxybiphenyl-3-yl)-3-(3-(4-hydroxy-1-methyl-2-oxo-1,2-dihydropyridin-3-yl)ureido)propanoate 1-136;

ethyl (S)-3-(3-(4-hydroxy-1-methyl-2-oxo-1,2-dihydropyridin-3-yl)ureido)-3-(5-methoxy-3'-(trifluoromethoxy)biphenyl-3-yl)propanoate 1-137;

ethyl (S)-3-(2',4'-difluoro-5-methoxybiphenyl-3-yl)-3-(3-(4-hydroxy-1-methyl-2-oxo-1,2-dihydropyridin-3-yl)ureido)propanoate 1-138;

ethyl (S)-3-(3',5-dimethoxybiphenyl-3-yl)-3-(3-(4-hydroxy-1,6-dimethyl-2-oxo-1,2-dihydropyridin-3-yl)ureido)propanoate 1-139;

ethyl (S)-3-(3-(4-hydroxy-1,6-dimethyl-2-oxo-1,2-dihydropyridin-3-yl)ureido)-3-(5-methoxy-3'-(trifluoromethoxy)biphenyl-3-yl)propanoate 1-140;

ethyl (S)-3-(3-(4-hydroxy-1,6-dimethyl-2-oxo-1,2-dihydropyridin-3-yl)ureido)-3-(3'-methoxy-6-methylbiphenyl-3-yl)propanoate 1-141;

ethyl (S)-3-(4-fluorobiphenyl-3-yl)-3-(3-(4-hydroxy-1-methyl-2-oxo-1,2-dihydro pyridin-3-yl)ureido)propanoate 1-142;

ethyl (S)-3-(3-(4-hydroxy-1-methyl-2-oxo-1,2-dihydropyridin-3-yl)ureido)-3-(6-phenylpyridin-2-yl)propanoate 1-143;

ethyl (S)-3-(3-(4-hydroxy-1-methyl-2-oxo-1,2-dihydropyridin-3-yl)ureido)-3-(5-methyl-3'-(trifluoromethoxy)biphenyl-3-yl)propanoate 1-144;

ethyl (S)-3-(3-(4-hydroxy-1-methyl-2-oxo-1,2-dihydropyridin-3-yl)ureido)-3-(6-methyl-3'-(trifluoromethoxy)biphenyl-3-yl)propanoate 1-148;

ethyl (S)-3-(3-(4-hydroxy-1,6-dimethyl-2-oxo-1,2-dihydropyridin-3-yl)ureido)-3-(6-methyl-3'-(trifluoromethoxy)biphenyl-3-yl)propanoate 1-149;

ethyl (S)-3-(6-fluoro-2',6'-dimethylbiphenyl-3-yl)-3-(3-(4-hydroxy-1,6-dimethyl-2-oxo-1,2-dihydropyridin-3-yl)ureido)propanoate 1-150;

ethyl (S)-3-(3-(4-hydroxy-1-methyl-2-oxo-1,2-dihydropyridin-3-yl)ureido)-3-(5-methoxy-2',6'-dimethylbiphenyl-3-yl)propanoate 1-151;

ethyl (S)-3-(3-(4-hydroxy-1,6-dimethyl-2-oxo-1,2-dihydropyridin-3-yl)ureido)-3-(5-methoxy-2',6'-dimethylbiphenyl-3-yl)propanoate 1-152;

ethyl (S)-3-(2',4'-difluoro-5-methoxybiphenyl-3-yl)-3-(3-(4-hydroxy-1,6-dimethyl-2-oxo-1,2-dihydropyridin-3-yl)ureido)propanoate 1-153;

ethyl (S)-3-(2',6'-dimethylbiphenyl-3-yl)-3-(3-(7-hydroxy-5-oxo-1,2,3,5-tetrahydro indolizin-6-yl)ureido)propanoate 1-155;

ethyl (S)-3-(3-(4-hydroxy-1-methyl-2-oxo-1,2-dihydropyridin-3-yl)ureido)-3-(4'-methyl-[2,3'-bithiophen]-5-yl)propanoate 1-156;

ethyl (S)-3-(3-(4-hydroxy-1,6-dimethyl-2-oxo-1,2-dihydropyridin-3-yl)ureido)-3-(4'-methyl-[2,3'-bithiophen]-5-yl)propanoate 1-157;

ethyl (S)-3-(3-(4-hydroxy-1,6-dimethyl-2-oxo-1,2-dihydropyridin-3-yl)ureido)-3-(3'-methoxy-5-methylbiphenyl-3-yl)propanoate 1-158;

ethyl (S)-3-(5-(2,6-dimethylphenyl)thiophen-2-yl)-3-(3-(4-hydroxy-1-methyl-2-oxo-1,2-dihydropyridin-3-yl)ureido)propanoate 1-159;

ethyl (S)-3-(5-(2,6-dimethylphenyl)thiophen-2-yl)-3-(3-(4-hydroxy-1,6-dimethyl-2-oxo-1,2-dihydropyridin-3-yl)ureido)propanoate 1-160;

ethyl (S)-3-(4-fluoro-2',6'-dimethylbiphenyl-3-yl)-3-(3-(4-hydroxy-1,6-dimethyl-2-oxo-1,2-dihydropyridin-3-yl)ureido)propanoate 1-161;

ethyl (S)-3-(4-fluoro-2',6'-dimethylbiphenyl-3-yl)-3-(3-(4-hydroxy-1-methyl-2-oxo-1,2-dihydropyridin-3-yl)ureido)propanoate 1-162;

ethyl (S)-3-(4-fluoro-3'-methoxybiphenyl-3-yl)-3-(3-(4-hydroxy-1-methyl-2-oxo-1,2-dihydropyridin-3-yl)ureido)propanoate 1-165;

ethyl (S)-3-(4-fluoro-3'-(trifluoromethoxy)biphenyl-3-yl)-3-(3-(4-hydroxy-1-methyl-2-oxo-1,2-dihydropyridin-3-yl)ureido)propanoate 1-166;

ethyl (S)-3-(4-fluoro-3'-(trifluoromethoxy)biphenyl-3-yl)-3-(3-(4-hydroxy-1,6-dimethyl-2-oxo-1,2-dihydropyridin-3-yl)ureido)propanoate 1-167;

ethyl (S)-3-(3-(4-hydroxy-1-methyl-2-oxo-1,2-dihydropyridin-3-yl)ureido)-3-(4-methoxybiphenyl-3-yl)propanoate 1-168;

ethyl (S)-3-(3-(4-hydroxy-1,6-dimethyl-2-oxo-1,2-dihydropyridin-3-yl)ureido)-3-(2',5,6'-trimethylbiphenyl-3-yl)propanoate 1-169;

ethyl (S)-3-(3-(4-hydroxy-1-methyl-2-oxo-1,2-dihydropyridin-3-yl)ureido)-3-(2'-methylbiphenyl-3-yl)propanoate 1-170;

ethyl (S)-3-(3-(4-hydroxy-1,6-dimethyl-2-oxo-1,2-dihydropyridin-3-yl)ureido)-3-(2'-methylbiphenyl-3-yl)propanoate 1-171;

ethyl (S)-3-(5-fluoro-2',6'-dimethylbiphenyl-3-yl)-3-(3-(4-hydroxy-1-methyl-2-oxo-1,2-dihydropyridin-3-yl)ureido)propanoate 1-172;

ethyl (S)-3-(3-(4-hydroxy-1-methyl-2-oxo-1,2-dihydropyridin-3-yl)ureido)-3-(5-(3-(trifluoromethoxy)phenyl)thiophen-2-yl)propanoate 1-173;

ethyl (S)-3-(3-(4-hydroxy-1-methyl-2-oxo-1,2-dihydropyridin-3-yl)ureido)-3-(4-methoxy-2',6'-dimethylbiphenyl-3-yl)propanoate 1-174;

ethyl (S)-3-(4-fluoro-3'-methoxybiphenyl-3-yl)-3-(3-(4-hydroxy-1,6-dimethyl-2-oxo-1,2-dihydropyridin-3-yl)ureido)propanoate 1-175;

ethyl (S)-3-(5-(3,5-dimethylisoxazol-4-yl)thiophen-2-yl)-3-(3-(4-hydroxy-1-methyl-2-oxo-1,2-dihydropyridin-3-yl)ureido)propanoate 1-180;

ethyl (S)-3-(3-(3,5-dimethylisoxazol-4-yl)phenyl)-3-(3-(4-hydroxy-1,6-dimethyl-2-oxo-1,2-dihydropyridin-3-yl)ureido)propanoate 1-181;

ethyl (S)-3-(3-(4-hydroxy-1-methyl-2-oxo-1,2-dihydropyridin-3-yl)ureido)-3-(5-phenylthiophen-2-yl)propanoate 1-185;

ethyl (S)-3-(5-(2,5-difluorophenyl)thiophen-2-yl)-3-(3-(4-hydroxy-1-methyl-2-oxo-1,2-dihydropyridin-3-yl)ureido)propanoate 1-186;

ethyl (S)-3-(3-(4-hydroxy-1-methyl-2-oxo-1,2-dihydropyridin-3-yl)ureido)-3-(5-(trifluoromethoxy)biphenyl-3-yl)propanoate 1-187;

ethyl (S)-3-(3-(4-hydroxy-1-methyl-2-oxo-1,2-dihydropyridin-3-yl)ureido)-3-(2'-methylbiphenyl-4-yl)propanoate 1-188;

ethyl (S)-3-(3-(7-hydroxy-5-oxo-1,2,3,5-tetrahydroindolizin-6-yl)ureido)-3-(5-methoxybiphenyl-3-yl)propanoate 1-189;

ethyl (S)-3-(3-(4-hydroxy-1-methyl-2-oxo-1,2-dihydropyridin-3-yl)ureido)-3-(5-(trifluoromethyl)biphenyl-3-yl)propanoate 1-190;

ethyl (S)-3-(5-(3-chlorophenyl)thiophen-2-yl)-3-(3-(4-hydroxy-1-methyl-2-oxo-1,2-dihydropyridin-3-yl)ureido)propanoate 1-191;

ethyl (S)-3-(5-(3-fluorophenyl)thiophen-2-yl)-3-(3-(4-hydroxy-1-methyl-2-oxo-1,2-dihydropyridin-3-yl)ureido)propanoate 1-192;

ethyl (S)-3-(3-(4-hydroxy-1-methyl-2-oxo-1,2-dihydropyridin-3-yl)ureido)-3-(2'-methyl-6-(trifluoromethoxy)biphenyl-3-yl)propanoate 1-196;

ethyl (S)-3-(3-(4-hydroxy-1,5-dimethyl-2-oxo-1,2-dihydropyridin-3-yl)ureido)-3-(4-phenylthiophen-2-yl)propanoate 1-200;

ethyl (S)-3-(3-(4-hydroxy-1,5-dimethyl-2-oxo-1,2-dihydropyridin-3-yl)ureido)-3-(5-phenylthiophen-2-yl)propanoate 1-201;

ethyl (S)-3-(2',4'-difluorobiphenyl-3-yl)-3-(3-(7-hydroxy-5-oxo-1,2,3,5-tetrahydroindolizin-6-yl)ureido)propanoate 1-202;

ethyl (S)-3-(3-(4-hydroxy-1-methyl-2-oxo-1,2-dihydropyridin-3-yl)ureido)-3-(3-(thiazol-2-yl)phenyl)propanoate 1-203;

ethyl (S)-3-(3-(4-hydroxy-1,6-dimethyl-2-oxo-1,2-dihydropyridin-3-yl)ureido)-3-(2',4',5-trifluorobiphenyl-3-yl)propanoate 1-205;

ethyl (S)-3-(3-(4-hydroxy-1-methyl-2-oxo-1,2-dihydropyridin-3-yl)ureido)-3-(2',4',5-trifluorobiphenyl-3-yl)propanoate 1-206;

ethyl (S)-3-(3-(4-hydroxy-1-methyl-2-oxo-1,2-dihydropyridin-3-yl)ureido)-3-(3'-methoxy-6-(trifluoromethoxy)biphenyl-3-yl)propanoate 1-207;

ethyl (S)-3-(3-(4-hydroxy-1,6-dimethyl-2-oxo-1,2-dihydropyridin-3-yl)ureido)-3-(3'-methoxy-6-(trifluoromethoxy)biphenyl-3-yl)propanoate 1-208;

ethyl (S)-3-(2',6'-dimethylbiphenyl-4-yl)-3-(3-(4-hydroxy-1-methyl-2-oxo-1,2-dihydropyridin-3-yl)ureido)propanoate 1-209;

ethyl (S)-3-(3-(4-hydroxy-1,6-dimethyl-2-oxo-1,2-dihydropyridin-3-yl)ureido)-3-(2'-methylbiphenyl-4-yl)propanoate 1-210;

ethyl (S)-3-(2',6'-dimethylbiphenyl-4-yl)-3-(3-(4-hydroxy-1,6-dimethyl-2-oxo-1,2-dihydropyridin-3-yl)ureido)propanoate 1-211;

ethyl (S)-3-(3-(4-hydroxy-1-methyl-2-oxo-1,2-dihydropyridin-3-yl)ureido)-3-(3-(pyridin-2-yl)phenyl)propanoate 1-212;

ethyl (S)-3-(3-(4-hydroxy-1-methyl-2-oxo-1,2-dihydropyridin-3-yl)ureido)-3-(3-(6-methoxypyridazin-3-yl)phenyl)propanoate 1-213;

tert-butyl (S)-3-(biphenyl-4-yl)-3-(3-(1,5-dimethyl-4-oxido-2-oxo-1,2-dihydropyridin-3-yl)ureido)propanoate 1-216;

ethyl (S)-3-(3-(4-hydroxy-1-methyl-2-oxo-1,2-dihydropyridin-3-yl)ureido)-3-(3-(6'-methoxypyridin-2-yl)phenyl)propanoate 1-217;

ethyl (S)-3-(3-(1H-imidazol-1-yl)phenyl)-3-(3-(4-hydroxy-1-methyl-2-oxo-1,2-dihydropyridin-3-yl)ureido)propanoate 1-219;

ethyl 3-(3-bromophenyl)-3-(3-(4-hydroxy-1,5-dimethyl-2-oxo-1,2-dihydropyridin-3-yl)ureido)propanoate 1-220, ethyl 3-(3-bromophenyl)-3-(3-(1-ethyl-4-hydroxy-5-methyl-2-oxo-1,2-dihydropyridin-3-yl)ureido)propanoate 1-221 ethyl (S)-3-(2',4'-difluorobiphenyl-4-yl)-3-(3-(4-hydroxy-1-methyl-2-oxo-1,2-dihydropyridin-3-yl)ureido)propanoate 1-222, ethyl (S)-3-(2',4'-difluorobiphenyl-4-yl)-3-(3-(4-hydroxy-1,6-dimethyl-2-oxo-1,2-di hydropyridin-3-yl)ureido)propanoate 1-223, The procedure was also modified by adding a base. This modification was used in all instances when the amine starting material had been isolated as a hydrochloride or acetic acid salt, but was also sometimes used on freebased amines. Sodium bicarbonate was used in the preparation of
ethyl (S)-3-(3-(4-hydroxy-1-methyl-2-oxo-1,2-dihydropyridin-3-yl)ureido)-3-(2',4,4'-trifluorobiphenyl-3-yl)propanoate 1-163;
ethyl (S)-3-(3-(4-hydroxy-1,6-dimethyl-2-oxo-1,2-dihydropyridin-3-yl)ureido)-3-(2',4,4'-trifluorobiphenyl-3-yl) propanoate 1-164;
ethyl (S)-3-(5-fluoro-3'-methoxybiphenyl-3-yl)-3-(3-(4-hydroxy-1-methyl-2-oxo-1,2-dihydropyridin-3-yl)ureido) propanoate 1-176;
ethyl (S)-3-(5-fluoro-3'-methoxybiphenyl-3-yl)-3-(3-(4-hydroxy-1,6-dimethyl-2-oxo-1,2-dihydropyridin-3-yl) ureido)propanoate 1-177;
ethyl (S)-3-(5-fluoro-3'-(trifluoromethoxy)biphenyl-3-yl)-3-(3-(4-hydroxy-1,6-dimethyl-2-oxo-1,2-dihydropyridin-3-yl)ureido)propanoate 1-178;
ethyl (S)-3-(5-fluoro-3'-(trifluoromethoxy)biphenyl-3-yl)-3-(3-(4-hydroxy-1-methyl-2-oxo-1,2-dihydropyridin-3-yl)ureido)propanoate 1-179;
ethyl (S)-3-(2-fluorobiphenyl-3-yl)-3-(3-(4-hydroxy-1,6-dimethyl-2-oxo-1,2-dihydro pyridin-3-yl)ureido)propanoate 1-182;
ethyl (S)-3-(6-fluoro-2'-methylbiphenyl-3-yl)-3-(3-(4-hydroxy-1,6-dimethyl-2-oxo-1,2-dihydropyridin-3-yl) ureido)propanoate 1-183;
and ethyl (S)-3-(6-fluoro-2'-methylbiphenyl-3-yl)-3-(3-(4-hydroxy-1-methyl-2-oxo-1,2-dihydropyridin-3-yl) ureido)propanoate 1-184;
ethyl 3-(3'-acetylbiphenyl-3-yl)-3-(3-(4-hydroxy-1,5-dimethyl-2-oxo-1,2-dihydropyridin-3-yl)ureido)propanoate 1-198;
and ethyl 3-(4'-acetylbiphenyl-3-yl)-3-(3-(4-hydroxy-1,5-dimethyl-2-oxo-1,2-dihydropyridin-3-yl)ureido)propanoate 1-199. Diisopropylethylamine was used to prepare ethyl (S)-3-(5-fluoro-2',6'-dimethylbiphenyl-3-yl)-3-(3-(4-hydroxy-1,6-dimethyl-2-oxo-1,2-dihydropyridin-3-yl) ureido)propanoate 1-215;
N-Methylmorpholine was used in the preparation of ethyl (S)-3-(3-(1H-indazol-1-yl)phenyl)-3-(3-(4-hydroxy-1-methyl-2-oxo-1,2-dihydropyridin-3-yl)ureido)propanoate 1-90;
ethyl (S)-3-(2',4'-difluorobiphenyl-3-yl)-3-(3-(4-hydroxy-1-methyl-2-oxo-1,2-dihydro-1,8-naphthyridin-3-yl)ureido) propanoate 1-98;
ethyl (S)-3-(3-(4-hydroxy-1-methyl-2-oxo-1,2-dihydropyridin-3-yl)ureido)-3-(2',5,6'-trimethylbiphenyl-3-yl)propanoate 1-145;
ethyl (S)-3-(2',4'-difluoro-5-methylbiphenyl-3-yl)-3-(3-(4-hydroxy-1-methyl-2-oxo-1,2-dihydropyridin-3-yl) ureido)propanoate 1-146;
ethyl (S)-3-(2',4'-difluoro-5-methylbiphenyl-3-yl)-3-(3-(4-hydroxy-1,6-dimethyl-2-oxo-1,2-dihydropyridin-3-yl) ureido)propanoate 1-147;
ethyl (S)-3-(3-(4-hydroxy-1-methyl-2-oxo-1,2-dihydropyridin-3-yl)ureido)-3-(3'-methoxy-5-methylbiphenyl-3-yl) propanoate 1-154;
tert-butyl (S)-3-(2',4'-difluorobiphenyl-4-yl)-3-(3-(4-hydroxy-1-methyl-2-oxo-1,2-dihydropyridin-3-yl)ureido) propanoate 1-193;
tert-butyl (S)-3-(2',4'-difluorobiphenyl-4-yl)-3-(3-(4-hydroxy-1,6-dimethyl-2-oxo-1,2-dihydropyridin-3-yl) ureido)propanoate 1-194;
ethyl (S)-3-(2',4'-difluorobiphenyl-3-yl)-3-(3-(4-hydroxy-1,6-dimethyl-2-oxo-1,2-dihydropyridin-3-yl)ureido)propanoate 1-195;
ethyl (S)-3-(3-(4-hydroxy-1,6-dimethyl-2-oxo-1,2-dihydropyridin-3-yl)ureido)-3-(5-methyl-3'-(trifluoromethoxy) biphenyl-3-yl)propanoate 1-204 and
ethyl (S)-3-(3-(4-hydroxy-1-methyl-2-oxo-1,2-dihydropyridin-3-yl)ureido)-3-(5-phenylpyridin-3-yl)propanoate 1-214; and Finally, triethylamine was used to prepare ethyl (S)-3-(3-(4-hydroxy-1,5-dimethyl-2-oxo-1,2-dihydropyridin-3-yl)ureido)-3-(2'-methoxybiphenyl-3-yl)propanoate 1-27;
ethyl (S)-3-(3-(4-hydroxy-1,5-dimethyl-2-oxo-1,2-dihydropyridin-3-yl)ureido)-3-(3'-methoxybiphenyl-3-yl)propanoate 1-32;
tert-butyl (S)-3-(2',4'-difluorobiphenyl-4-yl)-3-(3-(4-hydroxy-1,5-dimethyl-2-oxo-1,2-dihydropyridin-3-yl) ureido)propanoate 1-195;
ethyl (S)-3-(3-(4-hydroxy-1-methyl-2-oxo-1,2-dihydropyridin-3-yl)ureido)-3-(6-(trifluoro methoxy)biphenyl-3-yl) propanoate 1-197; and
ethyl (S)-3-(3-(4-hydroxy-1,5-dimethyl-2-oxo-1,2-dihydropyridin-3-yl)ureido)-3-(4'-methoxybiphenyl-3-yl)propanoate 1-218.

Step Ten: To a solution of 1-9 (120 mg, 0.266 mmol) in THF (4 mL) at room temperature sodium hydroxide (2 N, 2 mL) and methanol (1 mL) were added. The mixture was stirred for 2 hours, and the organic solvents were removed on the rotary evaporator. The remaining aqueous solution was diluted with water, and acidified with HCl (2N) The resulting suspension was filtered, washing with water. The solid was dried under vacuum to give (S)-3-(biphenyl-3-yl)-3-(3-(4-hydroxy-1,5-dimethyl-2-oxo-1,2-dihydropyridin-3-yl)ureido)propanoic acid (1-224, 96 mg).

This procedure was also used to prepare
(S)-3-(biphenyl-3-yl)-3-(3-(1-ethyl-4-hydroxy-5-methyl-2-oxo-1,2-dihydropyridin-3-yl)ureido)propanoic acid 1-225;
3-(3-(1-ethyl-4-hydroxy-5-methyl-2-oxo-1,2-dihydropyridin-3-yl)ureido)-3-(3-(2-oxo-3-phenylpyridin-1(2H)-yl) phenyl)propanoic acid 1-226;
(S)-3-(3-(4-hydroxy-1,5-dimethyl-2-oxo-1,2-dihydropyridin-3-yl)ureido)-3-(2'-methylbiphenyl-3-yl)propanoic acid 1-227;
(S)-3-(2'-fluorobiphenyl-3-yl)-3-(3-(4-hydroxy-1,5-dimethyl-2-oxo-1,2-dihydropyridin-3-yl)ureido)propanoic acid 1-228;
(S)-3-(6-fluorobiphenyl-3-yl)-3-(3-(4-hydroxy-1,5-dimethyl-2-oxo-1,2-dihydropyridin-3-yl)ureido)propanoic acid 1-229;
(S)-3-(3-(1-ethyl-4-hydroxy-5-methyl-2-oxo-1,2-dihydropyridin-3-yl)ureido)-3-(2'-methylbiphenyl-3-yl)propanoic acid 1-230;
(S)-3-(3-(1-ethyl-4-hydroxy-5-methyl-2-oxo-1,2-dihydropyridin-3-yl)ureido)-3-(4'-methylbiphenyl-3-yl)propanoic acid 1-231;
3-(3-(1H-pyrrol-1-yl)phenyl)-3-(3-(4-hydroxy-1,5-dimethyl-2-oxo-1,2-dihydropyridin-3-yl)ureido)propanoic acid 1-232;
(S)-3-(2',4'-difluorobiphenyl-3-yl)-3-(3-(4-hydroxy-1,5-dimethyl-2-oxo-1,2-dihydropyridin-3-yl)ureido)propanoic acid 1-233;
(S)-3-(2',5'-difluorobiphenyl-3-yl)-3-(3-(4-hydroxy-1,5-dimethyl-2-oxo-1,2-dihydropyridin-3-yl)ureido)propanoic acid 1-234;
(S)-3-(3-(4-hydroxy-1,5-dimethyl-2-oxo-1,2-dihydropyridin-3-yl)ureido)-3-(6-methyl biphenyl-3-yl)propanoic acid 1-235;

(S)-3-(3-(4-hydroxy-1,5-dimethyl-2-oxo-1,2-dihydropyridin-3-yl)ureido)-3-(6-methoxy biphenyl-3-yl)propanoic acid 1-236;
(S)-3-(3-(4-hydroxy-1,5-dimethyl-2-oxo-1,2-dihydropyridin-3-yl)ureido)-3-(4'-methyl biphenyl-3-yl)propanoic acid 1-237;
(S)-3-(3-(4-hydroxy-1,5-dimethyl-2-oxo-1,2-dihydropyridin-3-yl)ureido)-3-(3'-methyl biphenyl-3-yl)propanoic acid 1-238;
(S)-3-(3-(4-hydroxy-1,5-dimethyl-2-oxo-1,2-dihydropyridin-3-yl)ureido)-3-(3-(pyridin-3-yl)phenyl)propanoic acid 1-239;
(S)-3-(3',5'-difluorobiphenyl-3-yl)-3-(3-(4-hydroxy-1,5-dimethyl-2-oxo-1,2-dihydropyridin-3-yl)ureido)propanoic acid 1-240;
(S)-3-(3',5'-dimethylbiphenyl-3-yl)-3-(3-(4-hydroxy-1,5-dimethyl-2-oxo-1,2-dihydropyridin-3-yl)ureido)propanoic acid 1-241;
(S)-3-(3-(4-hydroxy-1,5-dimethyl-2-oxo-1,2-dihydropyridin-3-yl)ureido)-3-(4'-methoxy biphenyl-3-yl)propanoic acid 1-242;
(S)-3-(3-(4-hydroxy-1,5-dimethyl-2-oxo-1,2-dihydropyridin-3-yl)ureido)-3-(2'-methoxy biphenyl-3-yl)propanoic acid 1-243;
(S)-3-(3-(4-hydroxy-1,5-dimethyl-2-oxo-1,2-dihydropyridin-3-yl)ureido)-3-(4'-(trifluoromethyl)biphenyl-3-yl)propanoic acid 1-244;
(S)-3-(3-(4-hydroxy-1,5-dimethyl-2-oxo-1,2-dihydropyridin-3-yl)ureido)-3-(3'-methoxy biphenyl-3-yl)propanoic acid 1-245;
(S)-3-(3-(4-hydroxy-1,5-dimethyl-2-oxo-1,2-dihydropyridin-3-yl)ureido)-3-(3'-(trifluoromethoxy)biphenyl-3-yl)propanoic acid 1-246;
(S)-3-(3',4'-difluorobiphenyl-3-yl)-3-(3-(4-hydroxy-1,5-dimethyl-2-oxo-1,2-dihydropyridin-3-yl)ureido) propanoic acid 1-247;
(S)-3-(2',5'-dimethylbiphenyl-3-yl)-3-(3-(4-hydroxy-1,5-dimethyl-2-oxo-1,2-dihydropyridin-3-yl)ureido) propanoic acid 1-248;
(S)-3-(2',3'-dimethylbiphenyl-3-yl)-3-(3-(4-hydroxy-1,5-dimethyl-2-oxo-1,2-dihydropyridin-3-yl)ureido)propanoic acid 1-249;
3-(3-(4-hydroxy-1,5-dimethyl-2-oxo-1,2-dihydropyridin-3-yl)ureido)-3-(6-oxo-1-phenyl-1,6-dihydropyridin-3-yl)propanoic acid 1-250;
(S)-3-(2',6'-difluorobiphenyl-3-yl)-3-(3-(4-hydroxy-1,5-dimethyl-2-oxo-1,2-dihydropyridin-3-yl)ureido)propanoic acid 1-251;
(S)-3-(3'-fluorobiphenyl-3-yl)-3-(3-(4-hydroxy-1,5-dimethyl-2-oxo-1,2-dihydropyridin-3-yl)ureido)propanoic acid 1-252;
(S)-3-(4'-fluorobiphenyl-3-yl)-3-(3-(4-hydroxy-1,5-dimethyl-2-oxo-1,2-dihydropyridin-3-yl)ureido)propanoic acid 1-253;
(S)-3-(3-(4-hydroxy-1,5-dimethyl-2-oxo-1,2-dihydropyridin-3-yl)ureido)-3-(2'-(trifluoromethoxy)biphenyl-3-yl)propanoic acid 1-254;
(S)-3-(2',4'-dimethoxybiphenyl-3-yl)-3-(3-(4-hydroxy-1,5-dimethyl-2-oxo-1,2-dihydropyridin-3-yl)ureido)propanoic acid 1-255;
(S)-3-(3',4'-dimethoxybiphenyl-3-yl)-3-(3-(4-hydroxy-1,5-dimethyl-2-oxo-1,2-dihydropyridin-3-yl)ureido)propanoic acid 1-256;
(S)-3-(2',6'-dimethylbiphenyl-3-yl)-3-(3-(4-hydroxy-1,5-dimethyl-2-oxo-1,2-dihydropyridin-3-yl)ureido)propanoic acid 1-257;
3-(4'-chlorobiphenyl-3-yl)-3-(3-(4-hydroxy-1,5-dimethyl-2-oxo-1,2-dihydropyridin-3-yl)ureido)propanoic acid 1-258;
3-(3'-chlorobiphenyl-3-yl)-3-(3-(4-hydroxy-1,5-dimethyl-2-oxo-1,2-dihydropyridin-3-yl)ureido)propanoic acid 1-259;
3-(2'-chlorobiphenyl-3-yl)-3-(3-(4-hydroxy-1,5-dimethyl-2-oxo-1,2-dihydropyridin-3-yl)ureido)propanoic acid 1-260;
(S)-3-(3-(4-hydroxy-1,5-dimethyl-2-oxo-1,2-dihydropyridin-3-yl)ureido)-3-(2'-(trifluoromethyl)biphenyl-3-yl)propanoic acid 1-261;
(S)-3-(5,6-dimethoxybiphenyl-3-yl)-3-(3-(4-hydroxy-1,5-dimethyl-2-oxo-1,2-dihydropyridin-3-yl)ureido)propanoic acid 1-262;
(S)-3-(3-(4-hydroxy-1,5-dimethyl-2-oxo-1,2-dihydropyridin-3-yl)ureido)-3-(3-(6-methoxypyridin-3-yl)phenyl)propanoic acid 1-263;
(S)-3-(2',5'-dimethoxybiphenyl-3-yl)-3-(3-(4-hydroxy-1,5-dimethyl-2-oxo-1,2-dihydropyridin-3-yl)ureido)propanoic acid 1-264;
3-(3-(4-hydroxy-1,5-dimethyl-2-oxo-1,2-dihydropyridin-3-yl)ureido)-3-(3-(pyrimidin-5-yl)phenyl)propanoic acid 1-265;
(S)-3-(2',6'-dimethoxybiphenyl-3-yl)-3-(3-(4-hydroxy-1,5-dimethyl-2-oxo-1,2-dihydropyridin-3-yl)ureido)propanoic acid 1-266;
3-(3',4'-dichlorobiphenyl-3-yl)-3-(3-(1-ethyl-4-hydroxy-5-methyl-2-oxo-1,2-dihydropyridin-3-yl)ureido)propanoic acid 1-267;
3-(3',4'-dichlorobiphenyl-3-yl)-3-(3-(4-hydroxy-1,5-dimethyl-2-oxo-1,2-dihydropyridin-3-yl)ureido)propanoic acid 1-268;
(S)-3-(3-(4-hydroxy-1,5-dimethyl-2-oxo-1,2-dihydropyridin-3-yl)ureido)-3-(5-phenylfuran-2-yl)propanoic acid 1-269;
(S)-3-(3-(2,5-dimethyl-1H-pyrrol-1-yl)phenyl)-3-(3-(4-hydroxy-1,5-dimethyl-2-oxo-1,2-dihydropyridin-3-yl)ureido)propanoic acid 1-270;
3-(3'-chloro-4'-fluorobiphenyl-3-yl)-3-(3-(4-hydroxy-1,5-dimethyl-2-oxo-1,2-dihydropyridin-3-yl)ureido)propanoic acid 1-271;
3-(2',3'-dichlorobiphenyl-3-yl)-3-(3-(4-hydroxy-1,5-dimethyl-2-oxo-1,2-dihydropyridin-3-yl)ureido)propanoic acid 1-272;
3-(3',5'-dichlorobiphenyl-3-yl)-3-(3-(4-hydroxy-1,5-dimethyl-2-oxo-1,2-dihydropyridin-3-yl)ureido)propanoic acid 1-273;
(S)-3-(2',4'-difluorobiphenyl-3-yl)-3-(3-(4-hydroxy-1,6-dimethyl-2-oxo-1,2-dihydropyridin-3-yl)ureido)propanoic acid 1-274;
(S)-3-(2',4'-difluorobiphenyl-3-yl)-3-(3-(4-hydroxy-1-methyl-2-oxo-1,2-dihydropyridin-3-yl)ureido)propanoic acid 1-275;
(S)-3-(3-(4-hydroxy-1,5-dimethyl-2-oxo-1,2-dihydropyridin-3-yl)ureido)-3-(3'-methoxy-2'-methylbiphenyl-3-yl)propanoic acid 1-276;
(S)-3-(3-(4-hydroxy-1,5-dimethyl-2-oxo-1,2-dihydropyridin-3-yl)ureido)-3-(5'-methoxy-2'-methylbiphenyl-3-yl)propanoic acid 1-277;
3-(3-(4-hydroxy-1,5-dimethyl-2-oxo-1,2-dihydropyridin-3-yl)ureido)-3-(6-(2,2,2-trifluoroethoxy)biphenyl-3-yl)propanoic acid 1-278;
(S)-3-(2'-ethylbiphenyl-3-yl)-3-(3-(4-hydroxy-1,5-dimethyl-2-oxo-1,2-dihydropyridin-3-yl)ureido)propanoic acid 1-279;

(S)-3-(4-fluorobiphenyl-3-yl)-3-(3-(4-hydroxy-1,5-dimethyl-2-oxo-1,2-dihydropyridin-3-yl)ureido)propanoic acid 1-280;

(S)-3-(2',4'-difluorobiphenyl-3-yl)-3-(3-(4-hydroxy-2-oxo-1,2-dihydropyridin-3-yl)ureido)propanoic acid 1-281;

(S)-3-(3',4'-dimethylbiphenyl-3-yl)-3-(3-(4-hydroxy-1,5-dimethyl-2-oxo-1,2-dihydropyridin-3-yl)ureido)propanoic acid 1-282;

(S)-3-(2',3'-difluorobiphenyl-3-yl)-3-(3-(4-hydroxy-1,5-dimethyl-2-oxo-1,2-dihydropyridin-3-yl)ureido)propanoic acid 1-283;

(S)-3-(4'-fluoro-3'-methylbiphenyl-3-yl)-3-(3-(4-hydroxy-1,5-dimethyl-2-oxo-1,2-dihydropyridin-3-yl)ureido)propanoic acid 1-284;

(S)-3-(3-(4-hydroxy-1,5-dimethyl-2-oxo-1,2-dihydropyridin-3-yl)ureido)-3-(1-phenyl-1H-pyrrol-2-yl)propanoic acid 1-285;

(S)-3-(3'-chlorobiphenyl-3-yl)-3-(3-(4-hydroxy-1,5-dimethyl-2-oxo-1,2-dihydropyridin-3-yl)ureido)propanoic acid 1-286;

(S)-3-(3-(4-hydroxy-1,5-dimethyl-2-oxo-1,2-dihydropyridin-3-yl)ureido)-3-(2-methylbiphenyl-3-yl)propanoic acid 1-287;

(S)-3-(3-(4-hydroxy-1-methyl-2-oxo-1,2-dihydropyridin-3-yl)ureido)-3-(3'-methoxybiphenyl-3-yl)propanoic acid 1-288;

(S)-3-(2',6'-dimethylbiphenyl-3-yl)-3-(3-(4-hydroxy-1-methyl-2-oxo-1,2-dihydropyridin-3-yl)ureido)propanoic acid 1-289;

3-(5'-chloro-2',4'-difluorobiphenyl-3-yl)-3-(3-(4-hydroxy-1,5-dimethyl-2-oxo-1,2-dihydropyridin-3-yl)ureido)propanoic acid 1-290;

(S)-3-(2',3'-dimethoxybiphenyl-3-yl)-3-(3-(4-hydroxy-1,5-dimethyl-2-oxo-1,2-dihydropyridin-3-yl)ureido)propanoic acid 1-291;

(S)-3-(biphenyl-3-yl)-3-(3-(4-hydroxy-1-methyl-2-oxo-1,2-dihydropyridin-3-yl)ureido)propanoic acid 1-292;

(S)-3-(3'-chlorobiphenyl-3-yl)-3-(3-(4-hydroxy-1-methyl-2-oxo-1,2-dihydropyridin-3-yl)ureido)propanoic acid 1-293;

(S)-3-(3-(1H-pyrrol-1-yl)phenyl)-3-(3-(4-hydroxy-1-methyl-2-oxo-1,2-dihydropyridin-3-yl)ureido)propanoic acid 1-294;

(S)-3-(3-(4-hydroxy-1-methyl-2-oxo-1,2-dihydropyridin-3-yl)ureido)-3-(3-(6-methoxypyridin-3-yl)phenyl)propanoic acid 1-295;

(S)-3-(2'-fluoro-3'-methoxybiphenyl-3-yl)-3-(3-(4-hydroxy-1-methyl-2-oxo-1,2-dihydropyridin-3-yl)ureido)propanoic acid 1-296;

(S)-3-(3-(4-hydroxy-1-methyl-2-oxo-1,2-dihydropyridin-3-yl)ureido)-3-(4'-(trifluoromethoxy)biphenyl-3-yl)propanoic acid 1-297;

3-(2',4'-dichlorobiphenyl-3-yl)-3-(3-(4-hydroxy-1,5-dimethyl-2-oxo-1,2-dihydropyridin-3-yl)ureido)propanoic acid 1-298;

(S)-3-(3-(4-hydroxy-1-methyl-2-oxo-1,2-dihydropyridin-3-yl)ureido)-3-(2'-(trifluoromethoxy)biphenyl-3-yl)propanoic acid 1-299;

(S)-3-(2',4'-difluorobiphenyl-3-yl)-3-(3-(4-hydroxy-1-methyl-2-oxo-2,5,6,7-tetrahydro-1H-cyclopenta[b]pyridin-3-yl)ureido)propanoic acid 1-300;

(S)-3-(3-(4-hydroxy-1-methyl-2-oxo-1,2-dihydropyridin-3-yl)ureido)-3-(3'-(trifluoromethoxy)biphenyl-3-yl)propanoic acid 1-301;

(S)-3-(2',4'-difluorobiphenyl-3-yl)-3-(3-(7-hydroxy-4-methyl-5-oxo-4,5-dihydrothieno[3,2-b]pyridin-6-yl)ureido)propanoic acid 1-302;

(S)-3-(3-(benzo[d][1,3]dioxol-5-yl)phenyl)-3-(3-(4-hydroxy-1-methyl-2-oxo-1,2-dihydropyridin-3-yl)ureido)propanoic acid 1-303;

(S)-3-(3-(benzo[d][1,3]dioxol-5-yl)phenyl)-3-(3-(4-hydroxy-1,5-dimethyl-2-oxo-1,2-dihydropyridin-3-yl)ureido)propanoic acid 1-304;

(S)-3-(3-(1H-indazol-1-yl)phenyl)-3-(3-(4-hydroxy-1-methyl-2-oxo-1,2-dihydropyridin-3-yl)ureido)propanoic acid 1-305;

(S)-3-(2',4'-difluoro-6-methoxybiphenyl-3-yl)-3-(3-(4-hydroxy-1-methyl-2-oxo-1,2-dihydropyridin-3-yl)ureido)propanoic acid 1-306;

(S)-3-(3-(4-hydroxy-1-methyl-2-oxo-1,2-dihydropyridin-3-yl)ureido)-3-(4-phenylthiophen-2-yl)propanoic acid 1-307;

(S)-3-(3-(1-ethyl-1H-indol-6-yl)phenyl)-3-(3-(4-hydroxy-1-methyl-2-oxo-1,2-dihydropyridin-3-yl)ureido)propanoic acid 1-308;

(S)-3-(3-(1H-pyrazol-1-yl)phenyl)-3-(3-(4-hydroxy-1-methyl-2-oxo-1,2-dihydropyridin-3-yl)ureido)propanoic acid 1-309;

(S)-3-(4-(2,4-difluorophenyl)thiophen-2-yl)-3-(3-(4-hydroxy-1-methyl-2-oxo-1,2-dihydropyridin-3-yl)ureido)propanoic acid 1-310;

(S)-3-(3',6-dimethoxybiphenyl-3-yl)-3-(3-(4-hydroxy-1-methyl-2-oxo-1,2-dihydropyridin-3-yl)ureido)propanoic acid 1-311;

3-(2',5'-dichlorobiphenyl-3-yl)-3-(3-(4-hydroxy-1,5-dimethyl-2-oxo-1,2-dihydropyridin-3-yl)ureido)propanoic acid 1-312;

(S)-3-(2',4'-difluorobiphenyl-3-yl)-3-(3-(4-hydroxy-1-methyl-2-oxo-1,2-dihydro-1,8-naphthyridin-3-yl)ureido)propanoic acid 1-313;

(S)-3-(3',6-dimethoxybiphenyl-3-yl)-3-(3-(4-hydroxy-1,5-dimethyl-2-oxo-1,2-dihydropyridin-3-yl)ureido)propanoic acid 1-314;

(S)-3-(3-(4-hydroxy-1-methyl-2-oxo-1,2-dihydropyridin-3-yl)ureido)-3-(4-(3-methoxyphenyl)thiophen-2-yl)propanoic acid 1-315;

(S)-3-(3-(4-hydroxy-1-methyl-2-oxo-1,2-dihydropyridin-3-yl)ureido)-3-(6-methoxybiphenyl-3-yl)propanoic acid 1-316;

(S)-3-(4-(3-chlorophenyl)thiophen-2-yl)-3-(3-(4-hydroxy-1-methyl-2-oxo-1,2-dihydropyridin-3-yl)ureido)propanoic acid 1-317;

(S)-3-(2',4'-difluorobiphenyl-3-yl)-3-(3-(1-ethyl-4-hydroxy-2-oxo-1,2-dihydropyridin-3-yl)ureido)propanoic acid 1-318;

(S)-3-(3-(4-hydroxy-1-methyl-2-oxo-1,2-dihydropyridin-3-yl)ureido)-3-(3-(thiophen-2-yl)phenyl)propanoic acid 1-319;

(S)-3-(3-(4-hydroxy-1-methyl-2-oxo-1,2-dihydropyridin-3-yl)ureido)-3-(6-methoxy-2',6'-dimethylbiphenyl-3-yl)propanoic acid 1-320;

(S)-3-(3'-chloro-6-methoxybiphenyl-3-yl)-3-(3-(4-hydroxy-1-methyl-2-oxo-1,2-dihydropyridin-3-yl)ureido)propanoic acid 1-321;

(S)-3-(3-(4-hydroxy-1-methyl-2-oxo-1,2-dihydropyridin-3-yl)ureido)-3-(6-methoxy-3'-(trifluoromethoxy)biphenyl-3-yl)propanoic acid 1-322;

(S)-3-(3-(4-hydroxy-1-methyl-2-oxo-1,2-dihydropyridin-3-yl)ureido)-3-(6-methoxy-4'-(trifluoromethoxy)biphenyl-3-yl)propanoic acid 1-323;

(S)-3-(2',6'-dichlorobiphenyl-3-yl)-3-(3-(4-hydroxy-1-methyl-2-oxo-1,2-dihydropyridin-3-yl)ureido)propanoic acid 1-324;

(S)-3-(3-(5-chlorothiophen-2-yl)phenyl)-3-(3-(4-hydroxy-1-methyl-2-oxo-1,2-dihydropyridin-3-yl)ureido)propanoic acid 1-325;

(S)-3-(3-(1H-imidazol-1-yl)phenyl)-3-(3-(4-hydroxy-1-methyl-2-oxo-1,2-dihydropyridin-3-yl)ureido)propanoic acid 1-326;

(S)-3-(3-(4-hydroxy-1-methyl-2-oxo-1,2-dihydropyridin-3-yl)ureido)-3-(3-(4-methylthiophen-3-yl)phenyl)propanoic acid 1-327;

(S)-3-(2',4'-difluoro-6-methylbiphenyl-3-yl)-3-(3-(4-hydroxy-1-methyl-2-oxo-1,2-dihydropyridin-3-yl)ureido)propanoic acid 1-328;

(S)-3-(3-(4-hydroxy-1-methyl-2-oxo-1,2-dihydropyridin-3-yl)ureido)-3-(3'-methoxy-6-methylbiphenyl-3-yl)propanoic acid 1-329;

(S)-3-(4-(2,6-dimethylphenyl)thiophen-2-yl)-3-(3-(4-hydroxy-1-methyl-2-oxo-1,2-dihydropyridin-3-yl)ureido)propanoic acid 1-330;

(S)-3-(3-(1H-pyrrol-3-yl)phenyl)-3-(3-(4-hydroxy-1-methyl-2-oxo-1,2-dihydropyridin-3-yl)ureido)propanoic acid 1-331;

(S)-3-(3-(4-hydroxy-1-methyl-2-oxo-1,2-dihydropyridin-3-yl)ureido)-3-(2',6,6'-trimethylbiphenyl-3-yl)propanoic acid 1-332;

(S)-3-(3-(4-hydroxy-1-methyl-2-oxo-1,2-dihydropyridin-3-yl)ureido)-3-(2',6,6'-trifluorobiphenyl-3-yl)propanoic acid 1-333;

(S)-3-(6-fluoro-3'-methoxybiphenyl-3-yl)-3-(3-(4-hydroxy-1-methyl-2-oxo-1,2-dihydropyridin-3-yl)ureido)propanoic acid 1-334;

(S)-3-(3-(4-hydroxy-1-methyl-2-oxo-1,2-dihydropyridin-3-yl)ureido)-3-(3-(1-methyl-1H-pyrazol-4-yl)phenyl)propanoic acid 1-335;

(S)-3-(2',4'-difluorobiphenyl-3-yl)-3-(3-(5-hydroxy-2-methyl-3-oxo-2,3-dihydropyridazin-4-yl)ureido)propanoic acid 1-336;

(S)-3-(2',6'-dimethylbiphenyl-3-yl)-3-(3-(4-hydroxy-1,6-dimethyl-2-oxo-1,2-dihydropyridin-3-yl)ureido)propanoic acid 1-337;

(S)-3-(3',6-dimethoxybiphenyl-3-yl)-3-(3-(4-hydroxy-1,6-dimethyl-2-oxo-1,2-dihydropyridin-3-yl)ureido)propanoic acid 1-338;

(S)-3-(4-(2,4-difluorophenyl)thiophen-2-yl)-3-(3-(4-hydroxy-1,6-dimethyl-2-oxo-1,2-dihydropyridin-3-yl)ureido)propanoic acid 1-339;

(S)-3-(3-(4-hydroxy-1,6-dimethyl-2-oxo-1,2-dihydropyridin-3-yl)ureido)-3-(3'-methoxybiphenyl-3-yl)propanoic acid 1-340;

(S)-3-(3-(4-hydroxy-1,6-dimethyl-2-oxo-1,2-dihydropyridin-3-yl)ureido)-3-(6-methoxy-3'-(trifluoromethoxy)biphenyl-3-yl)propanoic acid 1-341;

(S)-3-(3'-chloro-6-methylbiphenyl-3-yl)-3-(3-(4-hydroxy-1-methyl-2-oxo-1,2-dihydropyridin-3-yl)ureido)propanoic acid 1-342;

(S)-3-(3'-chlorobiphenyl-3-yl)-3-(3-(4-hydroxy-1,6-dimethyl-2-oxo-1,2-dihydropyridin-3-yl)ureido)propanoic acid 1-343;

(S)-3-(2',4'-difluorobiphenyl-3-yl)-3-(3-(4-hydroxy-6-methyl-2-oxo-1,2-dihydropyridin-3-yl)ureido)propanoic acid 1-344;

(S)-3-(3-(4-hydroxy-1-methyl-2-oxo-1,2-dihydropyridin-3-yl)ureido)-3-(5-methoxybiphenyl-3-yl)propanoic acid 1-345;

(S)-3-(3-(furan-3-yl)phenyl)-3-(3-(4-hydroxy-1-methyl-2-oxo-1,2-dihydropyridin-3-yl)ureido)propanoic acid 1-346;

(S)-3-(3-(3,5-dimethylisoxazol-4-yl)phenyl)-3-(3-(4-hydroxy-1-methyl-2-oxo-1,2-dihydropyridin-3-yl)ureido)propanoic acid 1-347;

(S)-3-(6-fluoro-2',6'-dimethylbiphenyl-3-yl)-3-(3-(4-hydroxy-1-methyl-2-oxo-1,2-dihydropyridin-3-yl)ureido)propanoic acid 1-348;

(S)-3-(5-(2,4-difluorophenyl)thiophen-2-yl)-3-(3-(4-hydroxy-1-methyl-2-oxo-1,2-dihydropyridin-3-yl)ureido)propanoic acid 1-349;

(S)-3-(3-(4-hydroxy-1-methyl-2-oxo-1,2-dihydropyridin-3-yl)ureido)-3-(5-(3-methoxyphenyl)thiophen-2-yl)propanoic acid 1-350;

(S)-3-(3',5-dimethoxybiphenyl-3-yl)-3-(3-(4-hydroxy-1-methyl-2-oxo-1,2-dihydropyridin-3-yl)ureido)propanoic acid 1-351;

(S)-3-(3-(4-hydroxy-1-methyl-2-oxo-1,2-dihydropyridin-3-yl)ureido)-3-(5-methoxy-3'-(trifluoromethoxy)biphenyl-3-yl)propanoic acid 1-352;

(S)-3-(2',4'-difluoro-5-methoxybiphenyl-3-yl)-3-(3-(4-hydroxy-1-methyl-2-oxo-1,2-dihydropyridin-3-yl)ureido)propanoic acid 1-353;

(S)-3-(3',5-dimethoxybiphenyl-3-yl)-3-(3-(4-hydroxy-1,6-dimethyl-2-oxo-1,2-dihydropyridin-3-yl)ureido)propanoic acid 1-354;

(S)-3-(3-(4-hydroxy-1,6-dimethyl-2-oxo-1,2-dihydropyridin-3-yl)ureido)-3-(5-methoxy-3'-(trifluoromethoxy)biphenyl-3-yl)propanoic acid 1-355;

(S)-3-(3-(4-hydroxy-1,6-dimethyl-2-oxo-1,2-dihydropyridin-3-yl)ureido)-3-(3'-methoxy-6-methylbiphenyl-3-yl)propanoic acid 1-356;

(S)-3-(4-fluorobiphenyl-3-yl)-3-(3-(4-hydroxy-1-methyl-2-oxo-1,2-dihydropyridin-3-yl)ureido)propanoic acid 1-357;

(S)-3-(3-(4-hydroxy-1-methyl-2-oxo-1,2-dihydropyridin-3-yl)ureido)-3-(6-phenylpyridin-2-yl)propanoic acid 1-358;

(S)-3-(3-(4-hydroxy-1-methyl-2-oxo-1,2-dihydropyridin-3-yl)ureido)-3-(5-methyl-3'-(trifluoromethoxy)biphenyl-3-yl)propanoic acid 1-359;

(S)-3-(3-(4-hydroxy-1-methyl-2-oxo-1,2-dihydropyridin-3-yl)ureido)-3-(2',5,6'-trimethylbiphenyl-3-yl)propanoic acid 1-360;

(S)-3-(2',4'-difluoro-5-methylbiphenyl-3-yl)-3-(3-(4-hydroxy-1-methyl-2-oxo-1,2-dihydropyridin-3-yl)ureido)propanoic acid 1-361;

(S)-3-(2',4'-difluoro-5-methylbiphenyl-3-yl)-3-(3-(4-hydroxy-1,6-dimethyl-2-oxo-1,2-dihydropyridin-3-yl)ureido)propanoic acid 1-362;

(S)-3-(3-(4-hydroxy-1-methyl-2-oxo-1,2-dihydropyridin-3-yl)ureido)-3-(6-methyl-3'-(trifluoromethoxy)biphenyl-3-yl)propanoic acid 1-363;

(S)-3-(3-(4-hydroxy-1,6-dimethyl-2-oxo-1,2-dihydropyridin-3-yl)ureido)-3-(6-methyl-3'-(trifluoromethoxy)biphenyl-3-yl)propanoic acid 1-364;

(S)-3-(6-fluoro-2',6'-dimethylbiphenyl-3-yl)-3-(3-(4-hydroxy-1,6-dimethyl-2-oxo-1,2-dihydropyridin-3-yl)ureido)propanoic acid 1-365;

(S)-3-(3-(4-hydroxy-1-methyl-2-oxo-1,2-dihydropyridin-3-yl)ureido)-3-(5-methoxy-2',6'-dimethylbiphenyl-3-yl)propanoic acid 1-366;

(S)-3-(3-(4-hydroxy-1,6-dimethyl-2-oxo-1,2-dihydropyridin-3-yl)ureido)-3-(5-methoxy-2',6'-dimethylbiphenyl-3-yl)propanoic acid 1-367;

(S)-3-(2',4'-difluoro-5-methoxybiphenyl-3-yl)-3-(3-(4-hydroxy-1,6-dimethyl-2-oxo-1,2-dihydropyridin-3-yl)ureido)propanoic acid 1-368;

(S)-3-(3-(4-hydroxy-1-methyl-2-oxo-1,2-dihydropyridin-3-yl)ureido)-3-(3'-methoxy-5-methylbiphenyl-3-yl)propanoic acid 1-369;

(S)-3-(2',6'-dimethylbiphenyl-3-yl)-3-(3-(7-hydroxy-5-oxo-1,2,3,5-tetrahydroindolizin-6-yl)ureido)propanoic acid 1-370;

(S)-3-(3-(4-hydroxy-1-methyl-2-oxo-1,2-dihydropyridin-3-yl)ureido)-3-(4'-methyl-[2,3'-bithiophen]-5-yl)propanoic acid 1-371;

(S)-3-(3-(4-hydroxy-1,6-dimethyl-2-oxo-1,2-dihydropyridin-3-yl)ureido)-3-(4'-methyl-[2,3'-bithiophen]-5-yl)propanoic acid 1-372;

(S)-3-(3-(4-hydroxy-1,6-dimethyl-2-oxo-1,2-dihydropyridin-3-yl)ureido)-3-(3'-methoxy-5-methylbiphenyl-3-yl)propanoic acid 1-373;

(S)-3-(5-(2,6-dimethylphenyl)thiophen-2-yl)-3-(3-(4-hydroxy-1-methyl-2-oxo-1,2-dihydropyridin-3-yl)ureido)propanoic acid 1-374;

(S)-3-(5-(2,6-dimethylphenyl)thiophen-2-yl)-3-(3-(4-hydroxy-1,6-dimethyl-2-oxo-1,2-dihydropyridin-3-yl)ureido)propanoic acid 1-375;

(S)-3-(4-fluoro-2',6'-dimethylbiphenyl-3-yl)-3-(3-(4-hydroxy-1,6-dimethyl-2-oxo-1,2-dihydropyridin-3-yl)ureido)propanoic acid 1-376;

(S)-3-(4-fluoro-2',6'-dimethylbiphenyl-3-yl)-3-(3-(4-hydroxy-1-methyl-2-oxo-1,2-dihydropyridin-3-yl)ureido)propanoic acid 1-377;

(S)-3-(3-(4-hydroxy-1-methyl-2-oxo-1,2-dihydropyridin-3-yl)ureido)-3-(2',4,4'-trifluorobiphenyl-3-yl)propanoic acid 1-378;

(S)-3-(3-(4-hydroxy-1,6-dimethyl-2-oxo-1,2-dihydropyridin-3-yl)ureido)-3-(2',4,4'-trifluorobiphenyl-3-yl)propanoic acid 1-379;

(S)-3-(4-fluoro-3'-methoxybiphenyl-3-yl)-3-(3-(4-hydroxy-1-methyl-2-oxo-1,2-dihydropyridin-3-yl)ureido)propanoic acid 1-380;

(S)-3-(4-fluoro-3'-(trifluoromethoxy)biphenyl-3-yl)-3-(3-(4-hydroxy-1-methyl-2-oxo-1,2-dihydropyridin-3-yl)ureido)propanoic acid 1-381;

(S)-3-(4-fluoro-3'-(trifluoromethoxy)biphenyl-3-yl)-3-(3-(4-hydroxy-1,6-dimethyl-2-oxo-1,2-dihydropyridin-3-yl)ureido)propanoic acid 1-382;

(S)-3-(3-(4-hydroxy-1-methyl-2-oxo-1,2-dihydropyridin-3-yl)ureido)-3-(4-methoxybiphenyl-3-yl)propanoic acid 1-383;

(S)-3-(3-(4-hydroxy-1,6-dimethyl-2-oxo-1,2-dihydropyridin-3-yl)ureido)-3-(2',5,6'-trimethylbiphenyl-3-yl)propanoic acid 1-384;

(S)-3-(3-(4-hydroxy-1-methyl-2-oxo-1,2-dihydropyridin-3-yl)ureido)-3-(2'-methylbiphenyl-3-yl)propanoic acid 1-385;

(S)-3-(3-(4-hydroxy-1,6-dimethyl-2-oxo-1,2-dihydropyridin-3-yl)ureido)-3-(2'-methylbiphenyl-3-yl)propanoic acid 1-386;

(S)-3-(5-fluoro-2',6'-dimethylbiphenyl-3-yl)-3-(3-(4-hydroxy-1-methyl-2-oxo-1,2-dihydropyridin-3-yl)ureido)propanoic acid 1-387;

(S)-3-(3-(4-hydroxy-1-methyl-2-oxo-1,2-dihydropyridin-3-yl)ureido)-3-(5-(3-(trifluoromethoxy)phenyl)thiophen-2-yl)propanoic acid 1-388;

(S)-3-(3-(4-hydroxy-1-methyl-2-oxo-1,2-dihydropyridin-3-yl)ureido)-3-(4-methoxy-2',6'-dimethylbiphenyl-3-yl)propanoic acid 1-389;

(S)-3-(4-fluoro-3'-methoxybiphenyl-3-yl)-3-(3-(4-hydroxy-1,6-dimethyl-2-oxo-1,2-dihydropyridin-3-yl)ureido)propanoic acid 1-390;

(S)-3-(5-fluoro-3'-methoxybiphenyl-3-yl)-3-(3-(4-hydroxy-1-methyl-2-oxo-1,2-dihydropyridin-3-yl)ureido)propanoic acid 1-391;

(S)-3-(5-fluoro-3'-methoxybiphenyl-3-yl)-3-(3-(4-hydroxy-1,6-dimethyl-2-oxo-1,2-dihydropyridin-3-yl)ureido)propanoic acid 1-392;

(S)-3-(5-fluoro-3'-(trifluoromethoxy)biphenyl-3-yl)-3-(3-(4-hydroxy-1,6-dimethyl-2-oxo-1,2-dihydropyridin-3-yl)ureido)propanoic acid 1-393;

(S)-3-(5-fluoro-3'-(trifluoromethoxy)biphenyl-3-yl)-3-(3-(4-hydroxy-1-methyl-2-oxo-1,2-dihydropyridin-3-yl)ureido)propanoic acid 1-394;

(S)-3-(5-(3,5-dimethylisoxazol-4-yl)thiophen-2-yl)-3-(3-(4-hydroxy-1-methyl-2-oxo-1,2-dihydropyridin-3-yl)ureido)propanoic acid 1-395;

(S)-3-(3-(3,5-dimethylisoxazol-4-yl)phenyl)-3-(3-(4-hydroxy-1,6-dimethyl-2-oxo-1,2-dihydropyridin-3-yl)ureido)propanoic acid 1-396;

(S)-3-(2-fluorobiphenyl-3-yl)-3-(3-(4-hydroxy-1,6-dimethyl-2-oxo-1,2-dihydropyridin-3-yl)ureido)propanoic acid 1-397;

(S)-3-(6-fluoro-2'-methylbiphenyl-3-yl)-3-(3-(4-hydroxy-1,6-dimethyl-2-oxo-1,2-dihydropyridin-3-yl)ureido)propanoic acid 1-398;

(S)-3-(6-fluoro-2'-methylbiphenyl-3-yl)-3-(3-(4-hydroxy-1-methyl-2-oxo-1,2-dihydropyridin-3-yl)ureido)propanoic acid 1-399;

(S)-3-(3-(4-hydroxy-1-methyl-2-oxo-1,2-dihydropyridin-3-yl)ureido)-3-(5-phenylthiophen-2-yl)propanoic acid 1-400;

(S)-3-(5-(2,5-difluorophenyl)thiophen-2-yl)-3-(3-(4-hydroxy-1-methyl-2-oxo-1,2-dihydropyridin-3-yl)ureido)propanoic acid 1-401;

(S)-3-(3-(4-hydroxy-1-methyl-2-oxo-1,2-dihydropyridin-3-yl)ureido)-3-(5-(trifluoromethoxy)biphenyl-3-yl)propanoic acid 1-402;

(S)-3-(3-(4-hydroxy-1-methyl-2-oxo-1,2-dihydropyridin-3-yl)ureido)-3-(2'-methylbiphenyl-4-yl)propanoic acid 1-403;

(S)-3-(3-(7-hydroxy-5-oxo-1,2,3,5-tetrahydroindolizin-6-yl)ureido)-3-(5-methoxybiphenyl-3-yl)propanoic acid 1-404;

(S)-3-(3-(4-hydroxy-1-methyl-2-oxo-1,2-dihydropyridin-3-yl)ureido)-3-(5-(trifluoromethyl)biphenyl-3-yl)propanoic acid 1-405;

(S)-3-(5-(3-chlorophenyl)thiophen-2-yl)-3-(3-(4-hydroxy-1-methyl-2-oxo-1,2-dihydropyridin-3-yl)ureido)propanoic acid 1-406;

(S)-3-(5-(3-fluorophenyl)thiophen-2-yl)-3-(3-(4-hydroxy-1-methyl-2-oxo-1,2-dihydropyridin-3-yl)ureido)propanoic acid 1-407;

(S)-3-(2',4'-difluorobiphenyl-4-yl)-3-(3-(4-hydroxy-1-methyl-2-oxo-1,2-dihydropyridin-3-yl)ureido)propanoic acid 1-408;

(S)-3-(2',4'-difluorobiphenyl-4-yl)-3-(3-(4-hydroxy-1,6-dimethyl-2-oxo-1,2-dihydropyridin-3-yl)ureido)propanoic acid 1-409;

(S)-3-(2',4'-difluorobiphenyl-4-yl)-3-(3-(4-hydroxy-1,5-dimethyl-2-oxo-1,2-dihydropyridin-3-yl)ureido)propanoic acid 1-410;

(S)-3-(3-(4-hydroxy-1-methyl-2-oxo-1,2-dihydropyridin-3-yl)ureido)-3-(2'-methyl-6-(trifluoromethoxy)biphenyl-3-yl)propanoic acid 1-411;

(S)-3-(3-(4-hydroxy-1-methyl-2-oxo-1,2-dihydropyridin-3-yl)ureido)-3-(6-(trifluoromethoxy)biphenyl-3-yl)propanoic acid 1-412;

3-(3'-acetylbiphenyl-3-yl)-3-(3-(4-hydroxy-1,5-dimethyl-2-oxo-1,2-dihydropyridin-3-yl)ureido)propanoic acid 1-413;

3-(4'-acetylbiphenyl-3-yl)-3-(3-(4-hydroxy-1,5-dimethyl-2-oxo-1,2-dihydropyridin-3-yl)ureido)propanoic acid 1-414;

(S)-3-(3-(4-hydroxy-1,5-dimethyl-2-oxo-1,2-dihydropyridin-3-yl)ureido)-3-(4-phenylthiophen-2-yl)propanoic acid 1-415;

(S)-3-(3-(4-hydroxy-1,5-dimethyl-2-oxo-1,2-dihydropyridin-3-yl)ureido)-3-(5-phenylthiophen-2-yl)propanoic acid 1-416;

(S)-3-(2',4'-difluorobiphenyl-3-yl)-3-(3-(7-hydroxy-5-oxo-1,2,3,5-tetrahydroindolizin-6-yl)ureido)propanoic acid 1-417;

(S)-3-(3-(4-hydroxy-1-methyl-2-oxo-1,2-dihydropyridin-3-yl)ureido)-3-(3-(thiazol-2-yl)phenyl)propanoic acid 1-418;

(S)-3-(3-(4-hydroxy-1,6-dimethyl-2-oxo-1,2-dihydropyridin-3-yl)ureido)-3-(5-methyl-3'-(trifluoromethoxy)biphenyl-3-yl)propanoic acid 1-419;

(S)-3-(3-(4-hydroxy-1,6-dimethyl-2-oxo-1,2-dihydropyridin-3-yl)ureido)-3-(2',4',5-trifluorobiphenyl-3-yl)propanoic acid 1-420;

(S)-3-(3-(4-hydroxy-1-methyl-2-oxo-1,2-dihydropyridin-3-yl)ureido)-3-(2',4',5-trifluorobiphenyl-3-yl)propanoic acid 1-421;

(S)-3-(3-(4-hydroxy-1-methyl-2-oxo-1,2-dihydropyridin-3-yl)ureido)-3-(3'-methoxy-6-(trifluoromethoxy)biphenyl-3-yl)propanoic acid 1-422;

(S)-3-(3-(4-hydroxy-1,6-dimethyl-2-oxo-1,2-dihydropyridin-3-yl)ureido)-3-(3'-methoxy-6-(trifluoromethoxy)biphenyl-3-yl)propanoic acid 1-423;

(S)-3-(2',6'-dimethylbiphenyl-4-yl)-3-(3-(4-hydroxy-1-methyl-2-oxo-1,2-dihydropyridin-3-yl)ureido)propanoic acid 1-424;

(S)-3-(3-(4-hydroxy-1,6-dimethyl-2-oxo-1,2-dihydropyridin-3-yl)ureido)-3-(2'-methylbiphenyl-4-yl)propanoic acid 1-425;

(S)-3-(2',6'-dimethylbiphenyl-4-yl)-3-(3-(4-hydroxy-1,6-dimethyl-2-oxo-1,2-dihydropyridin-3-yl)ureido)propanoic acid 1-426;

(S)-3-(3-(4-hydroxy-1-methyl-2-oxo-1,2-dihydropyridin-3-yl)ureido)-3-(3-(pyridin-2-yl)phenyl)propanoic acid 1-427;

(S)-3-(3-(4-hydroxy-1-methyl-2-oxo-1,2-dihydropyridin-3-yl)ureido)-3-(3-(6-methoxypyridazin-3-yl)phenyl)propanoic acid 1-428;

(S)-3-(3-(4-hydroxy-1-methyl-2-oxo-1,2-dihydropyridin-3-yl)ureido)-3-(5-phenylpyridin-3-yl)propanoic acid 1-429;

(S)-3-(5-fluoro-2',6'-dimethylbiphenyl-3-yl)-3-(3-(4-hydroxy-1,6-dimethyl-2-oxo-1,2-dihydropyridin-3-yl)ureido)propanoic acid;

(S)-3-(biphenyl-4-yl)-3-(3-(1,5-dimethyl-4-oxido-2-oxo-1,2-dihydropyridin-3-yl)ureido)propanoic acid 1-430;

(S)-3-(3-(4-hydroxy-1-methyl-2-oxo-1,2-dihydropyridin-3-yl)ureido)-3-(3-(6'-methoxypyridin-2-yl)phenyl)propanoic acid 1-431;

(S)-3-(3-(4-hydroxy-1,5-dimethyl-2-oxo-1,2-dihydropyridin-3-yl)ureido)-3-(4'-methoxybiphenyl-3-yl)propanoic acid 1-432;

(S)-3-(3-(1H-imidazol-1-yl)phenyl)-3-(3-(4-hydroxy-1-methyl-2-oxo-1,2-dihydropyridin-3-yl)ureido)propanoic acid 1-433;

(S)-3-(3-(4-hydroxy-1-methyl-2-oxo-1,2-dihydropyridin-3-yl)ureido)-3-(3-(pyrazin-2-yl)phenyl)propanoic acid 1-434, 3-(3-bromophenyl)-3-(3-(4-hydroxy-1,5-dimethyl-2-oxo-1,2-dihydropyridin-3-yl)ureido)propanoic acid 1-435, 3-(3-bromophenyl)-3-(3-(1-ethyl-4-hydroxy-5-methyl-2-oxo-1,2-dihydropyridin-3-yl)ureido) propanoic acid 1-436, The product was crystallized from ethyl acetate during the preparation of (S)-3-(5-fluoro-2',6'-dimethylbiphenyl-3-yl)-3-(3-(4-hydroxy-1,6-dimethyl-2-oxo-1,2-dihydropyridin-3-yl)ureido)propanoic acid.

Step Eleven: To a solution of 1-224 (96 mg, 0.228 mmol) in inhibitor free tetrahydrofuran (2.5 mL), aqueous sodium hydroxide (0.1000 N, 4.57 mL, 0.457 mmol) was added. The mixture was heated briefly to 40° C. to give a homogeneous mixture, and the tetrahydrofuran was removed by rotary evaporation. The mixture was diluted with deionized water, then frozen in a dry ice/acetone bath and lyophilized to give sodium (S)-3-(biphenyl-3-yl)-3-(3-(1,5-dimethyl-4-oxido-2-oxo-1,2-dihydropyridin-3-yl) ureido)propanoate; (1-437, 115 mg) as a fluffy white powder. (MS $[M+H^+]^+$: Calculated: 422.17; Measured: 422.09; $IC_{50}$<20 nM).

This method was also used to prepare:

sodium (S)-3-(biphenyl-3-yl)-3-(3-(1-ethyl-5-methyl-4-oxido-2-oxo-1,2-dihydro pyridin-3-yl)ureido)propanoate 1-438 (MS $[M+H^+]^+$: Calculated: 436.19; Measured: 436.05; $\alpha 4\beta 1$ $IC_{50}$=<200 nM: $\alpha 4\beta 7$ $IC_{50}$=nd sodium 3-(3-(1-ethyl-5-methyl-4-oxido-2-oxo-1,2-dihydropyridin-3-yl)ureido)-3-(3-(2-oxo-3-phenylpyridin-1(2H)-yl)phenyl)propanoate 1-439 (MS $[M+H^+]^+$: Calculated: 529.21; Measured: 529.21); $\alpha 4\beta 1$ $IC_{50}$=>200 nM: $\alpha 4\beta 7$ $IC_{50}$=nd sodium (S)-3-(3-(1,5-dimethyl-4-oxido-2-oxo-1,2-dihydropyridin-3-yl)ureido)-3-(2'-methyl biphenyl-3-yl)propanoate 1-440 (MS $[M+H^+]^+$: Calculated: 436.19 Measured: 436.11; $\alpha 4\beta 1$ $IC_{50}$=<200 nM: $\alpha 4\beta 7$ $IC_{50}$=nd sodium (S)-3-(3-(1,5-dimethyl-4-oxido-2-oxo-1,2-dihydropyridin-3-yl)ureido)-3-(2'-fluorobiphenyl-3-yl)propanoate 1-441 (MS $[M+H^+]^+$: Calculated: 440.16; Measured: 440.04; $\alpha 4\beta 1$ $IC_{50}$=<20 nM: $\alpha 4\beta 7$ $IC_{50}$=nd sodium (S)-3-(3-(1,5-dimethyl-4-oxido-2-oxo-1,2-dihydropyridin-3-yl)ureido)-3-(6-fluorobiphenyl-3-yl)propanoate 1-442 (MS $[M+H^+]^+$: Calculated: 440.16; Measured: 440.10; $\alpha 4\beta 1$ $IC_{50}$=<20 nM: $\alpha 4\beta 7$ $IC_{50}$=nd;

sodium (S)-3-(3-(1-ethyl-5-methyl-4-oxido-2-oxo-1,2-dihydropyridin-3-yl)ureido)-3-(2'-methyl biphenyl-3-yl)propanoate 1-443 (MS $[M+H^+]^+$: Calculated: 450.20; Measured: 450.14; $\alpha 4\beta 1$ $IC_{50}$=<200 nM: $\alpha 4\beta 7$ $IC_{50}$=nd;

sodium (S)-3-(3-(1-ethyl-5-methyl-4-oxido-2-oxo-1,2-dihydropyridin-3-yl)ureido)-3-(4'-methylbiphenyl-3-yl)propanoate 1-444 (MS $[M+H^+]^+$: Calculated: 450.20; Measured: 450.11; $\alpha 4\beta 1$ $IC_{50}$=<200 nM: $\alpha 4\beta 7$ $IC_{50}$=nd;

sodium 3-(3-(1H-pyrrol-1-yl)phenyl)-3-(3-(1,5-dimethyl-4-oxido-2-oxo-1,2-dihydro pyridin-3-yl)ureido)propanoate 1-445 (MS $[M+H^+]^+$: Calculated: 411.17; Measured: 411.10; $\alpha 4\beta 1$ $IC_{50}$=<200 nM: $\alpha 4\beta 7$ $IC_{50}$=nd;

sodium (S)-3-(2',4'-difluorobiphenyl-3-yl)-3-(3-(1,5-dimethyl-4-oxido-2-oxo-1,2-dihydro pyridin-3-yl)ureido) propanoate 1-446 (MS $[M+H^+]^+$: Calculated: 458.15; Measured: 458.07; $\alpha 4\beta 1$ $IC_{50}$=<20 nM: $\alpha 4\beta 7$ $IC_{50}$=nd;

sodium (S)-3-(2',5'-difluorobiphenyl-3-yl)-3-(3-(1,5-dimethyl-4-oxido-2-oxo-1,2-di hydropyridin-3-yl)ureido) propanoate 1-447 (MS $[M+H^+]^+$: Calculated: 458.15; Measured: 458.06; $\alpha 4\beta 1$ $IC_{50}$=<20 nM: $\alpha 4\beta 7$ $IC_{50}$=nd;

sodium (S)-3-(3-(1,5-dimethyl-4-oxido-2-oxo-1,2-dihydropyridin-3-yl)ureido)-3-(6-methyl biphenyl-3-yl)propanoate 1-448 (MS $[M+H^+]^+$: Calculated: 436.19; Measured: 136.15; $\alpha 4\beta 1$ $IC_{50}$=<200 nM: $\alpha 4\beta 7$ $IC_{50}$=nd;

(S)-3-(3-(1,5-dimethyl-4-oxido-2-oxo-1,2-dihydropyridin-3-yl)ureido)-3-(6-methoxybiphenyl-3-yl)propanoate 1-449 (MS [M+H$^+$]$^+$: Calculated: 452.18; Measured: 452.11; α4β1 IC$_{50}$=<200 nM: α4β7 IC$_{50}$=nd;
sodium (S)-3-(3-(1,5-dimethyl-4-oxido-2-oxo-1,2-dihydropyridin-3-yl)ureido)-3-(4'-methyl biphenyl-3-yl)propanoate 1-450 (MS [M+H$^+$]$^+$: Calculated: 436.19; Measured: 436.07; α4β1 IC$_{50}$=<200 nM: α4β7 IC$_{50}$=nd;
sodium (S)-3-(3-(1,5-dimethyl-4-oxido-2-oxo-1,2-dihydropyridin-3-yl)ureido)-3-(3'-methyl biphenyl-3-yl)propanoate 1-451 (MS [M+H$^+$]$^+$: Calculated: 436.19; Measured: 435.96; α4β1 IC$_{50}$=<200 nM: α4β7 IC$_{50}$=nd;
sodium (S)-3-(3-(1,5-dimethyl-4-oxido-2-oxo-p1,2-dihydropyridin-3-yl)ureido)-3-(3-(pyridin-3-yl)phenyl)propanoate 1-452 (MS [M+H$^+$]$^+$: Calculated: 423.17; Measured: 423.15; α4β1 IC$_{50}$=<200 nM: α4β7 IC$_{50}$=nd;
sodium (S)-3-(3',5'-difluorobiphenyl-3-yl)-3-(3-(1,5-dimethyl-4-oxido-2-oxo-1,2-di hydropyridin-3-yl)ureido) propanoate 1-453 (MS [M+H$^+$]$^+$: Calculated: 458.15; Measured: 458.06; α4β1 IC$_{50}$=<20 nM: α4β7 IC$_{50}$=nd;
sodium (S)-3-(3-(1,5-dimethyl-4-oxido-2-oxo-1,2-dihydropyridin-3-yl)ureido)-3-(3',5'-dimethyl biphenyl-3-yl)propanoate 1-454 (MS [M+H$^+$]$^+$: Calculated: 450.20; Measured: 450.08; α4β1 IC$_{50}$=<200 nM: α4β7 IC$_{50}$=nd;
sodium (S)-3-(3-(1,5-dimethyl-4-oxido-2-oxo-1,2-dihydropyridin-3-yl)ureido)-3-(4'-methoxy biphenyl-3-yl)propanoate 1-455;
sodium (S)-3-(3-(1,5-dimethyl-4-oxido-2-oxo-1,2-dihydropyridin-3-yl)ureido)-3-(4'-(trifluoro methyl)biphenyl-3-yl)propanoate 1-457 (MS [M+H$^+$]$^+$: Calculated: 490.16; Measured: 490.10; α4β1 IC$_{50}$=<200 nM: α4β7 IC$_{50}$=nd;
sodium (S)-3-(3-(1,5-dimethyl-4-oxido-2-oxo-1,2-dihydropyridin-3-yl)ureido)-3-(4'-(trifluoro methoxy)biphenyl-3-yl)propanoate 1-457 (MS [M+H$^+$]$^+$: Calculated: 506.15; Measured: 506.14; α4β1 IC$_{50}$=<200 nM: α4β7 IC$_{50}$=nd;
sodium (S)-3-(3',4'-difluorobiphenyl-3-yl)-3-(3-(1,5-dimethyl-4-oxido-2-oxo-1,2-di hydropyridin-3-yl)ureido) propanoate 1-458 (MS [M+H$^+$]$^+$: Calculated: 458.15; Measured: 458.15; α4β1 IC$_{50}$=<20 nM: α4β7 IC$_{50}$=nd;
sodium (S)-3-(3-(1,5-dimethyl-4-oxido-2-oxo-1,2-dihydropyridin-3-yl)ureido)-3-(2',5'-dimethylbiphenyl-3-yl)propanoate 1-459 (MS [M+H$^+$]$^+$: Calculated: 450.20; Measured: 450.08; α4β1 IC$_{50}$=<20 nM: α4β7 IC$_{50}$=nd;
sodium (S)-3-(3-(1,5-dimethyl-4-oxido-2-oxo-1,2-dihydropyridin-3-yl)ureido)-3-(3'-(trifluoro methoxy)biphenyl-3-yl)propanoate 1-461 (MS [M+H$^+$]$^+$: Calculated: 506.15; Measured: 506.06; α4β1 IC$_{50}$=<200 nM: α4β7 IC$_{50}$=nd;
sodium (S)-3-(3-(1,5-dimethyl-4-oxido-2-oxo-1,2-dihydropyridin-3-yl)ureido)-3-(2',3'-dimethyl biphenyl-3-yl)propanoate 1-462 (MS [M+H$^+$]$^+$: Calculated: 450.20; Measured: 450.10; α4β1 IC$_{50}$=<200 nM: α4β7 IC$_{50}$=nd;
sodium (S)-3-(3-(1,5-dimethyl-4-oxido-2-oxo-1,2-dihydropyridin-3-yl)ureido)-3-(3'-(trifluoro methyl)biphenyl-3-yl)propanoate 1-461 (MS [M+H$^+$]$^+$: Calculated: 490.16; Measured: 490.08; α4β1 IC$_{50}$=<200 nM: α4β7 IC$_{50}$=nd;
sodium 3-(3-(1,5-dimethyl-4-oxido-2-oxo-1,2-dihydropyridin-3-yl)ureido)-3-(6-oxo-1-phenyl-1,6-dihydropyridin-3-yl)propanoate 1-463 (MS [M+H$^+$]$^+$: Calculated: 439.16; Measured: 438.98; α4β1 IC$_{50}$=<200 nM: α4β7 IC$_{50}$=nd;
sodium (S)-3-(2',6'-difluorobiphenyl-3-yl)-3-(3-(1,5-dimethyl-4-oxido-2-oxo-1,2-di hydropyridin-3-yl)ureido) propanoate 1-464 (MS [M+H$^+$]$^+$: Calculated: 458.15; Measured: 458.01; α4β1 IC$_{50}$=<20 nM: α4β7 IC$_{50}$=nd;
sodium (S)-3-(3-(1,5-dimethyl-4-oxido-2-oxo-1,2-dihydropyridin-3-yl)ureido)-3-(3'-fluorobiphenyl-3-yl)propanoate 1-465 (MS [M+H$^+$]$^+$: Calculated: 440.16; Measured: 440.05; α4β1 IC$_{50}$=<20 nM: α4β7 IC$_{50}$=nd;
sodium (S)-3-(3-(1,5-dimethyl-4-oxido-2-oxo-1,2-dihydropyridin-3-yl)ureido)-3-(4'-fluorobiphenyl-3-yl)propanoate 1-466 (MS [M+H$^+$]$^+$: Calculated: 440.16; Measured: 440.01; α4β1 IC$_{50}$=<20 nM: α4β7 IC$_{50}$=nd;
sodium (S)-3-(3-(1,5-dimethyl-4-oxido-2-oxo-1,2-dihydropyridin-3-yl)ureido)-3-(2'-(trifluoro methoxy)biphenyl-3-yl)propanoate 1-467 (MS [M+H$^+$]$^+$: Calculated: 506.15; Measured: 505.97; α4β1IC$_{50}$=<200 nM: α4β7 IC$_{50}$=nd;
sodium (S)-3-(2',4'-dimethoxybiphenyl-3-yl)-3-(3-(1,5-dimethyl-4-oxido-2-oxo-1,2-dihydropyridin-3-yl)ureido)propanoate 1-468 (MS [M+H$^+$]$^+$: Calculated: 482.19; Measured: 481.99; α4β1 IC$_{50}$=<200 nM: α4β7 IC$_{50}$=nd;
sodium (S)-3-(3',4'-dimethoxybiphenyl-3-yl)-3-(3-(1,5-dimethyl-4-oxido-2-oxo-1,2-dihydropyridin-3-yl)ureido)propanoate 1-469 (MS [M+H$^+$]$^+$: Calculated: 482.19; Measured: 482.00; α4β1 IC$_{50}$=<20 nM: α4β7 IC$_{50}$=nd;
sodium (S)-3-(3-(1,5-dimethyl-4-oxido-2-oxo-1,2-dihydropyridin-3-yl)ureido)-3-(2',6'-dimethyl biphenyl-3-yl)propanoate 1-470 (MS [M+H$^+$]$^+$: Calculated: 450.20; Measured: 449.97; α4β1 IC$_{50}$=<20 nM: α4β7 IC$_{50}$=<200 nM;
sodium 3-(4'-chlorobiphenyl-3-yl)-3-(3-(1,5-dimethyl-4-oxido-2-oxo-1,2-dihydropyridin-3-yl) ureido)propanoate 1-471 (MS [M+H$^+$]$^+$: Calculated: 456.13; Measured: 455.91; α4β1 IC$_{50}$=<200 nM: α4β7 IC$_{50}$=nd;
sodium 3-(3'-chlorobiphenyl-3-yl)-3-(3-(1,5-dimethyl-4-oxido-2-oxo-1,2-dihydropyridin-3-yl) ureido)propanoate 1-472 (MS [M+H$^+$]$^+$: Calculated: 456.13; Measured: 455.95; α4β1 IC$_{50}$=<200 nM: α4β7 IC$_{50}$=nd;
sodium 3-(2'-chlorobiphenyl-3-yl)-3-(3-(1,5-dimethyl-4-oxido-2-oxo-1,2-dihydropyridin-3-yl)ureido)propanoate 1-473 (MS [M+H$^+$]$^+$: Calculated: 456.13; Measured: 455.93; α4β1 IC$_{50}$=<20 nM: α4β7 IC$_{50}$=nd;
sodium (S)-3-(3-(1,5-dimethyl-4-oxido-2-oxo-1,2-dihydropyridin-3-yl)ureido)-3-(2'-(trifluoro methyl)biphenyl-3-yl)propanoate 1-474 (MS [M+H$^+$]$^+$: Calculated: 490.16; Measured: 489.96; α4β1 IC$_{50}$=<200 nM: α4β7 IC$_{50}$=nd;
sodium (S)-3-(5,6-dimethoxybiphenyl-3-yl)-3-(3-(1,5-dimethyl-4-oxido-2-oxo-1,2-dihydropyridin-3-yl)ureido)propanoate 1-475 (MS [M+H$^+$]$^+$: Calculated: 482.19; Measured: 481.95; α4β1 IC$_{50}$=<200 nM: α4β7 IC$_{50}$=nd;
sodium (S)-3-(3-(1,5-dimethyl-4-oxido-2-oxo-1,2-dihydropyridin-3-yl)ureido)-3-(3-(6-methoxy pyridin-3-yl)phenyl)propanoate 1-476 (MS [M+H$^+$]$^+$: Calculated: 453.18; Measured: 452.96; α4β1 IC$_{50}$=<20 nM: α4β7 IC$_{50}$=nd;
sodium (S)-3-(2',5'-dimethoxybiphenyl-3-yl)-3-(3-(1,5-dimethyl-4-oxido-2-oxo-1,2-dihydropyridin-3-yl)ureido)propanoate 1-477 (MS [M+H$^+$]$^+$: Calculated: 482.19; Measured: 481.96; α4β1 IC$_{50}$=<200 nM: α4β7 IC$_{50}$=nd;
sodium 3-(3-(1,5-dimethyl-4-oxido-2-oxo-1,2-dihydropyridin-3-yl)ureido)-3-(3-(pyrimidin-5-yl) phenyl)propanoate 1-478 (MS [M+H$^+$]$^+$: Calculated: 424.16; Measured: 423.92; α4β1 IC$_{50}$=<200 nM: α4β7 IC$_{50}$=nd;
sodium (S)-3-(2',6'-dimethoxybiphenyl-3-yl)-3-(3-(1,5-dimethyl-4-oxido-2-oxo-1,2-dihydropyridin-3-yl)ureido)propanoate 1-479 (MS [M+H$^+$]$^+$: Calculated: 482.19; Measured: 481.95; α4β1 IC$_{50}$=<200 nM: α4β7 IC$_{50}$=nd;
sodium (S)-3-(3-(1,5-dimethyl-4-oxido-2-oxo-1,2-dihydropyridin-3-yl)ureido)-3-(5-phenylfuran-2-yl)propanoate 1-482 (MS [M+H$^+$]$^+$: Calculated: 412.15; Measured: 411.90; α4β1 IC$_{50}$=<200 nM: α4β7 IC$_{50}$=nd;
sodium (S)-3-(3-(2,5-dimethyl-1H-pyrrol-1-yl)phenyl)-3-(3-(1,5-dimethyl-4-oxido-2-oxo-1,2-dihydropyridin-3-yl)ureido)propanoate 1-483 (MS [M+H$^+$]$^+$: Calculated: 439.20 Measured: 438.95; α4β1 IC$_{50}$=<20 nM: α4β7 IC$_{50}$=nd;

sodium 3-(3',5'-dichlorobiphenyl-3-yl)-3-(3-(1,5-dimethyl-4-oxido-2-oxo-1,2-dihydropyridin-3-yl)ureido)propanoate 1-486 (MS [M+H$^+$]$^+$: Calculated: 490.09; Measured: 489.87; α4β1 IC$_{50}$=<200 nM: α4β7 IC$_{50}$=nd;

sodium (S)-3-(2',4'-difluorobiphenyl-3-yl)-3-(3-(1,6-dimethyl-4-oxido-2-oxo-1,2-dihydropyridin-3-yl)ureido)propanoate 1-487 (MS [M+H$^+$]$^+$: Calculated: 458.15; Measured: 458.02; α4β1 IC$_{50}$=<20 nM: α4β7 IC$_{50}$=>200 nM;

sodium (S)-3-(2',4'-difluorobiphenyl-3-yl)-3-(3-(1-methyl-4-oxido-2-oxo-1,2-dihydropyridin-3-yl)ureido)propanoate 1-488 (MS [M+H$^+$]$^+$: Calculated: 444.14; Measured: 443.94; α4β1 IC$_{50}$=<20 nM: α4β7 IC$_{50}$=>200 nM sodium (S)-3-(3-(1,5-dimethyl-4-oxido-2-oxo-1,2-dihydropyridin-3-yl)ureido)-3-(3'-methoxy-2'-methylbiphenyl-3-yl)propanoate 1-489 (MS [M+H$^+$]$^+$: Calculated: 466.20; Measured: 465.97; α4β1 IC$_{50}$=<200 nM: α4β7 IC$_{50}$=nd;

sodium (S)-3-(3-(1,5-dimethyl-4-oxido-2-oxo-1,2-dihydropyridin-3-yl)ureido)-3-(5'-methoxy-2'-methylbiphenyl-3-yl)propanoate 1-490 (MS [M+H$^+$]$^+$: Calculated: 466.20; Measured: 465.96; α4β1 IC$_{50}$=<200 nM: α4β7 IC$_{50}$=nd;

sodium 3-(3-(1,5-dimethyl-4-oxido-2-oxo-1,2-dihydropyridin-3-yl)ureido)-3-(6-(2,2,2-trifluoro ethoxy)biphenyl-3-yl)propanoate 1-491 (MS [M+H$^+$]$^+$: Calculated: 520.17; Measured: 519.91; α4β1 IC$_{50}$=<200 nM: α4β7 IC$_{50}$=nd;

sodium (S)-3-(3-(1,5-dimethyl-4-oxido-2-oxo-1,2-dihydropyridin-3-yl)ureido)-3-(2'-ethylbiphenyl-3-yl)propanoate 1-492 (MS [M+H$^+$]$^+$: Calculated: 450.20; Measured: 449.95; α4β1 IC$_{50}$=<20 nM: α4β7 IC$_{50}$=nd;

sodium (S)-3-(3-(1,5-dimethyl-4-oxido-2-oxo-1,2-dihydropyridin-3-yl)ureido)-3-(4-fluorobiphenyl-3-yl)propanoate 1-493 (MS [M+H$^+$]$^+$: Calculated: 440.16; Measured: 439.93; α4β1 IC$_{50}$=<200 nM: α4β7 IC$_{50}$=nd;

sodium (S)-3-(2',4'-difluorobiphenyl-3-yl)-3-(3-(4-oxido-2-oxo-1,2-dihydropyridin-3-yl)ureido) propanoate 1-494 (MS [M+H$^+$]$^+$: Calculated: 430.12; Measured: 429.89; α4β1 IC$_{50}$=<20 nM: α4β7 IC$_{50}$=nd;

sodium (S)-3-(3-(1,5-dimethyl-4-oxido-2-oxo-1,2-dihydropyridin-3-yl)ureido)-3-(3',4'-dimethyl biphenyl-3-yl)propanoate 1-495 (MS [M+H$^+$]$^+$: Calculated: 450.20; Measured: 449.97; α4β1 IC$_{50}$=<200 nM: α4β7 IC$_{50}$=nd;

sodium (S)-3-(2',3'-difluorobiphenyl-3-yl)-3-(3-(1,5-dimethyl-4-oxido-2-oxo-1,2-dihydropyridin-3-yl)ureido)propanoate 1-496 (MS [M+H$^+$]$^+$: Calculated: 458.15; Measured: 457.90; α4β1 IC$_{50}$=<200 nM: α4β7 IC$_{50}$=nd;

sodium (S)-3-(3-(1,5-dimethyl-4-oxido-2-oxo-1,2-dihydropyridin-3-yl)ureido)-3-(4'-fluoro-3'-methylbiphenyl-3-yl) propanoate 1-497 (MS [M+H$^+$]$^+$: Calculated: 454.18; Measured: 453.91; α4β1 IC$_{50}$=<200 nM: α4β7 IC$_{50}$=nd;

sodium (S)-3-(3-(1,5-dimethyl-4-oxido-2-oxo-1,2-dihydropyridin-3-yl)ureido)-3-(1-phenyl-1H-pyrrol-2-yl)propanoate 1-498 (MS [M+H$^+$]$^+$: Calculated: 411.17; Measured: 410.87; α4β1 IC$_{50}$=>200 nM: α4β7 IC$_{50}$=nd;

sodium (S)-3-(3'-chlorobiphenyl-3-yl)-3-(3-(1,5-dimethyl-4-oxido-2-oxo-1,2-dihydropyridin-3-yl)ureido)propanoate 1-499 (MS [M+H$^+$]$^+$: Calculated: 456.13; Measured: 455.89; α4β1 IC$_{50}$=<20 nM: α4β7IC$_{50}$=nd;

sodium (S)-3-(3-(1,5-dimethyl-4-oxido-2-oxo-1,2-dihydropyridin-3-yl)ureido)-3-(2-methyl biphenyl-3-yl)propanoate 1-500 (MS [M+H$^+$]$^+$: Calculated: 436.19; Measured: 435.94; α4β1 IC$_{50}$=>200 nM: α4β7 IC$_{50}$=nd;

sodium (S)-3-(3'-methoxybiphenyl-3-yl)-3-(3-(1-methyl-4-oxido-2-oxo-1,2-dihydropyridin-3-yl)ureido)propanoate 1-501 (MS [M+H$^+$]$^+$: Calculated: 438.17; Measured: 437.93; α4β1 IC$_{50}$=<20 nM: α4β7 IC$_{50}$=nd;

sodium (S)-3-(2',6'-dimethylbiphenyl-3-yl)-3-(3-(1-methyl-4-oxido-2-oxo-1,2-dihydropyridin-3-yl) ureido)propanoate 1-502 (MS [M+H$^+$]$^+$: Calculated: 436.19; Measured: 436.03; α4β1 IC$_{50}$=<20 nM: α4β7 IC$_{50}$=<200 nM;

sodium 3-(5'-chloro-2',4'-difluorobiphenyl-3-yl)-3-(3-(1,5-dimethyl-4-oxido-2-oxo-1,2-dihydro pyridin-3-yl)ureido) propanoate 1-503 (MS [M+H$^+$]$^+$: Calculated: 492.11; Measured: 491.83; α4β1 IC$_{50}$=<200 nM: α4β7 IC$_{50}$=nd;

sodium (S)-3-(2',3'-dimethoxybiphenyl-3-yl)-3-(3-(1,5-dimethyl-4-oxido-2-oxo-1,2-dihydropyridin-3-yl)ureido)propanoate 1-504 (MS [M+H$^+$]$^+$: Calculated: 482.19; Measured: 482.01; α4β1 IC$_{50}$=<20 nM: α4β7 IC$_{50}$=nd;

sodium (S)-3-(biphenyl-3-yl)-3-(3-(1-methyl-4-oxido-2-oxo-1,2-dihydropyridin-3-yl)ureido) propanoate 1-505 (MS [M+H$^+$]$^+$: Calculated: 408.16; Measured: 407.93; α4β1 IC$_{50}$=<20 nM: α4β7 IC$_{50}$=nd;

sodium (S)-3-(3'-chlorobiphenyl-3-yl)-3-(3-(1-methyl-4-oxido-2-oxo-1,2-dihydro pyridin-3-yl)ureido)propanoate 1-506 (MS [M+H$^+$]$^+$: Calculated: 442.12; Measured: 441.85; α4β1 IC$_{50}$=<20 nM: α4β7 IC$_{50}$=nd;

sodium (S)-3-(3-(1H-pyrrol-1-yl)phenyl)-3-(3-(1-methyl-4-oxido-2-oxo-1,2-dihydro pyridin-3-yl)ureido)propanoate 1-507 (MS [M+H$^+$]$^+$: Calculated: 397.15; Measured: 396.90; α4β1 IC$_{50}$=<20 nM: α4β7 IC$_{50}$=nd;

sodium (S)-3-(3-(6-methoxypyridin-3-yl)phenyl)-3-(3-(1-methyl-4-oxido-2-oxo-1,2-dihydropyridin-3-yl)ureido) propanoate 1-508 (MS [M+H$^+$]$^+$: Calculated: 439.16; Measured: 439.01; α4β1 IC$_{50}$=<20 nM: α4β7IC$_{50}$=nd;

sodium (S)-3-(2'-fluoro-3'-methoxybiphenyl-3-yl)-3-(3-(1-methyl-4-oxido-2-oxo-1,2-dihydropyridin-3-yl)ureido) propanoate 1-509 (MS [M+H$^+$]$^+$: Calculated: 456.16; Measured: 456.00; α4β1 IC$_{50}$=<20 nM: α4β7 IC$_{50}$=nd;

sodium (S)-3-(3-(1-methyl-4-oxido-2-oxo-1,2-dihydropyridin-3-yl)ureido)-3-(4'-(trifluoromethoxy) biphenyl-3-yl) propanoate 1-510 (MS [M+H$^+$]$^+$: Calculated: 492.14; Measured: 491.97; α4β1IC$_{50}$=<20 nM: α4β7 IC$_{50}$=nd;

sodium 3-(2',4'-dichlorobiphenyl-3-yl)-3-(3-(1,5-dimethyl-4-oxido-2-oxo-1,2-dihydropyridin-3-yl)ureido)propanoate 1-511 (MS [M+H$^+$]$^+$: Calculated: 490.09; Measured: 489.97; α4β1 IC$_{50}$=<200 nM: α4β7 IC$_{50}$=nd;

sodium (S)-3-(3-(1-methyl-4-oxido-2-oxo-1,2-dihydropyridin-3-yl)ureido)-3-(2'-(trifluoromethoxy) biphenyl-3-yl) propanoate 1-512 (MS [M+H$^+$]$^+$: Calculated: 492.14; Measured: 492.00; α4β1 IC$_{50}$=<20 nM: α4β7 IC$_{50}$=nd;

sodium (S)-3-(2',4'-difluorobiphenyl-3-yl)-3-(3-(1-methyl-4-oxido-2-oxo-2,5,6,7-tetrahydro-1H-cyclopenta[b]pyridin-3-yl)ureido)propanoate 1-513 (MS [M+H$^+$]$^+$: Calculated: 484.17; Measured: 484.01; α4β1 IC$_{50}$=<20 nM: α4β7IC$_{50}$=nd;

sodium (S)-3-(3-(1-methyl-4-oxido-2-oxo-1,2-dihydropyridin-3-yl)ureido)-3-(3'-(trifluoromethoxy) biphenyl-3-yl) propanoate 1-514 (MS [M+H$^+$]$^+$: Calculated: 492.14; Measured: 492.02; α4β1 IC$_{50}$=<20 nM: α4β7 IC$_{50}$=nd;

sodium (S)-3-(2',4'-difluorobiphenyl-3-yl)-3-(3-(4-methyl-7-oxido-5-oxo-4,5-dihydrothieno[3,2-b]pyridin-6-yl) ureido)propanoate 1-515 (MS [M+H$^+$]$^+$: Calculated: 500.11; Measured: 499.95; α4β1 IC$_{50}$=<20 nM: α4β7 IC$_{50}$=nd;

sodium (S)-3-(3-(benzo[d][1,3]dioxol-5-yl)phenyl)-3-(3-(1-methyl-4-oxido-2-oxo-1,2-dihydro pyridin-3-yl)ureido) propanoate 1-516 (MS [M+H$^+$]$^+$: Calculated: 452.15; Measured: 452.00; α4β1 IC$_{50}$=<20 nM: α4β7 IC$_{50}$=nd;

sodium (S)-3-(3-(benzo[d][1,3]dioxol-5-yl)phenyl)-3-(3-(1,5-dimethyl-4-oxido-2-oxo-1,2-dihydropyridin-3-yl) ureido)propanoate 1-517 (MS [M+H$^+$]$^+$: Calculated: 466.16; Measured: 466.02; α4β1 IC$_{50}$=<20 nM: α4β7 IC$_{50}$=nd;

sodium (S)-3-(3-(1H-indazol-1-yl)phenyl)-3-(3-(1-methyl-4-oxido-2-oxo-1,2-dihydropyridin-3-yl)ureido)propanoate 1-518 (MS [M+H⁺]⁺: Calculated: 448.16; Measured: 448.05; α4β1 IC$_{50}$=<20 nM: α4β7 IC$_{50}$=nd;

sodium (S)-3-(2',4'-difluoro-6-methoxybiphenyl-3-yl)-3-(3-(1-methyl-4-oxido-2-oxo-1,2-dihydro pyridin-3-yl) ureido)propanoate 1-519 (MS [M+H⁺]⁺: Calculated: 474.15; Measured: 474.06; α4β1 IC$_{50}$=<20 nM: α4β7 IC$_{50}$=nd;

sodium (S)-3-(3-(1,5-dimethyl-4-oxido-2-oxo-1,2-dihydropyridin-3-yl)ureido)-3-(4-phenyl thiophen-2-yl)propanoate 1-520 (MS [M+H⁺]⁺: Calculated: 428.13; Measured: 427.92; α4β1 IC$_{50}$=<20 nM: α4β7 IC$_{50}$=nd;

sodium (S)-3-(3-(1-ethyl-1H-indol-6-yl)phenyl)-3-(3-(1-methyl-4-oxido-2-oxo-1,2-dihydropyridin-3-yl)ureido) propanoate 1-521 (MS [M+H⁺]⁺: Calculated: 475.20; Measured: 475.10; α4β1 IC$_{50}$=<20 nM: α4β7 IC$_{50}$=nd;

sodium (S)-3-(3-(1H-pyrazol-1-yl)phenyl)-3-(3-(1-methyl-4-oxido-2-oxo-1,2-dihydropyridin-3-yl) ureido)propanoate 1-522 (MS [M+H⁺]⁺: Calculated: 398.15; Measured: 398.02; α4β1IC$_{50}$=<20 nM: α4β7 IC$_{50}$=nd;

sodium (S)-3-(4-(2,4-difluorophenyl)thiophen-2-yl)-3-(3-(1-methyl-4-oxido-2-oxo-1,2-dihydro pyridin-3-yl) ureido)propanoate 1-523 (MS [M+H⁺]⁺: Calculated: 450.09; Measured: 449.92; α4β1 IC$_{50}$=<20 nM: α4β7 IC$_{50}$=nd;

sodium (S)-3-(3',6-dimethoxybiphenyl-3-yl)-3-(3-(1-methyl-4-oxido-2-oxo-1,2-di hydropyridin-3-yl)ureido) propanoate 1-524 (MS [M+H⁺]⁺: Calculated: 468.18; Measured: 468.05; α4β1 IC$_{50}$=<20 nM: α4β7 IC$_{50}$=nd;

sodium (S)-3-(2',4'-difluorobiphenyl-3-yl)-3-(3-(1-methyl-4-oxido-2-oxo-1,2-dihydro-1,8-naphthyridin-3-yl)ureido) propanoate 1-526 (MS [M+H⁺]⁺: Calculated: 495.15; Measured: 494.96; α4β1 IC$_{50}$=<200 nM: α4β7IC$_{50}$=nd;

sodium (S)-3-(3',6-dimethoxybiphenyl-3-yl)-3-(3-(1,5-dimethyl-4-oxido-2-oxo-1,2-dihydropyridin-3-yl)ureido)propanoate 1-527 (MS [M+H⁺]⁺: Calculated: 482.19; Measured: 482.02; α4β1 IC$_{50}$=<20 nM: α4β7 IC$_{50}$=>200 nM;

sodium (S)-3-(4-(3-methoxyphenyl)thiophen-2-yl)-3-(3-(1-methyl-4-oxido-2-oxo-1,2-dihydro pyridin-3-yl)ureido) propanoate 1-528 (MS [M+H⁺]⁺: Calculated: 444.12; Measured: 444.01; α4β1 IC$_{50}$=<20 nM: α4β7 IC$_{50}$=nd;

sodium (S)-3-(6-methoxybiphenyl-3-yl)-3-(3-(1-methyl-4-oxido-2-oxo-1,2-dihydro pyridin-3-yl)ureido)propanoate 1-529 (MS [M+H⁺]⁺: Calculated: 438.17; Measured: 438.02; α4β1 IC$_{50}$=<20 nM: α4β7 IC$_{50}$=nd;

sodium (S)-3-(4-(3-chlorophenyl)thiophen-2-yl)-3-(3-(1-methyl-4-oxido-2-oxo-1,2-dihydropyridin-3-yl)ureido) propanoate 1-530 (MS [M+H⁺]⁺: Calculated: 448.07; Measured: 447.99; α4β1 IC$_{50}$=<20 nM: α4β7 IC$_{50}$=nd;

sodium (S)-3-(2',4'-difluorobiphenyl-3-yl)-3-(3-(1-ethyl-4-oxido-2-oxo-1,2-dihydro pyridin-3-yl)ureido)propanoate 1-531 (MS [M+H⁺]⁺: Calculated: 458.15; Measured: 458.02; α4β1 IC$_{50}$=<20 nM: α4β7 IC$_{50}$=nd;

sodium (S)-3-(3-(1-methyl-4-oxido-2-oxo-1,2-dihydropyridin-3-yl)ureido)-3-(3-(thiophen-2-yl)phenyl)propanoate 1-532 (MS [M+H⁺]⁺: Calculated: 414.11; Measured: 414.00; α4β1 IC$_{50}$=<20 nM: α4β7 IC$_{50}$=nd;

sodium (S)-3-(6-methoxy-2',6'-dimethylbiphenyl-3-yl)-3-(3-(1-methyl-4-oxido-2-oxo-1,2-dihydro pyridin-3-yl) ureido)propanoate 1-533 (MS [M+H⁺]⁺: Calculated: 466.20; Measured: 466.01; α4β1 IC$_{50}$=<20 nM: α4β7 IC$_{50}$=<200 nM;

sodium (S)-3-(3'-chloro-6-methoxybiphenyl-3-yl)-3-(3-(1-methyl-4-oxido-2-oxo-1,2-dihydro pyridin-3-yl)ureido) propanoate 1-534 (MS [M+H⁺]⁺: Calculated: 472.13; Measured: 472.00; α4β1 IC$_{50}$=<20 nM: α4β7 IC$_{50}$=nd;

sodium (S)-3-(6-methoxy-3'-(trifluoromethoxy)biphenyl-3-yl)-3-(3-(1-methyl-4-oxido-2-oxo-1,2-dihydropyridin-3-yl)ureido)propanoate 1-535 (MS [M+H⁺]⁺: Calculated: 522.15; Measured: 521.95; α4β1 IC$_{50}$=<20 nM: α4β7 IC$_{50}$=nd;

sodium (S)-3-(6-methoxy-4'-(trifluoromethoxy)biphenyl-3-yl)-3-(3-(1-methyl-4-oxido-2-oxo-1,2-dihydropyridin-3-yl)ureido)propanoate 1-536 (MS [M+H⁺]⁺: Calculated: 522.15; Measured: 521.98; α4β1 IC$_{50}$=<20 nM: α4β7 IC$_{50}$=nd;

sodium (S)-3-(2',6'-dichlorobiphenyl-3-yl)-3-(3-(1-methyl-4-oxido-2-oxo-1,2-dihydropyridin-3-yl)ureido)propanoate 1-537 (MS [M+H⁺]⁺: Calculated: 476.08; Measured: 475.94; α4β1 IC$_{50}$=<20 nM: α4β7 IC$_{50}$=<200 nM;

sodium (S)-3-(3-(5-chlorothiophen-2-yl)phenyl)-3-(3-(1-methyl-4-oxido-2-oxo-1,2-dihydropyridin-3-yl)ureido) propanoate 1-538 (MS [M+H⁺]⁺: Calculated: 448.07; Measured: 447.92; α4β1 IC$_{50}$=<20 nM: α4β7 IC$_{50}$=nd;

sodium (S)-3-(3-(1H-imidazol-1-yl)phenyl)-3-(3-(1-methyl-4-oxido-2-oxo-1,2-dihydropyridin-3-yl)ureido) propanoate 1-539 (MS [M+H⁺]⁺: Calculated: 398.15; Measured: 398.07; α4β1 IC$_{50}$=<20 nM: α4β7 IC$_{50}$=nd;

sodium (S)-3-(3-(1-methyl-4-oxido-2-oxo-1,2-dihydropyridin-3-yl)ureido)-3-(3-(4-methylthiophen-3-yl)phenyl) propanoate 1-540 (MS [M+H⁺]⁺: Calculated: 428.13; Measured: 427.96; α4β1 IC$_{50}$=<20 nM: α4β7 IC$_{50}$=nd;

sodium (S)-3-(2',4'-difluoro-6-methylbiphenyl-3-yl)-3-(3-(1-methyl-4-oxido-2-oxo-1,2-dihydro pyridin-3-yl) ureido)propanoate 1-541 (MS [M+H⁺]⁺: Calculated: 458.15; Measured: 457.96; α4β1 IC$_{50}$=<20 nM: α4β7 IC$_{50}$=nd;

sodium (S)-3-(3'-methoxy-6-methylbiphenyl-3-yl)-3-(3-(1-methyl-4-oxido-2-oxo-1,2-dihydro pyridin-3-yl)ureido) propanoate 1-542 (MS [M+H⁺]⁺: Calculated: 452.18; Measured: 452.02; α4β1 IC$_{50}$=<20 nM: α4β7 IC$_{50}$=nd;

sodium (S)-3-(3-(1,5-dimethyl-4-oxido-2-oxo-1,2-dihydropyridin-3-yl)ureido)-3-(4-(2,6-dimethyl phenyl)thiophen-2-yl)propanoate 1-543 (MS [M+H⁺]⁺: Calculated: 442.14; Measured: 441.91; α4β1 IC$_{50}$=<20 nM: α4β7 IC$_{50}$=nd;

sodium (S)-3-(3-(1H-pyrrol-3-yl)phenyl)-3-(3-(1-methyl-4-oxido-2-oxo-1,2-dihydro pyridin-3-yl)ureido)propanoate 1-544 (MS [M+H⁺]⁺: Calculated: 397.15; Measured: 397.00; α4β1 IC$_{50}$=<20 nM: α4β7 IC$_{50}$=nd;

sodium (S)-3-(3-(1-methyl-4-oxido-2-oxo-1,2-dihydropyridin-3-yl)ureido)-3-(2',6,6'-trimethyl biphenyl-3-yl)propanoate 1-545 (MS [M+H⁺]⁺: Calculated: 450.20; Measured: 450.06; α4β1 IC$_{50}$=<20 nM: α4β7 IC$_{50}$=nd;

sodium (S)-3-(3-(1-methyl-4-oxido-2-oxo-1,2-dihydropyridin-3-yl)ureido)-3-(2',6,6'-trifluoro biphenyl-3-yl)propanoate 1-546 (MS [M+H⁺]⁺: Calculated: 462.13; Measured: 462.01; α4β1 IC$_{50}$=<20 nM: α4β7 IC$_{50}$=nd;

sodium (S)-3-(6-fluoro-3'-methoxybiphenyl-3-yl)-3-(3-(1-methyl-4-oxido-2-oxo-1,2-dihydro pyridin-3-yl)ureido) propanoate 1-547 (MS [M+H⁺]⁺: Calculated: 456.16; Measured: 456.04; α4β1 IC$_{50}$=<20 nM: α4β7 IC$_{50}$=nd;

sodium (S)-3-(3-(1-methyl-1H-pyrazol-4-yl)phenyl)-3-(3-(1-methyl-4-oxido-2-oxo-1,2-dihydro pyridin-3-yl) ureido)propanoate 1-548 (MS [M+H⁺]⁺: Calculated: 412.16; Measured: 411.98; α4β1 IC$_{50}$=<20 nM: α4β7 IC$_{50}$=nd;

sodium (S)-3-(2',4'-difluorobiphenyl-3-yl)-3-(3-(2-methyl-5-oxido-3-oxo-2,3-dihydropyridazin-4-yl)ureido)propanoate 1-549 (MS [M−H⁺]⁻: Calculated: 443.12; Measured: 443.10; α4β1IC$_{50}$=<20 nM: α4β7 IC$_{50}$=nd;

sodium (S)-3-(3-(1,6-dimethyl-4-oxido-2-oxo-1,2-dihydropyridin-3-yl)ureido)-3-(2',6'-dimethylbiphenyl-3-yl)propanoate 1-550 (MS [M+H⁺]⁺: Calculated: 450.20; Measured: 450.00; α4β1 IC$_{50}$=<20 nM: α4β7 IC$_{50}$=<200 nM;

sodium (S)-3-(3',6-dimethoxybiphenyl-3-yl)-3-(3-(1,6-dimethyl-4-oxido-2-oxo-1,2-dihydropyridin-3-yl)ureido)propanoate 1-551 (MS [M+H$^+$]$^+$: Calculated: 482.19; Measured: 481.99; α4β1 IC$_{50}$=<20 nM: α4β7 IC$_{50}$=nd;

sodium (S)-3-(4-(2,4-difluorophenyl)thiophen-2-yl)-3-(3-(1,6-dimethyl-4-oxido-2-oxo-1,2-dihydropyridin-3-yl)ureido)propanoate 1-552 (MS [M+H$^+$]$^+$: Calculated: 464.11; Measured: 463.98; α4β1 IC$_{50}$=<20 nM: α4β7 IC$_{50}$=nd;

sodium (S)-3-(3-(1,6-dimethyl-4-oxido-2-oxo-1,2-dihydropyridin-3-yl)ureido)-3-(3'-methoxy biphenyl-3-yl)propanoate 1-553 (MS [M+H$^+$]$^+$: Calculated: 452.18; Measured: 452.01; α4β1IC$_{50}$=<20 nM: α4β7 IC$_{50}$=nd;

sodium (S)-3-(3-(1,6-dimethyl-4-oxido-2-oxo-1,2-dihydropyridin-3-yl)ureido)-3-(6-methoxy-3'-(trifluoromethoxy)biphenyl-3-yl)propanoate 1-554 (MS [M+H$^+$]$^+$: Calculated: 536.16; Measured: 535.94; α4β1 IC$_{50}$=<20 nM: α4β7 IC$_{50}$=nd;

sodium (S)-3-(3'-chloro-6-methylbiphenyl-3-yl)-3-(3-(1-methyl-4-oxido-2-oxo-1,2-dihydropyridin-3-yl)ureido)propanoate 1-555 (MS [M+H$^+$]$^+$: Calculated: 456.13; Measured: 456.00; α4β1 IC$_{50}$=<20 nM: α4β7 IC$_{50}$=nd;

sodium (S)-3-(3'-chlorobiphenyl-3-yl)-3-(3-(1,6-dimethyl-4-oxido-2-oxo-1,2-dihydropyridin-3-yl)ureido)propanoate 1-556 (MS [M+H$^+$]$^+$: Calculated: 456.13; Measured: 455.99; α4β1 IC$_{50}$=<20 nM: α4β7 IC$_{50}$=nd;

sodium (S)-3-(2',4'-difluorobiphenyl-3-yl)-3-(3-(6-methyl-4-oxido-2-oxo-1,2-dihydropyridin-3-yl)ureido)propanoate 1-557 (MS [M+H$^+$]$^+$: Calculated: 444.14; Measured: 443.99; α4β1 IC$_{50}$=>200 nM: α4β7 IC$_{50}$=nd;

sodium (S)-3-(5-methoxybiphenyl-3-yl)-3-(3-(1-methyl-4-oxido-2-oxo-1,2-dihydropyridin-3-yl)ureido)propanoate 1-558 (MS [M+H$^+$]$^+$: Calculated: 438.17; Measured: 437.99; α4β1 IC$_{50}$=<20 nM: α4β7 IC$_{50}$=nd;

sodium (S)-3-(3-(furan-3-yl)phenyl)-3-(3-(1-methyl-4-oxido-2-oxo-1,2-dihydropyridin-3-yl)ureido) propanoate 1-559 (MS [M+H$^+$]$^+$: Calculated: 398.13; Measured: 397.93; α4β1 IC$_{50}$=<20 nM: α4β7 IC$_{50}$=nd;

sodium (S)-3-(3-(3,5-dimethylisoxazol-4-yl)phenyl)-3-(3-(1-methyl-4-oxido-2-oxo-1,2-dihydro pyridin-3-yl)ureido)propanoate 1-560 (MS [M+H$^+$]$^+$: Calculated: 427.16; Measured: 426.98; α4β1 IC$_{50}$=<20 nM: α4β7 IC$_{50}$=>200 nM;

sodium (S)-3-(6-fluoro-2',6'-dimethylbiphenyl-3-yl)-3-(3-(1-methyl-4-oxido-2-oxo-1,2-dihydro pyridin-3-yl)ureido)propanoate 1-561 (MS [M+H$^+$]$^+$: Calculated: 454.18; Measured: 453.99; α4β1 IC$_{50}$=<20 nM: α4β7 IC$_{50}$=<20 nM;

sodium (S)-3-(5-(2,4-difluorophenyl)thiophen-2-yl)-3-(3-(1-methyl-4-oxido-2-oxo-1,2-dihydro pyridin-3-yl)ureido)propanoate 1-562 (MS [M+H$^+$]$^+$: Calculated: 450.09; Measured: 449.95; α4β1 IC$_{50}$=<20 nM: α4β7 IC$_{50}$=>200 nM;

sodium (S)-3-(5-(3-methoxyphenyl)thiophen-2-yl)-3-(3-(1-methyl-4-oxido-2-oxo-1,2-dihydro pyridin-3-yl)ureido)propanoate 1-563 (MS [M+H$^+$]$^+$: Calculated: 444.12; Measured: 443.90; α4β1 IC$_{50}$=<20 nM: α4β7 IC$_{50}$=nd;

sodium (S)-3-(3',5-dimethoxybiphenyl-3-yl)-3-(3-(1-methyl-4-oxido-2-oxo-1,2-dihydropyridin-3-yl)ureido) propanoate 1-564 (MS [M+H$^+$]$^+$: Calculated: 468.18; Measured: 467.99; α4β1 IC$_{50}$=<20 nM: α4β7IC$_{50}$=nd;

sodium (S)-3-(5-methoxy-3'-(trifluoromethoxy)biphenyl-3-yl)-3-(3-(1-methyl-4-oxido-2-oxo-1,2-dihydropyridin-3-yl)ureido)propanoate 1-565 (MS [M+H$^+$]$^+$: Calculated: 522.15; Measured: 521.95; α4β1 IC$_{50}$=<20 nM: α4β7 IC$_{50}$=nd;

sodium (S)-3-(2',4'-difluoro-5-methoxybiphenyl-3-yl)-3-(3-(1-methyl-4-oxido-2-oxo-1,2-dihydropyridin-3-yl)ureido)propanoate 1-566 (MS [M+H$^+$]$^+$: Calculated: 474.15; Measured: 473.92; α4β1 IC$_{50}$=<20 nM: α4β7IC$_{50}$=nd;

sodium (S)-3-(3-(1,6-dimethyl-4-oxido-2-oxo-1,2-dihydropyridin-3-yl)ureido)-3-(5-methoxy-3'-(trifluoromethoxy)biphenyl-3-yl)propanoate 1-568 (MS [M+H$^+$]$^+$: Calculated: 536.16; Measured: 535.96; α4β1 IC$_{50}$=<20 nM: α4β7 IC$_{50}$=nd;

sodium (S)-3-(3-(1,6-dimethyl-4-oxido-2-oxo-1,2-dihydropyridin-3-yl)ureido)-3-(3'-methoxy-6-methylbiphenyl-3-yl)propanoate 1-569 (MS [M+H$^+$]$^+$: Calculated: 466.20; Measured: 465.99; α4β1 IC$_{50}$=<20 nM: α4β7 IC$_{50}$=nd;

sodium (S)-3-(4-fluorobiphenyl-3-yl)-3-(3-(1-methyl-4-oxido-2-oxo-1,2-dihydropyridin-3-yl)ureido)propanoate 1-570 (MS [M+H$^+$]$^+$: Calculated: 426.15; Measured: 425.98; α4β1 IC$_{50}$=<20 nM: α4β7 IC$_{50}$=nd;

sodium (S)-3-(3-(1-methyl-4-oxido-2-oxo-1,2-dihydropyridin-3-yl)ureido)-3-(6-phenylpyridin-2-yl)propanoate 1-571 (MS [M+H$^+$]$^+$: Calculated: 409.15; Measured: 408.99; α4β1 IC$_{50}$=<20 nM: α4β7 IC$_{50}$=nd;

sodium (S)-3-(5-methyl-3'-(trifluoromethoxy)biphenyl-3-yl)-3-(3-(1-methyl-4-oxido-2-oxo-1,2-dihydropyridin-3-yl)ureido)propanoate 1-572 (MS [M+H$^+$]$^+$: Calculated: 506.15; Measured: 506.12; α4β1 IC$_{50}$=<20 nM: α4β7 IC$_{50}$=>200 nM;

sodium (S)-3-(3-(1-methyl-4-oxido-2-oxo-1,2-dihydropyridin-3-yl)ureido)-3-(2',5,6'-trimethyl biphenyl-3-yl)propanoate 1-573 (MS [M+H$^+$]$^+$: Calculated: 450.20; Measured: 450.01; α4β1 IC$_{50}$=<20 nM: α4β7 IC$_{50}$=nd;

sodium (S)-3-(2',4'-difluoro-5-methylbiphenyl-3-yl)-3-(3-(1-methyl-4-oxido-2-oxo-1,2-dihydro pyridin-3-yl)ureido)propanoate 1-574 (MS [M+H$^+$]$^+$: Calculated: 458.15; Measured: 457.95; α4β1 IC$_{50}$=<20 nM: α4β7 IC$_{50}$=nd;

sodium (S)-3-(2',4'-difluoro-5-methylbiphenyl-3-yl)-3-(3-(1,6-dimethyl-4-oxido-2-oxo-1,2-dihydro pyridin-3-yl)ureido)propanoate 1-575 (MS [M+H$^+$]$^+$: Calculated: 472.17; Measured: 471.96; α4β1 IC$_{50}$=<20 nM: α4β7 IC$_{50}$=nd;

sodium (S)-3-(6-methyl-3'-(trifluoromethoxy)biphenyl-3-yl)-3-(3-(1-methyl-4-oxido-2-oxo-1,2-dihydropyridin-3-yl)ureido)propanoate 1-576 (MS [M+H$^+$]$^+$: Calculated: 506.15; Measured: 506.00; α4β1 IC$_{50}$=<20 nM: α4β7 IC$_{50}$=nd;

sodium (S)-3-(3-(1,6-dimethyl-4-oxido-2-oxo-1,2-dihydropyridin-3-yl)ureido)-3-(6-methyl-3'-(trifluoro methoxy)biphenyl-3-yl)propanoate 1-577 (MS [M+H$^+$]$^+$: Calculated: 520.17; Measured: 520.10; α4β1 IC$_{50}$=<20 nM: α4β7 IC$_{50}$=nd;

sodium (S)-3-(3-(1,6-dimethyl-4-oxido-2-oxo-1,2-dihydropyridin-3-yl)ureido)-3-(6-fluoro-2',6'-dimethylbiphenyl-3-yl)propanoate 1-578 (MS [M+H$^+$]$^+$: Calculated: 468.19; Measured: 468.03; α4β1 IC$_{50}$=<20 nM: α4β7 IC$_{50}$=nd;

sodium (S)-3-(5-methoxy-2',6'-dimethylbiphenyl-3-yl)-3-(3-(1-methyl-4-oxido-2-oxo-1,2-dihydro pyridin-3-yl)ureido)propanoate 1-579 (MS [M+H$^+$]$^+$: Calculated: 466.20; Measured: 466.05; α4β1 IC$_{50}$=<20 nM: α4β7 IC$_{50}$=<20 nM;

sodium (S)-3-(3-(1,6-dimethyl-4-oxido-2-oxo-1,2-dihydropyridin-3-yl)ureido)-3-(5-methoxy-2',6'-dimethylbiphenyl-3-yl)propanoate 1-580 (MS [M+H$^+$]$^+$: Calculated: 480.21; Measured: 480.03; α4β1 IC$_{50}$=<20 nM: α4β7 IC$_{50}$=<20 nM;

sodium (S)-3-(2',4'-difluoro-5-methoxybiphenyl-3-yl)-3-(3-(1,6-dimethyl-4-oxido-2-oxo-1,2-dihydropyridin-3-yl)ureido)propanoate 1-581 (MS [M+H$^+$]$^+$: Calculated: 488.16; Measured: 487.98; α4β1 IC$_{50}$=<20 nM: α4β7 IC$_{50}$=nd;

sodium (S)-3-(3'-methoxy-5-methylbiphenyl-3-yl)-3-(3-(1-methyl-4-oxido-2-oxo-1,2-dihydro pyridin-3-yl)ureido)propanoate 1-582 (MS [M+H$^+$]$^+$: Calculated: 452.18; Measured: 452.02; α4β1IC$_{50}$=<20 nM: α4β7 IC$_{50}$=<200 nM;

sodium (S)-3-(2',6'-dimethylbiphenyl-3-yl)-3-(3-(7-oxido-5-oxo-1,2,3,5-tetrahydro indolizin-6-yl)ureido)propanoate 1-583 (MS [M+H$^+$]$^+$: Calculated: 462.20; Measured: 462.28; α4β1 IC$_{50}$=<20 nM: α4β7 IC$_{50}$=<20 nM;

sodium (S)-3-(4'-methyl-2,3'-bithiophen-5-yl)-3-(3-(1-methyl-4-oxido-2-oxo-1,2-di hydropyridin-3-yl)ureido)propanoate 1-584 (MS [M+H$^+$]$^+$: Calculated: 434.08; Measured: 434.05; α4β1 IC$_{50}$=<20 nM: α4β7 IC$_{50}$=nd;

sodium (S)-3-(3-(1,6-dimethyl-4-oxido-2-oxo-1,2-dihydropyridin-3-yl)ureido)-3-(4'-methyl-2,3'-bithiophen-5-yl)propanoate 1-585 (MS [M+H$^+$]$^+$: Calculated: 448.10; Measured: 448.06; α4β1 IC$_{50}$=<20 nM: α4β7 IC$_{50}$=nd;

sodium (S)-3-(3-(1,6-dimethyl-4-oxido-2-oxo-1,2-dihydropyridin-3-yl)ureido)-3-(3'-methoxy-5-methylbiphenyl-3-yl)propanoate 1-586 (MS [M+H$^+$]$^+$: Calculated: 466.20; Measured: 466.39; α4β1 IC$_{50}$=<20 nM: α4β7IC$_{50}$=nd;

sodium (S)-3-(5-(2,6-dimethylphenyl)thiophen-2-yl)-3-(3-(1-methyl-4-oxido-2-oxo-1,2-dihydro pyridin-3-yl)ureido)propanoate 1-587 (MS [M+H$^+$]$^+$: Calculated: 442.14; Measured: 442.09; α4β1 IC$_{50}$=<20 nM: α4β7 IC$_{50}$=nd;

sodium (S)-3-(3-(1,6-dimethyl-4-oxido-2-oxo-1,2-dihydropyridin-3-yl)ureido)-3-(5-(2,6-dimethyl phenyl)thiophen-2-yl)propanoate 1-588 (MS [M+H$^+$]$^+$: Calculated: 456.16; Measured: 456.07; α4β1 IC$_{50}$=<20 nM: α4β7 IC$_{50}$=nd;

sodium (S)-3-(3-(1,6-dimethyl-4-oxido-2-oxo-1,2-dihydropyridin-3-yl)ureido)-3-(4-fluoro-2',6'-dimethylbiphenyl-3-yl)propanoate 1-589 (MS [M+H$^+$]$^+$: Calculated: 468.19; Measured: 468.32; α4β1 IC$_{50}$=<20 nM: α4β7 IC$_{50}$=nd;

sodium (S)-3-(4-fluoro-2',6'-dimethylbiphenyl-3-yl)-3-(3-(1-methyl-4-oxido-2-oxo-1,2-dihydro pyridin-3-yl)ureido)propanoate 1-590 (MS [M+H$^+$]$^+$: Calculated: 454.18; Measured: 454.32; α4β1 IC$_{50}$=<20 nM: α4β7 IC$_{50}$=<20 nM;

sodium (S)-3-(4-fluoro-3'-methoxybiphenyl-3-yl)-3-(3-(1-methyl-4-oxido-2-oxo-1,2-dihydropyridin-3-yl)ureido)propanoate 1-593 (MS [M+H$^+$]$^+$: Calculated: 456.16; Measured: 456.29; α4β1 IC$_{50}$=<20 nM: α4β7 IC$_{50}$=nd;

sodium (S)-3-(4-fluoro-3'-(trifluoromethoxy)biphenyl-3-yl)-3-(3-(1-methyl-4-oxido-2-oxo-1,2-dihydro pyridin-3-yl)ureido)propanoate 1-594 (MS [M+H$^+$]$^+$: Calculated: 510.13; Measured: 510.27; α4β1 IC$_{50}$=<20 nM: α4β7 IC$_{50}$=nd;

sodium (S)-3-(3-(1,6-dimethyl-4-oxido-2-oxo-1,2-dihydropyridin-3-yl)ureido)-3-(4-fluoro-3'-(trifluoro methoxy)biphenyl-3-yl)propanoate 1-595 (MS [M+H$^+$]$^+$: Calculated: 524.14; Measured: 524.27; α4β1 IC$_{50}$=<20 nM: α4β7 IC$_{50}$=nd;

sodium (S)-3-(4-methoxybiphenyl-3-yl)-3-(3-(1-methyl-4-oxido-2-oxo-1,2-dihydro pyridin-3-yl)ureido)propanoate 1-596 (MS [M+H$^+$]$^+$: Calculated: 438.17; Measured: 438.27; α4β1 IC$_{50}$=<20 nM: α4β7 IC$_{50}$=nd;

sodium (S)-3-(3-(1,6-dimethyl-4-oxido-2-oxo-1,2-dihydropyridin-3-yl)ureido)-3-(2',5,6'-trimethyl biphenyl-3-yl)propanoate 1-597 (MS [M+H$^+$]$^+$: Calculated: 464.22; Measured: 464.33; α4β1 IC$_{50}$=<20 nM: α4β7 IC$_{50}$=nd;

sodium (S)-3-(3-(1-methyl-4-oxido-2-oxo-1,2-dihydropyridin-3-yl)ureido)-3-(2'-methylbiphenyl-3-yl)propanoate 1-598 (MS [M+H$^+$]$^+$: Calculated: 422.17; Measured: 422.27; α4β1 IC$_{50}$=<20 nM: α4β7 IC$_{50}$=nd;

sodium (S)-3-(3-(1,6-dimethyl-4-oxido-2-oxo-1,2-dihydropyridin-3-yl)ureido)-3-(2'-methyl biphenyl-3-yl)propanoate 1-599 (MS [M+H$^+$]$^+$: Calculated: 436.19; Measured: 436.27; α4β1 IC$_{50}$=<20 nM: α4β7IC$_{50}$=nd;

sodium (S)-3-(5-fluoro-2',6'-dimethylbiphenyl-3-yl)-3-(3-(1-methyl-4-oxido-2-oxo-1,2-dihydro pyridin-3-yl)ureido)propanoate 1-600 (MS [M+H$^+$]$^+$: Calculated: 454.18; Measured: 454.09; α4β1 IC$_{50}$=<20 nM: α4β7 IC$_{50}$=nd;

sodium (S)-3-(3-(1-methyl-4-oxido-2-oxo-1,2-dihydropyridin-3-yl)ureido)-3-(5-(3-(trifluoro methoxy)phenyl)thiophen-2-yl)propanoate 1-601 (MS [M+H$^+$]$^+$: Calculated: 498.09; Measured: 498.02; α4β1 IC$_{50}$=<20 nM: α4β7 IC$_{50}$=nd;

sodium (S)-3-(4-methoxy-2',6'-dimethylbiphenyl-3-yl)-3-(3-(1-methyl-4-oxido-2-oxo-1,2-dihydropyridin-3-yl)ureido)propanoate 1-602 (MS [M+H$^+$]$^+$: Calculated: 466.20; Measured: 466.33; α4β1 IC$_{50}$=<20 nM: α4β7IC$_{50}$=nd;

sodium (S)-3-(3-(1,6-dimethyl-4-oxido-2-oxo-1,2-dihydropyridin-3-yl)ureido)-3-(4-fluoro-3'-methoxybiphenyl-3-yl)propanoate 1-603 (MS [M+H$^+$]$^+$: Calculated: 470.17; Measured: 470.32; α4β1 IC$_{50}$=<20 nM: α4β7 IC$_{50}$=nd;

sodium (S)-3-(5-fluoro-3'-methoxybiphenyl-3-yl)-3-(3-(1-methyl-4-oxido-2-oxo-1,2-dihydro pyridin-3-yl)ureido)propanoate 1-604 (MS [M+H$^+$]$^+$: Calculated: 456.16; Measured: 456.17; α4β1 IC$_{50}$=<20 nM: α4β7 IC$_{50}$=nd;

sodium (S)-3-(3-(1,6-dimethyl-4-oxido-2-oxo-1,2-dihydropyridin-3-yl)ureido)-3-(5-fluoro-3'-methoxybiphenyl-3-yl)propanoate 1-605 (MS [M+H$^+$]$^+$: Calculated: 470.17; Measured: 470.19; α4β1 IC$_{50}$=<20 nM: α4β7 IC$_{50}$=nd;

sodium (S)-3-(3-(1,6-dimethyl-4-oxido-2-oxo-1,2-dihydropyridin-3-yl)ureido)-3-(5-fluoro-3'-(trifluoromethoxy)biphenyl-3-yl)propanoate 1-606 (MS [M+H$^+$]$^+$: Calculated: 524.14; Measured: 524.18; α4β1 IC$_{50}$=<20 nM: α4β7 IC$_{50}$=nd;

sodium (S)-3-(5-fluoro-3'-(trifluoromethoxy)biphenyl-3-yl)-3-(3-(1-methyl-4-oxido-2-oxo-1,2-dihydropyridin-3-yl)ureido)propanoate 1-607 (MS [M+H$^+$]$^+$: Calculated: 510.13; Measured: 510.15; α4β1 IC$_{50}$=<20 nM: α4β7 IC$_{50}$=nd;

sodium (S)-3-(5-(3,5-dimethylisoxazol-4-yl)thiophen-2-yl)-3-(3-(1-methyl-4-oxido-2-oxo-1,2-dihydropyridin-3-yl)ureido)propanoate 1-608 (MS [M+H$^+$]$^+$: Calculated: 433.12; Measured: 433.00; α4β1 IC$_{50}$=<20 nM: α4β7 IC$_{50}$=nd;

sodium (S)-3-(3-(1,6-dimethyl-4-oxido-2-oxo-1,2-dihydropyridin-3-yl)ureido)-3-(3-(3,5-dimethyl isoxazol-4-yl)phenyl)propanoate 1-609 (MS [M+H$^+$]$^+$: Calculated: 441.18; Measured: 441.06; α4β1 IC$_{50}$=<20 nM: α4β7 IC$_{50}$=nd;

sodium (S)-3-(3-(1,6-dimethyl-4-oxido-2-oxo-1,2-dihydropyridin-3-yl)ureido)-3-(2-fluorobiphenyl-3-yl)propanoate 1-610 (MS [M+H$^+$]$^+$: Calculated: 440.16; Measured: 440.16; α4β1 IC$_{50}$=<20 nM: α4β7 IC$_{50}$=nd;

sodium (S)-3-(3-(1,6-dimethyl-4-oxido-2-oxo-1,2-dihydropyridin-3-yl)ureido)-3-(6-fluoro-2'-methylbiphenyl-3-yl)propanoate 1-611 (MS [M+H$^+$]$^+$: Calculated: 454.18; Measured: 454.16; α4β1 IC$_{50}$=<20 nM: α4β7 IC$_{50}$=nd;

sodium (S)-3-(6-fluoro-2'-methylbiphenyl-3-yl)-3-(3-(1-methyl-4-oxido-2-oxo-1,2-dihydropyridin-3-yl)ureido)

propanoate 1-612 (MS [M+H⁺]⁺: Calculated: 440.16; Measured: 440.14; α4β1 IC$_{50}$=<20 nM: α4β7 IC$_{50}$=nd;

sodium (S)-3-(3-(1-methyl-4-oxido-2-oxo-1,2-dihydropyridin-3-yl)ureido)-3-(5-phenylthiophen-2-yl)propanoate 1-613 (MS [M+H⁺]⁺: Calculated: 414.11; Measured: 414.07; α4β1 IC$_{50}$=<20 nM: α4β7 IC$_{50}$=nd;

sodium (S)-3-(5-(2,5-difluorophenyl)thiophen-2-yl)-3-(3-(1-methyl-4-oxido-2-oxo-1,2-dihydro pyridin-3-yl)ureido)propanoate 1-614 (MS [M+H⁺]⁺: Calculated: 450.09; Measured: 450.06; α4β1 IC$_{50}$=<20 nM: α4β7 IC$_{50}$=nd;

sodium (S)-3-(3-(1-methyl-4-oxido-2-oxo-1,2-dihydropyridin-3-yl)ureido)-3-(5-(trifluoromethoxy) biphenyl-3-yl)propanoate 1-615 (MS [M+H⁺]⁺: Calculated: 492.14; Measured: 492.09; α4β1 IC$_{50}$=<20 nM: α4β7 IC$_{50}$=nd;

sodium (S)-3-(3-(1-methyl-4-oxido-2-oxo-1,2-dihydropyridin-3-yl)ureido)-3-(2'-methylbiphenyl-4-yl)propanoate 1-616 (MS [M+H⁺]⁺: Calculated: 422.17; Measured: 422.14; α4β1 IC$_{50}$=<20 nM: α4β7 IC$_{50}$=nd;

sodium (S)-3-(5-methoxybiphenyl-3-yl)-3-(3-(7-oxido-5-oxo-1,2,3,5-tetrahydroindolizin-6-yl) ureido)propanoate 1-617 (MS [M+H⁺]⁺: Calculated: 464.18; Measured: 464.16), sodium (S)-3-(3-(1-methyl-4-oxido-2-oxo-1,2-dihydropyridin-3-yl)ureido)-3-(5-(trifluoromethyl) biphenyl-3-yl)propanoate 1-618 (MS [M+H⁺]⁺: Calculated: 476.14; Measured: 476.20), α4β1 IC$_{50}$=>200 nM: α4β7 IC$_{50}$=nd;

sodium (S)-3-(5-(3-chlorophenyl)thiophen-2-yl)-3-(3-(1-methyl-4-oxido-2-oxo-1,2-dihydro pyridin-3-yl)ureido) propanoate 1-619 (MS [M+H⁺]⁺: Calculated: 448.07; Measured: 448.12), α4β1 IC$_{50}$=<200 nM: α4β7 IC$_{50}$=nd;

sodium (S)-3-(5-(3-fluorophenyl)thiophen-2-yl)-3-(3-(1-methyl-4-oxido-2-oxo-1,2-dihydropyridin-3-yl)ureido) propanoate 1-620 (MS [M+H⁺]⁺: Calculated: 432.10; Measured: 432.06), α4β1 IC$_{50}$=<200 nM: α4β7 IC$_{50}$=nd;

sodium (S)-3-(2',4'-difluorobiphenyl-4-yl)-3-(3-(1-methyl-4-oxido-2-oxo-1,2-dihydropyridin-3-yl)ureido)propanoate 1-621 (MS [M+H⁺]⁺: Calculated: 444.14; Measured: 444.30; α4β1 IC$_{50}$=<20 nM: α4β7 IC$_{50}$=nd;

sodium (S)-3-(2',4'-difluorobiphenyl-4-yl)-3-(3-(1,6-dimethyl-4-oxido-2-oxo-1,2-dihydropyridin-3-yl)ureido)propanoate 1-622 (MS [M+H⁺]⁺: Calculated: 458.15; Measured: 458.30; α4β1 IC$_{50}$=<20 nM: α4β7 IC$_{50}$=nd;

sodium (S)-3-(2',4'-difluorobiphenyl-4-yl)-3-(3-(1,5-dimethyl-4-oxido-2-oxo-1,2-di hydropyridin-3-yl)ureido) propanoate 1-623 (MS [M+H⁺]⁺: Calculated: 458.15; Measured: 458.00; α4β1 IC$_{50}$=<20 nM: α4β7 IC$_{50}$=nd;

sodium (S)-3-(3-(1-methyl-4-oxido-2-oxo-1,2-dihydropyridin-3-yl)ureido)-3-(2'-methyl-6-(trifluoro methoxy)biphenyl-3-yl)propanoate 1-624 (MS [M+H⁺]⁺: Calculated: 506.15; Measured: 506.11; α4β1 IC$_{50}$=<20 nM: α4β7 IC$_{50}$=nd;

sodium (S)-3-(3-(1-methyl-4-oxido-2-oxo-1,2-dihydropyridin-3-yl)ureido)-3-(6-(trifluoromethoxy) biphenyl-3-yl)propanoate 1-625; α4β1 IC$_{50}$=<200 nM: α4β7 IC$_{50}$=nd;

sodium 3-(3'-acetylbiphenyl-3-yl)-3-(3-(1,5-dimethyl-4-oxido-2-oxo-1,2-dihydropyridin-3-yl) ureido)propanoate 1-626 (MS [M+H⁺]⁺: Calculated: 464.18; Measured: 463.99; α4β1 IC$_{50}$=<20 nM: α4β7 IC$_{50}$=nd;

sodium 3-(4'-acetylbiphenyl-3-yl)-3-(3-(1,5-dimethyl-4-oxido-2-oxo-1,2-dihydro pyridin-3-yl)ureido)propanoate 1-627 (MS [M+H⁺]⁺: Calculated: 464.18; Measured: 463.97; α4β1 IC$_{50}$=<200 nM: α4β7 IC$_{50}$=nd;

sodium (S)-3-(3-(1,5-dimethyl-4-oxido-2-oxo-1,2-dihydropyridin-3-yl)ureido)-3-(5-phenyl thiophen-2-yl)propanoate 1-628 (MS [M+H⁺]⁺: Calculated: 428.13; Measured: 427.92; α4β1 IC$_{50}$=<200 nM: α4β7 IC$_{50}$=nd;

sodium (S)-3-(3-(1,6-dimethyl-4-oxido-2-oxo-1,2-dihydropyridin-3-yl)ureido)-3-(5-methyl-3'-(trifluoromethoxy)biphenyl-3-yl)propanoate 1-631 (MS [M+H⁺]⁺: Calculated: 520.17; Measured: 520.40; α4β1 IC$_{50}$=<20 nM: α4β7 IC$_{50}$=nd;

sodium (S)-3-(3-(1,6-dimethyl-4-oxido-2-oxo-1,2-dihydropyridin-3-yl)ureido)-3-(2',4',5-trifluoro biphenyl-3-yl)propanoate 1-632 (MS [M+H⁺]⁺: Calculated: 476.14; Measured: 476.25; α4β1 IC$_{50}$=<20 nM: α4β7 IC$_{50}$=nd;

sodium (S)-3-(3-(1-methyl-4-oxido-2-oxo-1,2-dihydropyridin-3-yl)ureido)-3-(2',4',5-trifluoro biphenyl-3-yl)propanoate 1-633 (MS [M+H⁺]⁺: Calculated: 462.13; Measured: 462.29; α4β1 IC$_{50}$=<20 nM: α4β7 IC$_{50}$=nd;

sodium (S)-3-(3'-methoxy-6-(trifluoromethoxy)biphenyl-3-yl)-3-(3-(1-methyl-4-oxido-2-oxo-1,2-dihydropyridin-3-yl)ureido)propanoate 1-634 (MS [M+H⁺]⁺: Calculated: 522.15; Measured: 522.30; α4β1 IC$_{50}$=<20 nM: α4β7 IC$_{50}$=nd;

sodium (S)-3-(3-(1,6-dimethyl-4-oxido-2-oxo-1,2-dihydropyridin-3-yl)ureido)-3-(3'-methoxy-6-(trifluoromethoxy)biphenyl-3-yl)propanoate 1-635 (MS [M+H⁺]⁺: Calculated: 536.16; Measured: 536.34; α4β1 IC$_{50}$=<20 nM: α4β7IC$_{50}$=nd;

sodium (S)-3-(2',6'-dimethylbiphenyl-4-yl)-3-(3-(1-methyl-4-oxido-2-oxo-1,2-dihydropyridin-3-yl)ureido)propanoate 1-636 (MS [M+H⁺]⁺: Calculated: 436.19; Measured: 436.17; α4β1 IC$_{50}$=<200 nM: α4β7 IC$_{50}$=nd;

sodium (S)-3-(3-(1,6-dimethyl-4-oxido-2-oxo-1,2-dihydropyridin-3-yl)ureido)-3-(2'-methyl biphenyl-4-yl)propanoate 1-637 (MS [M+H⁺]⁺: Calculated: 436.19; Measured: 436.09; α4β1 IC$_{50}$=<20 nM: α4β7 IC$_{50}$=nd;

sodium (S)-3-(3-(1,6-dimethyl-4-oxido-2-oxo-1,2-dihydropyridin-3-yl)ureido)-3-(2',6'-dimethyl biphenyl-4-yl)propanoate 1-638 (MS [M+H⁺]⁺: Calculated: 450.20; Measured: 450.15; α4β1 IC$_{50}$=<200 nM: α4β7 IC$_{50}$=nd;

sodium (S)-3-(3-(1-methyl-4-oxido-2-oxo-1,2-dihydropyridin-3-yl)ureido)-3-(3-(pyridin-2-yl)phenyl)propanoate 1-639 (MS [M+H⁺]⁺: Calculated: 409.15; Measured: 409.01; α4β1 IC$_{50}$=<20 nM: α4β7 IC$_{50}$=nd;

sodium (S)-3-(3-(6-methoxypyridazin-3-yl)phenyl)-3-(3-(1-methyl-4-oxido-2-oxo-1,2-dihydro pyridin-3-yl)ureido) propanoate 1-640 (MS [M+H⁺]⁺: Calculated: 440.16; Measured: 440.00; α4β1 IC$_{50}$=<20 nM: α4β7 IC$_{50}$=nd;

sodium (S)-3-(3-(1-methyl-4-oxido-2-oxo-1,2-dihydropyridin-3-yl)ureido)-3-(5-phenylpyridin-3-yl)propanoate 1-641 (MS [M+H⁺]⁺: Calculated: 409.15; Measured: 409.00; α4β1 IC$_{50}$=<20 nM: α4β7 IC$_{50}$=nd;

sodium (S)-3-(3-(1,6-dimethyl-4-oxido-2-oxo-1,2-dihydropyridin-3-yl)ureido)-3-(5-fluoro-2',6'-dimethylbiphenyl-3-yl)propanoate 1-642 (MS [M+H⁺]⁺: Calculated: 468.19; Measured: 468.11; α4β1 IC$_{50}$=<20 nM: α4β7 IC$_{50}$=<20 nM;

sodium (S)-3-(biphenyl-4-yl)-3-(3-(1,5-dimethyl-4-oxido-2-oxo-1,2-dihydropyridin-3-yl)ureido) propanoate 1-643 (MS [M+H⁺]⁺: Calculated: 422.17; Measured: 421.95; α4β1IC$_{50}$=<200 nM: α4β7 IC$_{50}$=nd;

sodium (S)-3-(3-(1H-imidazol-1-yl)phenyl)-3-(3-(1-methyl-4-oxido-2-oxo-1,2-dihydropyridin-3-yl)ureido) propanoate 1-646;

sodium (S)-3-(3-(4-hydroxy-1-methyl-2-oxo-1,2-dihydropyridin-3-yl)ureido)-3-(3-(pyrazin-2-yl)phenyl) propanoate 1-647;

sodium 3-(3-bromophenyl)-3-(3-(4-hydroxy-1,5-dimethyl-2-oxo-1,2-dihydro pyridin-3-yl) ureido) propanoate 1-;

sodium 3-(3-bromophenyl)-3-(3-(1-ethyl-4-hydroxy-5-methyl-2-oxo-1,2-dihydropyridin-3-yl)ureido) propanoate 1-649.

This transformation was also accomplished using acetonitrile or methanol in place of tetrahydrofuran without affecting the outcome. This procedure was also used to prepare sodium (S)-3-(3',5-dimethoxybiphenyl-3-yl)-3-(3-(1,6-dimethyl-4-oxido-2-oxo-1,2-dihydropyridin-3-yl)ureido)propanoate 1-567 (MS [M+H$^+$]$^+$: Calculated: 482.19; Measured: 482.01; α4β1 IC$_{50}$=<20 nM: α4β7 IC$_{50}$=nd;

sodium (S)-3-(3-(1-methyl-4-oxido-2-oxo-1,2-dihydropyridin-3-yl)ureido)-3-(2',4,4'-trifluorobiphenyl-3-yl)propanoate 1-591 (MS [M+H$^+$]$^+$: Calculated: 462.13; Measured: 462.28; α4β1 IC$_{50}$=<20 nM: α4β7 IC$_{50}$=nd;

sodium (S)-3-(3-(1,6-dimethyl-4-oxido-2-oxo-1,2-dihydropyridin-3-yl)ureido)-3-(2',4,4'-trifluorobiphenyl-3-yl) propanoate 1-592 (MS [M+H$^+$]$^+$: Calculated: 476.14; Measured: 476.31; α4β1 IC$_{50}$=<20 nM: α4β7 IC$_{50}$=nd;

This reaction could be accomplished without the aid of an organic solvent. The starting acid was taken up in an appropriate amount of sodium hydroxide, and stirred until dissolved, with mild heating as necessary. The resulting solution was lyophilized to give sodium (S)-3-(3-(1,5-dimethyl-4-oxido-2-oxo-1,2-dihydropyridin-3-yl)ureido)-3-(4'-methoxybiphenyl-3-yl) propanoate 1-645 (MS [M+H$^+$]$^+$: Calculated: 452.18; Measured: 452.08; α4β1 IC$_{50}$=<200 nM: α4β7 IC$_{50}$=nd;

sodium (S)-3-(3-(1,5-dimethyl-4-oxido-2-oxo-1,2-dihydropyridin-3-yl)ureido)-3-(2'-methoxy biphenyl-3-yl)propanoate 1-456 (MS [M+H$^+$]$^+$: Calculated: 452.18; Measured: 452.09; α4β1 IC$_{50}$=<200 nM: α4β7 IC$_{50}$=nd;

sodium (S)-3-(3-(1,5-dimethyl-4-oxido-2-oxo-1,2-dihydropyridin-3-yl)ureido)-3-(3'-methoxybiphenyl-3-yl)propanoate 1-460 (MS [M+H$^+$]$^+$: Calculated: 452.18; Measured: 452.09; α4β1 IC$_{50}$=<200 nM: α4β7 IC$_{50}$=nd;

sodium 3-(3',4'-dichlorobiphenyl-3-yl)-3-(3-(1-ethyl-5-methyl-4-oxido-2-oxo-1,2-dihydropyridin-3-yl)ureido) propanoate 1-480 (MS [M+H$^+$]$^+$: Calculated: 504.11; Measured: 503.86; α4β1 IC$_{50}$=<200 nM: α4β7 IC$_{50}$=nd;

sodium 3-(3',4'-dichlorobiphenyl-3-yl)-3-(3-(1,5-dimethyl-4-oxido-2-oxo-1,2-dihydropyridin-3-yl)ureido)propanoate 1-481 (MS [M+H$^+$]$^+$: Calculated: 490.09; Measured: 489.95; α4β1 IC$_{50}$=<200 nM: α4β7 IC$_{50}$=nd;

sodium 3-(3'-chloro-4'-fluorobiphenyl-3-yl)-3-(3-(1,5-dimethyl-4-oxido-2-oxo-1,2-dihydropyridin-3-yl)ureido)propanoate 1-484 (MS [M+H$^+$]$^+$: Calculated: 474.12; Measured: 473.90; α4β1 IC$_{50}$=<200 nM: α4β7 IC$_{50}$=nd;

sodium 3-(2',3'-dichlorobiphenyl-3-yl)-3-(3-(1,5-dimethyl-4-oxido-2-oxo-1,2-dihydropyridin-3-yl)ureido)propanoate 1-485 (MS [M+H$^+$]$^+$: Calculated: 490.09; Measured: 489.91; α4β1 IC$_{50}$=<200 nM: α4β7 IC$_{50}$=nd;

sodium (S)-3-(2',4'-difluorobiphenyl-3-yl)-3-(3-(7-oxido-5-oxo-1,2,3,5-tetrahydroindolizin-6-yl)ureido)propanoate 1-629 (MS [M+H$^+$]$^+$: Calculated: 470.15; Measured: 470.02; α4β1 IC$_{50}$=<20 nM: α4β7 IC$_{50}$=>200 nM;

sodium (S)-3-(3-(1-methyl-4-oxido-2-oxo-1,2-dihydropyridin-3-yl)ureido)-3-(3-(thiazol-2-yl) phenyl)propanoate 1-630 (MS [M+H$^+$]$^+$: Calculated: 415.11; Measured: 414.96; α4β1 IC$_{50}$=<20 nM: α4β7 IC$_{50}$=nd;

Example 2

Synthesis of ethyl 3-amino-3-(3-(2-oxo-3-phenylpyridin-1(2H)-yl)phenyl)propanoate (2-9)

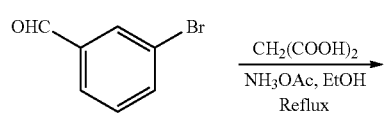

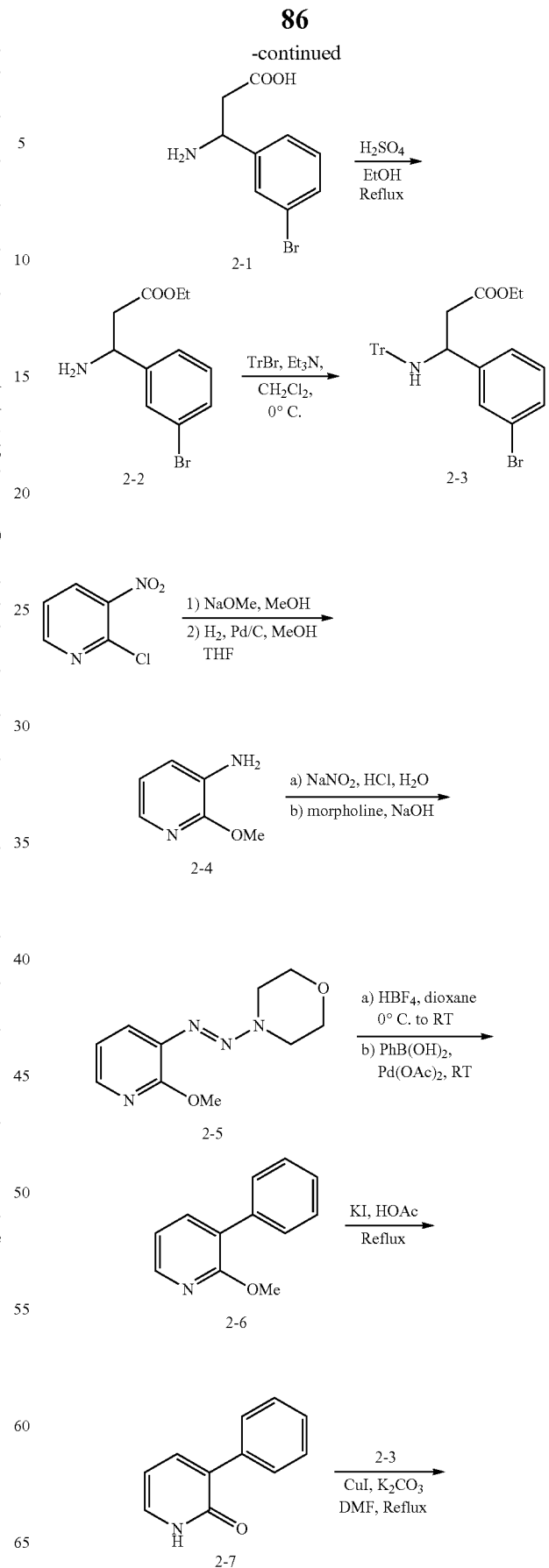

-continued

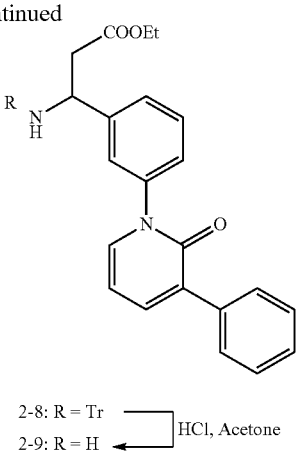

2-8: R = Tr
2-9: R = H
HCl, Acetone

Step One: A solution of 3-bromobenzaldehyde (50 mL, 0.43 mol), malonic acid (49.09 g, 0.47 mol) and ammonium acetate (49.73 g, 0.65 mol) in absolute ethanol (300 mL) was refluxed overnight then cooled to room temperature. The suspension was filtered, washing with hexanes. The solid was dried under vacuum to give 3-amino-3-(3-bromophenyl)propanoic acid (2-1, 94.74 g) as a white solid.

This procedure was also used to make 3-amino-3-(3-iodophenyl)propanoic acid;
3-amino-3-(6-oxo-1,6-dihydropyridin-3-yl)propanoic acid; and
3-amino-3-(3-bromo-4-(2,2,2-trifluoroethoxy)phenyl)propanoic acid.

Step Two: To a mixture of 2-1 (50 g, 0.21 mol) in absolute ethanol (400 mL), concentrated sulfuric acid (12.8 mL) was added slowly. The mixture was refluxed overnight, then cooled to room temperature and carefully quenched with saturated aqueous sodium bicarbonate. The mixture was diluted with water then extracted with ethyl acetate. The organic layer was extracted twice with aqueous HCl (2N). The aqueous layer was basified with aqueous NaOH (2N) and extracted three times with ethyl acetate. These three organic layers were combined, washed with brine, dried over magnesium sulfate, filtered and concentrated under reduced pressure to give ethyl 3-amino-3-(3-bromophenyl) propanoate; (2-2, 25 g).

This procedure was modified by using thionyl chloride instead of sulfuric acid. This modifications was used to make ethyl 3-amino-3-(3-iodophenyl)propanoate;
ethyl 3-amino-3-(6-oxo-1,6-dihydropyridin-3-yl)propanoate; and
ethyl 3-amino-3-(3-bromo-4-(2,2,2-trifluoroethoxy)phenyl) propanoate.

Step Three: To a solution of 2-2 (5.0 g, 18.4 mmol) in dichloromethane (50 mL) under nitrogen, tritylbromide (5.64 g, 17.5 mmol) was added. The mixture was cooled to 0° C., and triethylamine (7.68 mL, 55.1 mmol) was added dropwise over the course of 15 minutes. The mixture was stirred for 2 hours then was poured into saturated aqueous ammonium chloride. The aqueous layer was extracted twice with dichloromethane, and the combined organic layers were washed with brine, dried over magnesium sulfate, filtered, and concentrated under reduced pressure to give ethyl 3-(3-bromophenyl)-3-(tritylamino)propanoate (2-3) as a white paste.

This procedure was also used to make ethyl 3-(3-iodophenyl)-3-(tritylamino)propanoate (3-1);

ethyl 3-(6-oxo-1,6-dihydropyridin-3-yl)-3-(tritylamino)propanoate (5-1), and
ethyl 3-(3-bromo-4-(2,2,2-trifluoroethoxy)phenyl)-3-(tritylamino)propanoate.

Step Four: To a suspension of 2-chloro-3-nitropyridine (5.00 g, 31.5 mmol) in anhydrous methanol (20 mL) at 0° C. under nitrogen, a solution of sodium methoxide in methanol (25%, 14.4 mL, 63.1 mmol) was added dropwise over 30 minutes. The mixture was allowed to warm to room temperature and was stirred for 3 hours then was poured into saturated aqueous ammonium chloride. The resulting mixture was extracted three times with ethyl acetate. The combined organic layers were dried over magnesium sulfate, filtered and concentrated under reduced pressure. The residue was taken up in tetrahydrofuran (7 mL) and methanol (7 mL), and palladium on carbon (10%, catalytic amount) was added. The mixture was placed under a hydrogen atmosphere (toggle between vacuum and hydrogen gas from a balloon several times) and stirred overnight. The reaction was not complete, so the reaction mixture was filtered through Celite® and the filtrate was treated with fresh palladium on carbon and placed under hydrogen as before. The mixture was stirred for 7 hours, then filtered through Celite® and concentrated to give 2-methoxypyridin-3-amine (2-4, 3.91 g).

Step Five: A mixture of 2-4 (500 mg, 4.03 mmol) and aqueous hydrochloric acid (6 M, 2.28 mL) was briefly warmed to give a homogeneous solution then was cooled to 0° C. To the resulting mixture, a solution of sodium nitrite (305 mg, 4.43 nnol) in deionized water (0.5 mL) was added dropwise over 5 minutes. The mixture was stirred for 20 minutes and morpholine (0.356 mL, 4.43 mmol) was added dropwise followed by deionized water (0.5 mL). The solution was adjusted to pH 7 with the addition of aqueous sodium hydroxide (1N) then the mixture was stirred for 1 hour. The resulting suspension was filtered to give (E)-4-((2-methoxypyridin-3-yl)diazenyl)morpholine (2-5, 517 mg) as a rust colored solid.

Step Six: To a solution of 2-5 (300 mg, 1.35 mmol) in dioxane (1 mL) at 0° C. under nitrogen, tetrafluoroboric acid (40% in water, 0.64 mL, 4.1 mmol) was added dropwise. The mixture was warmed to room temperature and palladium diacetate (30 mg, 0.14 mmol) and phenylboronic acid (329 mg, 2.70 mmol) were added. The mixture was stirred under nitrogen for 4 hours then was diluted with ethyl acetate and filtered through Celite®. The filtrate was concentrated and the residue was purified by column chromatography on silica gel, eluting with hexanes followed by 5% ethyl acetate in hexanes to give 2-methoxy-3-phenylpyridine (2-6, 81 mg) as a yellow oil.

Step Seven: To a solution of 2-6 (800 mg, 4.32 mmol) in glacial acetic acid (20 mL), potassium iodide (2.15 g, 13.0 mmol) was added. The mixture was heated to reflux for 6 hours then was cooled to room temperature and concentrated. The residue was taken up in chloroform and washed with saturated aqueous sodium bicarbonate and brine. The organic layer was dried over magnesium sulfate, filtered, and concentrated under reduced pressure to give 3-phenylpyridin-2(1H)-one (2-7, 350 mg) as a yellow powder.

This procedure was also used to make 6-oxo-1,6-dihydropyridine-3-carbaldehyde (from 6-methoxy-3-pyridinecarboxaldehyde).

Step Eight: To a flask containing 2-3 (750 mg, 1.45 mmol), 2-7 (373 mg, 2.19 mmol), copper(I) iodide (38 mg, 0.29 mmol), and potassium carbonate (302 mg, 2.19 mmol), N,N-dimethylformamide (2 mL) was added and the reaction was heated to reflux for 6 hours. The reaction was cooled to room temperature, diluted with saturated ammonium chloride and extracted three times with ethyl acetate. The combined organic layers were washed with brine, dried over magnesium sulfate, filtered, and concentrated under reduced pressure. The residue was purified by silica gel chromatography, eluting with hexanes then 10% ethyl acetate in hexanes increasing to 20% to give ethyl 3-(3-(2-oxo-3-phenylpyridin-1(2H)-yl)phenyl)-3-(tritylamino)propanoate (2-8, 220 mg).

Step Nine: To a solution of 2-8 (202 mg, 0.334 mmol) in acetone (2 mL) at room temperature, aqueous hydrochloric acid (2N, 2 mL) was added. The mixture was stirred for 4 hours, diluted with chloroform, and extracted three times with aqueous hydrochloric acid. The combined aqueous layers were adjusted to pH 8 with the addition of solid potassium carbonate and extracted three time with ethyl acetate. The organic layers were combined and concentrated under reduced pressure to give ethyl 3-amino-3-(3-(2-oxo-3-phenylpyridin-1(2H)-yl)phenyl)propanoate (2-9, 0.237 mmol). This material was used directly in the next step.

This procedure was also use to make ethyl 3-(3-(1H-pyrrol-1-yl)phenyl)-3-aminopropanoate;
ethyl 3-amino-3-(6-(2,2,2-trifluoroethoxy)biphenyl-3-yl)propanoate;
and ethyl 3-amino-3-(5'-chloro-2',4'-difluorobiphenyl-3-yl)propanoate.

This procedure was modified by using acetonitrile in place of acetone to make ethyl 3-amino-3-(6-oxo-1-phenyl-1,6-dihydropyridin-3-yl)propanoate. The workup for this modification was altered by concentrating the crude mixture and washing the solid residue with ether to isolate the product by filtration as a hydrochloride salt to give
ethyl 3-(3'-acetylbiphenyl-3-yl)-3-aminopropanoate hydrochloride; and
ethyl 3-(4'-acetylbiphenyl-3-yl)-3-aminopropanoate hydrochloride.

Example 3

Synthesis of ethyl 3-(3-(1H-pyrrol-1-yl)phenyl)-3-(tritylamino)propanoate (3-2)

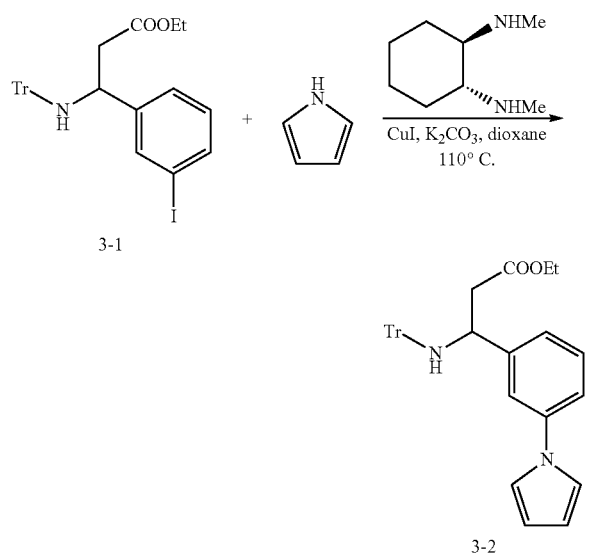

Step One: To a flask containing potassium carbonate (259 mg, 1.87 mmol) and copper(I) iodide (1.6 mg, 0.008 mmol) under an argon atmosphere, a solution of 3-1 (500 mg, 0.891 mmol, prepared by steps 1 to 3 of example 2) in dioxane (0.9 mL), pyrrole (0.074 mL, 1.07 mmol), and (1R,2R)-(−)-N,N'-dimethyl-1,2-cyclohexanediamine (0.0107 mL, 0.0891 mmol) were added. The mixture was heated to 110° C. overnight then was cooled to room temperature, diluted with ethyl acetate, and washed with water and brine. The organic layer was dried over magnesium sulfate, filtered and concentrated under reduced pressure. The residue was purified by silica gel chromatography, eluting with 10% ethyl acetate in hexanes to give ethyl 3-(3-(1H-pyrrol-1-yl)phenyl)-3-(tritylamino)propanoate (3-2, 250 mg).

This procedure was also used to make (S)-ethyl 3-(3-(1H-indazol-1-yl)phenyl)-3-(benzyl((R)-1-phenylethyl)amino)propanoate; and
ethyl (S)-3-(3-(1H-pyrazol-1-yl)phenyl)-3-(benzyl((R)-1-phenylethyl)amino) propanoate. This procedure was modified to use tribasic potassium phosphate instead of potassium carbonate in preparing ethyl (S)-3-(3-(1H-imidazol-1-yl)phenyl)-3-(benzyl((R)-1-phenylethyl)amino)propanoate.

Example 4

Synthesis of ethyl (E)-3-(3-bromo-4-methylphenyl)acrylate (4-1)

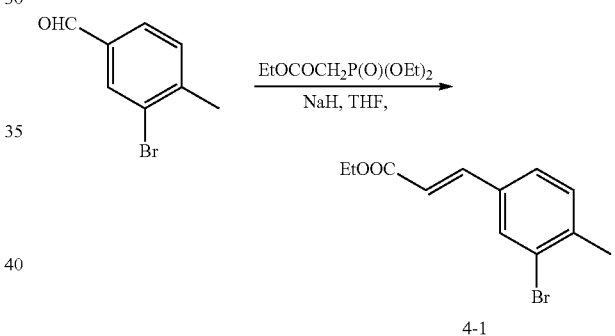

Step One: To a solution of triethyl phosphonoacetate (3.59 g, 16.0 mmol) in tetrahydrofuran (5 mL) cooled to 0° C., sodium hydride (60% dispersion in mineral oil, 0.69 g, 17.3 mmol) was added in portions. The resulting mixture was warmed to room temperature and stirred for 15 minutes. To this mixture, a solution of 3-bromo-4-methylbenzaldehyde (2.65 g, 13.3 mmol) in tetrahydrofuran (5 mL) was added by syringe. The mixture was stirred for 1 hour, carefully quenched with aqueous hydrochloric acid (2N), and extracted with ethyl acetate. The organic layer was dried, filtered and concentrated to give ethyl (E)-3-(3-bromo-4-methylphenyl)acrylate (4-1, 3.58 g).

This procedure was also used to make (E)-ethyl 3-(3-bromo-4-methoxyphenyl)acrylate;
ethyl (E)-3-(5,6-dimethoxybiphenyl-3-yl)acrylate;
ethyl (E)-3-(5-bromo-2-fluorophenyl)acrylate;
ethyl (E)-3-(2-methylbiphenyl-3-yl)acrylate;
ethyl (E)-3-(3-iodophenyl)acrylate;
ethyl (E)-3-(3-(1-ethyl-1H-indol-6-yl)phenyl)acrylate;
ethyl (E)-3-(6-methoxy-2',6'-dimethylbiphenyl-3-yl)acrylate;
ethyl (E)-3-(5-bromo-2-methoxyphenyl)acrylate;
ethyl (E)-3-(3-iodo-4-(trifluoromethoxy)phenyl)acrylate;

ethyl (E)-3-(2'-methyl-6-(trifluoromethoxy)biphenyl-3-yl) acrylate;
ethyl (E)-3-(2-fluoro-3-iodophenyl)acrylate;
and ethyl (E)-3-(3-bromo-5-(trifluoromethoxy)phenyl)acrylate.

Example 5

Synthesis of ethyl 3-(6-oxo-1-phenyl-1,6-dihydropyridin-3-yl)-3-(tritylamino)propanoate (5-2)

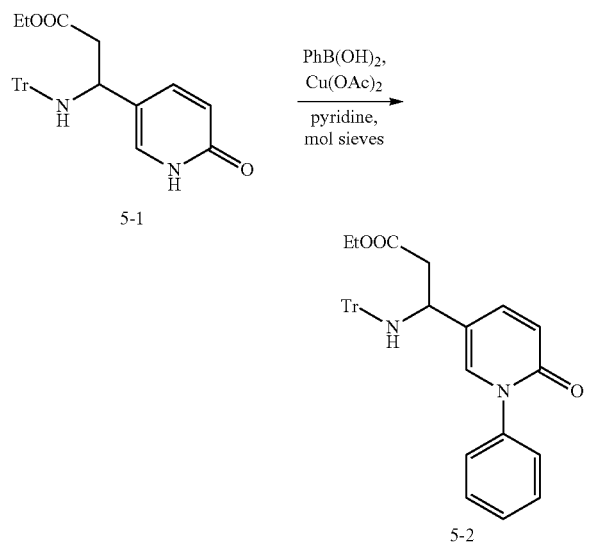

Step One: To a solution of 5-1 (150 mg, 0.33 mmol) prepared from 6-methoxy-3-pyridinecarboxaldehyde following step 7 then steps 1 to 3 of example 2) and phenylboronic acid (80 mg, 0.66 mmol) in dichloromethane (1.3 mL) at room temperature, 4 Å molecular sieves (0.6 g), pyridine (0.5 mL) and copper(II) acetate (12 mg, 0.066 mmol) were added sequentially. Air was gently pulled from a drying tube packed with calcium chloride through the resulting mixture with stirring overnight. The resulting mixture was diluted with ammonium hydroxide and extracted three times with dichloromethane. The organic layers were combined, dried, filtered and concentrated under reduced pressure to give ethyl 3-(6-oxo-1-phenyl-1,6-dihydropyridin-3-yl)-3-(tritylamino)propanoate (5-2, 151 mg) as a white foam. This material was used without further purification.

Example 6

Synthesis of ethyl (S)-3-amino-3-(5-phenylfuran-2-yl)propanoate (6-3)

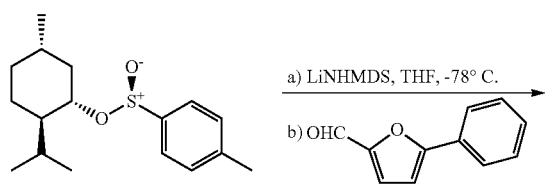

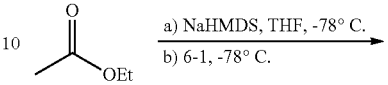

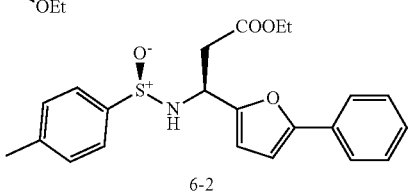

Step One: To a solution of (+)-(1S)-menthyl (R)-p-toluenesulfinate (500 mg, 1.70 mmol) in tetrahydrofuran (8 mL) at −78° C. under nitrogen, lithium hexamethyldisilazide (1.0 M in tetrahydrofuran, 2.22 mL, 2.22 mmol) was added by syringe. The mixture was stirred for 8 hours then a solution of 5-phenyl-2-furaldehyde (322 mg, 1.87 mmol) in tetrahydrofuran (5 mL) was added by syringe. The mixture was stirred at −78° C. for three hours then was diluted with water and ether. The aqueous layer was extracted twice with ethyl acetate and the combined organic layers were washed with brine, dried over magnesium sulfate, filtered and concentrated. The residue was purified by silica gel column chromatography, eluting with 5% ethyl acetate in hexanes to give (R,E)-4-methyl-N-((5-phenylfuran-2-yl)methylene)benzenesulfinamide (6-1, 292 mg) as an oil.

This procedure was also used to make (R,E)-4-methyl-N-((1-phenyl-1H-pyrrol-2-yl)methylene)benzenesulfinamide;
(R,E)-4-methyl-N-((4-phenylthiophen-2-yl)methylene)benzenesulfinamide;
(R,E)-4-methyl-N-((5-phenylthiophen-2-yl)methylene)benzenesulfinamide;
(R,E)-N-((4-(2,4-difluorophenyl)thiophen-2-yl)methylene)-4-methylbenzene sulfonamide;
(R,E)-N-((4-(3-methoxyphenyl)thiophen-2-yl)methylene)-4-methylbenzene sulfonamide;
(R,E)-N-((4-(3-chlorophenyl)thiophen-2-yl)methylene)-4-methylbenzene sulfonamide;
(R,E)-N-((3'-chloro-6-methoxybiphenyl-3-yl)methylene)-4-methylbenzene sulfonamide;
(R,E)-4-methyl-N-(3-(pyrazin-2-yl)benzylidene)benzenesulfinamide;
(R,E)-N-(3-(6-methoxypyridin-2-yl)benzylidene)-4-methylbenzenesulfinamide;
(R,E)-N-((4-(2,6-dimethylphenyl)thiophen-2-yl)methylene)-4-methylbenzene sulfonamide;
(R,E)-4-methyl-N-(3-(1-(triisopropylsilyl)-1H-pyrrol-3-yl)benzylidene)benzene sulfonamide;

(R,E)-4-methyl-N-(3-(1-methyl-1H-pyrazol-4-yl)benzylidene)benzenesulfinamide;
(R,E)-N-((3'-chloro-6-methylbiphenyl-3-yl)methylene)-4-methylbenzene sulfonamide;
(R,E)-4-methyl-N-(3-(thiazol-2-yl)benzylidene)benzenesulfinamide;
(R,E)-N-(3-(3,5-dimethylisoxazol-4-yl)benzylidene)-4-methylbenzenesulfinamide (19-1);
(R,E)-4-methyl-N-((4'-methyl-2,3'-bithiophen-5-yl)methylene)benzenesulfinamide;
(R,E)-N-((5-(2,6-dimethylphenyl)thiophen-2-yl)methylene)-4-methylbenzenesulfonamide;
(R,E)-4-methyl-N-((5-(3-(trifluoromethoxy)phenyl)thiophen-2-yl)methylene) benzenesulfinamide;
(R,E)-N-((5-(3,5-dimethylisoxazol-4-yl)thiophen-2-yl)methylene)-4-methylbenzene sulfonamide;
(R,E)-N-((5-(2,5-difluorophenyl)thiophen-2-yl)methylene)-4-methylbenzene sulfonamide;
(R,E)-4-methyl-N-((6-(trifluoromethoxy)biphenyl-3-yl)methylene)benzene sulfonamide;
(R,E)-N-((5-(3-chlorophenyl)thiophen-2-yl)methylene)-4-methylbenzene sulfonamide; and
(R,E)-N-((5-(3-fluorophenyl)thiophen-2-yl)methylene)-4-methylbenzene sulfinamide.

Step Two: To a solution of ethyl acetate (0.154 mL, 1.58 mmol) in tetrahydrofuran (3 mL) at −78° C. under nitrogen, sodium hexamethyldisilazide (1.0 M in tetrahydrofuran, 1.58 mL, 1.58 mmol) was added by syringe. The resulting mixture was stirred for 30 minutes, then a solution of 6-1 (292 mg, 1.05 mmol) in tetrahydrofuran (4 mL) was added. The mixture was stirred at −78° C. for 4 hours then was quenched with saturated aqueous ammonium chloride. The mixture was warmed to room temperature and extracted with ethyl acetate. The organic layer was dried over magnesium sulfate, filtered and concentrated. The residue was purified by silica gel column chromatography, eluting with 30% to 50% ethyl acetate in hexanes to give ethyl (S)-3-((R)-4-methylphenylsulfinamido)-3-(5-phenylfuran-2-yl)propanoate; (6-2, 270 mg).

This procedure was also used to make ethyl (S)-3-((R)-4-methylphenylsulfinamido)-3-(1-phenyl-1H-pyrrol-2-yl)propanoate;
ethyl (S)-3-((R)-4-methylphenylsulfinamido)-3-(4-phenylthiophen-2-yl)propanoate;
ethyl (S)-3-((R)-5-methylphenylsulfinamido)-3-(4-phenylthiophen-2-yl)propanoate;
ethyl (S)-3-(4-(2,4-difluorophenyl)thiophen-2-yl)-3-((R)-4-methylphenylsulfinamido)propanoate;
ethyl (S)-3-(4-(3-methoxyphenyl)thiophen-2-yl)-3-((R)-4-methylphenylsulfinamido)propanoate;
ethyl (S)-3-(4-(3-chlorophenyl)thiophen-2-yl)-3-((R)-4-methylphenylsulfinamido)propanoate;
ethyl (S)-3-(3'-chloro-6-methoxybiphenyl-3-yl)-3-((R)-4-methylphenylsulfinamido)propanoate;
ethyl (S)-3-((R)-4-methylphenylsulfinamido)-3-(3-(pyrazin-2-yl)phenyl)propanoate;
ethyl (S)-3-(3-(6-methoxypyridin-2-yl) phenyl)-3-((R)-4-methylphenylsulfinamido)propanoate;
ethyl (S)-3-(4-(2,6-dimethylphenyl)thiophen-2-yl)-3-((R)-4-methylphenylsulfinamido)propanoate;
ethyl (S)-3-((R)-4-methylphenylsulfinamido)-3-(3-(1-(triisopropylsilyl)-1H-pyrrol-3-yl)phenyl)propanoate;
ethyl (S)-3-(3-(1-methyl-1H-pyrazol-4-yl)phenyl)-3-((R)-4-methylphenylsulfinamido)propanoate;
ethyl (S)-3-(3'-chloro-6-methylbiphenyl-3-yl)-3-((R)-4-methylphenylsulfinamido) propanoate;
ethyl (S)-3-((R)-4-methylphenylsulfinamido)-3-(3-(thiazol-2-yl)phenyl)propanoate;
ethyl (S)-3-((R)-4-methylphenylsulfinamido)-3-(5-(3-(trifluoromethoxy)phenyl) thiophen-2-yl)propanoate; and
ethyl (S)-3-((R)-4-methylphenylsulfinamido)-3-(6-(trifluoromethoxy)biphenyl-3-yl)propanoate. This procedure was modified to use ether as a co-solvent with tetrahydrofuran.

This modification was used to prepare ethyl (S)-3-(5-(2,6-dimethylphenyl)thiophen-2-yl)-3-((R)-4-methylphenylsulfinamido)propanoate;
ethyl (S)-3-(5-(3,5-dimethylisoxazol-4-yl)thiophen-2-yl)-3-((R)-4-methylphenylsulfinamido)propanoate;
ethyl (S)-3-(4'-methyl-2,3'-bithiophen-5-yl)-3-((R)-4-methylphenylsulfinamido) propanoate;
ethyl (S)-3-(5-(2,5-difluorophenyl)thiophen-2-yl)-3-((R)-4-methylphenylsulfinamido)propanoate;
ethyl (S)-3-(5-(3-chlorophenyl)thiophen-2-yl)-3-((R)-4-methylphenylsulfinamido) propanoate; and
ethyl (S)-3-(5-(3-fluorophenyl)thiophen-2-yl)-3-((R)-4-methylphenylsulfinamido) propanoate.

Step Three: To a solution of 6-2 (200 mg, 0.50 mmol) in ethanol, trifluoroacetic acid (0.077 mL, 1.0 mmol) was added. The mixture was stirred for 2 hours, diluted with saturated aqueous sodium bicarbonate, and extracted with ethyl acetate. The organic layer was washed with brine, dried over magnesium sulfate, filtered and concentrated to give ethyl (S)-3-amino-3-(5-phenylfuran-2-yl)propanoate; (6-3, 110 mg) as a yellow oil.

This procedure was also used to make
ethyl (S)-3-amino-3-(1-phenyl-1H-pyrrol-2-yl)propanoate;
ethyl (S)-3-amino-3-(4-phenylthiophen-2-yl)propanoate;
ethyl (S)-3-amino-3-(5-phenylthiophen-2-yl)propanoate;
ethyl (S)-3-amino-3-(3-(pyrazin-2-yl)phenyl)propanoate;
ethyl (S)-3-amino-3-(3-(6-methoxypyridin-2-yl)phenyl)propanoate;
and ethyl (S)-3-amino-3-(3-(thiazol-2-yl)phenyl)propanoate.

This procedure was altered by using 2N hydrochloric acid instead of trifluoroacetic acid. This modification was used to make ethyl (S)-3-(3-(1H-pyrrol-3-yl)phenyl)-3-aminopropanoate; (from ethyl (S)-3-((R)-4-methylphenylsulfinamido)-3-(3-(1-(triisopropylsilyl)-1H-pyrrol-3-yl)phenyl) propanoate triisopropylsilyl group also removed),
ethyl (S)-3-amino-3-(4-(2,4-difluorophenyl)thiophen-2-yl) propanoate;
ethyl (S)-3-amino-3-(4-(3-methoxyphenyl)thiophen-2-yl) propanoate;
ethyl (S)-3-amino-3-(4-(3-chlorophenyl)thiophen-2-yl)propanoate;
ethyl (S)-3-amino-3-(3'-chloro-6-methoxybiphenyl-3-yl) propanoate;
ethyl (S)-3-amino-3-(4-(2,6-dimethylphenyl)thiophen-2-yl) propanoate;
ethyl (S)-3-amino-3-(3-(1-methyl-1H-pyrazol-4-yl)phenyl) propanoate;
ethyl (S)-3-amino-3-(3'-chloro-6-methylbiphenyl-3-yl)propanoate;
ethyl (S)-3-amino-3-(3-(furan-3-yl)phenyl)propanoate;
ethyl (S)-3-amino-3-(3-(3,5-dimethylisoxazol-4-yl)phenyl) propanoate;
ethyl (S)-3-amino-3-(4'-methyl-[2,3'-bithiophen]-5-yl)propanoate;
ethyl (S)-3-amino-3-(5-(2,6-dimethylphenyl)thiophen-2-yl) propanoate;
ethyl (S)-3-amino-3-(5-(3-(trifluoromethoxy)phenyl)thiophen-2-yl)propanoate;

ethyl (S)-3-amino-3-(5-(3,5-dimethylisoxazol-4-yl)thiophen-2-yl)propanoate;
ethyl (S)-3-amino-3-(5-(2,5-difluorophenyl)thiophen-2-yl)propanoate;
ethyl (S)-3-amino-3-(6-(trifluoromethoxy)biphenyl-3-yl)propanoate;
ethyl (S)-3-amino-3-(5-(trifluoromethyl)biphenyl-3-yl)propanoate;
ethyl (S)-3-amino-3-(5-(3-chlorophenyl)thiophen-2-yl)propanoate;
and ethyl (S)-3-amino-3-(5-(3-fluorophenyl)thiophen-2-yl)propanoate.

In another modification, 4M hydrogen chloride in dioxane was used in place of trifluoroacetic acid. This modification was used to prepare ethyl (S)-3-amino-3-(3-(6-methoxypyridazin-3-yl)phenyl)propanoate;
ethyl (S)-3-amino-3-(5-(2,4-difluorophenyl)thiophen-2-yl)propanoate;
ethyl (S)-3-amino-3-(5-(3-methoxyphenyl)thiophen-2-yl)propanoate;
ethyl (S)-3-amino-3-(6-phenylpyridin-2-yl)propanoate;
ethyl (S)-3-amino-3-(3-(thiophen-2-yl)phenyl)propanoate;
ethyl (S)-3-amino-3-(2',6'-dichlorobiphenyl-3-yl)propanoate;
ethyl (S)-3-amino-3-(3-(5-chlorothiophen-2-yl)phenyl)propanoate;
ethyl (S)-3-amino-3-(3-(4-methylthiophen-3-yl)phenyl)propanoate;
and ethyl (S)-3-amino-3-(3'-chlorobiphenyl-3-yl)propanoate.

When preparing ethyl (S)-3-amino-3-(5-phenylpyridin-3-yl)propanoate dihydrochloride by this modification, the crude reaction mixture was concentrated to give the hydrochloride salt.

Example 7

Synthesis of ethyl (S)-3-(3-(2,5-dimethyl-1H-pyrrol-1-yl)phenyl)-3-(3-(4-hydroxy-1,5-dimethyl-2-oxo-1,2-dihydropyridin-3-yl)ureido)propanoate (7-5)

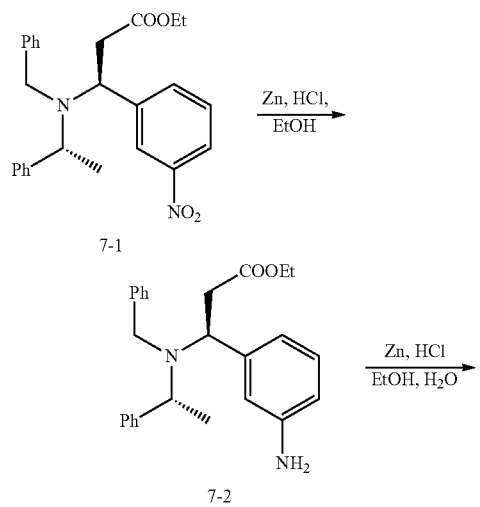

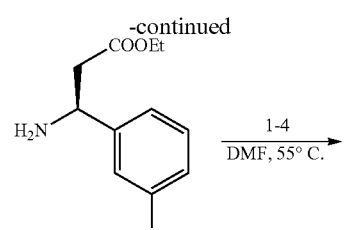

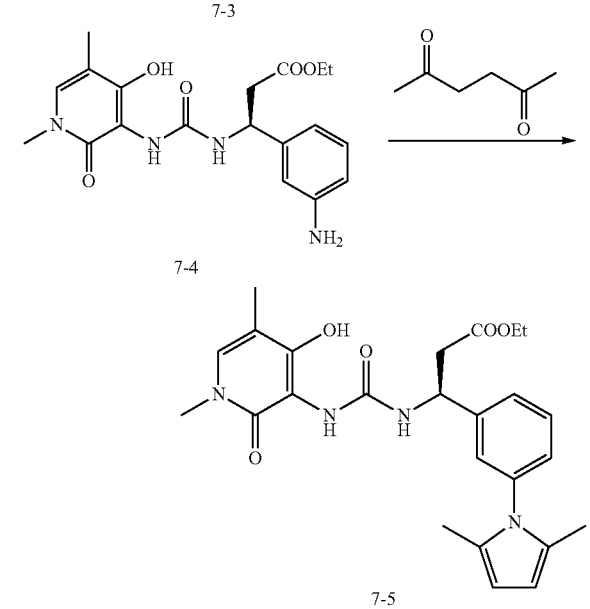

Step One: To a solution of 7-1 (13.1 g, 30.29 mmol, prepared according to steps 5 and 6 of example 1 from 3-nitrocinnamic acid) in ethanol (136 mL), zinc dust (11.88 g, 181.7 mmol) and aqueous hydrochloric acid (136 mL) were added. The resulting mixture was stirred at room temperature for 2 hours and was adjusted to pH 4 and filtered through Celite®. The filtrate was concentrated to give ethyl (S)-3-(3-aminophenyl)-3-(benzyl((R)-1-phenylethyl)amino)propanoate (7-2, 10.6 g) as a solid.

Step Two: To a solution of 7-2 (1.00 g, 2.28 mmol) in ethanol (9 mL) under nitrogen, palladium on carbon (10%, 500 mg) was added. The atmosphere was exchanged for hydrogen (toggle between vacuum and hydrogen from a balloon several times) and the mixture was stirred for 1 hour then was filtered through Celite® and concentrated. The residue was taken up in ether and extracted three times with aqueous hydrochloric acid (1N). The combined aqueous layers were basified with saturated aqueous sodium bicarbonate then extracted three times with ethyl acetate. The combined organic layers were washed with brine, dried, filtered and concentrated to give ethyl (S)-3-amino-3-(3-aminophenyl)propanoate (7-3, 352 mg).

Step Three: A mixture of 1-4 (100 mg, 0.52 mmol) and 7-3 (161 mg, 0.77 mmol) in N,N-dimethylformamide (2.5 mL) was heated to 60° C. for 6 hours then cooled to room temperature. The mixture was diluted with ethyl acetate, washed with aqueous hydrochloric acid (2N), water, and brine. The organic layer was dried over magnesium sulfate, filtered, and concentrated. The residue was purified by silica gel column chromatography, eluting with 10-20% methanol in chloroform to give ethyl (S)-3-(3-aminophenyl)-3-(3-(4-hydroxy-1,5-dimethyl-2-oxo-1,2-dihydropyridin-3-yl)ureido) propanoate (7-4, 166 mg).

This procedure was also used to prepare ethyl (S)-3-(3-aminophenyl)-3-(3-(4-hydroxy-1-methyl-2-oxo-1,2-dihydropyridin-3-yl)ureido)propanoate (13-1, from 7-3 and 5-methyloxazolo[4,5-c]pyridine-2,4(3H,5H)-dione).

Step Four: To a mixture of 7-4 (91 mg, 0.23 mmol) in glacial acetic acid (1 mL), 2,5-hexanedione (0.040 mL, 0.34 mmol) was added and the mixture was heated to 85° C. for 1 hour. The mixture was diluted with saturated aqueous sodium bicarbonate and was extracted three times with chloroform. The combined organic layers were dried, filtered and concentrated to give ethyl (S)-3-(3-(2,5-dimethyl-1H-pyrrol-1-yl)phenyl)-3-(3-(4-hydroxy-1,5-dimethyl-2-oxo-1,2-dihydropyridin-3-yl)ureido)propanoate (7-5, 71 mg). This material was used without purification.

Example 8

Synthesis of 5,6-dimethyloxazolo[4,5-c]pyridine-2,4 (3H,5H)-dione (8-2)

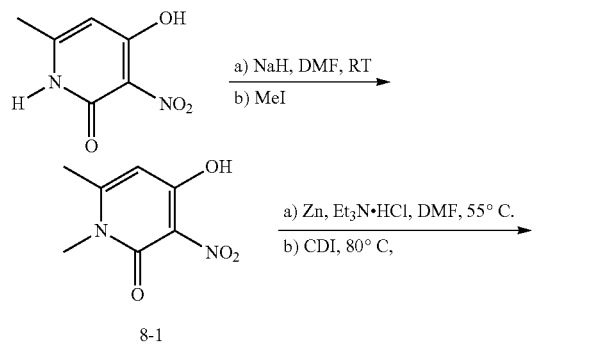

Step One: To a solution of 4-hydroxy-6-methyl-3-nitropyridone (998 mg, 5.87 mmol) in N,N-dimethylformamide at room temperature under argon, sodium hydride (60% dispersion in mineral oil, 517 mg, 12.9 mmol) was added in three portions. The resulting mixture was stirred for 1 hour and iodomethane (0.44 mL, 7.04 mmol) was added by syringe. The mixture was stirred overnight, during which time a solid had formed. The mixture was poured into 50% ethyl acetate in hexanes, washing the reaction flask with ethyl acetate. The resulting suspension was stirred for 30 minutes then filtered, washing with 50% ethyl acetate in hexanes. The solid cake was air dried for 15 minutes then was dissolved in water (40 mL) and acidified with aqueous hydrocholoric acid (2N, 10 mL). The resulting mixture was stirred for 30 minutes, during which time a yellow solid had formed. The mixture was filtered, washing with water, and the solid was dried under vacuum overnight to give 4-hydroxy-1,6-dimethyl-3-nitropyridin-2(1H)-one (8-1, 865 mg) as a yellow powder.

This procedure was also used to prepare 4-hydroxy-1-methyl-3-nitropyridin-2(1H)-one, and 4-chloro-5-methoxy-2-methylpyridazin-3(2H)-one (29-2, from 29-1).

In another reaction, the workup was modified by diluting the crude reaction mixture with 2 N hydrochloric acid and extracting several times with dichloromethane. The organic layer was dried, filtered and concentrated. The residue was taken up in ether to give a suspension, which was filtered to give 1-ethyl-4-hydroxy-3-nitropyridin-2(1H)-one as a solid.

Step Two: To a solution of 8-1 (860 mg, 4.67 mmol) in N,N-dimethylformamide (15.6 mL) at room temperature under argon, zinc dust (1.374 g, 21.0 mmol) and trimethylamine hydrochloride (3.536 g, 25.7 mmol) were added. The mixture was heated to 60° C. for 3 hours then cooled to room temperature, and 1,1'-carbonyldiimidazole (2.27 g, 14.0 mmol) was added in one portion (gas evolution). The mixture was heated under argon to 80° C. for 2 hours then filtered hot to remove the unreacted zinc, washing with N,N-dimethylformamide. The filtrate was concentrated under reduced pressure and the residue was taken up in aqueous hydrochloric acid (1N, 50 mL). The flask was vigorously swirled for 5 minutes then the resulting suspension was filtered, washing with water. The solid was dried under vacuum to give 5,6-dimethyloxazolo[4,5-c]pyridine-2,4(3H,5H)-dione (8-2, 637 mg) as a cream colored powder.

This procedure was also used to prepare 5-methyloxazolo[4,5-c]pyridine-2,4(3H,5H)-dione.

The procedure was modified by using 4 M hydrogen chloride in dioxane instead of trimethylamine hydrochloride to prepare 5-ethyloxazolo[4,5-c]pyridine-2,4(3H,5H)-dione and oxazolo[4,5-c]pyridine-2,4(3H,5H)-dione.

Example 9

Synthesis of 4-hydroxy-1-methyl-6,7-dihydro-1H-cyclopenta[b]pyridin-2(5H)-one (9-3)

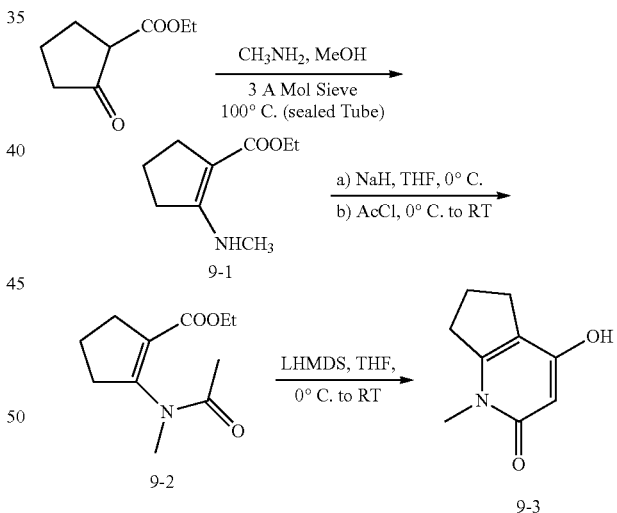

Step One: A mixture of ethyl 2-oxocyclopentanecarboxylate (5.0 mL, 33.7 mmol) and molecular sieves (3 Å) in methylamine (2 M in tetrahydrofuran, 17.0 mL, 34 mmol) was heated to 100° C. in a sealed tube overnight. The resulting mixture was cooled to room temperature, diluted with ethyl acetate, and filtered through Celite®, washing with ethyl acetate. The filtrate was concentrated to give ethyl 2-(methylamino)cyclopent-1-enecarboxylate (9-1, 5.35 g) as a yellow solid.

Step Two: To a solution of 9-1 (5.35 g, 31.6 mmol) in tetrahydrofuran (63 mL) at 0° C. under nitrogen, sodium hydride (60% dispersion in mineral oil, 1.39 g, 34.8 mmol)

was added in portions. The resulting mixture was stirred 15 minutes then acetyl chloride (3.2 mL, 45.0 mmol) was added dropwise. The reaction was stirred for 15 minutes then removed from the ice bath and stirred another two hours. The mixture was diluted with saturated aqueous ammonium chloride, and extracted three times with ethyl acetate. The combined organic layers were dried over magnesium sulfate, filtered and concentrated to give ethyl 2-(N-methylacetamido)cyclopent-1-enecarboxylate (9-2, 6.04 g) as a dark yellow oil. This material contained mineral oil and other minor impurities but was used without purification.

This reaction could also be performed using DMF as solvent, This modification was used to prepare methyl 3-(N-methylacetamido)thiophene-2-carboxylate; and methyl 2-(N-methylacetamido)nicotinate.

Step Three: To a solution of 9-2 (6.04 g, crude material from previous step) in tetrahydrofuran (36 mL) at 0° C. under nitrogen, lithium hexamethyldisilazide (1.0 M in tetrahydrofuran, 72.0 mL, 72.0 mmol) was added slowly by syringe. The reaction was stirred for 15 minutes then removed from the ice bath and stirred 4 hours. The reaction was quenched by adding glacial acetic acid (4.1 mL) then concentrated. The residue was taken up in 30% methanol in chloroform and filtered through Celite®. The filtrate was concentrated and the residue was purified by silica gel chromatography, eluting with 10% methanol in chloroform.

Fractions containing product were taken up in chloroform to give a suspension, which was filtered. The solid was dried under vacuum to give 4-hydroxy-1-methyl-6,7-dihydro-1H-cyclopenta[b]pyridin-2(5H)-one (9-3, 2.107 g).

This procedure was also used to prepare 4-hydroxy-1-methyl-6,7-dihydro-1H-cyclopenta[b]pyridin-2(5H)-one; 4-hydroxy-1-methyl-1,8-naphthyridin-2(1H)-one; and 7-hydroxy-4-methylthieno[3,2-b]pyridin-5(4H)-one.

Example 10

Synthesis of ethyl (S)-3-(benzyl((R)-1-phenylethyl)amino)-3-(3'-methoxy-2'-methylbiphenyl-3-yl)propanoate (10-4)

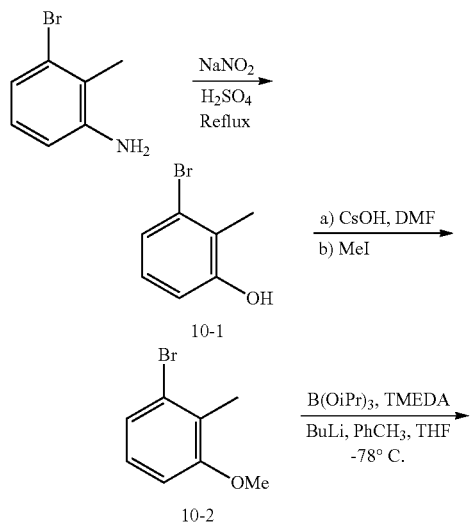

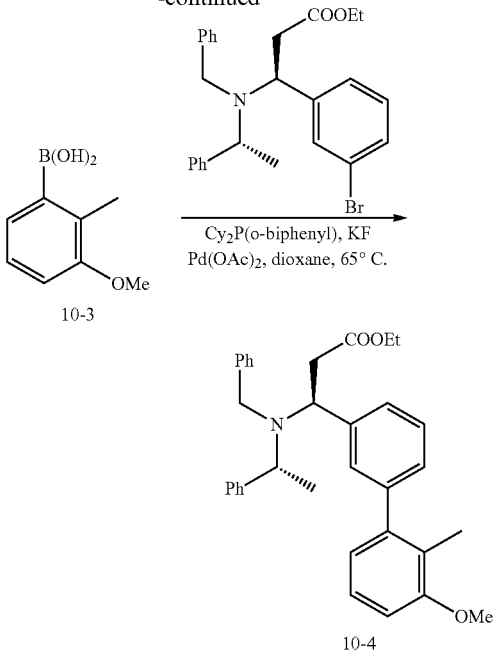

Step One: To a flask containing aqueous sulfuric acid (14%, 260 mL), 3-bromo-2-methylaniline (5.00 mL, 40.6 mmol) was added. The mixture was brought to reflux, and a solution of sodium nitrite (3.08 g, 44.6 mmol) in water (minimum amount required to dissolve) was added dropwise over the course of 1 hour. The mixture was refluxed an additional 30 minutes, cooled to room temperature, and extracted three times with chloroform. The combined chloroform layeres were extracted three times with aqueous sodium hydroxide (1 M). The aqueous layers were acidified with concentrated hydrochloric acid and extracted three times with chloroform. These three chloroform extracts were combined, dried over magnesium sulfate, filtered, and concentrated to give 3-bromo-2-methylphenol (10-1, 5.63 g) as a brown solid.

This procedure was also used to prepare 3-bromo-4-methylphenol.

Step Two: After stirring a mixture of cesium hydroxide hydrate (6.57 g, 39.1 mmol) and molecular sieves (4 Å, 15.06 g) in N,N-dimethylformamide (75 mL) at room temperature for 15 minutes, 10-1 (5.63 g, 30.1 mmol) was added. The mixture was stirred for 30 minutes and iodomethane (2.44 mL, 39.1 mmol) was added. The reaction was stirred 4 hours then diluted with ethyl acetate and filtered through Celite®. The filtrate was diluted with water and the aqueous layer was adjusted to pH 9 with aqueous sodium hydroxide (1N). The organic layer was washed with brine, dried over magnesium sulfate, filtered and concentrated. The residue was taken up in 5% ethyl acetate in hexanes (250 mL) and filtered through a short plug of silica gel. The filtrate was concentrated to give 1-bromo-3-methoxy-2-methylbenzene (10-2, 4.57 g) as a yellow liquid. This procedure was also used to prepare 2-bromo-4-methoxy-1-methylbenzene.

The reaction could also be performed using potassium carbonate in place of cesium carbonate at reflux in a sealed tube. This variation was used to prepare 3-bromo-4-(2,2,2-trifluoroethoxy)benzaldehyde (from 2,2,2-trifluoroethyl iodide).

Step Three: To a mixture of 10-2 (1.00 g, 4.97 mmol) and triisopropyl borate (1.72 mL, 6.46 mmol) in toluene (8 mL) and tetrahydrofuran (2 mL) and tetramethylethylenediamine (0.99 mL, 6.46 mmol) at −78° C. under nitrogen, butyllithium (2.5 M in hexanes, 2.58 mL, 6.46 mmol) was added dropwise by syringe over the course of 1 hour. The reaction was stirred for 1 hour, warmed to −20° C., quenched with aqueous hydrochloric acid (2N, 20 mL), and warmed to room temperature and stirred 45 minutes. The resulting mixture was diluted with ethyl acetate and the organic layer was washed with brine, dried over magnesium sulfate, and filtered. The filtrate was concentrated and the residue was taken up in hexanes and the resulting suspension was filtered. After standing overnight, more solid precipitated from the filtrate, and was collected by filtration. The combined solids were dried under vacuum to give 3-methoxy-2-methylphenylboronic acid (10-3, 517 mg).

This procedure was also used to prepare 5-methoxy-2-methylphenylboronic acid.

Step Four: To a screw cap thick-wall tube containing 10-3 (500 mg, 3.01 mmol), potassium fluoride (350 mg, 6.03 mmol), palladium(II) acetate (34 mg, 0.15 mmol) and 2-(dicyclohexylphosphino)biphenyl (106 mg, 0.301 mmol), a solution of 1-6 (993 mg, 2.01 mmol) in dioxane (3 mL) was added. The mixture was placed under nitrogen, sealed and heated to 65° C. for 16 hours. The mixture was cooled to room temperature, diluted with ethyl acetate, filtered through Celite®, and concentrated. The residue was purified by silica gel chromatography, eluting with 5% ethyl acetate in hexanes to give ethyl (S)-3-(benzyl((R)-1-phenylethyl)amino)-3-(3'-methoxy-2'-methylbiphenyl-3-yl)propanoate; (10-4, 891 mg).

This procedure was also used to prepare ethyl (S)-3-(benzyl((R)-1-phenylethyl)amino)-3-(5'-methoxy-2'-methylbiphenyl-3-yl)propanoate;
ethyl (S)-3-(3'-chlorobiphenyl-3-yl)-3-((R)-1,1-dimethylethylsulfinamido)propanoate;
tert-butyl (S)-3-(benzyl((R)-1-phenylethyl)amino)-3-(2',4'-difluorobiphenyl-4-yl)propanoate;
ethyl (S)-3-(benzyl((R)-1-phenylethyl)amino)-3-(2'-ethylbiphenyl-3-yl)propanoate (from 26-2 and 1-bromo-2-ethylbenzene Example 11

Synthesis of 1-phenyl-1H-pyrrole-2-carbaldehyde (11-1)

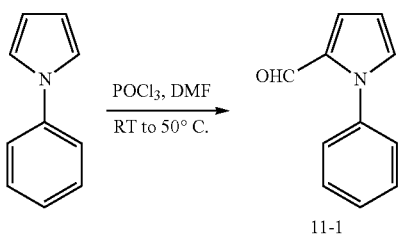 [SMILES: c1ccc(-n2cccc2)cc1 ; O=Cc1cccn1-c1ccccc1]

Step One: Phosphorousoxychloride (1.30 mL, 14.0 mmol) and N,N-dimethylformamide (1.08 mL, 14.0 mmol) were combined at 0° C. under nitrogen, warmed to room temperature and stirred for 15 minutes. To the resulting mixture, a solution of 1-phenylpyrrole (2.00 g, 14.0 mmol) in N,N-dimethylformamide (1 mL) was added dropwise by syringe. The reaction was heated to 50° C. for 3 hours, cooled to room temperature, diluted with saturated aqueous bicarbonate, and stirred for 10 minutes. The mixture was extracted with ethyl acetate and the organic layer was dried over magnesium sulfate, filtered and concentrated. The residue was purified by silica gel chromatography, eluting with 10% ethyl acetate in hexanes to give 1-phenyl-1H-pyrrole-2-carbaldehyde (11-1, 581 mg).

Example 12 ethyl (S)-3-(3-bromophenyl)-3-((R)-1,1-dimethylethylsulfinamido)propanoate (12-2)

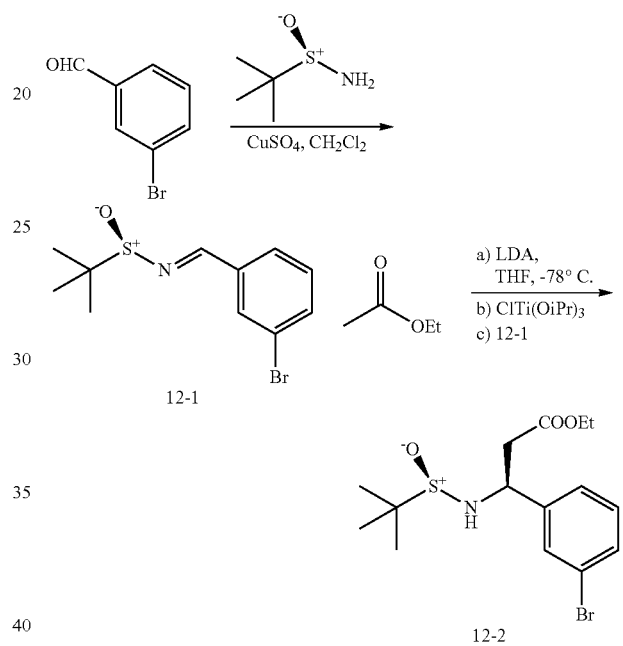

Step One: To a solution of 3-bromobenzaldehyde (0.33 mL, 2.72 mmol) and (R)-(+)-2-methyl-2-propanesulfinamide (300 mg, 2.49 mmol) in dichloromethane (5 mL) at room temperature under nitrogen, copper(II) sulfate (788 mg, 4.94 mmol) was added. The mixture was stirred overnight, filtered through Celite®, and concentrated. The residue was purified by silica gel chromatography to give (R,E)-N-(3-bromobenzylidene)-2-methylpropane-2-sulfinamide (12-1, 561 mg) as a pale yellow oil.

This material was also used to prepare (R,E)-2-methyl-N-(3-(thiophen-2-yl)benzylidene)propane-2-sulfinamide;
(R,E)-N-((2',6'-dichlorobiphenyl-3-yl)methylene)-2-methylpropane-2-sulfinamide;
(R,E)-N-(3-(5-chlorothiophen-2-yl)benzylidene)-2-methylpropane-2-sulfinamide;
(R,E)-2-methyl-N-(3-(4-methylthiophen-3-yl)benzylidene)propane-2-sulfinamide;
(R,E)-N-(3-(6-methoxypyridazin-3-yl)benzylidene)-2-methylpropane-2-sulfinamide;
(R,E)-N-(3-(furan-3-yl)benzylidene)-2-methylpropane-2-sulfinamide;
(R,E)-N-((5-(2,4-difluorophenyl)thiophen-2-yl)methylene)-2-methylpropane-2-sulfinamide; and
(R,E)-N-((5-(3-methoxyphenyl)thiophen-2-yl)methylene)-2-methylpropane-2-sulfinamide.

Step Two: To a solution of diisopropylamine (0.612 mL, 4.37 mmol) in tetrahydrofuran (10 mL) at 0° C. under nitrogen, n-butyllithium (2.5 M in hexanes, 1.75 mL, 4.38 mmol) was added by syringe. The resulting mixture was stirred for 30 minutes, was cooled to −78° C., and ethyl acetate (0.406 mL, 4.16 mmol) was added dropwise. The reaction was stirred for 30 minutes and chlorotriisopropoxytitanium(IV) (1.0 M in hexanes, 8.73 mL, 8.73 mmol) was added and the mixture was stirred another 30 minutes. To the resulting mixture, a solution of 12-1 (600 mg, 2.08 mmol) in tetrahydrofuran (8 mL) was added. The reaction was stirred for 3 hours at −78° C., saturated aqueous ammonium chloride (10 mL) was added and the mixture was allowed to warm to room temperature. The organic layer was decanted and saved. The remainder of the mixture was diluted with ethyl acetate and water and stirred 20 minutes. The phases were separated and the aqueous layer was extracted three times with ethyl acetate. All organic phases were combined, washed with brine, dried over magnesium sulfate, filtered and concentrated. The residue was purified by silica gel chromatography to give ethyl (S)-3-(3-bromophenyl)-3-((R)-1,1-dimethylethylsulfinamido)propanoate (12-2, 600 mg) as a clear oil.

This reaction was also used to prepare ethyl (S)-3-((R)-1,1-dimethylethylsulfinamido)-3-(3-(thiophen-2-yl)phenyl) propanoate;
ethyl (S)-3-(2',6'-dichlorobiphenyl-3-yl)-3-((R)-1,1-dimethylethylsulfinamido)propanoate;
ethyl (S)-3-(3-(5-chlorothiophen-2-yl)phenyl)-3-((R)-1,1-dimethylethylsulfinamido) propanoate;
ethyl (S)-3-((R)-1,1-dimethylethylsulfinamido)-3-(3-(4-methylthiophen-3-yl)phenyl) propanoate;
ethyl (S)-3-((R)-1,1-dimethylethylsulfinamido)-3-(3-(furan-3-yl)phenyl)propanoate;
ethyl (S)-3-(5-bromopyridin-3-yl)-3-((R)-1,1-dimethylethylsulfinamido)propanoate (20-2); and
ethyl (S)-3-((R)-1,1-dimethylethylsulfinamido)-3-(6-phenylpyridin-2-yl)propanoate.

Example 13

Synthesis of ethyl (S)-3-(3-(1H-pyrrol-1-yl)phenyl)-3-(3-(4-hydroxy-1-methyl-2-oxo-1,2-dihydropyridin-3-yl)ureido)propanoate (13-2)

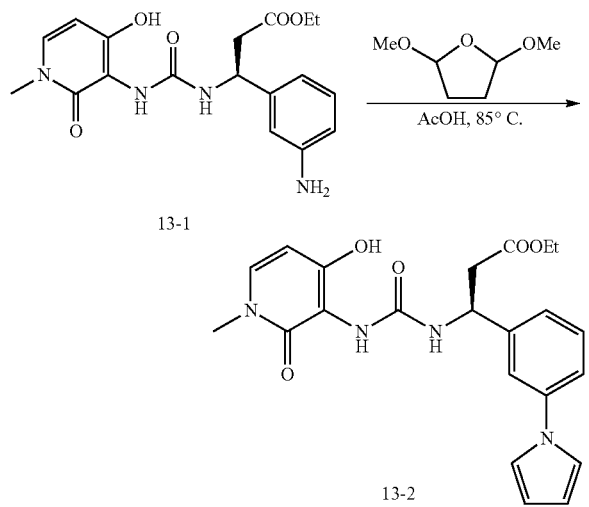

Step One: To a solution of 13-1 (181 mg, 0.484 mmol, prepared from 7-3 and 5-methyloxazolo[4,5-c]pyridine-2,4 (3H,5H)-dione according to the procedure described in step 3 of example 7) in tetrahydrofuran (1.7 mL), glacial acetic acid (2.2 mL) and 2,5-dimethoxytetrahydrofuran (0.100 mL, 0.774 mmol) were added. The mixture was heated to 75° C. overnight, cooled to room temperature, diluted with water, basified by the careful addition of solid sodium bicarbonate, and extracted three times with chloroform. The combined organic layers were dried over magnesium sulfate, filtered and concentrated. The residue was purified by silica gel chromatography, eluting with ethyl acetate to give ethyl (S)-3-(3-(1H-pyrrol-1-yl)phenyl)-3-(3-(4-hydroxy-1-methyl-2-oxo-1,2-dihydropyridin-3-yl)ureido)propanoate (13-2, 87.5 mg).

Example 14

Synthesis of 3-(thiophen-2-yl)benzaldehyde (14-1)

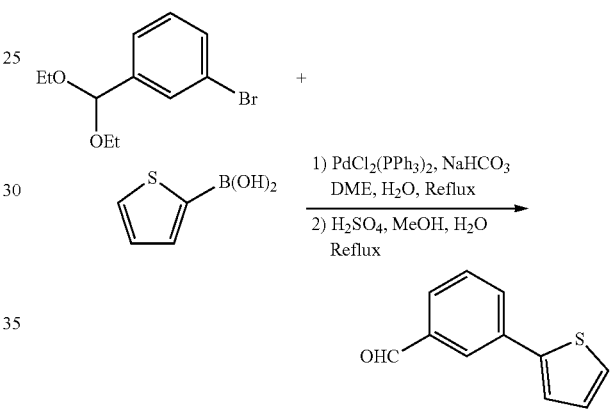

Step One: To a mixture of 3-bromobenzaldehyde diethylacetal (1.495 g, 5.77 mmol) and bis(triphenylphoshine) palladium(II) dichloride (206 mg, 0.29 mmol) in dimethoxyethane (30 mL) at room temperature under nitrogen, 2-thiopheneboronic acid (1.189 g, 9.29 mmol) and aquesou sodium bicarbonate (1M, 29 mL) were added. The mixture was heated to reflux overnight, cooled to room temperature, and diluted with ethyl acetate. The organic layer was washed with water and brine, dried over magnesium sulfate, filtered, and concentrated. The residue was purified by silica gel chromatography to give a mixture of 2-(3-(diethoxymethyl) phenyl)thiophene and 14-1. This material was taken up in 1:1 methanol:water (30 mL) and concentrated sulfuric acid (1 mL) was added. The mixture was heated to reflux for 2 hours, cooled to room temperature and concentrated. The residue was taken up in ethyl acetate, washed with saturated aqueous sodium bicarbonate, water and brine, dried over magnesium sulfate, filtered and concentrated. The residue was purified by silica gel chromatography, eluting with 10% ethyl acetate in hexanes to give 3-(thiophen-2-yl)benzaldehyde (14-1, 661 mg) as a yellow oil.

In a modification of this procedure, the crude reaction mixture in the first step was acidified with 2 N hydrochloric acid to hydrolyze the acetal. The workup for the second step was then employed once the hydrolysis was complete to give 3-(5-chlorothiophen-2-yl)benzaldehyde.

Example 15

Synthesis of Sodium (S)-3-(3-(1-methyl-4-oxido-2-oxo-1,2-dihydropyridin-3-yl)ureido)-3-(3-(pyrazin-2-yl)phenyl)propanoate (15-2)

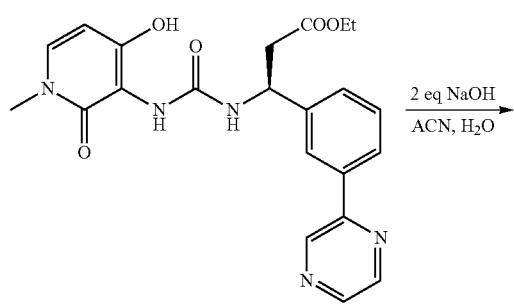

15-1

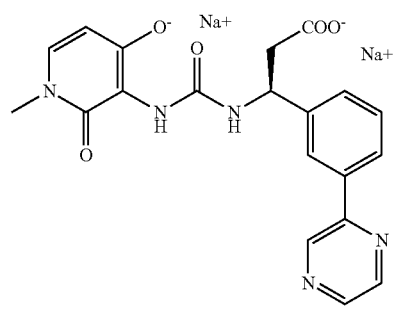

15-2

Step One: To a solution of 15-1 (30.4 mg, 0.0695 mmol, prepared from ethyl (S)-3-amino-3-(3-(pyrazin-2-yl)phenyl)propanoate and 5-methyloxazolo[4,5-c]pyridine-2,4(3H,5H)-dione according to the procedure described in step 9 of example 1) in acetonitrile (0.25 mL), aqueous sodium hydroxide (0.1004N, 0.69 mL, 0.0693 mmol) was added. The mixture was stirred overnight, and additional aqueous sodium hydroxide (0.1004N, 0.69 mL, 0.0693 mmol) was added. The mixture was stirred at room temperature for 3 hours then at 35° C. for 3 hours. The resulting mixture was extracted with diethyl ether and the aqueous layer was separated, frozen, and lyophilized to give sodium (S)-3-(3-(1-methyl-4-oxido-2-oxo-1,2-dihydropyridin-3-yl)ureido)-3-(3-(pyrazin-2-yl)phenyl)propanoate (15-2, 30.3 mg, MS [M+H$^+$]$^+$: Calculated: 410.15; Measured: 410.02; α4β1 IC$_{50}$=<20 nM: α4β7 IC$_{50}$=nd; as an off-white solid.

This procedure was also used to prepare sodium (S)-3-(3-(6-methoxypyridin-2-yl)phenyl)-3-(3-(1-methyl-4-oxido-2-oxo-1,2-dihydropyridin-3-yl)ureido)propanoate (MS [M+H$^+$]$^+$: Calculated: 439.16; Measured: 439.00; α4β1 IC$_{50}$=<20 nM: α4β7 IC$_{50}$=nd.

Example 16

Synthesis of 4-iodo-1-methyl-1H-pyrazole (16-1)

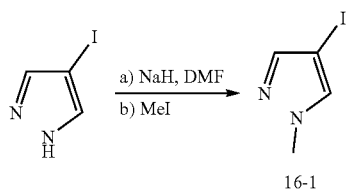

16-1

Step One: To a mixture of 4-iodopyrazole (675 mg, 3.48 mmol) in N,N-dimethylformamide (13 mL) at 0° C. under nitrogen, sodium hydride (60% dispersion in mineral oil, 167 mg, 4.18 mmol) was added. The resulting mixture was stirred for 30 minutes and iodomethane (0.217 mL, 3.48 mmol) was added. The resulting mixture was allowed to warm to room temperature and stirred overnight. The mixture was quenched by the careful addition of aqueous hydrochloric acid (2N), then basified with aqueous sodium bicarbonate and extracted three times with chloroform. The organic layers were combined, dried over magnesium sulfate, filtered and concentrated to give 4-iodo-1-methyl-1H-pyrazole (16-1). This material contained mineral oil and other impurities but was used without purification.

This procedure was also used to prepare 6-bromo-1-ethyl-1H-indole;
methyl 3-(methylamino)thiophene-2-carboxylate (from methyl 3-aminothiophene-2-carboxylate); and
methyl 2-(methylamino)nicotinate (from methyl 2-aminonicotinate).

Example 17

Synthesis of ethyl (E)-3-(3-bromo-5-methoxyphenyl)acrylate (17-1)

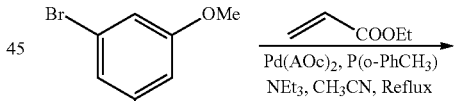

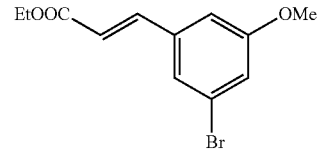

17-1

Step One: To a solution of 3,5-dibromoanisole (1.01 g, 3.79 mmol) in acetonitrile (20 mL) at room temperature under nitrogen, palladium(II) acetate (42 mg, 0.19 mmol), tri(o-tolyl)phosphine (116 mg, 0.38 mmol), ethyl acrylate (0.36 mL, 3.38 mmol) and triethylamine (2.10 ml, 15.1 mmol) were added sequentially. The mixture was heated to reflux 4 hours, cooled to room temperature, diluted with ethyl acetate, and washed with water and brine. The organic layer was dried over magnesium sulfate, filtered and concentrated. The residue was purified by silica gel chromatography, eluting with 5% ethyl acetate in hexanes. Fractions containing product were combined, concentrated and the residue was rechromatographed, eluting with 3% increasing to 5% ethyl acetate in hexanes to give ethyl (E)-3-(3-bromo-5-methoxyphenyl)acrylate (17-1, 354 mg) as a yellow oil.

This procedure was also used to prepare ethyl (E)-3-(3-bromo-5-methylphenyl)acrylate.

In instances where only one bromine was present, an excess of the acrylate (1.25 equivalents) could be used. This variation was used to prepare ethyl (E)-3-(2',4',5-trifluoro-biphenyl-3-yl)acrylate;
ethyl (E)-3-(5-fluoro-3'-methoxybiphenyl-3-yl)acrylate;
and ethyl (E)-3-(5-fluoro-3'-(trifluoromethoxy)biphenyl-3-yl)acrylate.

Example 18

Synthesis of 7-hydroxy-2,3-dihydroindolizin-5(1H)-one (18-3)

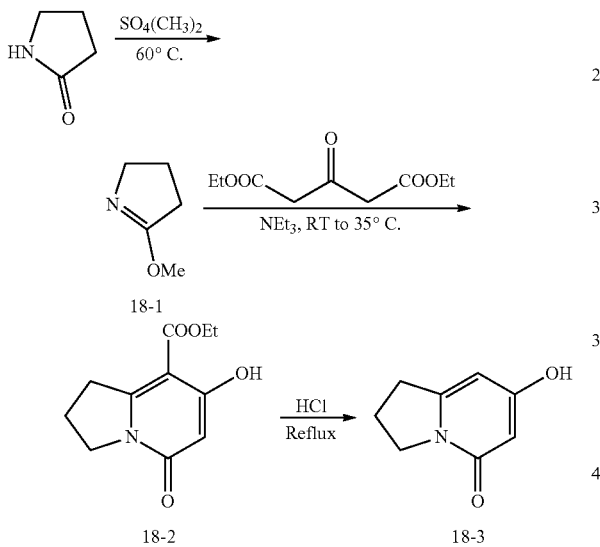

Step One: To a flask containing dimethyl sulfate (8.90 mL, 139 mmol) at room temperature under nitrogen, 2-pyrrolidinone (7.20 mL, 94 mmol) was added slowly over the course of 2 hours. The resulting mixture was heated to 60° C. overnight then was cooled to room temperature and poured into sodium carbonate in ice-water. The mixture was extracted twice with ethyl ether with a small amount of ethyl acetate and twice with dichloromethane. The ether extracts were dried, filtered, and concentrated to give 5-methoxy-3,4-dihydro-2H-pyrrole (18-1, 7.8 g). The dichloromethane extracts were separately dried, filtered and concentrated to give additional 18-1 (2.87 g). The material from the dichloromethane extracts contained fewer impurities than the material from the ether extracts and was used without purification.

Step Two: To a flask containing 18-1 (2.87 g, 28.9 mmol) at room temperature, diethyl 1,3-acetonedicarboxylate (7.90 mL, 43.4 mmol) and triethylamine (0.45 mL, 3.2 mmol) were added. The mixture was stirred at room temperature overnight then was heated to 35° C. for 3 days. The mixture was cooled to room temperature and diluted with ether. The resulting suspension was filtered, washing with ether. Additional solid precipitated from the filtrate which was collected by filtration. The combined solids were dried under vacuum to give ethyl 7-hydroxy-5-oxo-1,2,3,5-tetrahydroindolizine-8-carboxylate (18-2, 2.52 g) as a white solid.

Step Three: A solution of 18-2 (1.00 g, 4.5 mmol) in concentrated hydrochloric acid (15 mL) was heated to reflux overnight then concentrated to dryness to give 7-hydroxy-2,3-dihydroindolizin-5(1H)-one (18-3, 700 mg). This material was used without purification.

Example 19

Synthesis of ethyl (S)-3-(3-(3,5-dimethylisoxazol-4-yl)phenyl)-3-((R)-4-methylphenyl sulfinamido) propanoate (19-2)

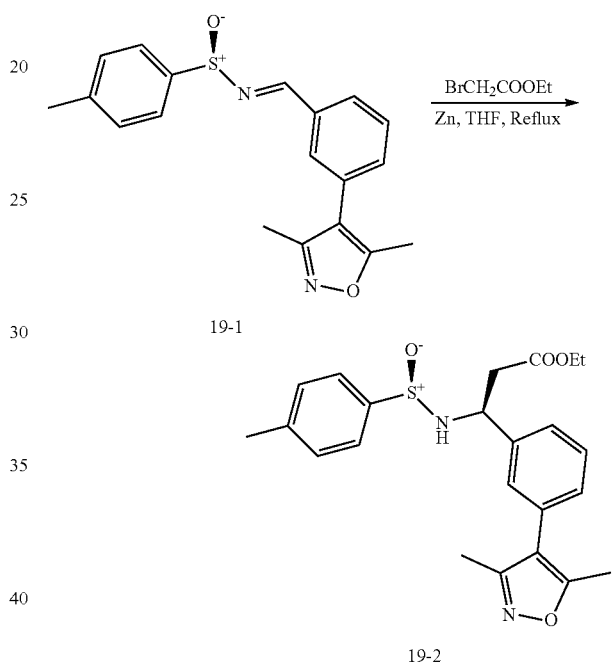

Step One: To a mixture of zinc dust (300 mg, 4.65 mmol) in tetrahydrofuran at room temperature under nitrogen, a catalytic amount of 1,2-dibromoethane was added and the mixture was heated to reflux for 10 minutes. To this refluxing mixture, a solution of 19-1 (630 mg, 1.86 mmol, prepared from 3-(3,5-dimethylisoxazol-4-yl)benzaldehyde according to the procedure described in Example 6, Step One) and ethyl bromoacetate (810 mg, 4.84 mmol) in tetrahydrofuran (6 mL) was added dropwise by syringe. The mixture was refluxed for 2 hours, cooled to room temperature, diluted with 25% ethyl acetate in hexanes, and washed with saturated aqueous ammonium chloride and brine. The organic layer was dried over sodium sulfate, and filtered. The filtrate was passed through a plug of silica gel, washing with 25% then 33% and finally 50% ethyl acetate in hexanes to give ethyl (S)-3-(3-(3,5-dimethylisoxazol-4-yl)phenyl)-3-((R)-4-methylphenylsulfinamido)propanoate (19-2, 360 mg) as a clear glass.

This procedure was also used to prepare (S)-ethyl 3-((R)-1,1-dimethylethylsulfinamido)-3-(3-(6-methoxypyridazin-3-yl)phenyl)propanoate;
ethyl (S)-3-(5-(2,4-difluorophenyl)thiophen-2-yl)-3-((R)-1,1-dimethylethylsulfinamido)propanoate;

ethyl (S)-3-((R)-1,1-dimethylethylsulfinamido)-3-(5-(3-methoxyphenyl)thiophen-2-yl)propanoate; and
ethyl (S)-3-((R)-1,1-dimethylethylsulfinamido)-3-(5-(trifluoromethyl)biphenyl-3-yl)propanoate.

Example 20

Synthesis of ethyl (S)-3-((R)-1,1-dimethylethylsulfinamido)-3-(5-phenylpyridin-3-yl) propanoate (20-3)

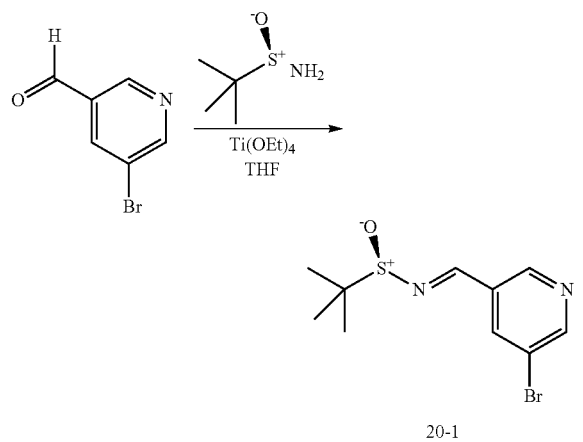

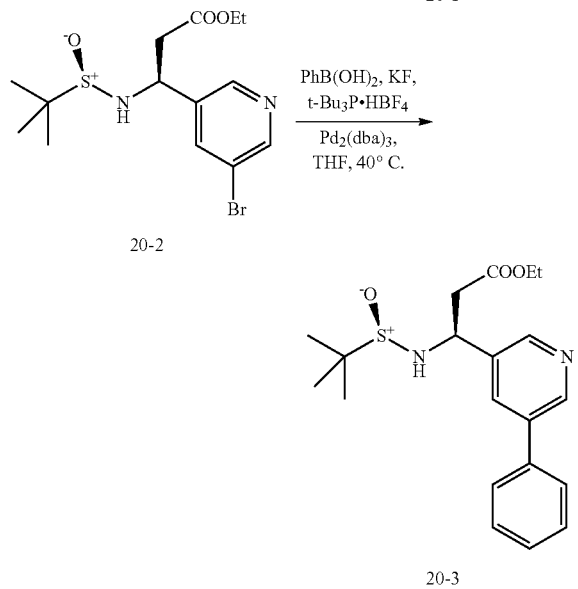

Step One: To a solution of 5-bromonicotinaldehyde (500 mg, 2.69 mmol) in tetrahydrofuran (10 mL) at room temperature under nitrogen, and (R)-(+)-2-methyl-2-propanesulfinamide (358 mg, 2.95 mmol) and titanium(IV) ethoxide (1.11 mL, 5.38 mmol) were added. The resulting mixture was stirred overnight, diluted with ethyl acetate and brine, stirred an additional 20 minutes, and filtered through Celite®. The organic layer from the filtrate was separated, dried over magnesium sulfate, filtered and concentrated to give (R,E)-N-((5-bromopyridin-3-yl)methylene)-2-methylpropane-2-sulfinamide (20-1, 771 mg) as a yellow solid.

This procedure was also used to prepare (R,E)-2-methyl-N-((6-phenylpyridin-2-yl)methylene)propane-2-sulfinamide; and
(R,E)-2-methyl-N-((5-(trifluoromethyl)biphenyl-3-yl)methylene)propane-2-sulfinamide.

Step Two: To a screw cap, thick-walled tube containing 20-2 (250 mg, 0.66 mmol, prepared using 20-1 according to the procedure described in Example 12, Step 2), phenylboronic acid (121 mg, 0.99 mmol), potassium fluoride (193 mg, 2.19 mmol), tris(dibenzylideneacetone)dipalladium(0) (9 mg, 0.01 mmol) and tri-tert-butylphosponium tetrafluoroborate (6 mg, 0.02 mmol) under nitrogen, tetrahydrofuran (2 mL) was added. The tube was sealed, heated to 60° C. overnight then cooled to room temperature. The resulting mixture was diluted with ethyl acetate and filtered through Celite®, washing with ethyl acetate. The filtrate was concentrated and the residue was purified by silica gel column chromatography, eluting with 10% methanol in dichloromethane to give ethyl (S)-3-((R)-1,1-dimethylethylsulfinamido)-3-(5-phenylpyridin-3-yl)propanoate (20-3, 227 mg) as a white solid.

This procedure was modified by using cesium carbonate instead of potassium fluoride in dioxane instead of THF to prepare ethyl (S)-3-(benzyl((R)-1-phenylethyl)amino)-3-(2',3'-dimethylbiphenyl-3-yl)propanoate; and
ethyl (S)-3-(benzyl((R)-1-phenylethyl)amino)-3-(2',5'-dimethylbiphenyl-3-yl)propanoate.

Example 21

Synthesis of 6-phenylpicolinaldehyde (21-2)

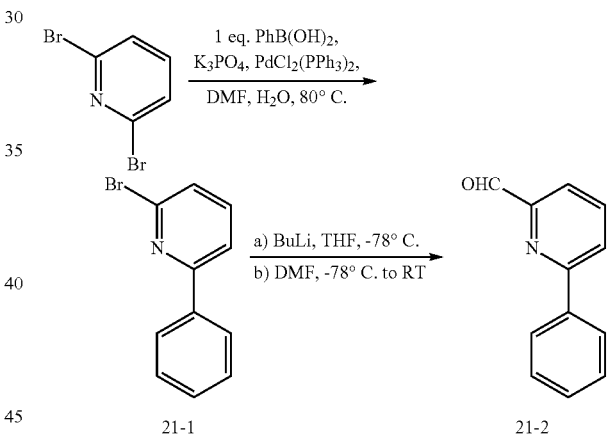

Step One: To a mixture of 2,6-dibromopyridine (3.50 g, 14.8 mmol) and phenylboronic acid (1.80 g, 14.8 mmol) in N,N-dimethylformamide (20 mL) at room temperature under nitrogen, a solution of tribasic potassium phosphate (7.80 g, 36.7 mmol) in water (14 mL) and bis(triphenylphoshine)palladium(II) dichloride (518 mg, 0.74 mmol) were added. The mixture was deoxygenated (toggle between vacuum and nitrogen gas 5 times) and heated to 80° C. overnight. The mixture was cooled, diluted with ethyl acetate, and washed with water and brine. The organic layer was dried, filtered and concentrated. The residue was purified by column chromatography on silica gel, eluting with 5% ethyl acetate in hexanes to give a mixture containing 2-bromo-6-phenylpyridine (21-1, 2.70 g) that was used without further purification.

This procedure was also used to prepare 3-bromo-5-fluoro-3'-methoxybiphenyl (from 1,3-dibromo-5-fluorobenzene);
3-bromo-5-fluoro-3'-(trifluoromethoxy)biphenyl; and
3'-bromo-2,4,5'-trifluorobiphenyl.

Step Two: To a solution of 21-1 (2.70 g, mixture from previous step) in tetrahydrofuran (50 mL) cooled to −78° C. under nitrogen, n-butyllithium (2.5 M in hexanes, 5.8 mL, 14.5 mmol) was added dropwise. The mixture was stirred for 45 minutes then N,N-dimethylformamide (1.80 mL, 23 mmol) was added. The mixture was stirred at −78° C. for 1 hour, warmed to room temperature, quenched with water, and extracted with ethyl acetate. The organic layer was washed three times with water, once with brine, dried over sodium sulfate, filtered and concentrated. The residue was purified by silica gel column chromatography, eluting with 2.5% followed by 5% ethyl acetate in hexanes to give 6-phenylpicolinaldehyde (21-2, 1.24 g) as a yellow oil.

Example 22

Synthesis of (S)-3-(biphenyl-4-yl)-3-(3-(4-hydroxy-1,5-dimethyl-2-oxo-1,2-dihydro pyridin-3-yl)ureido)propanoic acid (22-3)

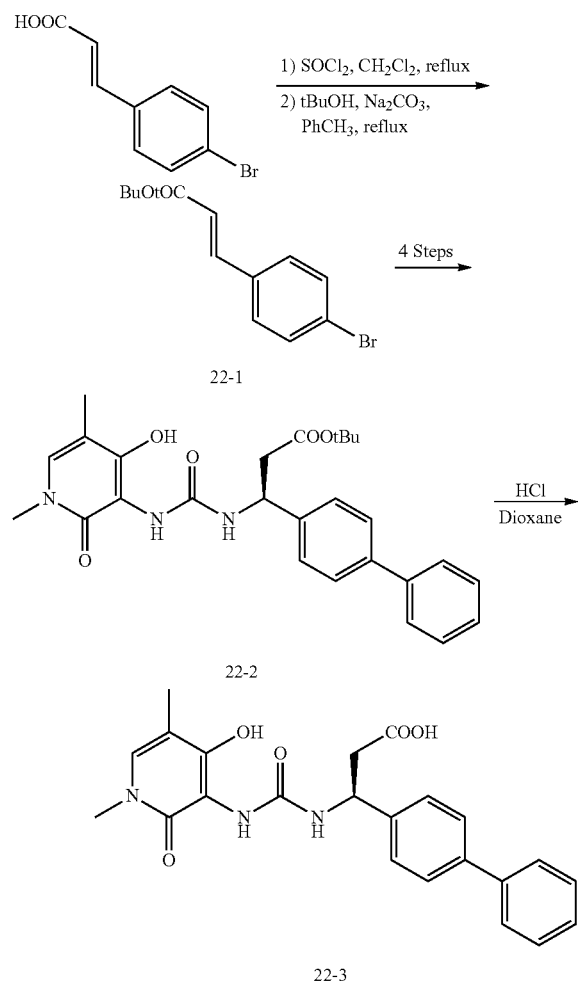

Step One: To a mixture of 4-bromocinnamic acid (51.1 g, 225 mmol) in dichloromethane (750 mL) under nitrogen, thionyl chloride (33 mL, 450 mmol) was added. The mixture was heated to reflux overnight, cooled to room temperature and concentrated. The residue was taken up in toluene (600 mL) and tert-butanol (110 mL, 1.15 mol) and sodium carbonate (29 g, 270 mmol) were added. The mixture was heated to reflux for 8 hours, cooled to room temperature and concentrated. The residue was taken up in ethyl acetate and washed with water and brine. The organic layer was dried over magnesium sulfate, filtered and concentrated to give tert-butyl (E)-3-(4-bromophenyl)acrylate (22-1, 42.6 g).

Step Two: A solution of 22-2 (259 mg, 0.542 mmol, prepared in 4 steps from 22-1 according to the procedures described in Steps 6-9 of Example 1) in hydrogen chloride in dioxane (8 M, 7 mL, 56 mmol) was stirred at room temperature for 4 hours. The mixture was diluted with aqueous sodium hydroxide and extracted twice with chloroform. The aqueous layer was acidified with concentrated hydrochloric acid and extracted twice with ethyl acetate. The ethyl acetate layers were combined, washed with brine, dried over magnesium sulfate, filtered and concentrated to give (S)-3-(biphenyl-4-yl)-3-(3-(4-hydroxy-1,5-dimethyl-2-oxo-1,2-dihydropyridin-3-yl)ureido)propanoic acid (22-3, 161 mg) as a white solid.

This procedure was also used to prepare (S)-3-(2',4'-difluorobiphenyl-4-yl)-3-(3-(4-hydroxy-1,5-dimethyl-2-oxo-1,2-dihydropyridin-3-yl)ureido)propanoic acid (from (S)-tert-butyl 3-(2',4'-difluorobiphenyl-4-yl)-3-(3-(4-hydroxy-1,5-dimethyl-2-oxo-1,2-dihydro pyridin-3-yl)ureido)propanoate.

Example 23

Synthesis of ethyl (E)-3-(3-bromo-5-fluorophenyl)acrylate (23-1)

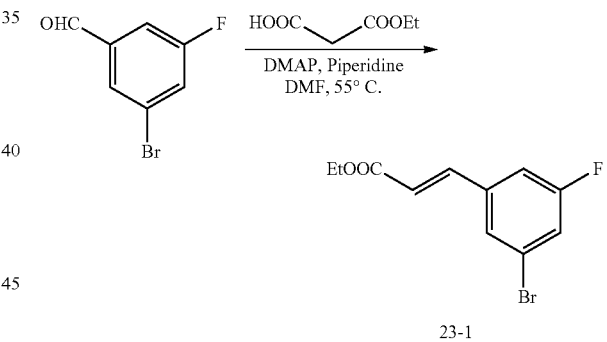

Step One: To a solution of N,N-dimethylaminopyridine (211 mg, 1.73 mmol) in N,N-dimethylformamide (40 mL) at room temperature under argon, ethyl hydrogen malonate (3.43 g, 26.0 mmol) was added. The resulting mixture was added to a flask containing 3-bromo-5-fluorobenzaldehyde (3.52 g, 17.3 mmol) under argon, along with a N,N-dimethylformamide (3 mL) rinse. To the resulting mixture, piperidine (0.17 mL, 1.7 mmol) was added. The mixture was heated to 55° C. overnight, cooled to room temperature, and diluted with 20% ethyl acetate in hexanes and water. The organic layer was washed with saturated aqueous sodium bicarbonate, saturated aqueous ammonium chloride, water (twice), and brine. The resulting organic layer was dried over magnesium sulfate, filtered, and concentrated. The residue was purified by silica gel chromatography (Biotage® SNAP 100 KP-Sil cartridge) to give ethyl (E)-3-(3-bromo-5-fluorophenyl)acrylate (23-1, 3.51 g) as a white solid.

Example 24

Synthesis of 3-iodo-4-(trifluoromethoxy)benzaldehyde (24-1)

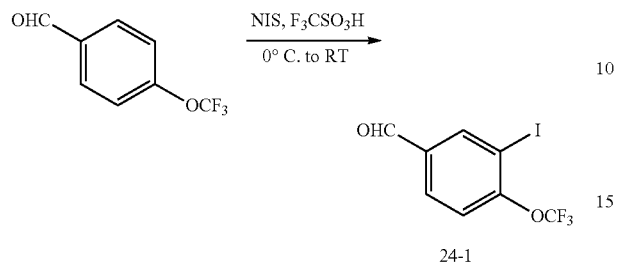

Step One: To a mixture of 4-(trifluoromethoxy)benzaldehyde (5.00 g, 26.3 mmol) in trifluoromethansulfonic acid (11.6 mL, 132 mmol) at 0° C., N-iodosuccinimide (5.92 g, 26.3 mmol) was added. The mixture was allowed to warm to room temperature, was stirred overnight, and was diluted with water and ethyl acetate. The organic layer was washed with water and brine, dried over magnesium sulfate, filtered and concentrated. The residue was purified by silica gelchromatography, eluting with 5% ethyl acetate in hexanes to give 3-iodo-4-(trifluoromethoxy)benzaldehyde (24-1, 3.42 g).

Example 25

Synthesis of 5-(trifluoromethyl)biphenyl-3-carbaldehyde (25-7)

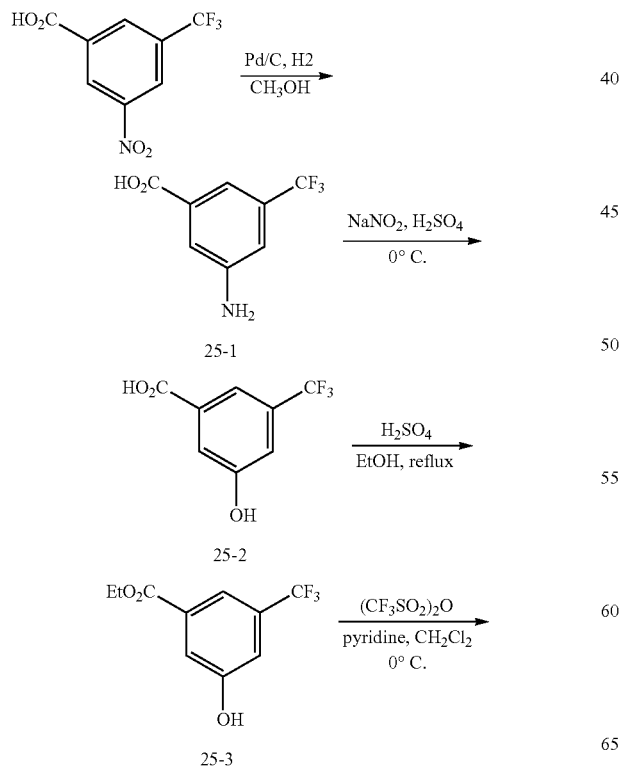

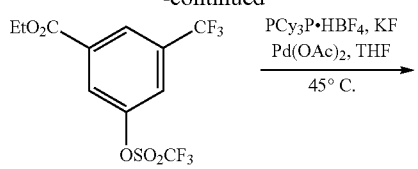

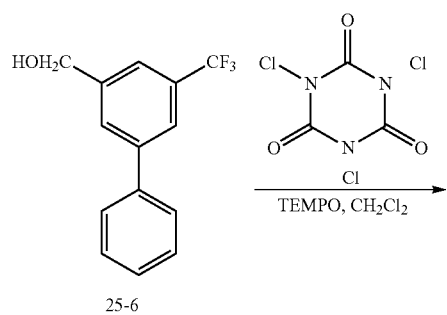

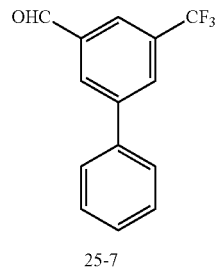

Step One: To a solution of 3-nitro-5-trifluoromethylbenzoic acid (5.00 g, 21.3 mmol) in methanol (75 mL), palladium metal on carbon (10%, 1.0 g). The atmosphere was replaced with hydrogen (toggling between vacuum and hydrogen from a balloon several times) and the reaction was stirred 6 hours. The mixture was filtered through Celite® and the filtrate was concentrated under reduced pressure to give 3-amino-5-(trifluoromethyl)benzoic acid (25-1, 4.36 g) as a pale yellow solid.

Step Two: To a suspension of 25-1 (4.36 g, 21.3 mmol) in water at 0° C., concentrated sulfuric acid (10.6 mL, 191 mmol) was added. The mixture was stirred until the solid had completely dissolved and a solution of sodium nitrite (1.47 g, 21.3 mmol) in water (40 mL) was added dropwise. The mixture was stirred at 0° C. for 15 minutes then brought to reflux for an additional 15 minutes. The mixture was cooled to room temperature and extracted three times with ethyl ether. The organic layers were combined, washed with brine, dried over magnesium sulfate, filtered and concentrated to give 3-hydroxy-5-(trifluoromethyl)benzoic acid (25-2, 4.06 g) as a yellow solid.

Step Three: To a solution of 25-2 (2.90 g, 14.1 mmol) in absolute ethanol, concentrated sulfuric acid (0.04 mL, catalytic) was added. The resulting mixture was heated to reflux for 3 days, cooled to room temperature, concentrated to about 10 mL, and diluted with ethyl acetate. The mixture was washed with water and brine, dried over magnesium sulfate, filtered, and concentrated to give ethyl 3-hydroxy-5-(trifluoromethyl)benzoate (25-3, 3.16 g) as an orange solid.

Step Four: To a solution of 25-3 (2.90 g, 12.4 mmol) and pyridine (1.20 mL, 15.0 mmol) in dichloromethane (24 mL) at 0° C. under nitrogen, trifluoromethanesulfonic anhydride (2.29 mL, 13.6 mmol) was added dropwise by syringe. The mixture was stirred at 0° C. for 1 hour then at room temperature for 30 minutes. The mixture was diluted with dichloromethane and washed with hydrochloric acid (0.5 N) and water. The two aqueous washes were combined and extracted with dichloromethane. The organic layers were combined, dried over magnesium sulfate and concentrated. The residue was filtered through a short pad of silica gel, washing with 15% ethyl acetate in hexanes. The filtrate was concentrated to give ethyl 3-(trifluoromethyl)-5-(((trifluoromethyl)sulfonyl)oxy)benzoate (25-4, 3.65 g) as a yellow oil.

Step Five: To a pressure vessel containing phenylboronic acid (1.16 g, 9.50 mmol), potassium fluoride (1.52 g, 26.1 mmol), palladium acetate (35 mg, 0.16 mmol), and tricylcohexylphosphine tetrafluoroborate (61 mg, 0.17 mmol) under nitrogen, tetrahydrofuran (12 mL) and 25-4 (2.90 g, 7.92 mmol) were added. The vessel was sealed and heated to 45° C. overnight, cooled to room temperature, diluted with ether, and filtered through Celite®. The filtrate was concentrated and the residue was purified by silica gel chromatography, eluting with hexanes increasing to 5% ether in hexanes to give ethyl 5-(trifluoromethyl)biphenyl-3-carboxylate (25-5, 2.40 g) as a white solid.

Step Six: To a solution of 25-5 (2.40 g, 8.15 mmol) in tetrahydrofuran (16 mL) at 0° C. under nitrogen, lithium aluminum hydride (1.0 M in tetrahydrofuran, 16.3 mL, 16.3 mmol) was added dropwise. The mixture was allowed to gradually warm to room temperature overnight, then was carefully poured into an ice cold aqueous sulfuric acid (10%). The resulting mixture was extracted three times with ethyl acetate and the combined organic layers were washed with brine, dried over magnesium sulfate, filtered, and concentrated. The residue was purified by silica gel chromatography, eluting with 15% ethyl acetate in hexanes to give (5-(trifluoromethyl)biphenyl-3-yl)methanol (25-6, 1.74 g) as a white solid.

Step Seven: To a solution of 25-6 (1.70 g, 6.74 mmol) in dichloromethane (12 mL) at 0° C. under nitrogen, trichloroisocyanuric acid (1.72 g, 7.41 mmol) and 2,2,6,6-tetramethylpiperidine 1-oxyl (TEMPO, 20 mg, 0.13 mmol) were added. The mixture was warmed to room temperature, stirred for 30 minutes then diluted with dichlormethane and filtered through Celite®. The filtrate was washed with saturated aqueous sodium bicarbonate, aqueous hydrochloric acid (1 N), and brine. The organic layer was dried over magnesium sulfate, filtered and concentrated to give 5-(trifluoromethyl)biphenyl-3-carbaldehyde (25-7, 1.49 g) as a yellow oil).

Example 26

Synthesis of ethyl (S)-3-amino-3-(3-(pyridin-2-yl)phenyl)propanoate (26-4)

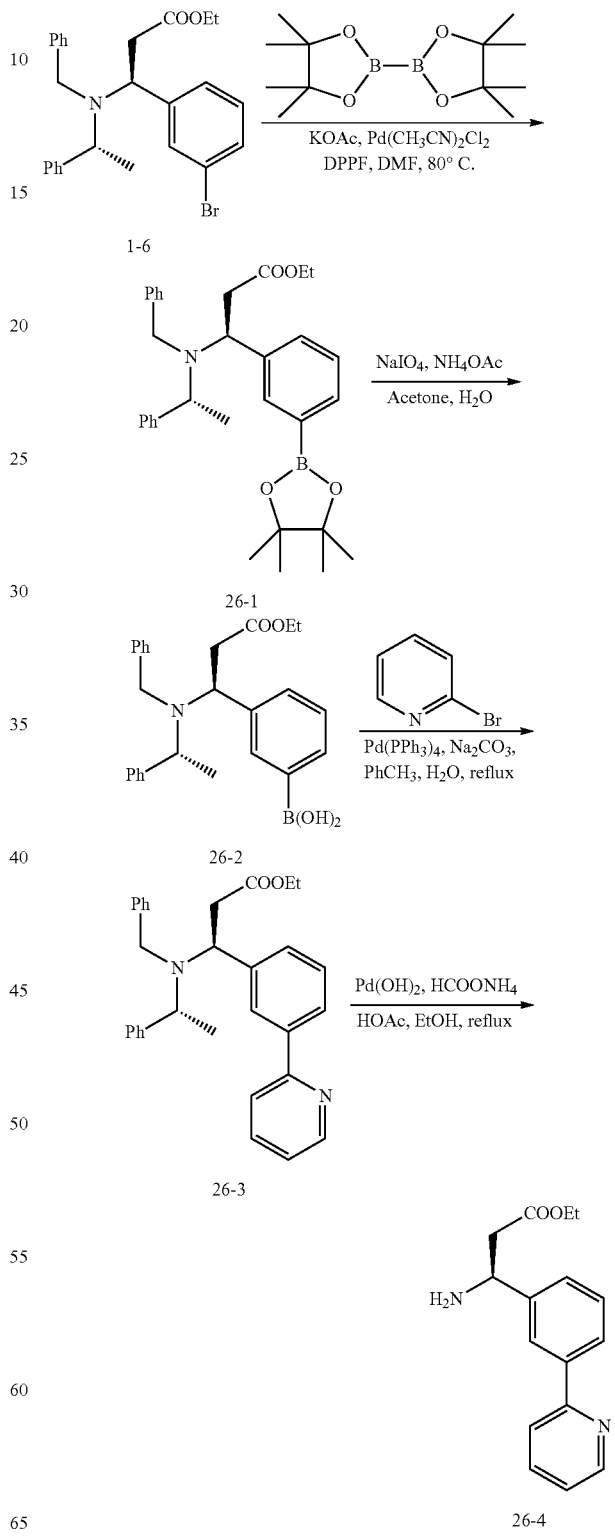

Step One: A mixture of Pd(CH$_3$CN)$_2$Cl$_2$ (39 mg, 0.15 mmol) and DPPF (84 mg, 0.15 mmol) in DMF (5 mL) at room temperature under nitrogen was stirred for 30 minutes. To the resulting mixture, a solution of 1-6 (2.50 g, 5.05 mmol) in DMF (15 mL), bis(pinacolato)diboron (1.41 g, 5.56 mmol), and potassium acetate (1.49 g, 15.2 mmol) were added. The resulting mixture was heated to 80° C. under nitrogen overnight then was cooled to room temperature and diluted with ethyl acetate. The mixture was washed with saturated aqueous ammonium chloride and brine, dried over magnesium sulfate, filtered and concentrated. The residue was purified by silica gel chromatography to give ethyl (S)-3-(benzyl((R)-1-phenylethyl)amino)-3-(3-(4,4,5,5-tetramethyl-1,3,2-dioxaborolan-2-yl)phenyl)propanoate (26-1, 2.42 g).

Step Two: To a solution of 26-1 (1.00 g, 1.84 mmol) in acetone (50 mL), sodium periodate (789 mg, 3.69 mmol), ammonium acetate (284 mg, 3.69 mmol) and water (50 mL) were added. The resulting mixture was stirred at room temperature for 2 days then the acetone was removed by rotary evaporation. The aqueous mixture was extracted three times with chloroform and the combined organic layers were washed with brine, dried over magnesium sulfate, filtered and concentrated to give 3-((S)-1-(benzyl((R)-1-phenylethyl)amino)-3-ethoxy-3-oxopropyl)phenylboronic acid (26-2, 689 mg) as a brown foam.

Step Three: To a mixture of toluene (2 mL) and aqueous sodium carbonate (2M, 0.93 mL, 1.86 mmol) that had been deoxygenated with argon (toggle between vacuum and argon several times) at room temperature, 26-2 (400 mg, 0.927 mmol), 2-bromopyridine (0.132 mL, 1.39 mmol), and Pd(PPh$_3$)$_4$(107 mg, 0.093 mmol) were added. The mixture was heated to reflux under argon for 18 hours, cooled to room temperature and diluted with ethyl acetate. The mixture was washed with brine, dried over magnesium sulfate, filtered and concentrated to give ethyl (S)-3-(benzyl((R)-1-phenylethyl)amino)-3-(3-(pyridin-2-yl)phenyl)propanoate (26-3, 239 mg) as a clear oil.

This procedure was also used to prepare 3-(6-methoxypyridazin-3-yl)benzaldehyde (from 3-formylphenylboronic acid and 3-chloro-6-methoxypyridazine).

Step Four: To a solution of 26-3 (239 mg, 0.514 mmol) in ethanol, Pd(OH)$_2$ (20% on carbon, 293 mg, 0.417 mmol), ammonium formate (105 mg, 1.67 mmol) and glacial acetic acid (0.064 mL, 1.1 mmol) were added. The mixture was heated to reflux for 2.3 hours, cooled to room temperature, diluted with ethyl acetate, and filtered through Celite®. The filtrate was washed with saturated aqueous sodium bicarbonate and brine, dried over magnesium sulfate, filtered and concentrated. The residue was purified by silica gel column chromatography to give ethyl (S)-3-amino-3-(3-(pyridin-2-yl)phenyl)propanoate (26-4, 115 mg) as a clear oil.

Example 27

Synthesis of 3-bromo-2-methylbenzaldehyde (27-2)

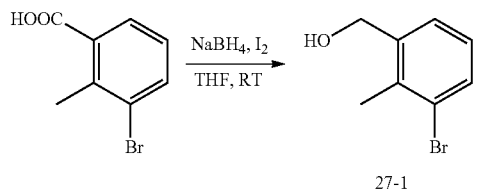

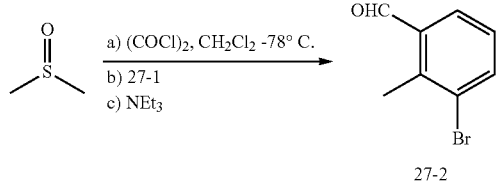

Step One: To a suspension of sodium borohydride (0.630 g, 16.7 mmol) in THF (82 mL), 3-bromo-2-methylbenzoic acid (3.00 g, 14.0 mmol) was added. The mixture was stirred until gas evolution ceased and iodine (1.77 g, 6.98 mmol) was added in small portions. The mixture was stirred at room temperature for 2 hours then the reaction was carefully quenched by the slow addition of aqueous HCl (2N). The resulting mixture was diluted with water and extracted with ether. The organic layer was washed three times with aqueous NaOH (2N), once with brine, dried over magnesium sulfate, filtered and concentrated to give (3-bromo-2-methylphenyl)methanol (27-1, 2.79 g) as a white solid.

Step Two: To a solution of dimethylsulfoxide (2.99 mL, 41.8 mmol) in dichloromethane (55 mL) cooled to −78° C. under nitrogen, oxalyl chloride (2.0 M in dichloromethane, 10.4 mL, 20.8 mmol) was added slowly. The mixture was stirred at −78° C. for 30 minutes then a solution of 27-1 (2.79 g, 13.9 mmol) in dichloromethane (15 mL) was added dropwise by cannula. The mixture was stirred for 1 hour, triethylamine (5.8 mL, 41.8 mmol) was added slowly, and the reaction was allowed to warm to room temperature. The mixture was washed with saturated aqueous sodium bicarbonate, water, and brine. The organic layer was dried over magnesium sulfate, filtered and concentrated to give 3-bromo-2-methylbenzaldehyde (27-2, 2.76 g).

Example 28

Synthesis of 3-(1-ethyl-1H-indol-6-yl)benzaldehyde (28-3)

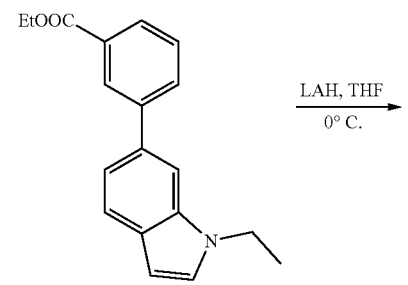

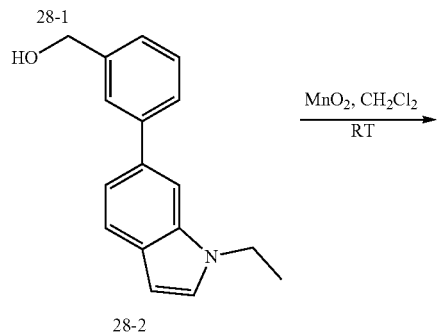

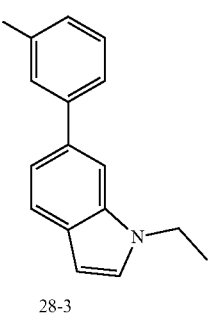

28-3

Step One: To a solution of 28-1 (prepared from 6-bromo-1-ethyl-1H-indole and 3-ethoxycarbonylphenylboronic acid following the procedure of example 1 step 7, 330 mg, 1.12 mmol) in THF at 0° C. under nitrogen, lithium aluminum hydride (1.0 M in THF, 1.23 mL, 1.23 mmol) was added by syringe. The mixture was allowed to warm to room temperature and was stirred for 3.5 hours. The mixture was quenched by adding ice to the reaction and the resulting mixture was dried over sodium sulfate and filtered. The filtrate was concentrated to give (3-(1-ethyl-1H-indol-6-yl)phenyl)methanol (28-2, 0.30 g) as a light yellow solid.

Step Two: To a solution of 28-2 (0.30 g, 1.19 mmol) in dichloromethane (40 mL) at room temperature under nitrogen, activated manganese dioxide (85%, 1.46 g, 14.3 mmol) was added. The mixture was stirred at room temperature overnight, filtered through Celite®, and concentrated to give 3-(1-ethyl-1H-indol-6-yl)benzaldehyde (28-3, 0.29 g) as a yellow-brown oil.

Example 29

Synthesis of 5-hydroxy-2-methylpyridazin-3(2H)-one (29-4)

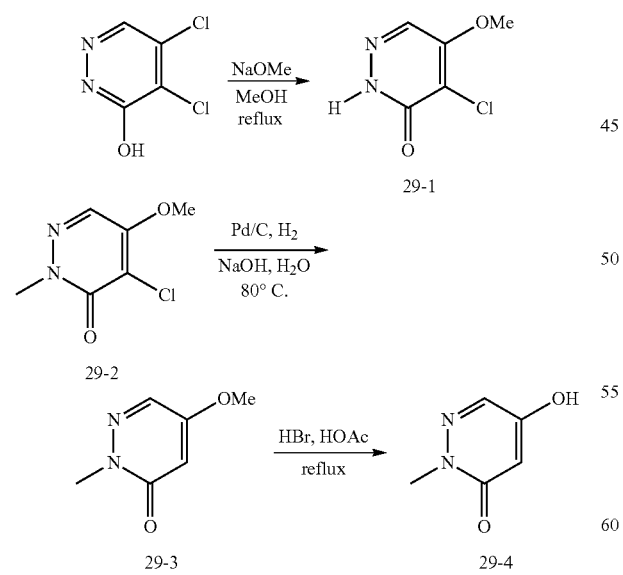

Step One: To a suspension of 4,5-dichloro-2-hydroxypyradizine (5.00 g, 30.3 mmol) in methanol (90 mL) at room temperature, sodium methoxide (30% in methanol, 32.8 mL, 182 mmol) was added. The mixture was heated to reflux for 2 days then was concentrated to dryness. The residue was dissolved in water and acidified with glacial acetic acid. The white precipitate that formed was collected by filtration, washing with water. The solid was dried under vacuum to give 4-chloro-5-methoxypyridazin-3(2H)-one (29-1, 2.99 g).

This procedure was also used to prepare 3-chloro-6-methoxypyridazine from 3,6-dichloropyridazine using potassium carbonate in refluxing methanol instead of sodium hydroxide.

Step Two: To a suspension of 29-2 (prepared from 29-1 following the procedure of example 8 step 1, 2.18 g, 12.5 mmol) in aqueous sodium hydroxide (90 mL) heated to 80° C. under nitrogen, palladium (10% on carbon, 9.0 g, 8.45 mmol) was added. The atmosphere was replaced with hydrogen (toggle between vacuum and hydrogen from a balloon several times) and the mixture was stirred at 80° C. for 3.5 hours. The mixture was filtered through Celite®, washing with hot water. The filtrate was cooled to room temperature, filtered through Celite® again then concentrated to approximately 20 mL and extracted with ethyl acetate. The organic layer was washed with brine, dried over sodium sulfate, filtered and concentrated to give 5-methoxy-2-methylpyridazin-3(2H)-one (29-3, 0.46 g) as a white solid.

Step Three: To a solution of 29-3 (0.46 g, 3.29 mmol) in glacial acetic acid (11 mL), concentrated hydrobromic acid (48%, 11 mL) was added. The mixture was heated to reflux overnight then was cooled to room temperature, diluted with water, and basified with solid sodium bicarbonate (added in portions). The resulting mixture was extracted with ethyl acetate. The aqueous layer was acidified with aqueous HCl (2N) and concentrated. The residue suspended in hot ethyl acetate and filtered. The solid was resuspended on hot methanol and filtered. The two filtrates were dried over sodium sulfate, reduced in volume then adsorbed onto silica gel. The adsorbed material was placed on a silica gel column and eluted with 10% methanol in dichloromethane to give 5-hydroxy-2-methylpyridazin-3(2H)-one (29-4, 264 mg) as a white solid.

The present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. Also, the terms in the claims have their plain, ordinary meaning unless otherwise explicitly and clearly defined by the patentee.

What is claimed is:

1. A compound of formula I having a chemical structure of

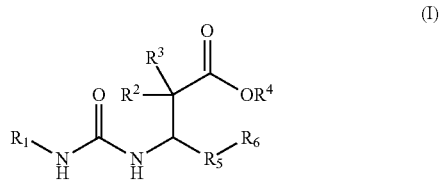

wherein $R^1$ is

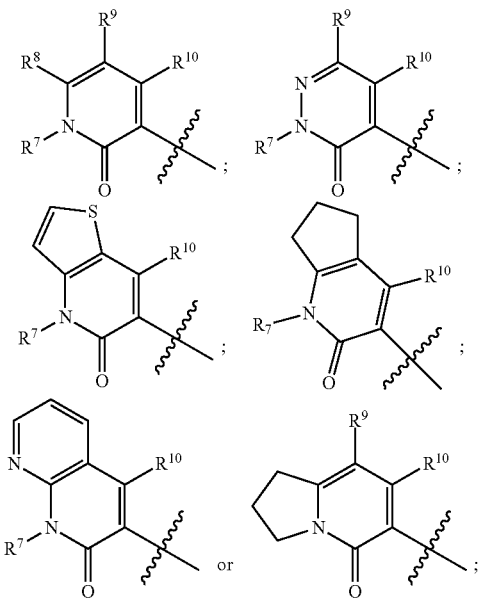

$R^2$ and $R^3$ are independently hydrogen or $C_{1-4}$ alkyl;

$R^4$ is H or $C_{1-4}$ alkyl;

$R^5$ is phenyl, or aryl, any of which is substituted with one or more of hydrogen, $C_{1-4}$ alkyl, alkoxy, oxo, halogen, haloalkoxy, —$CF_3$, hydroxyl, —$OCF_3$, aryl, —$OCF_2H$, —$OCF_2CF_2H$, —$O(C_{3-6}$ cycloalkyl), —$OCH_2CF_3$, thioalkoxy, dialkylamino, $C_{3-6}$ cycloalkyl or haloalkyl;

$R^6$ is phenyl, or aryl, any of which is substituted with one or more of hydrogen, $C_{1-4}$ alkyl, alkoxy, halogen, oxo, acetyl, haloalkoxy, —$CF_3$, hydroxyl, —$OCF_3$, aryl, —$OCF_2H$, —$OCF_2CF_2H$, —$O(C_{3-6}$ cycloalkyl), —$OCH_2CF_3$, thioalkoxy, dialkylamino, $C_{3-6}$ cycloalkyl or haloalkyl;

$R^7$ is H or $C_{1-4}$ alkyl;

$R^8$ and $R^9$ are independently hydrogen, $C_{1-4}$ alkyl, or hydroxyl;

$R^{10}$ is hydroxyl;

or a pharmaceutically acceptable salt or stereoisomer thereof.

2. The compound of claim 1, wherein $R^2$ and $R^3$ are each hydrogen.

3. The compound of claim 1, wherein $R^4$ is hydrogen; methyl, ethyl or t-butyl.

4. The compound of claim 1, wherein $R^7$ is hydrogen, methyl or ethyl.

5. The compound of claim 1, wherein $R^8$ and $R^9$ are independently hydrogen or methyl.

6. The compound of claim 1, wherein $R^{10}$ is hydroxyl.

7. The compound of claim 1, wherein the stereoisomer is of the (S)-configuration.

8. The compound of claim 1, wherein the compound of formula I is the compound of formula I A having a chemical structure of

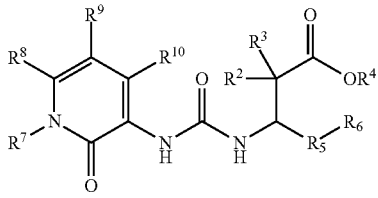

wherein, $R^2$, $R^3$, $R^4$, $R^5$, $R^6$, $R^7$, $R^8$, $R^9$ and $R^{10}$ are as defined in claim 1; or a pharmaceutically acceptable salt or stereoisomers thereof.

9. The compound of claim 1, wherein the compound of formula I is the compound of formula I B having a chemical structure of

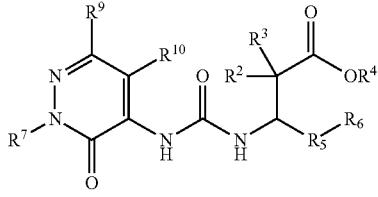

wherein, $R^2$, $R^3$, $R^4$, $R^5$, $R^6$, $R^7$, $R^9$ and $R^{10}$ are as defined in claim 1; or the pharmaceutically acceptable salt or stereoisomers thereof.

10. The compound of claim 1, wherein the compound of formula I is the compound of formula I C having a chemical structure of

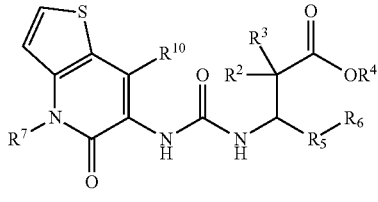

wherein, $R^2$, $R^3$, $R^4$, $R^5$, $R^6$, $R^7$ and $R^{10}$ are as defined in claim 1; or a pharmaceutically acceptable salt or stereoisomers thereof.

11. The compound of claim 1, wherein the compound of formula I is the compound of formula I D having a chemical structure of)

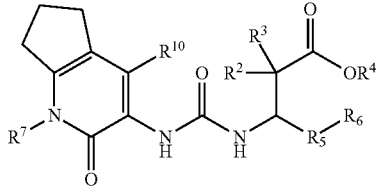

wherein, $R^2$, $R^3$, $R^4$, $R^5$, $R^6$, $R^7$ and $R^{10}$ are as defined in claim 1; or a pharmaceutically acceptable salt or stereoisomers thereof.

12. The compound of claim 1, wherein the compound of formula I is the compound of formula IE having a chemical structure of (IE)

wherein, $R^2$, $R^3$, $R^4$, $R^5$, $R^6$, $R^7$ and $R^{10}$ are as defined in claim 1; or a pharmaceutically acceptable salt or stereoisomers thereof.

13. The compound of claim 1, wherein the compound of formula I is the compound of formula IF having a chemical structure of (IF)

wherein, $R^2$, $R^3$, $R^4$, $R^5$, $R^6$, $R^9$ and $R^{10}$ are as defined in claim 1; or a pharmaceutically acceptable salt or stereoisomers thereof.

14. The compound of claim 1, wherein the pharmaceutically acceptable salt is the mono or disodium sodium salt.

15. A pharmaceutical composition, comprising at least one compound of claim 1 and one or more pharmaceutically acceptable carriers.

16. A compound of formula I having a chemical structure of (I)

wherein $R^1$ is $R^2$ and $R^3$ are independently hydrogen;
$R^4$ is hydrogen; methyl, ethyl or t-butyl;
$R^5$ is phenyl, or aryl, which is substituted with one or more of hydrogen, $C_{1-4}$ alkyl, alkoxy, oxo, halogen, haloalkoxy, —$CF_3$, hydroxyl, —$OCF_3$, aryl, —$OCF_2H$, —$OCF_2CF_2H$, —$O(C_{3-6}$ cycloalkyl), —$OCH_2CF_3$, thioalkoxy, dialkylamino, $C_{3-6}$ cycloalkyl or haloalkyl
$R^6$ is phenyl, or aryl which is substituted with one or more of hydrogen, $C_{1-4}$ alkyl, alkoxy, halogen, oxo, acetyl, haloalkoxy, —$CF_3$, hydroxyl, —$OCF_3$, aryl, —$OCF_2H$, —$OCF_2CF_2H$, —$O(C_{3-6}$ cycloalkyl), —$OCH_2CF_3$, thioalkoxy, dialkylamino, $C_{3-6}$ cycloalkyl or haloalkyl;
$R^7$ is hydrogen; methyl or ethyl
$R_8$ and $R^9$ are independently hydrogen or methyl and
or a pharmaceutically acceptable salt or stereoisomers thereof.

17. A compound that is:
ethyl (S)-3-(biphenyl-3-yl)-3-(3-(4-hydroxy-1,5-dimethyl-2-oxo-1,2-dihydro pyridin-3-yl)ureido)propanoate;
ethyl (S)-3-(biphenyl-3-yl)-3-(3-(1-ethyl-4-hydroxy-5-methyl-2-oxo-1,2-dihydropyridin-3-yl)ureido)propanoate;
ethyl 3-(3-(1-ethyl-4-hydroxy-5-methyl-2-oxo-1,2-dihydropyridin-3-yl)ureido)-3-(3-(2-oxo-3-phenylpyridin-1(2H)-yl)phenyl)propanoate;
ethyl (S)-3-(3-(4-hydroxy-1,5-dimethyl-2-oxo-1,2-dihydropyridin-3-yl)ureido)-3-(2'-methylbiphenyl-3-yl) propanoate;
ethyl (S)-3-(2'-fluorobiphenyl-3-yl)-3-(3-(4-hydroxy-1,5-dimethyl-2-oxo-1,2-dihydro pyridin-3-yl)ureido)propanoate;
ethyl (S)-3-(6-fluorobiphenyl-3-yl)-3-(3-(4-hydroxy-1,5-dimethyl-2-oxo-1,2-dihydro pyridin-3-yl)ureido)propanoate;
ethyl (S)-3-(3-(1-ethyl-4-hydroxy-5-methyl-2-oxo-1,2-dihydropyridin-3-yl)ureido)-3-(2'-methylbiphenyl-3-yl)propanoate;
ethyl (S)-3-(3-(1-ethyl-4-hydroxy-5-methyl-2-oxo-1,2-dihydropyridin-3-yl)ureido)-3-(4'-methylbiphenyl-3-yl)propanoate;
ethyl 3-(3-(1H-pyrrol-1-yl)phenyl)-3-(3-(4-hydroxy-1,5-dimethyl-2-oxo-1,2-dihydro pyridin-3-yl)ureido)propanoate;
ethyl (S)-3-(2',4'-difluorobiphenyl-3-yl)-3-(3-(4-hydroxy-1,5-dimethyl-2-oxo-1,2-di hydropyridin-3-yl)ureido)propanoate;

ethyl (S)-3-(2',5'-difluorobiphenyl-3-yl)-3-(3-(4-hydroxy-1,5-dimethyl-2-oxo-1,2-di hydropyridin-3-yl)ureido)propanoate;

ethyl (S)-3-(3-(4-hydroxy-1,5-dimethyl-2-oxo-1,2-dihydropyridin-3-yl)ureido)-3-(6-methylbiphenyl-3-yl)propanoate;

ethyl (S)-3-(3-(4-hydroxy-1,5-dimethyl-2-oxo-1,2-dihydropyridin-3-yl)ureido)-3-(6-methoxybiphenyl-3-yl)propanoate;

ethyl (S)-3-(3-(4-hydroxy-1,5-di methyl-2-oxo-1,2-dihydropyridin-3-yl)ureido)-3-(4'-methylbiphenyl-3-yl)propanoate;

ethyl (S)-3-(3-(4-hydroxy-1,5-dimethyl-2-oxo-1,2-dihydropyridin-3-yl)ureido)-3-(3'-methylbiphenyl-3-yl)propanoate;

ethyl (S)-3-(3-(4-hydroxy-1,5-dimethyl-2-oxo-1,2-dihydropyridin-3-yl)ureido)-3-(3-(pyridin-3-yl)phenyl)propanoate;

ethyl (S)-3-(3',5'-difluorobiphenyl-3-yl)-3-(3-(4-hydroxy-1,5-dimethyl-2-oxo-1,2-dihydropyridin-3-yl)ureido)propanoate;

ethyl (S)-3-(3',5'-dimethylbiphenyl-3-yl)-3-(3-(4-hydroxy-1,5-dimethyl-2-oxo-1,2-di hydropyridin-3-yl)ureido)propanoate;

ethyl (S)-3-(3-(4-hydroxy-1,5-di methyl-2-oxo-1,2-dihydropyridin-3-yl)ureido)-3-(4'-methoxybiphenyl-3-yl)propanoate;

ethyl (S)-3-(3-(4-hydroxy-1,5-dimethyl-2-oxo-1,2-dihydropyridin-3-yl)ureido)-3-(2'-methoxybiphenyl-3-yl)propanoate;

ethyl (S)-3-(3-(4-hydroxy-1-methyl-2-oxo-1,2-dihydropyridin-3-yl)ureido)-3-(3-(pyrazin-2-yl)phenyl)propanoate, ethyl (S)-3-(3-(4-hydroxy-1,5-di methyl-2-oxo-1,2-dihydropyridin-3-yl)ureido)-3-(4'-(trifluoromethoxy)biphenyl-3-yl)propanoate;

ethyl (S)-3-(3',4'-difluorobiphenyl-3-yl)-3-(3-(4-hydroxy-1,5-dimethyl-2-oxo-1,2-dihydropyridin-3-yl)ureido)propanoate;

ethyl (S)-3-(2',5'-dimethylbiphenyl-3-yl)-3-(3-(4-hydroxy-1,5-dimethyl-2-oxo-1,2-dihydropyridin-3-yl)ureido)propanoate;

ethyl (S)-3-(3-(4-hydroxy-1,5-dimethyl-2-oxo-1,2-dihydropyridin-3-yl)ureido)-3-(3'-methoxybiphenyl-3-yl)propanoate;

ethyl (S)-3-(3-(4-hydroxy-1,5-dim ethyl-2-oxo-1,2-dihydropyridin-3-yl)ureido)-3-(3'-(trifluoromethoxy)biphenyl-3-yl)propanoate;

ethyl (S)-3-(2',3'-dimethylbiphenyl-3-yl)-3-(3-(4-hydroxy-1,5-dimethyl-2-oxo-1,2-dihydropyridin-3-yl)ureido)propanoate;

ethyl 3-(3-(4-hydroxy-1,5-dimethyl-2-oxo-1,2-dihydropyridin-3-yl)ureido)-3-(6-oxo-1-phenyl-1,6-dihydropyridin-3-yl)propanoate;

ethyl (S)-3-(2',6'-difluorobiphenyl-3-yl)-3-(3-(4-hydroxy-1,5-dimethyl-2-oxo-1,2-di hydropyridin-3-yl)ureido)propanoate;

ethyl (S)-3-(3'-fluorobiphenyl-3-yl)-3-(3-(4-hydroxy-1,5-dim ethyl-2-oxo-1,2-di hydropyridin-3-yl)ureido)propanoate;

ethyl (S)-3-(4'-fluorobiphenyl-3-yl)-3-(3-(4-hydroxy-1,5-dimethyl-2-oxo-1,2-dihydro pyridin-3-yl)ureido)propanoate;

ethyl (S)-3-(3-(4-hydroxy-1,5-dimethyl-2-oxo-1,2-dihydropyridin-3-yl)ureido)-3-(2'-(trifluoromethoxy)biphenyl-3-yl)propanoate;

ethyl (S)-3-(2',4'-dimethoxybiphenyl-3-yl)-3-(3-(4-hydroxy-1,5-dimethyl-2-oxo-1,2-dihydropyridin-3-yl)ureido)propanoate;

ethyl (S)-3-(3',4'-dimethoxybiphenyl-3-yl)-3-(3-(4-hydroxy-1,5-dimethyl-2-oxo-1,2-dihydropyridin-3-yl)ureido)propanoate;

ethyl (S)-3-(2',6'-dimethylbiphenyl-3-yl)-3-(3-(4-hydroxy-1,5-dimethyl-2-oxo-1,2-di hydropyridin-3-yl)ureido)propanoate;

ethyl 3-(4'-chlorobiphenyl-3-yl)-3-(3-(4-hydroxy-1,5-dim ethyl-2-oxo-1,2-dihydropyridin-3-yl)ureido)propanoate;

ethyl (S)-3-(3'-chlorobiphenyl-3-yl)-3-(3-(4-hydroxy-1,5-dimethyl-2-oxo-1,2-dihydropyridin-3-yl)ureido)propanoate;

ethyl 3-(2'-chlorobiphenyl-3-yl)-3-(3-(4-hydroxy-1,5-dim ethyl-2-oxo-1,2-dihydropyridin-3-yl)ureido)propanoate;

ethyl (S)-3-(3-(4-hydroxy-1,5-dimethyl-2-oxo-1,2-dihydropyridin-3-yl)ureido)-3-(2'-(trifluoromethyl)biphenyl-3-yl)propanoate;

ethyl (S)-3-(5,6-dimethoxybiphenyl-3-yl)-3-(3-(4-hydroxy-1,5-dimethyl-2-oxo-1,2-dihydropyridin-3-yl)ureido)propanoate;

ethyl (S)-3-(3-(4-hydroxy-1,5-dimethyl-2-oxo-1,2-dihydropyridin-3-yl)ureido)-3-(3-(6-methoxypyridin-3-yl)phenyl)propanoate;

ethyl (S)-3-(2',5'-dimethoxybiphenyl-3-yl)-3-(3-(4-hydroxy-1,5-dimethyl-2-oxo-1,2-dihydropyridin-3-yl)ureido)propanoate;

ethyl 3-(3-(4-hydroxy-1,5-dimethyl-2-oxo-1,2-dihydropyridin-3-yl)ureido)-3-(3-(pyrimidin-5-yl)phenyl)propanoate;

ethyl (S)-3-(2',6'-dimethoxybiphenyl-3-yl)-3-(3-(4-hydroxy-1,5-dimethyl-2-oxo-1,2-dihydropyridin-3-yl)ureido)propanoate;

ethyl 3-(3',4'-dichlorobiphenyl-3-yl)-3-(3-(1-ethyl-4-hydroxy-5-methyl-2-oxo-1,2-dihydro pyridin-3-yl)ureido) propanoate;

ethyl 3-(3',4'-dichlorobiphenyl-3-yl)-3-(3-(4-hydroxy-1,5-dimethyl-2-oxo-1,2-dihydropyridin-3-yl)ureido)propanoate;

ethyl (S)-3-(3-(4-hydroxy-1,5-dimethyl-2-oxo-1,2-dihydropyridin-3-yl)ureido)-3-(5-phenylfuran-2-yl)propanoate;

ethyl (S)-3-(3-(2,5-dimethyl-1H-pyrrol-1-yl)phenyl)-3-(3-(4-hydroxy-1,5-dimethyl-2-oxo-1,2-dihydropyridin-3-yl)ureido)propanoate;

ethyl 3-(3'-chloro-4'-fluorobiphenyl-3-yl)-3-(3-(4-hydroxy-1,5-dim ethyl-2-oxo-1,2-dihydropyridin-3-yl)ureido)propanoate;

ethyl 3-(2',3'-dichlorobiphenyl-3-yl)-3-(3-(4-hydroxy-1,5-dimethyl-2-oxo-1,2-dihydropyridin-3-yl)ureido)propanoate;

ethyl 3-(3',5'-dichlorobiphenyl-3-yl)-3-(3-(4-hydroxy-1,5-dimethyl-2-oxo-1,2-dihydropyridin-3-yl)ureido)propanoate;

ethyl (S)-3-(2',4'-difluorobiphenyl-3-yl)-3-(3-(4-hydroxy-1,6-dimethyl-2-oxo-1,2-dihydropyridin-3-yl)ureido)propanoate;

ethyl (S)-3-(2',4'-difluorobiphenyl-3-yl)-3-(3-(4-hydroxy-1-methyl-2-oxo-1,2-dihydropyridin-3-yl)ureido)propanoate;

ethyl (S)-3-(3-(4-hydroxy-1,5-dimethyl-2-oxo-1,2-dihydropyridin-3-yl)ureido)-3-(3'-methoxy-2'-methylbiphenyl-3-yl)propanoate;

ethyl (S)-3-(3-(4-hydroxy-1,5-dimethyl-2-oxo-1,2-dihydropyridin-3-yl)ureido)-3-(5'-methoxy-2'-methylbiphenyl-3-yl)propanoate;

ethyl 3-(3-(4-hydroxy-1,5-dimethyl-2-oxo-1,2-dihydropyridin-3-yl)ureido)-3-(6-(2,2,2-trifluoroethoxy)biphenyl-3-yl)propanoate;

ethyl (S)-3-(2'-ethylbiphenyl-3-yl)-3-(3-(4-hydroxy-1,5-dimethyl-2-oxo-1,2-dihydro pyridin-3-yl)ureido)propanoate;

ethyl (S)-3-(4-fluorobiphenyl-3-yl)-3-(3-(4-hydroxy-1,5-dimethyl-2-oxo-1,2-dihydro pyridin-3-yl)ureido)propanoate;

ethyl (S)-3-(2',4'-difluorobiphenyl-3-yl)-3-(3-(4-hydroxy-2-oxo-1,2-dihydropyridin-3-yl)ureido)propanoate;

ethyl (S)-3-(3',4'-dimethylbiphenyl-3-yl)-3-(3-(4-hydroxy-1,5-dimethyl-2-oxo-1,2-di hydropyridin-3-yl)ureido)propanoate;

ethyl (S)-3-(2',3'-difluorobiphenyl-3-yl)-3-(3-(4-hydroxy-1,5-dimethyl-2-oxo-1,2-di hydropyridin-3-yl)ureido)propanoate;

ethyl (S)-3-(4'-fluoro-3'-methylbiphenyl-3-yl)-3-(3-(4-hydroxy-1,5-dim ethyl-2-oxo-1,2-dihydropyridin-3-yl)ureido)propanoate;

ethyl (S)-3-(3-(4-hydroxy-1,5-dimethyl-2-oxo-1,2-dihydropyridin-3-yl)ureido)-3-(1-phenyl-1H-pyrrol-2-yl)propanoate;

ethyl (S)-3-(3'-chlorobiphenyl-3-yl)-3-(3-(4-hydroxy-1,5-dimethyl-2-oxo-1,2-dihydropyridin-3-yl)ureido)propanoate ethyl (S)-3-(3-(4-hydroxy-1,5-dimethyl-2-oxo-1,2-dihydropyridin-3-yl)ureido)-3-(2-methylbiphenyl-3-yl)propanoate;

ethyl (S)-3-(3-(4-hydroxy-1-methyl-2-oxo-1,2-dihydropyridin-3-yl)ureido)-3-(3'-methoxybiphenyl-3-yl)propanoate;

ethyl (S)-3-(2',6'-dimethylbiphenyl-3-yl)-3-(3-(4-hydroxy-1-methyl-2-oxo-1,2-dihydropyridin-3-yl)ureido)propanoate;

ethyl 3-(5'-chloro-2',4'-difluorobiphenyl-3-yl)-3-(3-(4-hydroxy-1,5-dim ethyl-2-oxo-1,2-dihydropyridin-3-yl)ureido)propanoate;

ethyl (S)-3-(2',3'-dimethoxybiphenyl-3-yl)-3-(3-(4-hydroxy-1,5-dimethyl-2-oxo-1,2-dihydropyridin-3-yl)ureido)propanoate;

ethyl (S)-3-(biphenyl-3-yl)-3-(3-(4-hydroxy-1-methyl-2-oxo-1,2-dihydropyridin-3-yl)ureido)propanoate;

ethyl (S)-3-(3'-chlorobiphenyl-3-yl)-3-(3-(4-hydroxy-1-methyl-2-oxo-1,2-dihydropyridin-3-yl)ureido)propanoate;

ethyl (S)-3-(3-(1H-pyrrol-1-yl)phenyl)-3-(3-(4-hydroxy-1-methyl-2-oxo-1,2-dihydropyridin-3-yl)ureido)propanoate;

ethyl (S)-3-(3-(4-hydroxy-1-methyl-2-oxo-1,2-dihydropyridin-3-yl)ureido)-3-(3-(6-methoxypyridin-3-yl)phenyl)propanoate;

ethyl (S)-3-(2'-fluoro-3'-m ethoxybiphenyl-3-yl)-3-(3-(4-hydroxy-1-methyl-2-oxo-1,2-dihydropyridin-3-yl)ureido)propanoate;

ethyl (S)-3-(3-(4-hydroxy-1-methyl-2-oxo-1,2-dihydropyridin-3-yl)ureido)-3-(4'-(trifluoromethoxy)biphenyl-3-yl)propanoate;

ethyl 3-(2',4'-dichlorobiphenyl-3-yl)-3-(3-(4-hydroxy-1,5-dimethyl-2-oxo-1,2-dihydropyridin-3-yl)ureido)propanoate;

ethyl (S)-3-(3-(4-hydroxy-1-methyl-2-oxo-1,2-dihydropyridin-3-yl)ureido)-3-(2'-(trifluoromethoxy)biphenyl-3-yl)propanoate;

ethyl (S)-3-(2',4'-difluorobiphenyl-3-yl)-3-(3-(4-hydroxy-1-methyl-2-oxo-2,5,6,7-tetrahydro-1H-cyclopenta[b]pyridin-3-yl)ureido)propanoate;

ethyl (S)-3-(3-(4-hydroxy-1-methyl-2-oxo-1,2-dihydropyridin-3-yl)ureido)-3-(3'-(trifluoromethoxy)biphenyl-3-yl)propanoate;

ethyl (S)-3-(2',4'-difluorobiphenyl-3-yl)-3-(3-(7-hydroxy-4-methyl-5-oxo-4,5-dihydrothieno[3,2-b]pyridin-6-yl)ureido)propanoate;

ethyl (S)-3-(3-(benzo[d][1,3]dioxol-5-yl)phenyl)-3-(3-(4-hydroxy-1-methyl-2-oxo-1,2-dihydropyridin-3-yl)ureido)propanoate;

ethyl (S)-3-(3-(benzo[d][1,3]dioxol-5-yl)phenyl)-3-(3-(4-hydroxy-1,5-dimethyl-2-oxo-1,2-dihydropyridin-3-yl)ureido)propanoate;

ethyl (S)-3-(3-(1H-indazol-1-yl)phenyl)-3-(3-(4-hydroxy-1-methyl-2-oxo-1,2-dihydropyridin-3-yl)ureido)propanoate;

ethyl (S)-3-(2',4'-difluoro-6-methoxybiphenyl-3-yl)-3-(3-(4-hydroxy-1-methyl-2-oxo-1,2-dihydropyridin-3-yl)ureido)propanoate;

ethyl (S)-3-(3-(4-hydroxy-1-methyl-2-oxo-1,2-dihydropyridin-3-yl)ureido)-3-(4-phenylthiophen-2-yl)propanoate;

ethyl (S)-3-(3-(1-ethyl-1H-indol-6-yl)phenyl)-3-(3-(4-hydroxy-1-methyl-2-oxo-1,2-dihydropyridin-3-yl)ureido)propanoate;

ethyl (S)-3-(3-(1H-pyrazol-1-yl)phenyl)-3-(3-(4-hydroxy-1-methyl-2-oxo-1,2-dihydropyridin-3-yl)ureido)propanoate;

ethyl (S)-3-(4-(2,4-difluorophenyl)thiophen-2-yl)-3-(3-(4-hydroxy-1-methyl-2-oxo-1,2-dihydropyridin-3-yl)ureido)propanoate;

ethyl (S)-3-(3',6-dimethoxybiphenyl-3-yl)-3-(3-(4-hydroxy-1-methyl-2-oxo-1,2-dihydropyridin-3-yl)ureido)propanoate;

ethyl 3-(2',5'-dichlorobiphenyl-3-yl)-3-(3-(4-hydroxy-1,5-dimethyl-2-oxo-1,2-dihydropyridin-3-yl)ureido)propanoate;

ethyl (S)-3-(2',4'-difluorobiphenyl-3-yl)-3-(3-(4-hydroxy-1-methyl-2-oxo-1,2-dihydro-1,8-naphthyridin-3-yl)ureido)propanoate;

ethyl (S)-3-(3',6-dimethoxybiphenyl-3-yl)-3-(3-(4-hydroxy-1,5-dimethyl-2-oxo-1,2-dihydropyridin-3-yl)ureido)propanoate;

ethyl (S)-3-(3-(4-hydroxy-1-methyl-2-oxo-1,2-dihydropyridin-3-yl)ureido)-3-(4-(3-methoxyphenyl)thiophen-2-yl)propanoate;

ethyl (S)-3-(3-(4-hydroxy-1-methyl-2-oxo-1,2-dihydropyridin-3-yl)ureido)-3-(6-methoxybiphenyl-3-yl)propanoate;

ethyl (S)-3-(4-(3-chlorophenyl)thiophen-2-yl)-3-(3-(4-hydroxy-1-methyl-2-oxo-1,2-dihydropyridin-3-yl)ureido)propanoate;

ethyl (S)-3-(2',4'-difluorobiphenyl-3-yl)-3-(3-(1-ethyl-4-hydroxy-2-oxo-1,2-dihydro pyridin-3-yl)ureido)propanoate;

ethyl (S)-3-(3-(4-hydroxy-1-methyl-2-oxo-1,2-dihydropyridin-3-yl)ureido)-3-(3-(thiophen-2-yl)phenyl)propanoate;

ethyl (S)-3-(3-(4-hydroxy-1-methyl-2-oxo-1,2-dihydropyridin-3-yl)ureido)-3-(6-methoxy-2',6'-dimethylbiphenyl-3-yl)propanoate;

ethyl (S)-3-(3'-chloro-6-methoxybiphenyl-3-yl)-3-(3-(4-hydroxy-1-methyl-2-oxo-1,2-dihydropyridin-3-yl)ureido)propanoate;
ethyl (S)-3-(3-(4-hydroxy-1-methyl-2-oxo-1,2-dihydropyridin-3-yl)ureido)-3-(6-methoxy-3'-(trifluoromethoxy)biphenyl-3-yl)propanoate;
ethyl (S)-3-(3-(4-hydroxy-1-methyl-2-oxo-1,2-dihydropyridin-3-yl)ureido)-3-(6-methoxy-4'-(trifluoromethoxy)biphenyl-3-yl)propanoate;
ethyl (S)-3-(2',6'-dichlorobiphenyl-3-yl)-3-(3-(4-hydroxy-1-methyl-2-oxo-1,2-dihydropyridin-3-yl)ureido)propanoate;
ethyl (S)-3-(3-(5-chlorothiophen-2-yl)phenyl)-3-(3-(4-hydroxy-1-methyl-2-oxo-1,2-dihydropyridin-3-yl)ureido)propanoate;
ethyl (S)-3-(3-(1H-imidazol-1-yl)phenyl)-3-(3-(4-hydroxy-1-methyl-2-oxo-1,2-dihydropyridin-3-yl)ureido)propanoate;
ethyl (S)-3-(3-(4-hydroxy-1-methyl-2-oxo-1,2-dihydropyridin-3-yl)ureido)-3-(3-(4-methylthiophen-3-yl)phenyl)propanoate;
ethyl (S)-3-(2',4'-difluoro-6-methyl biphenyl-3-yl)-3-(3-(4-hydroxy-1-methyl-2-oxo-1,2-dihydropyridin-3-yl)ureido)propanoate;
ethyl (S)-3-(3-(4-hydroxy-1-methyl-2-oxo-1,2-dihydropyridin-3-yl)ureido)-3-(3'-methoxy-6-methylbiphenyl-3-yl)propanoate;
ethyl (S)-3-(4-(2,6-dimethylphenyl)thiophen-2-yl)-3-(3-(4-hydroxy-1-methyl-2-oxo-1,2-dihydropyridin-3-yl)ureido)propanoate;
ethyl (S)-3-(3-(1H-pyrrol-3-yl)phenyl)-3-(3-(4-hydroxy-1-methyl-2-oxo-1,2-dihydro pyridin-3-yl)ureido)propanoate;
ethyl (S)-3-(3-(4-hydroxy-1-methyl-2-oxo-1,2-dihydropyridin-3-yl)ureido)-3-(2',6,6'-trimethylbiphenyl-3-yl)propanoate;
ethyl (S)-3-(3-(4-hydroxy-1-methyl-2-oxo-1,2-dihydropyridin-3-yl)ureido)-3-(2',6,6'-trifluorobiphenyl-3-yl)propanoate;
ethyl (S)-3-(6-fluoro-3'-methoxybiphenyl-3-yl)-3-(3-(4-hydroxy-1-methyl-2-oxo-1,2-dihydropyridin-3-yl)ureido)propanoate;
ethyl (S)-3-(3-(4-hydroxy-1-methyl-2-oxo-1,2-dihydropyridin-3-yl)ureido)-3-(3-(1-methyl-1H-pyrazol-4-yl)phenyl)propanoate;
ethyl (S)-3-(2',4'-difluorobiphenyl-3-yl)-3-(3-(5-hydroxy-2-methyl-3-oxo-2,3-dihydropyridazin-4-yl)ureido)propanoate;
ethyl (S)-3-(2',6'-dimethylbiphenyl-3-yl)-3-(3-(4-hydroxy-1,6-dimethyl-2-oxo-1,2-dihydropyridin-3-yl)ureido)propanoate;
ethyl (S)-3-(3',6-dimethoxybiphenyl-3-yl)-3-(3-(4-hydroxy-1,6-dimethyl-2-oxo-1,2-dihydropyridin-3-yl)ureido)propanoate;
ethyl (S)-3-(4-(2,4-difluorophenyl)thiophen-2-yl)-3-(3-(4-hydroxy-1,6-dimethyl-2-oxo-1,2-dihydropyridin-3-yl)ureido)propanoate;
ethyl (S)-3-(3-(4-hydroxy-1,6-dimethyl-2-oxo-1,2-dihydropyridin-3-yl)ureido)-3-(3'-methoxybiphenyl-3-yl)propanoate;
ethyl (S)-3-(3-(4-hydroxy-1,6-dimethyl-2-oxo-1,2-dihydropyridin-3-yl)ureido)-3-(6-methoxy-3'-(trifluoromethoxy)biphenyl-3-yl)propanoate;
ethyl (S)-3-(3'-chloro-6-methylbiphenyl-3-yl)-3-(3-(4-hydroxy-1-methyl-2-oxo-1,2-dihydropyridin-3-yl)ureido)propanoate;
ethyl (S)-3-(3'-chlorobiphenyl-3-yl)-3-(3-(4-hydroxy-1,6-dimethyl-2-oxo-1,2-dihydropyridin-3-yl)ureido)propanoate;
ethyl (S)-3-(2',4'-difluorobiphenyl-3-yl)-3-(3-(4-hydroxy-6-methyl-2-oxo-1,2-dihydropyridin-3-yl)ureido)propanoate;
ethyl (S)-3-(3-(4-hydroxy-1-methyl-2-oxo-1,2-dihydropyridin-3-yl)ureido)-3-(5-methoxybiphenyl-3-yl)propanoate;
ethyl (S)-3-(3-(furan-3-yl)phenyl)-3-(3-(4-hydroxy-1-methyl-2-oxo-1,2-dihydro pyridin-3-yl)ureido)propanoate;
ethyl (S)-3-(3-(3,5-dimethylisoxazol-4-yl)phenyl)-3-(3-(4-hydroxy-1-methyl-2-oxo-1,2-dihydropyridin-3-yl)ureido)propanoate;
ethyl (S)-3-(6-fluoro-2',6'-dimethylbiphenyl-3-yl)-3-(3-(4-hydroxy-1-methyl-2-oxo-1,2-dihydropyridin-3-yl)ureido)propanoate;
ethyl (S)-3-(5-(2,4-difluorophenyl)thiophen-2-yl)-3-(3-(4-hydroxy-1-methyl-2-oxo-1,2-dihydropyridin-3-yl)ureido)propanoate;
ethyl (S)-3-(3-(4-hydroxy-1-methyl-2-oxo-1,2-dihydropyridin-3-yl)ureido)-3-(5-(3-methoxyphenyl)thiophen-2-yl)propanoate;
ethyl (S)-3-(3',5-dimethoxybiphenyl-3-yl)-3-(3-(4-hydroxy-1-methyl-2-oxo-1,2-dihydropyridin-3-yl)ureido)propanoate;
ethyl (S)-3-(3-(4-hydroxy-1-methyl-2-oxo-1,2-dihydropyridin-3-yl)ureido)-3-(5-methoxy-3'-(trifluoromethoxy)biphenyl-3-yl)propanoate;
ethyl (S)-3-(2',4'-difluoro-5-methoxybiphenyl-3-yl)-3-(3-(4-hydroxy-1-methyl-2-oxo-1,2-dihydropyridin-3-yl)ureido)propanoate;
ethyl (S)-3-(3',5-dimethoxybiphenyl-3-yl)-3-(3-(4-hydroxy-1,6-dimethyl-2-oxo-1,2-dihydropyridin-3-yl)ureido)propanoate;
ethyl (S)-3-(3-(4-hydroxy-1,6-dimethyl-2-oxo-1,2-dihydropyridin-3-yl)ureido)-3-(5-methoxy-3'-(trifluoromethoxy)biphenyl-3-yl)propanoate;
ethyl (S)-3-(3-(4-hydroxy-1,6-dimethyl-2-oxo-1,2-dihydropyridin-3-yl)ureido)-3-(3'-methoxy-6-methylbiphenyl-3-yl)propanoate;
ethyl (S)-3-(4-fluorobiphenyl-3-yl)-3-(3-(4-hydroxy-1-methyl-2-oxo-1,2-dihydro pyridin-3-yl)ureido)propanoate;
ethyl (S)-3-(3-(4-hydroxy-1-methyl-2-oxo-1,2-dihydropyridin-3-yl)ureido)-3-(6-phenylpyridin-2-yl)propanoate;
ethyl (S)-3-(3-(4-hydroxy-1-methyl-2-oxo-1,2-dihydropyridin-3-yl)ureido)-3-(5-methyl-3'-(trifluoromethoxy)biphenyl-3-yl)propanoate;
ethyl (S)-3-(3-(4-hydroxy-1-methyl-2-oxo-1,2-dihydropyridin-3-yl)ureido)-3-(2',5,6'-trimethylbiphenyl-3-yl)propanoate;
ethyl (S)-3-(2',4'-difluoro-5-methyl biphenyl-3-yl)-3-(3-(4-hydroxy-1-methyl-2-oxo-1,2-dihydropyridin-3-yl)ureido)propanoate;
ethyl (S)-3-(2',4'-difluoro-5-methylbiphenyl-3-yl)-3-(3-(4-hydroxy-1,6-dimethyl-2-oxo-1,2-dihydropyridin-3-yl)ureido)propanoate;
ethyl (S)-3-(3-(4-hydroxy-1-methyl-2-oxo-1,2-dihydropyridin-3-yl)ureido)-3-(6-methyl-3'-(trifluoromethoxy)biphenyl-3-yl)propanoate;
ethyl (S)-3-(3-(4-hydroxy-1,6-dimethyl-2-oxo-1,2-dihydropyridin-3-yl)ureido)-3-(6-methyl-3'-(trifluoromethoxy)biphenyl-3-yl)propanoate;

ethyl (S)-3-(6-fluoro-2',6'-dimethylbiphenyl-3-yl)-3-(3-(4-hydroxy-1,6-dimethyl-2-oxo-1,2-dihydropyridin-3-yl)ureido)propanoate;

ethyl (S)-3-(3-(4-hydroxy-1-methyl-2-oxo-1,2-dihydropyridin-3-yl)ureido)-3-(5-methoxy-2',6'-dimethylbiphenyl-3-yl)propanoate;

ethyl (S)-3-(3-(4-hydroxy-1,6-dimethyl-2-oxo-1,2-dihydropyridin-3-yl)ureido)-3-(5-methoxy-2',6'-dimethylbiphenyl-3-yl)propanoate;

ethyl (S)-3-(2',4'-difluoro-5-methoxybiphenyl-3-yl)-3-(3-(4-hydroxy-1,6-dimethyl-2-oxo-1,2-dihydropyridin-3-yl)ureido)propanoate;

ethyl (S)-3-(3-(4-hydroxy-1-methyl-2-oxo-1,2-dihydropyridin-3-yl)ureido)-3-(3'-methoxy-5-methylbiphenyl-3-yl)propanoate;

ethyl (S)-3-(2',6'-dimethylbiphenyl-3-yl)-3-(3-(7-hydroxy-5-oxo-1,2,3,5-tetrahydro indolizin-6-yl)ureido)propanoate;

ethyl (S)-3-(3-(4-hydroxy-1-methyl-2-oxo-1,2-dihydropyridin-3-yl)ureido)-3-(4'-methyl-[2,3'-bithiophen]-5-yl)propanoate;

ethyl (S)-3-(3-(4-hydroxy-1,6-dimethyl-2-oxo-1,2-dihydropyridin-3-yl)ureido)-3-(4'-methyl-[2,3'-bithiophen]-5-yl)propanoate;

ethyl (S)-3-(3-(4-hydroxy-1,6-dimethyl-2-oxo-1,2-dihydropyridin-3-yl)ureido)-3-(3'-methoxy-5-methylbiphenyl-3-yl)propanoate;

ethyl (S)-3-(5-(2,6-dimethylphenyl)thiophen-2-yl)-3-(3-(4-hydroxy-1-methyl-2-oxo-1,2-dihydropyridin-3-yl)ureido)propanoate;

ethyl (S)-3-(5-(2,6-dimethylphenyl)thiophen-2-yl)-3-(3-(4-hydroxy-1,6-dimethyl-2-oxo-1,2-dihydropyridin-3-yl)ureido)propanoate;

ethyl (S)-3-(4-fluoro-2',6'-dimethylbiphenyl-3-yl)-3-(3-(4-hydroxy-1,6-dimethyl-2-oxo-1,2-dihydropyridin-3-yl)ureido)propanoate;

ethyl (S)-3-(4-fluoro-2',6'-dimethylbiphenyl-3-yl)-3-(3-(4-hydroxy-1-methyl-2-oxo-1,2-dihydropyridin-3-yl)ureido)propanoate;

ethyl (S)-3-(3-(4-hydroxy-1-methyl-2-oxo-1,2-dihydropyridin-3-yl)ureido)-3-(2',4,4'-trifluorobiphenyl-3-yl)propanoate;

ethyl (S)-3-(3-(4-hydroxy-1,6-dimethyl-2-oxo-1,2-dihydropyridin-3-yl)ureido)-3-(2',4,4'-trifluorobiphenyl-3-yl)propanoate;

ethyl (S)-3-(4-fluoro-3'-m ethoxybiphenyl-3-yl)-3-(3-(4-hydroxy-1-methyl-2-oxo-1,2-dihydropyridin-3-yl)ureido)propanoate;

ethyl (S)-3-(4-fluoro-3'-(trifluoromethoxy)biphenyl-3-yl)-3-(3-(4-hydroxy-1-methyl-2-oxo-1,2-dihydropyridin-3-yl)ureido)propanoate;

ethyl (S)-3-(4-fluoro-3'-(trifluoromethoxy)biphenyl-3-yl)-3-(3-(4-hydroxy-1,6-dimethyl-2-oxo-1,2-dihydropyridin-3-yl)ureido)propanoate;

ethyl (S)-3-(3-(4-hydroxy-1-methyl-2-oxo-1,2-dihydropyridin-3-yl)ureido)-3-(4-methoxybiphenyl-3-yl)propanoate;

ethyl (S)-3-(3-(4-hydroxy-1,6-dimethyl-2-oxo-1,2-dihydropyridin-3-yl)ureido)-3-(2',5,6'-trimethylbiphenyl-3-yl)propanoate;

ethyl (S)-3-(3-(4-hydroxy-1-methyl-2-oxo-1,2-dihydropyridin-3-yl)ureido)-3-(2'-methylbiphenyl-3-yl)propanoate;

ethyl (S)-3-(3-(4-hydroxy-1,6-dimethyl-2-oxo-1,2-dihydropyridin-3-yl)ureido)-3-(2'-methylbiphenyl-3-yl)propanoate;

ethyl (S)-3-(5-fluoro-2',6'-dimethylbiphenyl-3-yl)-3-(3-(4-hydroxy-1-methyl-2-oxo-1,2-dihydropyridin-3-yl)ureido)propanoate;

ethyl (S)-3-(3-(4-hydroxy-1-methyl-2-oxo-1,2-dihydropyridin-3-yl)ureido)-3-(5-(3-(trifluoromethoxy)phenyl)thiophen-2-yl)propanoate;

ethyl (S)-3-(3-(4-hydroxy-1-methyl-2-oxo-1,2-dihydropyridin-3-yl)ureido)-3-(4-methoxy-2',6'-dimethylbiphenyl-3-yl)propanoate;

ethyl (S)-3-(4-fluoro-3'-m ethoxybiphenyl-3-yl)-3-(3-(4-hydroxy-1,6-dim ethyl-2-oxo-1,2-dihydropyridin-3-yl)ureido)propanoate;

ethyl (S)-3-(5-fluoro-3'-m ethoxybiphenyl-3-yl)-3-(3-(4-hydroxy-1-methyl-2-oxo-1,2-dihydropyridin-3-yl)ureido)propanoate;

ethyl (S)-3-(5-fluoro-3'-m ethoxybiphenyl-3-yl)-3-(3-(4-hydroxy-1,6-dim ethyl-2-oxo-1,2-dihydropyridin-3-yl)ureido)propanoate;

ethyl (S)-3-(5-fluoro-3'-(trifluoromethoxy)biphenyl-3-yl)-3-(3-(4-hydroxy-1,6-dimethyl-2-oxo-1,2-dihydropyridin-3-yl)ureido)propanoate;

ethyl (S)-3-(5-fluoro-3'-(trifluoromethoxy)biphenyl-3-yl)-3-(3-(4-hydroxy-1-methyl-2-oxo-1,2-dihydropyridin-3-yl)ureido)propanoate;

ethyl (S)-3-(5-(3,5-dimethylisoxazol-4-yl)thiophen-2-yl)-3-(3-(4-hydroxy-1-methyl-2-oxo-1,2-dihydropyridin-3-yl)ureido)propanoate;

ethyl (S)-3-(3-(3,5-dim ethyl isoxazol-4-yl)phenyl)-3-(3-(4-hydroxy-1,6-dimethyl-2-oxo-1,2-dihydropyridin-3-yl)ureido)propanoate;

ethyl (S)-3-(2-fluorobiphenyl-3-yl)-3-(3-(4-hydroxy-1,6-dimethyl-2-oxo-1,2-dihydro pyridin-3-yl)ureido)propanoate;

ethyl (S)-3-(6-fluoro-2'-methylbiphenyl-3-yl)-3-(3-(4-hydroxy-1,6-dimethyl-2-oxo-1,2-dihydropyridin-3-yl)ureido)propanoate;

ethyl (S)-3-(6-fluoro-2'-methylbiphenyl-3-yl)-3-(3-(4-hydroxy-1-methyl-2-oxo-1,2-dihydropyridin-3-yl)ureido)propanoate;

ethyl (S)-3-(3-(4-hydroxy-1-methyl-2-oxo-1,2-dihydropyridin-3-yl)ureido)-3-(5-phenylthiophen-2-yl)propanoate;

ethyl (S)-3-(5-(2,5-difluorophenyl)thiophen-2-yl)-3-(3-(4-hydroxy-1-methyl-2-oxo-1,2-dihydropyridin-3-yl)ureido)propanoate;

ethyl (S)-3-(3-(4-hydroxy-1-methyl-2-oxo-1,2-dihydropyridin-3-yl)ureido)-3-(5-(tri fluoromethoxy)biphenyl-3-yl)propanoate;

ethyl (S)-3-(3-(4-hydroxy-1-methyl-2-oxo-1,2-dihydropyridin-3-yl)ureido)-3-(2'-methylbiphenyl-4-yl)propanoate;

ethyl (S)-3-(3-(7-hydroxy-5-oxo-1,2,3,5-tetrahydroindolizin-6-yl)ureido)-3-(5-methoxybiphenyl-3-yl)propanoate;

ethyl (S)-3-(3-(4-hydroxy-1-methyl-2-oxo-1,2-dihydropyridin-3-yl)ureido)-3-(5-(tri fluoromethyl)biphenyl-3-yl)propanoate;

ethyl (S)-3-(5-(3-chlorophenyl)thiophen-2-yl)-3-(3-(4-hydroxy-1-methyl-2-oxo-1,2-dihydropyridin-3-yl)ureido)propanoate;

ethyl (S)-3-(5-(3-fluorophenyl)thiophen-2-yl)-3-(3-(4-hydroxy-1-methyl-2-oxo-1,2-dihydropyridin-3-yl)ureido)propanoate;

tert-butyl (S)-3-(2',4'-difluorobiphenyl-4-yl)-3-(3-(4-hydroxy-1-methyl-2-oxo-1,2-dihydropyridin-3-yl)ureido)propanoate;

tert-butyl (S)-3-(2',4'-difluorobiphenyl-4-yl)-3-(3-(4-hydroxy-1,6-dimethyl-2-oxo-1,2-dihydropyridin-3-yl)ureido)propanoate;

tert-butyl (S)-3-(2',4'-difluorobiphenyl-4-yl)-3-(3-(4-hydroxy-1,5-dimethyl-2-oxo-1,2-dihydropyridin-3-yl)ureido)propanoate;

ethyl (S)-3-(3-(4-hydroxy-1-methyl-2-oxo-1,2-dihydropyridin-3-yl)ureido)-3-(2'-methyl-6-(trifluoromethoxy)biphenyl-3-yl)propanoate;

ethyl (S)-3-(3-(4-hydroxy-1-methyl-2-oxo-1,2-dihydropyridin-3-yl)ureido)-3-(6-(trifluoromethoxy)biphenyl-3-yl)propanoate;

ethyl 3-(3'-acetylbiphenyl-3-yl)-3-(3-(4-hydroxy-1,5-dimethyl-2-oxo-1,2-dihydropyridin-3-yl)ureido)propanoate;

ethyl 3-(4'-acetylbiphenyl-3-yl)-3-(3-(4-hydroxy-1,5-dimethyl-2-oxo-1,2-dihydropyridin-3-yl)ureido)propanoate;

ethyl (S)-3-(3-(4-hydroxy-1,5-dimethyl-2-oxo-1,2-dihydropyridin-3-yl)ureido)-3-(4-phenylthiophen-2-yl)propanoate;

ethyl (S)-3-(3-(4-hydroxy-1,5-dimethyl-2-oxo-1,2-dihydropyridin-3-yl)ureido)-3-(5-phenylthiophen-2-yl)propanoate;

ethyl (S)-3-(2',4'-difluorobiphenyl-3-yl)-3-(3-(7-hydroxy-5-oxo-1,2,3,5-tetrahydroindolizin-6-yl)ureido)propanoate;

ethyl (S)-3-(3-(4-hydroxy-1-methyl-2-oxo-1,2-dihydropyridin-3-yl)ureido)-3-(3-(thiazol-2-yl)phenyl)propanoate;

ethyl (S)-3-(3-(4-hydroxy-1,6-dimethyl-2-oxo-1,2-dihydropyridin-3-yl)ureido)-3-(5-methyl-3'-(trifluoromethoxy)biphenyl-3-yl)propanoate;

ethyl (S)-3-(3-(4-hydroxy-1,6-dimethyl-2-oxo-1,2-dihydropyridin-3-yl)ureido)-3-(2',4', 5-trifluorobiphenyl-3-yl)propanoate;

ethyl (S)-3-(3-(4-hydroxy-1-methyl-2-oxo-1,2-dihydropyridin-3-yl)ureido)-3-(2',4', 5-trifluorobiphenyl-3-yl)propanoate;

ethyl (S)-3-(3-(4-hydroxy-1-methyl-2-oxo-1,2-dihydropyridin-3-yl)ureido)-3-(3'-methoxy-6-(trifluoromethoxy)biphenyl-3-yl)propanoate;

ethyl (S)-3-(3-(4-hydroxy-1,6-dimethyl-2-oxo-1,2-dihydropyridin-3-yl)ureido)-3-(3'-methoxy-6-(trifluoromethoxy)biphenyl-3-yl)propanoate;

ethyl (S)-3-(2',6'-dimethylbiphenyl-4-yl)-3-(3-(4-hydroxy-1-methyl-2-oxo-1,2-dihydropyridin-3-yl)ureido)propanoate;

ethyl (S)-3-(3-(4-hydroxy-1,6-dimethyl-2-oxo-1,2-dihydropyridin-3-yl)ureido)-3-(2'-methylbiphenyl-4-yl)propanoate;

ethyl (S)-3-(2',6'-dimethylbiphenyl-4-yl)-3-(3-(4-hydroxy-1,6-dimethyl-2-oxo-1,2-dihydropyridin-3-yl)ureido)propanoate;

ethyl (S)-3-(3-(4-hydroxy-1-methyl-2-oxo-1,2-dihydropyridin-3-yl)ureido)-3-(3-(pyridin-2-yl)phenyl)propanoate;

ethyl (S)-3-(3-(4-hydroxy-1-methyl-2-oxo-1,2-dihydropyridin-3-yl)ureido)-3-(3-(6-methoxypyridazin-3-yl)phenyl)propanoate;

ethyl (S)-3-(3-(4-hydroxy-1-methyl-2-oxo-1,2-dihydropyridin-3-yl)ureido)-3-(5-phenylpyridin-3-yl)propanoate;

(S)-ethyl 3-(5-fluoro-2',6'-dimethylbiphenyl-3-yl)-3-(3-(4-hydroxy-1,6-dimethyl-2-oxo-1,2-dihydropyridin-3-yl)ureido)propanoate;

tert-butyl (S)-3-(biphenyl-4-yl)-3-(3-(1,5-dimethyl-4-oxido-2-oxo-1,2-dihydropyridin-3-yl)ureido)propanoate;

ethyl (S)-3-(3-(4-hydroxy-1-methyl-2-oxo-1,2-dihydropyridin-3-yl)ureido)-3-(3-(6'-methoxypyridin-2-yl)phenyl)propanoate;

ethyl (S)-3-(3-(4-hydroxy-1,5-di methyl-2-oxo-1,2-dihydropyridin-3-yl)ureido)-3-(4'-methoxybiphenyl-3-yl)propanoate;

ethyl (S)-3-(3-(1H-imidazol-1-yl)phenyl)-3-(3-(4-hydroxy-1-methyl-2-oxo-1,2-dihydropyridin-3-yl)ureido)propanoate;

ethyl 3-(3-bromophenyl)-3-(3-(4-hydroxy-1,5-dimethyl-2-oxo-1,2-dihydropyridin-3-yl)ureido)propanoate, ethyl 3-(3-bromophenyl)-3-(3-(1-ethyl-4-hydroxy-5-methyl-2-oxo-1,2-dihydro pyridin-3-yl)ureido)propanoate;

ethyl (S)-3-(2',4'-difluorobiphenyl-4-yl)-3-(3-(4-hydroxy-1-methyl-2-oxo-1,2-di hydropyridin-3-yl)ureido)propanoate, ethyl (S)-3-(2',4'-difluorobiphenyl-4-yl)-3-(3-(4-hydroxy-1,6-dimethyl-2-oxo-1,2-di hydropyridin-3-yl)ureido)propanoate (S)-3-(biphenyl-3-yl)-3-(3-(4-hydroxy-1,5-dimethyl-2-oxo-1,2-dihydropyridin-3-yl)ureido)propanoic acid (S)-3-(biphenyl-3-yl)-3-(3-(1-ethyl-4-hydroxy-5-methyl-2-oxo-1,2-dihydropyridin-3-yl)ureido)propanoic acid;

3-(3-(1-ethyl-4-hydroxy-5-methyl-2-oxo-1,2-dihydropyridin-3-yl)ureido)-3-(3-(2-oxo-3-phenylpyridin-1(2H)-yl)phenyl)propanoic acid;

(S)-3-(3-(4-hydroxy-1,5-dimethyl-2-oxo-1,2-dihydropyridin-3-yl)ureido)-3-(2'-methylbiphenyl-3-yl)propanoic acid;

(S)-3-(2'-fluorobiphenyl-3-yl)-3-(3-(4-hydroxy-1,5-dimethyl-2-oxo-1,2-dihydropyridin-3-yl)ureido)propanoic acid;

(S)-3-(6-fluorobiphenyl-3-yl)-3-(3-(4-hydroxy-1,5-dimethyl-2-oxo-1,2-dihydropyridin-3-yl)ureido)propanoic acid;

(S)-3-(3-(1-ethyl-4-hydroxy-5-methyl-2-oxo-1,2-dihydropyridin-3-yl)ureido)-3-(2'-methylbiphenyl-3-yl)propanoic acid;

(S)-3-(3-(1-ethyl-4-hydroxy-5-methyl-2-oxo-1,2-dihydropyridin-3-yl)ureido)-3-(4'-methylbiphenyl-3-yl)propanoic acid;

3-(3-(1H-pyrrol-1-yl)phenyl)-3-(3-(4-hydroxy-1,5-dimethyl-2-oxo-1,2-dihydropyridin-3-yl)ureido)propanoic acid;

(S)-3-(2',4'-difluorobiphenyl-3-yl)-3-(3-(4-hydroxy-1,5-dimethyl-2-oxo-1,2-dihydropyridin-3-yl)ureido)propanoic acid;

(S)-3-(2',5'-difluorobiphenyl-3-yl)-3-(3-(4-hydroxy-1,5-dimethyl-2-oxo-1,2-dihydropyridin-3-yl)ureido)propanoic acid;

(S)-3-(3-(4-hydroxy-1,5-dimethyl-2-oxo-1,2-dihydropyridin-3-yl)ureido)-3-(6-methylbiphenyl-3-yl)propanoic acid;

(S)-3-(3-(4-hydroxy-1,5-dimethyl-2-oxo-1,2-dihydropyridin-3-yl)ureido)-3-(6-methoxybiphenyl-3-yl)propanoic acid;

(S)-3-(3-(4-hydroxy-1,5-dimethyl-2-oxo-1,2-dihydropyridin-3-yl)ureido)-3-(4'-methylbiphenyl-3-yl)propanoic acid;

(S)-3-(3-(4-hydroxy-1,5-dimethyl-2-oxo-1,2-dihydropyridin-3-yl)ureido)-3-(3'-methylbiphenyl-3-yl)propanoic acid;

(S)-3-(3-(4-hydroxy-1,5-dimethyl-2-oxo-1,2-dihydropyridin-3-yl)ureido)-3-(3-(pyridin-3-yl)phenyl)propanoic acid;
(S)-3-(3',5'-difluorobiphenyl-3-yl)-3-(3-(4-hydroxy-1,5-dimethyl-2-oxo-1,2-dihydropyridin-3-yl)ureido)propanoic acid;
(S)-3-(3',5'-dimethylbiphenyl-3-yl)-3-(3-(4-hydroxy-1,5-dimethyl-2-oxo-1,2-dihydropyridin-3-yl)ureido)propanoic acid;
(S)-3-(3-(4-hydroxy-1,5-dimethyl-2-oxo-1,2-dihydropyridin-3-yl)ureido)-3-(4'-methoxybiphenyl-3-yl)propanoic acid;
(S)-3-(3-(4-hydroxy-1,5-dimethyl-2-oxo-1,2-dihydropyridin-3-yl)ureido)-3-(2'-methoxybiphenyl-3-yl)propanoic acid;
(S)-3-(3-(4-hydroxy-1,5-dimethyl-2-oxo-1,2-dihydropyridin-3-yl)ureido)-3-(4'-(trifluoromethyl)biphenyl-3-yl)propanoic acid;
(S)-3-(3-(4-hydroxy-1,5-dimethyl-2-oxo-1,2-dihydropyridin-3-yl)ureido)-3-(3'-methoxybiphenyl-3-yl)propanoic acid;
(S)-3-(3-(4-hydroxy-1,5-dimethyl-2-oxo-1,2-dihydropyridin-3-yl)ureido)-3-(3'-(trifluoromethoxy)biphenyl-3-yl)propanoic acid;
(S)-3-(3',4'-difluorobiphenyl-3-yl)-3-(3-(4-hydroxy-1,5-dimethyl-2-oxo-1,2-dihydropyridin-3-yl)ureido)propanoic acid;
(S)-3-(2',5'-dimethylbiphenyl-3-yl)-3-(3-(4-hydroxy-1,5-dimethyl-2-oxo-1,2-dihydropyridin-3-yl)ureido)propanoic acid;
(S)-3-(2',3'-dimethylbiphenyl-3-yl)-3-(3-(4-hydroxy-1,5-dimethyl-2-oxo-1,2-dihydropyridin-3-yl)ureido)propanoic acid;
3-(3-(4-hydroxy-1,5-dimethyl-2-oxo-1,2-dihydropyridin-3-yl)ureido)-3-(6-oxo-1-phenyl-1,6-dihydropyridin-3-yl)propanoic acid;
(S)-3-(2',6'-difluorobiphenyl-3-yl)-3-(3-(4-hydroxy-1,5-dimethyl-2-oxo-1,2-dihydropyridin-3-yl)ureido)propanoic acid;
(S)-3-(3'-fluorobiphenyl-3-yl)-3-(3-(4-hydroxy-1,5-dimethyl-2-oxo-1,2-dihydropyridin-3-yl)ureido)propanoic acid;
(S)-3-(4'-fluorobiphenyl-3-yl)-3-(3-(4-hydroxy-1,5-dimethyl-2-oxo-1,2-dihydropyridin-3-yl)ureido)propanoic acid;
(S)-3-(3-(4-hydroxy-1,5-dimethyl-2-oxo-1,2-dihydropyridin-3-yl)ureido)-3-(2'-(trifluoromethoxy)biphenyl-3-yl)propanoic acid;
(S)-3-(2',4'-dimethoxybiphenyl-3-yl)-3-(3-(4-hydroxy-1,5-dimethyl-2-oxo-1,2-dihydropyridin-3-yl)ureido)propanoic acid;
(S)-3-(3',4'-dimethoxybiphenyl-3-yl)-3-(3-(4-hydroxy-1,5-dimethyl-2-oxo-1,2-dihydropyridin-3-yl)ureido)propanoic acid;
(S)-3-(2',6'-dimethylbiphenyl-3-yl)-3-(3-(4-hydroxy-1,5-dimethyl-2-oxo-1,2-dihydropyridin-3-yl)ureido)propanoic acid;
3-(4'-chlorobiphenyl-3-yl)-3-(3-(4-hydroxy-1,5-dimethyl-2-oxo-1,2-dihydropyridin-3-yl)ureido)propanoic acid;
3-(3'-chlorobiphenyl-3-yl)-3-(3-(4-hydroxy-1,5-dimethyl-2-oxo-1,2-dihydropyridin-3-yl)ureido)propanoic acid;
3-(2'-chlorobiphenyl-3-yl)-3-(3-(4-hydroxy-1,5-dimethyl-2-oxo-1,2-dihydropyridin-3-yl)ureido)propanoic acid;
(S)-3-(3-(4-hydroxy-1,5-dimethyl-2-oxo-1,2-dihydropyridin-3-yl)ureido)-3-(2'-(trifluoromethyl)biphenyl-3-yl)propanoic acid;
(S)-3-(5,6-dimethoxybiphenyl-3-yl)-3-(3-(4-hydroxy-1,5-dimethyl-2-oxo-1,2-dihydropyridin-3-yl)ureido)propanoic acid;
(S)-3-(3-(4-hydroxy-1,5-dimethyl-2-oxo-1,2-dihydropyridin-3-yl)ureido)-3-(3-(6-methoxypyridin-3-yl)phenyl)propanoic acid;
(S)-3-(2',5'-dimethoxybiphenyl-3-yl)-3-(3-(4-hydroxy-1,5-dimethyl-2-oxo-1,2-dihydropyridin-3-yl)ureido)propanoic acid;
3-(3-(4-hydroxy-1,5-dimethyl-2-oxo-1,2-dihydropyridin-3-yl)ureido)-3-(3-(pyrimidin-5-yl)phenyl)propanoic acid;
(S)-3-(2',6'-dimethoxybiphenyl-3-yl)-3-(3-(4-hydroxy-1,5-dimethyl-2-oxo-1,2-dihydropyridin-3-yl)ureido)propanoic acid;
3-(3',4'-dichlorobiphenyl-3-yl)-3-(3-(1-ethyl-4-hydroxy-5-methyl-2-oxo-1,2-dihydropyridin-3-yl)ureido)propanoic acid;
3-(3',4'-dichlorobiphenyl-3-yl)-3-(3-(4-hydroxy-1,5-dimethyl-2-oxo-1,2-dihydropyridin-3-yl)ureido)propanoic acid;
(S)-3-(3-(4-hydroxy-1,5-dimethyl-2-oxo-1,2-dihydropyridin-3-yl)ureido)-3-(5-phenylfuran-2-yl)propanoic acid;
(S)-3-(3-(2,5-dimethyl-1H-pyrrol-1-yl)phenyl)-3-(3-(4-hydroxy-1,5-dimethyl-2-oxo-1,2-dihydropyridin-3-yl)ureido)propanoic acid;
3-(3'-chloro-4'-fluorobiphenyl-3-yl)-3-(3-(4-hydroxy-1,5-dimethyl-2-oxo-1,2-dihydropyridin-3-yl)ureido)propanoic acid;
3-(2',3'-dichlorobiphenyl-3-yl)-3-(3-(4-hydroxy-1,5-dimethyl-2-oxo-1,2-dihydropyridin-3-yl)ureido)propanoic acid;
3-(3',5'-dichlorobiphenyl-3-yl)-3-(3-(4-hydroxy-1,5-dimethyl-2-oxo-1,2-dihydropyridin-3-yl)ureido)propanoic acid;
(S)-3-(2',4'-difluorobiphenyl-3-yl)-3-(3-(4-hydroxy-1,6-dimethyl-2-oxo-1,2-dihydropyridin-3-yl)ureido)propanoic acid;
(S)-3-(2',4'-difluorobiphenyl-3-yl)-3-(3-(4-hydroxy-1-methyl-2-oxo-1,2-dihydropyridin-3-yl)ureido)propanoic acid;
(S)-3-(3-(4-hydroxy-1,5-dimethyl-2-oxo-1,2-dihydropyridin-3-yl)ureido)-3-(3'-methoxy-2'-methylbiphenyl-3-yl)propanoic acid;
(S)-3-(3-(4-hydroxy-1,5-dimethyl-2-oxo-1,2-dihydropyridin-3-yl)ureido)-3-(5'-methoxy-2'-methylbiphenyl-3-yl)propanoic acid;
3-(3-(4-hydroxy-1,5-dimethyl-2-oxo-1,2-dihydropyridin-3-yl)ureido)-3-(6-(2,2,2-trifluoroethoxy)biphenyl-3-yl)propanoic acid;
(S)-3-(2'-ethylbiphenyl-3-yl)-3-(3-(4-hydroxy-1,5-dimethyl-2-oxo-1,2-dihydropyridin-3-yl)ureido)propanoic acid;
(S)-3-(4-fluorobiphenyl-3-yl)-3-(3-(4-hydroxy-1,5-dimethyl-2-oxo-1,2-dihydropyridin-3-yl)ureido)propanoic acid;
(S)-3-(2',4'-difluorobiphenyl-3-yl)-3-(3-(4-hydroxy-2-oxo-1,2-dihydropyridin-3-yl)ureido)propanoic acid;
(S)-3-(3',4'-dimethylbiphenyl-3-yl)-3-(3-(4-hydroxy-1,5-dimethyl-2-oxo-1,2-dihydropyridin-3-yl)ureido)propanoic acid;

(S)-3-(2',3'-difluorobiphenyl-3-yl)-3-(3-(4-hydroxy-1,5-dimethyl-2-oxo-1,2-dihydropyridin-3-yl)ureido)propanoic acid;

(S)-3-(4'-fluoro-3'-methylbiphenyl-3-yl)-3-(3-(4-hydroxy-1,5-dimethyl-2-oxo-1,2-dihydropyridin-3-yl)ureido)propanoic acid;

(S)-3-(3-(4-hydroxy-1,5-dimethyl-2-oxo-1,2-dihydropyridin-3-yl)ureido)-3-(1-phenyl-1H-pyrrol-2-yl)propanoic acid;

(S)-3-(3'-chlorobiphenyl-3-yl)-3-(3-(4-hydroxy-1,5-dimethyl-2-oxo-1,2-dihydropyridin-3-yl)ureido)propanoic acid;

(S)-3-(3-(4-hydroxy-1,5-dimethyl-2-oxo-1,2-dihydropyridin-3-yl)ureido)-3-(2-methylbiphenyl-3-yl)propanoic acid;

(S)-3-(3-(4-hydroxy-1-methyl-2-oxo-1,2-dihydropyridin-3-yl)ureido)-3-(3'-methoxybiphenyl-3-yl)propanoic acid;

(S)-3-(2',6'-dimethylbiphenyl-3-yl)-3-(3-(4-hydroxy-1-methyl-2-oxo-1,2-dihydropyridin-3-yl)ureido)propanoic acid;

3-(5'-chloro-2',4'-difluorobiphenyl-3-yl)-3-(3-(4-hydroxy-1,5-dimethyl-2-oxo-1,2-dihydropyridin-3-yl)ureido)propanoic acid;

(S)-3-(2',3'-dimethoxybiphenyl-3-yl)-3-(3-(4-hydroxy-1,5-dimethyl-2-oxo-1,2-dihydropyridin-3-yl)ureido)propanoic acid;

(S)-3-(biphenyl-3-yl)-3-(3-(4-hydroxy-1-methyl-2-oxo-1,2-dihydropyridin-3-yl)ureido)propanoic acid;

(S)-3-(3'-chlorobiphenyl-3-yl)-3-(3-(4-hydroxy-1-methyl-2-oxo-1,2-dihydropyridin-3-yl)ureido)propanoic acid;

(S)-3-(3-(1H-pyrrol-1-yl)phenyl)-3-(3-(4-hydroxy-1-methyl-2-oxo-1,2-dihydropyridin-3-yl)ureido)propanoic acid;

(S)-3-(3-(4-hydroxy-1-methyl-2-oxo-1,2-dihydropyridin-3-yl)ureido)-3-(3-(6-methoxypyridin-3-yl)phenyl)propanoic acid;

(S)-3-(2'-fluoro-3'-methoxybiphenyl-3-yl)-3-(3-(4-hydroxy-1-methyl-2-oxo-1,2-dihydropyridin-3-yl)ureido)propanoic acid;

(S)-3-(3-(4-hydroxy-1-methyl-2-oxo-1,2-dihydropyridin-3-yl)ureido)-3-(4'-(trifluoromethoxy)biphenyl-3-yl)propanoic acid;

3-(2',4'-dichlorobiphenyl-3-yl)-3-(3-(4-hydroxy-1,5-dimethyl-2-oxo-1,2-dihydropyridin-3-yl)ureido)propanoic acid;

(S)-3-(3-(4-hydroxy-1-methyl-2-oxo-1,2-dihydropyridin-3-yl)ureido)-3-(2'-(trifluoromethoxy)biphenyl-3-yl)propanoic acid;

(S)-3-(2',4'-difluorobiphenyl-3-yl)-3-(3-(4-hydroxy-1-methyl-2-oxo-2,5,6,7-tetrahydro-1H-cyclopenta[b]pyridin-3-yl)ureido)propanoic acid;

(S)-3-(3-(4-hydroxy-1-methyl-2-oxo-1,2-dihydropyridin-3-yl)ureido)-3-(3'-(trifluoromethoxy)biphenyl-3-yl)propanoic acid;

(S)-3-(2',4'-difluorobiphenyl-3-yl)-3-(3-(7-hydroxy-4-methyl-5-oxo-4,5-dihydrothieno[3,2-b]pyridin-6-yl)ureido)propanoic acid;

(S)-3-(3-(benzo[d][1,3]dioxol-5-yl)phenyl)-3-(3-(4-hydroxy-1-methyl-2-oxo-1,2-dihydropyridin-3-yl)ureido)propanoic acid;

(S)-3-(3-(benzo[d][1,3]dioxol-5-yl)phenyl)-3-(3-(4-hydroxy-1,5-dimethyl-2-oxo-1,2-dihydropyridin-3-yl)ureido)propanoic acid;

(S)-3-(3-(1H-indazol-1-yl)phenyl)-3-(3-(4-hydroxy-1-methyl-2-oxo-1,2-dihydropyridin-3-yl)ureido)propanoic acid;

(S)-3-(2',4'-difluoro-6-methoxybiphenyl-3-yl)-3-(3-(4-hydroxy-1-methyl-2-oxo-1,2-dihydropyridin-3-yl)ureido)propanoic acid;

(S)-3-(3-(4-hydroxy-1-methyl-2-oxo-1,2-dihydropyridin-3-yl)ureido)-3-(4-phenylthiophen-2-yl)propanoic acid;

(S)-3-(3-(1-ethyl-1H-indol-6-yl)phenyl)-3-(3-(4-hydroxy-1-methyl-2-oxo-1,2-dihydropyridin-3-yl)ureido)propanoic acid;

(S)-3-(3-(1H-pyrazol-1-yl)phenyl)-3-(3-(4-hydroxy-1-methyl-2-oxo-1,2-dihydropyridin-3-yl)ureido)propanoic acid;

(S)-3-(4-(2,4-difluorophenyl)thiophen-2-yl)-3-(3-(4-hydroxy-1-methyl-2-oxo-1,2-dihydropyridin-3-yl)ureido)propanoic acid;

(S)-3-(3',6-dimethoxybiphenyl-3-yl)-3-(3-(4-hydroxy-1-methyl-2-oxo-1,2-dihydropyridin-3-yl)ureido)propanoic acid;

3-(2',5'-dichlorobiphenyl-3-yl)-3-(3-(4-hydroxy-1,5-dimethyl-2-oxo-1,2-dihydropyridin-3-yl)ureido)propanoic acid;

(S)-3-(2',4'-difluorobiphenyl-3-yl)-3-(3-(4-hydroxy-1-methyl-2-oxo-1,2-dihydro-1,8-naphthyridin-3-yl)ureido)propanoic acid;

(S)-3-(3',6-dimethoxybiphenyl-3-yl)-3-(3-(4-hydroxy-1,5-dimethyl-2-oxo-1,2-dihydropyridin-3-yl)ureido)propanoic acid;

(S)-3-(3-(4-hydroxy-1-methyl-2-oxo-1,2-dihydropyridin-3-yl)ureido)-3-(4-(3-methoxyphenyl)thiophen-2-yl)propanoic acid;

(S)-3-(3-(4-hydroxy-1-methyl-2-oxo-1,2-dihydropyridin-3-yl)ureido)-3-(6-methoxybiphenyl-3-yl)propanoic acid;

(S)-3-(4-(3-chlorophenyl)thiophen-2-yl)-3-(3-(4-hydroxy-1-methyl-2-oxo-1,2-dihydropyridin-3-yl)ureido)propanoic acid;

(S)-3-(2',4'-difluorobiphenyl-3-yl)-3-(3-(1-ethyl-4-hydroxy-2-oxo-1,2-dihydropyridin-3-yl)ureido)propanoic acid;

(S)-3-(3-(4-hydroxy-1-methyl-2-oxo-1,2-dihydropyridin-3-yl)ureido)-3-(3-(thiophen-2-yl)phenyl)propanoic acid;

(S)-3-(3-(4-hydroxy-1-methyl-2-oxo-1,2-dihydropyridin-3-yl)ureido)-3-(6-methoxy-2',6'-dimethylbiphenyl-3-yl)propanoic acid;

(S)-3-(3'-chloro-6-methoxybiphenyl-3-yl)-3-(3-(4-hydroxy-1-methyl-2-oxo-1,2-dihydropyridin-3-yl)ureido)propanoic acid;

(S)-3-(3-(4-hydroxy-1-methyl-2-oxo-1,2-dihydropyridin-3-yl)ureido)-3-(6-methoxy-3'-(trifluoromethoxy)biphenyl-3-yl)propanoic acid;

(S)-3-(3-(4-hydroxy-1-methyl-2-oxo-1,2-dihydropyridin-3-yl)ureido)-3-(6-methoxy-4'-(trifluoromethoxy)biphenyl-3-yl)propanoic acid;

(S)-3-(2',6'-dichlorobiphenyl-3-yl)-3-(3-(4-hydroxy-1-methyl-2-oxo-1,2-dihydropyridin-3-yl)ureido)propanoic acid;

(S)-3-(3-(5-chlorothiophen-2-yl)phenyl)-3-(3-(4-hydroxy-1-methyl-2-oxo-1,2-dihydropyridin-3-yl)ureido)propanoic acid;

(S)-3-(3-(1H-imidazol-1-yl)phenyl)-3-(3-(4-hydroxy-1-methyl-2-oxo-1,2-dihydropyridin-3-yl)ureido)propanoic acid;

(S)-3-(3-(4-hydroxy-1-methyl-2-oxo-1,2-dihydropyridin-3-yl)ureido)-3-(3-(4-methylthiophen-3-yl)phenyl)propanoic acid;
(S)-3-(2',4'-difluoro-6-methylbiphenyl-3-yl)-3-(3-(4-hydroxy-1-methyl-2-oxo-1,2-dihydropyridin-3-yl)ureido)propanoic acid;
(S)-3-(3-(4-hydroxy-1-methyl-2-oxo-1,2-dihydropyridin-3-yl)ureido)-3-(3'-methoxy-6-methylbiphenyl-3-yl)propanoic acid;
(S)-3-(4-(2,6-dimethylphenyl)thiophen-2-yl)-3-(3-(4-hydroxy-1-methyl-2-oxo-1,2-dihydropyridin-3-yl)ureido)propanoic acid;
(S)-3-(3-(1H-pyrrol-3-yl)phenyl)-3-(3-(4-hydroxy-1-methyl-2-oxo-1,2-dihydropyridin-3-yl)ureido)propanoic acid;
(S)-3-(3-(4-hydroxy-1-methyl-2-oxo-1,2-dihydropyridin-3-yl)ureido)-3-(2',6,6'-trimethylbiphenyl-3-yl)propanoic acid;
(S)-3-(3-(4-hydroxy-1-methyl-2-oxo-1,2-dihydropyridin-3-yl)ureido)-3-(2',6,6'-trifluorobiphenyl-3-yl)propanoic acid;
(S)-3-(6-fluoro-3'-methoxybiphenyl-3-yl)-3-(3-(4-hydroxy-1-methyl-2-oxo-1,2-dihydropyridin-3-yl)ureido)propanoic acid;
(S)-3-(3-(4-hydroxy-1-methyl-2-oxo-1,2-dihydropyridin-3-yl)ureido)-3-(3-(1-methyl-1H-pyrazol-4-yl)phenyl)propanoic acid;
(S)-3-(2',4'-difluorobiphenyl-3-yl)-3-(3-(5-hydroxy-2-methyl-3-oxo-2,3-dihydropyridazin-4-yl)ureido)propanoic acid;
(S)-3-(2',6'-dimethylbiphenyl-3-yl)-3-(3-(4-hydroxy-1,6-dimethyl-2-oxo-1,2-dihydropyridin-3-yl)ureido)propanoic acid;
(S)-3-(3',6-dimethoxybiphenyl-3-yl)-3-(3-(4-hydroxy-1,6-dimethyl-2-oxo-1,2-dihydropyridin-3-yl)ureido)propanoic acid;
(S)-3-(4-(2,4-difluorophenyl)thiophen-2-yl)-3-(3-(4-hydroxy-1,6-dimethyl-2-oxo-1,2-dihydropyridin-3-yl)ureido)propanoic acid;
(S)-3-(3-(4-hydroxy-1,6-dimethyl-2-oxo-1,2-dihydropyridin-3-yl)ureido)-3-(3'-methoxybiphenyl-3-yl)propanoic acid;
(S)-3-(3-(4-hydroxy-1,6-dimethyl-2-oxo-1,2-dihydropyridin-3-yl)ureido)-3-(6-methoxy-3'-(trifluoromethoxy)biphenyl-3-yl)propanoic acid;
(S)-3-(3'-chloro-6-methylbiphenyl-3-yl)-3-(3-(4-hydroxy-1-methyl-2-oxo-1,2-dihydropyridin-3-yl)ureido)propanoic acid;
(S)-3-(3'-chlorobiphenyl-3-yl)-3-(3-(4-hydroxy-1,6-dimethyl-2-oxo-1,2-dihydropyridin-3-yl)ureido)propanoic acid;
(S)-3-(2',4'-difluorobiphenyl-3-yl)-3-(3-(4-hydroxy-6-methyl-2-oxo-1,2-dihydropyridin-3-yl)ureido)propanoic acid;
(S)-3-(3-(4-hydroxy-1-methyl-2-oxo-1,2-dihydropyridin-3-yl)ureido)-3-(5-methoxybiphenyl-3-yl)propanoic acid;
(S)-3-(3-(furan-3-yl)phenyl)-3-(3-(4-hydroxy-1-methyl-2-oxo-1,2-dihydropyridin-3-yl)ureido)propanoic acid;
(S)-3-(3-(3,5-dimethylisoxazol-4-yl)phenyl)-3-(3-(4-hydroxy-1-methyl-2-oxo-1,2-dihydropyridin-3-yl)ureido)propanoic acid;
(S)-3-(6-fluoro-2',6'-dimethylbiphenyl-3-yl)-3-(3-(4-hydroxy-1-methyl-2-oxo-1,2-dihydropyridin-3-yl)ureido)propanoic acid;
(S)-3-(5-(2,4-difluorophenyl)thiophen-2-yl)-3-(3-(4-hydroxy-1-methyl-2-oxo-1,2-dihydropyridin-3-yl)ureido)propanoic acid;
(S)-3-(3-(4-hydroxy-1-methyl-2-oxo-1,2-dihydropyridin-3-yl)ureido)-3-(5-(3-methoxyphenyl)thiophen-2-yl)propanoic acid;
(S)-3-(3',5-dimethoxybiphenyl-3-yl)-3-(3-(4-hydroxy-1-methyl-2-oxo-1,2-dihydropyridin-3-yl)ureido)propanoic acid;
(S)-3-(3-(4-hydroxy-1-methyl-2-oxo-1,2-dihydropyridin-3-yl)ureido)-3-(5-methoxy-3'-(trifluoromethoxy)biphenyl-3-yl)propanoic acid;
(S)-3-(2',4'-difluoro-5-methoxybiphenyl-3-yl)-3-(3-(4-hydroxy-1-methyl-2-oxo-1,2-dihydropyridin-3-yl)ureido)propanoic acid;
(S)-3-(3',5-dimethoxybiphenyl-3-yl)-3-(3-(4-hydroxy-1,6-dimethyl-2-oxo-1,2-dihydropyridin-3-yl)ureido)propanoic acid;
(S)-3-(3-(4-hydroxy-1,6-dimethyl-2-oxo-1,2-dihydropyridin-3-yl)ureido)-3-(5-methoxy-3'-(trifluoromethoxy)biphenyl-3-yl)propanoic acid;
(S)-3-(3-(4-hydroxy-1,6-dimethyl-2-oxo-1,2-dihydropyridin-3-yl)ureido)-3-(3'-methoxy-6-methylbiphenyl-3-yl)propanoic acid 1;
(S)-3-(4-fluorobiphenyl-3-yl)-3-(3-(4-hydroxy-1-methyl-2-oxo-1,2-dihydropyridin-3-yl)ureido)propanoic acid;
(S)-3-(3-(4-hydroxy-1-methyl-2-oxo-1,2-dihydropyridin-3-yl)ureido)-3-(6-phenylpyridin-2-yl)propanoic acid;
(S)-3-(3-(4-hydroxy-1-methyl-2-oxo-1,2-dihydropyridin-3-yl)ureido)-3-(5-methyl-3'-(trifluoromethoxy)biphenyl-3-yl)propanoic acid;
(S)-3-(3-(4-hydroxy-1-methyl-2-oxo-1,2-dihydropyridin-3-yl)ureido)-3-(2',5,6'-trimethylbiphenyl-3-yl)propanoic acid;
(S)-3-(2',4'-difluoro-5-methylbiphenyl-3-yl)-3-(3-(4-hydroxy-1-methyl-2-oxo-1,2-dihydropyridin-3-yl)ureido)propanoic acid;
(S)-3-(2',4'-difluoro-5-methylbiphenyl-3-yl)-3-(3-(4-hydroxy-1,6-dimethyl-2-oxo-1,2-dihydropyridin-3-yl)ureido)propanoic acid;
(S)-3-(3-(4-hydroxy-1-methyl-2-oxo-1,2-dihydropyridin-3-yl)ureido)-3-(6-methyl-3'-(trifluoromethoxy)biphenyl-3-yl)propanoic acid;
(S)-3-(3-(4-hydroxy-1,6-dimethyl-2-oxo-1,2-dihydropyridin-3-yl)ureido)-3-(6-methyl-3'-(trifluoromethoxy)biphenyl-3-yl)propanoic acid;
(S)-3-(6-fluoro-2',6'-dimethylbiphenyl-3-yl)-3-(3-(4-hydroxy-1,6-dimethyl-2-oxo-1,2-dihydropyridin-3-yl)ureido)propanoic acid;
(S)-3-(3-(4-hydroxy-1-methyl-2-oxo-1,2-dihydropyridin-3-yl)ureido)-3-(5-methoxy-2',6'-dimethylbiphenyl-3-yl)propanoic acid;
(S)-3-(3-(4-hydroxy-1,6-dimethyl-2-oxo-1,2-dihydropyridin-3-yl)ureido)-3-(5-methoxy-2',6'-dimethylbiphenyl-3-yl)propanoic acid;
(S)-3-(2',4'-difluoro-5-methoxybiphenyl-3-yl)-3-(3-(4-hydroxy-1,6-dimethyl-2-oxo-1,2-dihydropyridin-3-yl)ureido)propanoic acid;
(S)-3-(3-(4-hydroxy-1-methyl-2-oxo-1,2-dihydropyridin-3-yl)ureido)-3-(3'-methoxy-5-methylbiphenyl-3-yl)propanoic acid;
(S)-3-(2',6'-dimethylbiphenyl-3-yl)-3-(3-(7-hydroxy-5-oxo-1,2,3,5-tetrahydroindolizin-6-yl)ureido)propanoic acid;
(S)-3-(3-(4-hydroxy-1-methyl-2-oxo-1,2-dihydropyridin-3-yl)ureido)-3-(4'-methyl-[2,3'-bithiophen]-5-yl)propanoic acid;

(S)-3-(3-(4-hydroxy-1,6-dimethyl-2-oxo-1,2-dihydropyridin-3-yl)ureido)-3-(4'-methyl-[2,3'-bithiophen]-5-yl)propanoic acid;
(S)-3-(3-(4-hydroxy-1,6-dimethyl-2-oxo-1,2-dihydropyridin-3-yl)ureido)-3-(3'-methoxy-5-methylbiphenyl-3-yl)propanoic acid;
(S)-3-(5-(2,6-dimethylphenyl)thiophen-2-yl)-3-(3-(4-hydroxy-1-methyl-2-oxo-1,2-dihydropyridin-3-yl)ureido)propanoic acid;
(S)-3-(5-(2,6-dimethylphenyl)thiophen-2-yl)-3-(3-(4-hydroxy-1,6-dimethyl-2-oxo-1,2-dihydropyridin-3-yl)ureido)propanoic acid;
(S)-3-(4-fluoro-2',6'-dimethylbiphenyl-3-yl)-3-(3-(4-hydroxy-1,6-dimethyl-2-oxo-1,2-dihydropyridin-3-yl)ureido)propanoic acid;
(S)-3-(4-fluoro-2',6'-dimethylbiphenyl-3-yl)-3-(3-(4-hydroxy-1-methyl-2-oxo-1,2-dihydropyridin-3-yl)ureido)propanoic acid;
(S)-3-(3-(4-hydroxy-1-methyl-2-oxo-1,2-dihydropyridin-3-yl)ureido)-3-(2',4,4'-trifluorobiphenyl-3-yl)propanoic acid;
(S)-3-(3-(4-hydroxy-1,6-dimethyl-2-oxo-1,2-dihydropyridin-3-yl)ureido)-3-(2',4,4'-trifluorobiphenyl-3-yl)propanoic acid;
(S)-3-(4-fluoro-3'-methoxybiphenyl-3-yl)-3-(3-(4-hydroxy-1-methyl-2-oxo-1,2-dihydropyridin-3-yl)ureido)propanoic acid;
(S)-3-(4-fluoro-3'-(trifluoromethoxy)biphenyl-3-yl)-3-(3-(4-hydroxy-1-methyl-2-oxo-1,2-dihydropyridin-3-yl)ureido)propanoic acid;
(S)-3-(4-fluoro-3'-(trifluoromethoxy)biphenyl-3-yl)-3-(3-(4-hydroxy-1,6-dimethyl-2-oxo-1,2-dihydropyridin-3-yl)ureido)propanoic acid;
(S)-3-(3-(4-hydroxy-1-methyl-2-oxo-1,2-dihydropyridin-3-yl)ureido)-3-(4-methoxybiphenyl-3-yl)propanoic acid;
(S)-3-(3-(4-hydroxy-1,6-dimethyl-2-oxo-1,2-dihydropyridin-3-yl)ureido)-3-(2',5,6'-trimethylbiphenyl-3-yl)propanoic acid;
(S)-3-(3-(4-hydroxy-1-methyl-2-oxo-1,2-dihydropyridin-3-yl)ureido)-3-(2'-methylbiphenyl-3-yl)propanoic acid;
(S)-3-(3-(4-hydroxy-1,6-dimethyl-2-oxo-1,2-dihydropyridin-3-yl)ureido)-3-(2'-methylbiphenyl-3-yl)propanoic acid;
(S)-3-(5-fluoro-2',6'-dimethylbiphenyl-3-yl)-3-(3-(4-hydroxy-1-methyl-2-oxo-1,2-dihydropyridin-3-yl)ureido)propanoic acid;
(S)-3-(3-(4-hydroxy-1-methyl-2-oxo-1,2-dihydropyridin-3-yl)ureido)-3-(5-(3-(trifluoromethoxy)phenyl)thiophen-2-yl)propanoic acid;
(S)-3-(3-(4-hydroxy-1-methyl-2-oxo-1,2-dihydropyridin-3-yl)ureido)-3-(4-methoxy-2',6'-dimethylbiphenyl-3-yl)propanoic acid;
(S)-3-(4-fluoro-3'-methoxybiphenyl-3-yl)-3-(3-(4-hydroxy-1,6-dimethyl-2-oxo-1,2-dihydropyridin-3-yl)ureido)propanoic acid;
(S)-3-(5-fluoro-3'-methoxybiphenyl-3-yl)-3-(3-(4-hydroxy-1-methyl-2-oxo-1,2-dihydropyridin-3-yl)ureido)propanoic acid;
(S)-3-(5-fluoro-3'-methoxybiphenyl-3-yl)-3-(3-(4-hydroxy-1,6-dimethyl-2-oxo-1,2-dihydropyridin-3-yl)ureido)propanoic acid;
(S)-3-(5-fluoro-3'-(trifluoromethoxy)biphenyl-3-yl)-3-(3-(4-hydroxy-1,6-dimethyl-2-oxo-1,2-dihydropyridin-3-yl)ureido)propanoic acid;
(S)-3-(5-fluoro-3'-(trifluoromethoxy)biphenyl-3-yl)-3-(3-(4-hydroxy-1-methyl-2-oxo-1,2-dihydropyridin-3-yl)ureido)propanoic acid;
(S)-3-(5-(3,5-dimethylisoxazol-4-yl)thiophen-2-yl)-3-(3-(4-hydroxy-1-methyl-2-oxo-1,2-dihydropyridin-3-yl)ureido)propanoic acid;
(S)-3-(3-(3,5-dimethylisoxazol-4-yl)phenyl)-3-(3-(4-hydroxy-1,6-dimethyl-2-oxo-1,2-dihydropyridin-3-yl)ureido)propanoic acid;
(S)-3-(2-fluorobiphenyl-3-yl)-3-(3-(4-hydroxy-1,6-dimethyl-2-oxo-1,2-dihydropyridin-3-yl)ureido)propanoic acid;
(S)-3-(6-fluoro-2'-methylbiphenyl-3-yl)-3-(3-(4-hydroxy-1,6-dimethyl-2-oxo-1,2-dihydropyridin-3-yl)ureido)propanoic acid;
(S)-3-(6-fluoro-2'-methylbiphenyl-3-yl)-3-(3-(4-hydroxy-1-methyl-2-oxo-1,2-dihydropyridin-3-yl)ureido)propanoic acid;
(S)-3-(3-(4-hydroxy-1-methyl-2-oxo-1,2-dihydropyridin-3-yl)ureido)-3-(5-phenylthiophen-2-yl)propanoic acid;
(S)-3-(5-(2,5-difluorophenyl)thiophen-2-yl)-3-(3-(4-hydroxy-1-methyl-2-oxo-1,2-dihydropyridin-3-yl)ureido)propanoic acid;
(S)-3-(3-(4-hydroxy-1-methyl-2-oxo-1,2-dihydropyridin-3-yl)ureido)-3-(5-(trifluoromethoxy)biphenyl-3-yl)propanoic acid;
(S)-3-(3-(4-hydroxy-1-methyl-2-oxo-1,2-dihydropyridin-3-yl)ureido)-3-(2'-methylbiphenyl-4-yl)propanoic acid;
(S)-3-(3-(7-hydroxy-5-oxo-1,2,3,5-tetrahydroindolizin-6-yl)ureido)-3-(5-methoxybiphenyl-3-yl)propanoic acid;
(S)-3-(3-(4-hydroxy-1-methyl-2-oxo-1,2-dihydropyridin-3-yl)ureido)-3-(5-(trifluoromethyl)biphenyl-3-yl)propanoic acid;
(S)-3-(5-(3-chlorophenyl)thiophen-2-yl)-3-(3-(4-hydroxy-1-methyl-2-oxo-1,2-dihydropyridin-3-yl)ureido)propanoic acid;
(S)-3-(5-(3-fluorophenyl)thiophen-2-yl)-3-(3-(4-hydroxy-1-methyl-2-oxo-1,2-dihydropyridin-3-yl)ureido)propanoic acid;
(S)-3-(2',4'-difluorobiphenyl-4-yl)-3-(3-(4-hydroxy-1-methyl-2-oxo-1,2-dihydropyridin-3-yl)ureido)propanoic acid;
(S)-3-(2',4'-difluorobiphenyl-4-yl)-3-(3-(4-hydroxy-1,6-dimethyl-2-oxo-1,2-dihydropyridin-3-yl)ureido)propanoic acid;
(S)-3-(2',4'-difluorobiphenyl-4-yl)-3-(3-(4-hydroxy-1,5-dimethyl-2-oxo-1,2-dihydropyridin-3-yl)ureido)propanoic acid;
(S)-3-(3-(4-hydroxy-1-methyl-2-oxo-1,2-dihydropyridin-3-yl)ureido)-3-(2'-methyl-6-(trifluoromethoxy)biphenyl-3-yl)propanoic acid;
(S)-3-(3-(4-hydroxy-1-methyl-2-oxo-1,2-dihydropyridin-3-yl)ureido)-3-(6-(trifluoromethoxy)biphenyl-3-yl)propanoic acid;
3-(3'-acetylbiphenyl-3-yl)-3-(3-(4-hydroxy-1,5-dimethyl-2-oxo-1,2-dihydropyridin-3-yl)ureido)propanoic acid;
3-(4'-acetylbiphenyl-3-yl)-3-(3-(4-hydroxy-1,5-dimethyl-2-oxo-1,2-dihydropyridin-3-yl)ureido)propanoic acid;
(S)-3-(3-(4-hydroxy-1,5-dimethyl-2-oxo-1,2-dihydropyridin-3-yl)ureido)-3-(4-phenylthiophen-2-yl)propanoic acid;
(S)-3-(3-(4-hydroxy-1,5-dimethyl-2-oxo-1,2-dihydropyridin-3-yl)ureido)-3-(5-phenylthiophen-2-yl)propanoic acid;

(S)-3-(2',4'-difluorobiphenyl-3-yl)-3-(3-(7-hydroxy-5-oxo-1,2,3,5-tetrahydroindolizin-6-yl)ureido)propanoic acid;

(S)-3-(3-(4-hydroxy-1-methyl-2-oxo-1,2-dihydropyridin-3-yl)ureido)-3-(3-(thiazol-2-yl)phenyl)propanoic acid;

(S)-3-(3-(4-hydroxy-1,6-dimethyl-2-oxo-1,2-dihydropyridin-3-yl)ureido)-3-(5-methyl-3'-(trifluoromethoxy)biphenyl-3-yl)propanoic acid;

(S)-3-(3-(4-hydroxy-1,6-dimethyl-2-oxo-1,2-dihydropyridin-3-yl)ureido)-3-(2',4',5-trifluorobiphenyl-3-yl)propanoic acid;

(S)-3-(3-(4-hydroxy-1-methyl-2-oxo-1,2-dihydropyridin-3-yl)ureido)-3-(2',4',5-trifluorobiphenyl-3-yl)propanoic acid;

(S)-3-(3-(4-hydroxy-1-methyl-2-oxo-1,2-dihydropyridin-3-yl)ureido)-3-(3'-methoxy-6-(trifluoromethoxy)biphenyl-3-yl)propanoic acid;

(S)-3-(3-(4-hydroxy-1,6-dimethyl-2-oxo-1,2-dihydropyridin-3-yl)ureido)-3-(3'-methoxy-6-(trifluoromethoxy)biphenyl-3-yl)propanoic acid;

(S)-3-(2',6'-dimethylbiphenyl-4-yl)-3-(3-(4-hydroxy-1-methyl-2-oxo-1,2-dihydropyridin-3-yl)ureido)propanoic acid;

(S)-3-(3-(4-hydroxy-1,6-dimethyl-2-oxo-1,2-dihydropyridin-3-yl)ureido)-3-(2'-methylbiphenyl-4-yl)propanoic acid;

(S)-3-(2',6'-dimethylbiphenyl-4-yl)-3-(3-(4-hydroxy-1,6-dimethyl-2-oxo-1,2-dihydropyridin-3-yl)ureido)propanoic acid;

(S)-3-(3-(4-hydroxy-1-methyl-2-oxo-1,2-dihydropyridin-3-yl)ureido)-3-(3-(pyridin-2-yl)phenyl)propanoic acid;

(S)-3-(3-(4-hydroxy-1-methyl-2-oxo-1,2-dihydropyridin-3-yl)ureido)-3-(3-(6-methoxypyridazin-3-yl)phenyl)propanoic acid;

(S)-3-(3-(4-hydroxy-1-methyl-2-oxo-1,2-dihydropyridin-3-yl)ureido)-3-(5-phenylpyridin-3-yl)propanoic acid;

(S)-3-(5-fluoro-2',6'-dimethylbiphenyl-3-yl)-3-(3-(4-hydroxy-1,6-dimethyl-2-oxo-1,2-dihydropyridin-3-yl)ureido)propanoic acid;

(S)-3-(biphenyl-4-yl)-3-(3-(1,5-dimethyl-4-oxido-2-oxo-1,2-dihydropyridin-3-yl)ureido)propanoic acid;

(S)-3-(3-(4-hydroxy-1-methyl-2-oxo-1,2-dihydropyridin-3-yl)ureido)-3-(3-(6'-methoxypyridin-2-yl)phenyl)propanoic acid;

(S)-3-(3-(4-hydroxy-1,5-dimethyl-2-oxo-1,2-dihydropyridin-3-yl)ureido)-3-(4'-methoxybiphenyl-3-yl)propanoic acid;

(S)-3-(3-(1H-imidazol-1-yl)phenyl)-3-(3-(4-hydroxy-1-methyl-2-oxo-1,2-dihydropyridin-3-yl)ureido)propanoic acid;

(S)-3-(3-(4-hydroxy-1-methyl-2-oxo-1,2-dihydropyridin-3-yl)ureido)-3-(3-(pyrazin-2-yl)phenyl)propanoic acid, 3-(3-bromophenyl)-3-(3-(4-hydroxy-1,5-dimethyl-2-oxo-1,2-dihydropyridin-3-yl)ureido) propanoic acid, 3-(3-bromophenyl)-3-(3-(1-ethyl-4-hydroxy-5-methyl-2-oxo-1,2-dihydropyridin-3-yl)ureido) propanoic acid, sodium (S)-3-(biphenyl-3-yl)-3-(3-(1,5-dimethyl-4-oxido-2-oxo-1,2-dihydropyridin-3-yl) ureido)propanoate;

sodium (S)-3-(biphenyl-3-yl)-3-(3-(1-ethyl-5-methyl-4-oxido-2-oxo-1,2-dihydropyridin-3-yl)ureido)propanoate;

sodium 3-(3-(1-ethyl-5-methyl-4-oxido-2-oxo-1,2-dihydropyridin-3-yl)ureido)-3-(3-(2-oxo-3-phenylpyridin-1(2H)-yl)phenyl)propanoate;

sodium (S)-3-(3-(1,5-dimethyl-4-oxido-2-oxo-1,2-dihydropyridin-3-yl)ureido)-3-(2'-methylbiphenyl-3-yl)propanoate;

sodium (S)-3-(3-(1,5-dimethyl-4-oxido-2-oxo-1,2-dihydropyridin-3-yl)ureido)-3-(2'-fluorobiphenyl-3-yl)propanoate;

sodium (S)-3-(3-(1,5-dimethyl-4-oxido-2-oxo-1,2-dihydropyridin-3-yl)ureido)-3-(6-fluorobiphenyl-3-yl)propanoate;

sodium (S)-3-(3-(1-ethyl-5-methyl-4-oxido-2-oxo-1,2-dihydropyridin-3-yl)ureido)-3-(2'-methylbiphenyl-3-yl)propanoate;

sodium (S)-3-(3-(1-ethyl-5-methyl-4-oxido-2-oxo-1,2-dihydropyridin-3-yl)ureido)-3-(4'-methylbiphenyl-3-yl)propanoate;

sodium 3-(3-(1H-pyrrol-1-yl)phenyl)-3-(3-(1,5-dimethyl-4-oxido-2-oxo-1,2-dihydro pyridin-3-yl)ureido)propanoate;

sodium (S)-3-(2',4'-difluorobiphenyl-3-yl)-3-(3-(1,5-dimethyl-4-oxido-2-oxo-1,2-dihydropyridin-3-yl)ureido) propanoate;

sodium (S)-3-(2',5'-difluorobiphenyl-3-yl)-3-(3-(1,5-dimethyl-4-oxido-2-oxo-1,2-di hydropyridin-3-yl)ureido) propanoate;

sodium (S)-3-(3-(1,5-dimethyl-4-oxido-2-oxo-1,2-dihydropyridin-3-yl)ureido)-3-(6-methylbiphenyl-3-yl)propanoate;

sodium (S)-3-(3-(1,5-dimethyl-4-oxido-2-oxo-1,2-dihydropyridin-3-yl)ureido)-3-(6-methoxybiphenyl-3-yl) propanoate;

sodium (S)-3-(3-(1,5-dimethyl-4-oxido-2-oxo-1,2-dihydropyridin-3-yl)ureido)-3-(4'-methylbiphenyl-3-yl) propanoate;

sodium (S)-3-(3-(1,5-dimethyl-4-oxido-2-oxo-1,2-dihydropyridin-3-yl)ureido)-3-(3'-methylbiphenyl-3-yl) propanoate;

sodium (S)-3-(3-(1,5-dimethyl-4-oxido-2-oxo-1,2-dihydropyridin-3-yl)ureido)-3-(3-(pyridin-3-yl)phenyl)propanoate;

sodium (S)-3-(3',5'-difluorobiphenyl-3-yl)-3-(3-(1,5-dimethyl-4-oxido-2-oxo-1,2-di hydropyridin-3-yl)ureido) propanoate;

sodium (S)-3-(3-(1,5-dimethyl-4-oxido-2-oxo-1,2-dihydropyridin-3-yl)ureido)-3-(3',5'-dimethylbiphenyl-3-yl)propanoate;

sodium (S)-3-(3-(1,5-dimethyl-4-oxido-2-oxo-1,2-dihydropyridin-3-yl)ureido)-3-(4'-methoxybiphenyl-3-yl) propanoate;

sodium (S)-3-(3-(1,5-dimethyl-4-oxido-2-oxo-1,2-dihydropyridin-3-yl)ureido)-3-(2'-methoxybiphenyl-3-yl) propanoate;

sodium (S)-3-(3-(1,5-dimethyl-4-oxido-2-oxo-1,2-dihydropyridin-3-yl)ureido)-3-(4'-(trifluoromethyl)biphenyl-3-yl)propanoate;

sodium (S)-3-(3',4'-difluorobiphenyl-3-yl)-3-(3-(1,5-dimethyl-4-oxido-2-oxo-1,2-di hydropyridin-3-yl)ureido) propanoate;

sodium (S)-3-(3-(1,5-dimethyl-4-oxido-2-oxo-1,2-dihydropyridin-3-yl)ureido)-3-(2',5'-dimethylbiphenyl-3-yl)propanoate;

sodium (S)-3-(3-(1,5-dimethyl-4-oxido-2-oxo-1,2-dihydropyridin-3-yl)ureido)-3-(3'-methoxybiphenyl-3-yl) propanoate;

sodium (S)-3-(3-(1,5-dimethyl-4-oxido-2-oxo-1,2-dihydropyridin-3-yl)ureido)-3-(3'-(trifluoromethoxy)biphenyl-3-yl)propanoate;

sodium (S)-3-(3-(1,5-dimethyl-4-oxido-2-oxo-1,2-dihydropyridin-3-yl)ureido)-3-(2',3'-dimethylbiphenyl-3-yl)propanoate;
sodium 3-(3-(1,5-dimethyl-4-oxido-2-oxo-1,2-dihydropyridin-3-yl)ureido)-3-(6-oxo-1-phenyl-1,6-dihydropyridin-3-yl)propanoate;
sodium (S)-3-(2',6'-difluorobiphenyl-3-yl)-3-(3-(1,5-dimethyl-4-oxido-2-oxo-1,2-di hydropyridin-3-yl)ureido)propanoate;
sodium (S)-3-(3-(1,5-dimethyl-4-oxido-2-oxo-1,2-dihydropyridin-3-yl)ureido)-3-(3'-fluorobiphenyl-3-yl)propanoate;
sodium (S)-3-(3-(1,5-dimethyl-4-oxido-2-oxo-1,2-dihydropyridin-3-yl)ureido)-3-(4'-fluorobiphenyl-3-yl)propanoate;
sodium (S)-3-(3-(1,5-dimethyl-4-oxido-2-oxo-1,2-dihydropyridin-3-yl)ureido)-3-(2'-(trifluoromethoxy)biphenyl-3-yl)propanoate;
sodium (S)-3-(2',4'-dimethoxybiphenyl-3-yl)-3-(3-(1,5-dimethyl-4-oxido-2-oxo-1,2-dihydropyridin-3-yl)ureido)propanoate;
sodium (S)-3-(3',4'-dimethoxybiphenyl-3-yl)-3-(3-(1,5-dimethyl-4-oxido-2-oxo-1,2-dihydropyridin-3-yl)ureido)propanoate;
sodium (S)-3-(3-(1,5-dimethyl-4-oxido-2-oxo-1,2-dihydropyridin-3-yl)ureido)-3-(2',6'-dimethylbiphenyl-3-yl)propanoate;
sodium 3-(4'-chlorobiphenyl-3-yl)-3-(3-(1,5-dimethyl-4-oxido-2-oxo-1,2-dihydropyridin-3-yl)ureido)propanoate;
sodium 3-(3'-chlorobiphenyl-3-yl)-3-(3-(1,5-dimethyl-4-oxido-2-oxo-1,2-dihydropyridin-3-yl)ureido)propanoate;
sodium 3-(2'-chlorobiphenyl-3-yl)-3-(3-(1,5-dimethyl-4-oxido-2-oxo-1,2-dihydropyridin-3-yl)ureido)propanoate;
sodium (S)-3-(3-(1,5-dimethyl-4-oxido-2-oxo-1,2-dihydropyridin-3-yl)ureido)-3-(2'-(trifluoromethyl)biphenyl-3-yl)propanoate;
sodium (S)-3-(5,6-dimethoxybiphenyl-3-yl)-3-(3-(1,5-dimethyl-4-oxido-2-oxo-1,2-dihydropyridin-3-yl)ureido)propanoate;
sodium (S)-3-(3-(1,5-dimethyl-4-oxido-2-oxo-1,2-dihydropyridin-3-yl)ureido)-3-(3-(6-methoxypyridin-3-yl)phenyl)propanoate;
sodium (S)-3-(2',5'-dimethoxybiphenyl-3-yl)-3-(3-(1,5-dimethyl-4-oxido-2-oxo-1,2-dihydropyridin-3-yl)ureido)propanoate;
sodium 3-(3-(1,5-dimethyl-4-oxido-2-oxo-1,2-dihydropyridin-3-yl)ureido)-3-(3-(pyrimidin-5-yl)phenyl)propanoate;
sodium (S)-3-(2',6'-dimethoxybiphenyl-3-yl)-3-(3-(1,5-dimethyl-4-oxido-2-oxo-1,2-dihydropyridin-3-yl)ureido)propanoate;
sodium 3-(3',4'-dichlorobiphenyl-3-yl)-3-(3-(1-ethyl-5-methyl-4-oxido-2-oxo-1,2-dihydropyridin-3-yl)ureido)propanoate;
sodium 3-(3',4'-dichlorobiphenyl-3-yl)-3-(3-(1,5-dimethyl-4-oxido-2-oxo-1,2-dihydropyridin-3-yl)ureido)propanoate;
sodium (S)-3-(3-(1,5-dimethyl-4-oxido-2-oxo-1,2-dihydropyridin-3-yl)ureido)-3-(5-phenylfuran-2-yl)propanoate;
sodium (S)-3-(3-(2,5-dimethyl-1H-pyrrol-1-yl)phenyl)-3-(3-(1,5-dimethyl-4-oxido-2-oxo-1,2-dihydropyridin-3-yl)ureido)propanoate;
sodium 3-(3'-chloro-4'-fluorobiphenyl-3-yl)-3-(3-(1,5-dimethyl-4-oxido-2-oxo-1,2-dihydropyridin-3-yl)ureido)propanoate;
sodium 3-(2',3'-dichlorobiphenyl-3-yl)-3-(3-(1,5-dimethyl-4-oxido-2-oxo-1,2-dihydropyridin-3-yl)ureido)propanoate;
sodium 3-(3',5'-dichlorobiphenyl-3-yl)-3-(3-(1,5-dimethyl-4-oxido-2-oxo-1,2-dihydropyridin-3-yl)ureido)propanoate;
sodium (S)-3-(2',4'-difluorobiphenyl-3-yl)-3-(3-(1,6-dimethyl-4-oxido-2-oxo-1,2-dihydropyridin-3-yl)ureido)propanoate;
sodium (S)-3-(2',4'-difluorobiphenyl-3-yl)-3-(3-(1-methyl-4-oxido-2-oxo-1,2-dihydropyridin-3-yl)ureido)propanoate;
sodium (S)-3-(3-(1,5-dimethyl-4-oxido-2-oxo-1,2-dihydropyridin-3-yl)ureido)-3-(3'-methoxy-2'-methylbiphenyl-3-yl)propanoate;
sodium (S)-3-(3-(1,5-dimethyl-4-oxido-2-oxo-1,2-dihydropyridin-3-yl)ureido)-3-(5'-methoxy-2'-methylbiphenyl-3-yl)propanoate;
sodium 3-(3-(1,5-dimethyl-4-oxido-2-oxo-1,2-dihydropyridin-3-yl)ureido)-3-(6-(2,2,2-trifluoroethoxy)biphenyl-3-yl)propanoate;
sodium (S)-3-(3-(1,5-dimethyl-4-oxido-2-oxo-1,2-dihydropyridin-3-yl)ureido)-3-(2'-ethylbiphenyl-3-yl)propanoate;
sodium (S)-3-(3-(1,5-dimethyl-4-oxido-2-oxo-1,2-dihydropyridin-3-yl)ureido)-3-(4-fluorobiphenyl-3-yl)propanoate;
sodium (S)-3-(2',4'-difluorobiphenyl-3-yl)-3-(3-(4-oxido-2-oxo-1,2-dihydropyridin-3-yl)ureido)propanoate;
sodium (S)-3-(3-(1,5-dimethyl-4-oxido-2-oxo-1,2-dihydropyridin-3-yl)ureido)-3-(3',4'-dimethylbiphenyl-3-yl)propanoate;
sodium (S)-3-(2',3'-difluorobiphenyl-3-yl)-3-(3-(1,5-dimethyl-4-oxido-2-oxo-1,2-dihydropyridin-3-yl)ureido)propanoate;
sodium (S)-3-(3-(1,5-dimethyl-4-oxido-2-oxo-1,2-dihydropyridin-3-yl)ureido)-3-(4'-fluoro-3'-methylbiphenyl-3-yl)propanoate;
sodium (S)-3-(3-(1,5-dimethyl-4-oxido-2-oxo-1,2-dihydropyridin-3-yl)ureido)-3-(1-phenyl-1H-pyrrol-2-yl)propanoate;
sodium (S)-3-(3'-chlorobiphenyl-3-yl)-3-(3-(1,5-dimethyl-4-oxido-2-oxo-1,2-dihydropyridin-3-yl)ureido)propanoate;
sodium (S)-3-(3-(1,5-dimethyl-4-oxido-2-oxo-1,2-dihydropyridin-3-yl)ureido)-3-(2-methylbiphenyl-3-yl)propanoate;
sodium (S)-3-(3'-methoxybiphenyl-3-yl)-3-(3-(1-methyl-4-oxido-2-oxo-1,2-dihydro pyridin-3-yl)ureido)propanoate;
sodium (S)-3-(2',6'-dimethylbiphenyl-3-yl)-3-(3-(1-methyl-4-oxido-2-oxo-1,2-dihydropyridin-3-yl)ureido)propanoate;
sodium 3-(5'-chloro-2',4'-difluorobiphenyl-3-yl)-3-(3-(1,5-dimethyl-4-oxido-2-oxo-1,2-dihydropyridin-3-yl)ureido)propanoate;
sodium (S)-3-(2',3'-dimethoxybiphenyl-3-yl)-3-(3-(1,5-dimethyl-4-oxido-2-oxo-1,2-dihydropyridin-3-yl)ureido)propanoate;
sodium (S)-3-(biphenyl-3-yl)-3-(3-(1-methyl-4-oxido-2-oxo-1,2-dihydropyridin-3-yl)ureido)propanoate;
sodium (S)-3-(3'-chlorobiphenyl-3-yl)-3-(3-(1-methyl-4-oxido-2-oxo-1,2-dihydro pyridin-3-yl)ureido)propanoate;

sodium (S)-3-(3-(1H-pyrrol-1-yl)phenyl)-3-(3-(1-methyl-4-oxido-2-oxo-1,2-dihydro pyridin-3-yl)ureido)propanoate;

sodium (S)-3-(3-(6-methoxypyridin-3-yl)phenyl)-3-(3-(1-methyl-4-oxido-2-oxo-1,2-dihydropyridin-3-yl)ureido)propanoate;

sodium (S)-3-(2'-fluoro-3'-methoxybiphenyl-3-yl)-3-(3-(1-methyl-4-oxido-2-oxo-1,2-dihydropyridin-3-yl)ureido)propanoate;

sodium (S)-3-(3-(1-methyl-4-oxido-2-oxo-1,2-dihydropyridin-3-yl)ureido)-3-(4'-(trifluoromethoxy)biphenyl-3-yl)propanoate;

sodium 3-(2',4'-dichlorobiphenyl-3-yl)-3-(3-(1,5-dimethyl-4-oxido-2-oxo-1,2-dihydropyridin-3-yl)ureido)propanoate;

sodium (S)-3-(3-(1-methyl-4-oxido-2-oxo-1,2-dihydropyridin-3-yl)ureido)-3-(2'-(trifluoromethoxy)biphenyl-3-yl)propanoate;

sodium (S)-3-(2',4'-difluorobiphenyl-3-yl)-3-(3-(1-methyl-4-oxido-2-oxo-2,5,6,7-tetrahydro-1H-cyclopenta[b]pyridin-3-yl)ureido)propanoate;

sodium (S)-3-(3-(1-methyl-4-oxido-2-oxo-1,2-dihydropyridin-3-yl)ureido)-3-(3'-(trifluoromethoxy)biphenyl-3-yl)propanoate;

sodium (S)-3-(2',4'-difluorobiphenyl-3-yl)-3-(3-(4-methyl-7-oxido-5-oxo-4,5-dihydrothieno[3,2-b]pyridin-6-yl)ureido)propanoate;

sodium (S)-3-(3-(benzo[d][1,3]dioxol-5-yl)phenyl)-3-(3-(1-methyl-4-oxido-2-oxo-1,2-dihydropyridin-3-yl)ureido)propanoate;

sodium (S)-3-(3-(benzo[d][1,3]dioxol-5-yl)phenyl)-3-(3-(1,5-dimethyl-4-oxido-2-oxo-1,2-dihydropyridin-3-yl)ureido)propanoate;

sodium (S)-3-(3-(1H-indazol-1-yl)phenyl)-3-(3-(1-methyl-4-oxido-2-oxo-1,2-dihydro pyridin-3-yl)ureido)propanoate;

sodium (S)-3-(2',4'-difluoro-6-methoxybiphenyl-3-yl)-3-(3-(1-methyl-4-oxido-2-oxo-1,2-dihydropyridin-3-yl)ureido)propanoate;

sodium (S)-3-(3-(4-hydroxy-1-methyl-2-oxo-1,2-dihydropyridin-3-yl)ureido)-3-(4-phenyl thiophen-2-yl)propanoate;

sodium (S)-3-(3-(1-ethyl-1H-indol-6-yl)phenyl)-3-(3-(1-methyl-4-oxido-2-oxo-1,2-dihydro pyridin-3-yl)ureido)propanoate;

sodium (S)-3-(3-(1H-pyrazol-1-yl)phenyl)-3-(3-(1-methyl-4-oxido-2-oxo-1,2-dihydro pyridin-3-yl)ureido)propanoate;

sodium (S)-3-(4-(2,4-difluorophenyl)thiophen-2-yl)-3-(3-(1-methyl-4-oxido-2-oxo-1,2-dihydropyridin-3-yl)ureido)propanoate;

sodium (S)-3-(3',6-dimethoxybiphenyl-3-yl)-3-(3-(1-methyl-4-oxido-2-oxo-1,2-dihydro pyridin-3-yl)ureido)propanoate;

sodium 3-(2',5'-dichlorobiphenyl-3-yl)-3-(3-(4-hydroxy-1,5-dimethyl-2-oxo-1,2-dihydro pyridin-3-yl)ureido)propanoate;

sodium (S)-3-(2',4'-difluorobiphenyl-3-yl)-3-(3-(1-methyl-4-oxido-2-oxo-1,2-dihydro-1,8-naphthyridin-3-yl)ureido)propanoate;

sodium (S)-3-(3',6-dimethoxybiphenyl-3-yl)-3-(3-(1,5-dimethyl-4-oxido-2-oxo-1,2-dihydropyridin-3-yl)ureido)propanoate;

sodium (S)-3-(4-(3-methoxyphenyl)thiophen-2-yl)-3-(3-(1-methyl-4-oxido-2-oxo-1,2-dihydro pyridin-3-yl)ureido)propanoate;

sodium (S)-3-(6-methoxybiphenyl-3-yl)-3-(3-(1-methyl-4-oxido-2-oxo-1,2-dihydro pyridin-3-yl)ureido)propanoate;

sodium (S)-3-(4-(3-chlorophenyl)thiophen-2-yl)-3-(3-(1-methyl-4-oxido-2-oxo-1,2-dihydro pyridin-3-yl)ureido)propanoate;

sodium (S)-3-(2',4'-difluorobiphenyl-3-yl)-3-(3-(1-ethyl-4-oxido-2-oxo-1,2-dihydropyridin-3-yl)ureido)propanoate;

sodium (S)-3-(3-(1-methyl-4-oxido-2-oxo-1,2-dihydropyridin-3-yl)ureido)-3-(3-(thiophen-2-yl)phenyl)propanoate;

sodium (S)-3-(6-methoxy-2',6'-dimethylbiphenyl-3-yl)-3-(3-(1-methyl-4-oxido-2-oxo-1,2-dihydropyridin-3-yl)ureido)propanoate;

sodium (S)-3-(3'-chloro-6-methoxybiphenyl-3-yl)-3-(3-(1-methyl-4-oxido-2-oxo-1,2-dihydropyridin-3-yl)ureido)propanoate;

sodium (S)-3-(6-methoxy-3'-(trifluoromethoxy)biphenyl-3-yl)-3-(3-(1-methyl-4-oxido-2-oxo-1,2-dihydropyridin-3-yl)ureido)propanoate;

sodium (S)-3-(6-methoxy-4'-(trifluoromethoxy)biphenyl-3-yl)-3-(3-(1-methyl-4-oxido-2-oxo-1,2-dihydropyridin-3-yl)ureido)propanoate;

sodium (S)-3-(2',6'-dichlorobiphenyl-3-yl)-3-(3-(1-methyl-4-oxido-2-oxo-1,2-dihydropyridin-3-yl)ureido)propanoate;

sodium (S)-3-(3-(5-chlorothiophen-2-yl)phenyl)-3-(3-(1-methyl-4-oxido-2-oxo-1,2-dihydropyridin-3-yl)ureido)propanoate;

sodium (S)-3-(3-(1H-imidazol-1-yl)phenyl)-3-(3-(1-methyl-4-oxido-2-oxo-1,2-dihydropyridin-3-yl)ureido)propanoate;

sodium (S)-3-(3-(1-methyl-4-oxido-2-oxo-1,2-dihydropyridin-3-yl)ureido)-3-(3-(4-methylthiophen-3-yl)phenyl)propanoate;

sodium (S)-3-(2',4'-difluoro-6-methylbiphenyl-3-yl)-3-(3-(1-methyl-4-oxido-2-oxo-1,2-dihydropyridin-3-yl)ureido)propanoate;

sodium (S)-3-(3'-methoxy-6-methylbiphenyl-3-yl)-3-(3-(1-methyl-4-oxido-2-oxo-1,2-dihydropyridin-3-yl)ureido)propanoate;

sodium (S)-3-(3-(1,5-dimethyl-4-oxido-2-oxo-1,2-dihydropyridin-3-yl)ureido)-3-(4-(2,6-dimethylphenyl)thiophen-2-yl)propanoate;

sodium (S)-3-(3-(1H-pyrrol-3-yl)phenyl)-3-(3-(1-methyl-4-oxido-2-oxo-1,2-dihydro pyridin-3-yl)ureido)propanoate;

sodium (S)-3-(3-(1-methyl-4-oxido-2-oxo-1,2-dihydropyridin-3-yl)ureido)-3-(2',6,6'-trimethylbiphenyl-3-yl)propanoate;

sodium (S)-3-(3-(1-methyl-4-oxido-2-oxo-1,2-dihydropyridin-3-yl)ureido)-3-(2',6,6'-trifluorobiphenyl-3-yl)propanoate;

sodium (S)-3-(6-fluoro-3'-methoxybiphenyl-3-yl)-3-(3-(1-methyl-4-oxido-2-oxo-1,2-dihydropyridin-3-yl)ureido)propanoate;

sodium (S)-3-(3-(1-methyl-1H-pyrazol-4-yl)phenyl)-3-(3-(1-methyl-4-oxido-2-oxo-1,2-dihydropyridin-3-yl)ureido)propanoate;

sodium (S)-3-(2',4'-difluorobiphenyl-3-yl)-3-(3-(2-methyl-5-oxido-3-oxo-2,3-dihydropyridazin-4-yl)ureido)propanoate;

sodium (S)-3-(3-(1,6-dimethyl-4-oxido-2-oxo-1,2-dihydropyridin-3-yl)ureido)-3-(2',6'-dimethylbiphenyl-3-yl)propanoate;

sodium (S)-3-(3',6-dimethoxybiphenyl-3-yl)-3-(3-(1,6-dimethyl-4-oxido-2-oxo-1,2-dihydropyridin-3-yl)ureido)propanoate;

sodium (S)-3-(4-(2,4-difluorophenyl)thiophen-2-yl)-3-(3-(1,6-dimethyl-4-oxido-2-oxo-1,2-dihydropyridin-3-yl)ureido)propanoate;

sodium (S)-3-(3-(1,6-dimethyl-4-oxido-2-oxo-1,2-dihydropyridin-3-yl)ureido)-3-(3'-methoxybiphenyl-3-yl)propanoate;

sodium (S)-3-(3-(1,6-dimethyl-4-oxido-2-oxo-1,2-dihydropyridin-3-yl)ureido)-3-(6-methoxy-3'-(trifluoromethoxy)biphenyl-3-yl)propanoate;

sodium (S)-3-(3'-chloro-6-methylbiphenyl-3-yl)-3-(3-(1-methyl-4-oxido-2-oxo-1,2-dihydropyridin-3-yl)ureido)propanoate;

sodium (S)-3-(3'-chlorobiphenyl-3-yl)-3-(3-(1,6-dimethyl-4-oxido-2-oxo-1,2-dihydropyridin-3-yl)ureido)propanoate;

sodium (S)-3-(2',4'-difluorobiphenyl-3-yl)-3-(3-(6-methyl-4-oxido-2-oxo-1,2-dihydropyridin-3-yl)ureido)propanoate;

sodium (S)-3-(5-methoxybiphenyl-3-yl)-3-(3-(1-methyl-4-oxido-2-oxo-1,2-dihydropyridin-3-yl)ureido)propanoate;

sodium (S)-3-(3-(furan-3-yl)phenyl)-3-(3-(1-methyl-4-oxido-2-oxo-1,2-dihydropyridin-3-yl)ureido)propanoate;

sodium (S)-3-(3-(3,5-dimethylisoxazol-4-yl)phenyl)-3-(3-(1-methyl-4-oxido-2-oxo-1,2-dihydropyridin-3-yl)ureido)propanoate;

sodium (S)-3-(6-fluoro-2',6'-dimethylbiphenyl-3-yl)-3-(3-(1-methyl-4-oxido-2-oxo-1,2-dihydropyridin-3-yl)ureido)propanoate;

sodium (S)-3-(5-(2,4-difluorophenyl)thiophen-2-yl)-3-(3-(1-methyl-4-oxido-2-oxo-1,2-dihydropyridin-3-yl)ureido)propanoate;

sodium (S)-3-(5-(3-methoxyphenyl)thiophen-2-yl)-3-(3-(1-methyl-4-oxido-2-oxo-1,2-dihydropyridin-3-yl)ureido)propanoate;

sodium (S)-3-(3',5-dimethoxybiphenyl-3-yl)-3-(3-(1-methyl-4-oxido-2-oxo-1,2-dihydropyridin-3-yl)ureido)propanoate;

sodium (S)-3-(5-methoxy-3'-(trifluoromethoxy)biphenyl-3-yl)-3-(3-(1-methyl-4-oxido-2-oxo-1,2-dihydropyridin-3-yl)ureido)propanoate;

sodium (S)-3-(2',4'-difluoro-5-methoxybiphenyl-3-yl)-3-(3-(1-methyl-4-oxido-2-oxo-1,2-dihydropyridin-3-yl)ureido)propanoate;

sodium (S)-3-(3',5-dimethoxybiphenyl-3-yl)-3-(3-(1,6-dimethyl-4-oxido-2-oxo-1,2-dihydropyridin-3-yl)ureido)propanoate;

sodium (S)-3-(3-(1,6-dimethyl-4-oxido-2-oxo-1,2-dihydropyridin-3-yl)ureido)-3-(5-methoxy-3'-(trifluoromethoxy)biphenyl-3-yl)propanoate;

sodium (S)-3-(3-(1,6-dimethyl-4-oxido-2-oxo-1,2-dihydropyridin-3-yl)ureido)-3-(3'-methoxy-6-methylbiphenyl-3-yl)propanoate;

sodium (S)-3-(4-fluorobiphenyl-3-yl)-3-(3-(1-methyl-4-oxido-2-oxo-1,2-dihydropyridin-3-yl)ureido)propanoate;

sodium (S)-3-(3-(1-methyl-4-oxido-2-oxo-1,2-dihydropyridin-3-yl)ureido)-3-(6-phenylpyridin-2-yl)propanoate;

sodium (S)-3-(5-methyl-3'-(trifluoromethoxy)biphenyl-3-yl)-3-(3-(1-methyl-4-oxido-2-oxo-1,2-dihydropyridin-3-yl)ureido)propanoate;

sodium (S)-3-(3-(1-methyl-4-oxido-2-oxo-1,2-dihydropyridin-3-yl)ureido)-3-(2',5,6'-trimethylbiphenyl-3-yl)propanoate;

sodium (S)-3-(2',4'-difluoro-5-methylbiphenyl-3-yl)-3-(3-(1-methyl-4-oxido-2-oxo-1,2-dihydropyridin-3-yl)ureido)propanoate;

sodium (S)-3-(2',4'-difluoro-5-methylbiphenyl-3-yl)-3-(3-(1,6-dimethyl-4-oxido-2-oxo-1,2-dihydropyridin-3-yl)ureido)propanoate;

sodium (S)-3-(6-methyl-3'-(trifluoromethoxy)biphenyl-3-yl)-3-(3-(1-methyl-4-oxido-2-oxo-1,2-dihydropyridin-3-yl)ureido)propanoate;

sodium (S)-3-(3-(1,6-dimethyl-4-oxido-2-oxo-1,2-dihydropyridin-3-yl)ureido)-3-(6-methyl-3'-(trifluoromethoxy)biphenyl-3-yl)propanoate;

sodium (S)-3-(3-(1,6-dimethyl-4-oxido-2-oxo-1,2-dihydropyridin-3-yl)ureido)-3-(6-fluoro-2',6'-dimethylbiphenyl-3-yl)propanoate;

sodium (S)-3-(5-methoxy-2',6'-dimethylbiphenyl-3-yl)-3-(3-(1-methyl-4-oxido-2-oxo-1,2-dihydropyridin-3-yl)ureido)propanoate;

sodium (S)-3-(3-(1,6-dimethyl-4-oxido-2-oxo-1,2-dihydropyridin-3-yl)ureido)-3-(5-methoxy-2',6'-dimethylbiphenyl-3-yl)propanoate;

sodium (S)-3-(2',4'-difluoro-5-methoxybiphenyl-3-yl)-3-(3-(1,6-dimethyl-4-oxido-2-oxo-1,2-dihydropyridin-3-yl)ureido)propanoate;

sodium (S)-3-(3'-methoxy-5-methylbiphenyl-3-yl)-3-(3-(1-methyl-4-oxido-2-oxo-1,2-dihydropyridin-3-yl)ureido)propanoate;

sodium (S)-3-(2',6'-dimethylbiphenyl-3-yl)-3-(3-(7-oxido-5-oxo-1,2,3,5-tetrahydro indolizin-6-yl)ureido)propanoate;

sodium (S)-3-(4'-methyl-2,3'-bithiophen-5-yl)-3-(3-(1-methyl-4-oxido-2-oxo-1,2-di hydropyridin-3-yl)ureido)propanoate;

sodium (S)-3-(3-(1,6-dimethyl-4-oxido-2-oxo-1,2-dihydropyridin-3-yl)ureido)-3-(4'-methyl-2,3'-bithiophen-5-yl)propanoate;

sodium (S)-3-(3-(1,6-dimethyl-4-oxido-2-oxo-1,2-dihydropyridin-3-yl)ureido)-3-(3'-methoxy-5-methylbiphenyl-3-yl)propanoate;

sodium (S)-3-(5-(2,6-dimethylphenyl)thiophen-2-yl)-3-(3-(1-methyl-4-oxido-2-oxo-1,2-dihydropyridin-3-yl)ureido)propanoate;

sodium (S)-3-(3-(1,6-dimethyl-4-oxido-2-oxo-1,2-dihydropyridin-3-yl)ureido)-3-(5-(2,6-dimethylphenyl)thiophen-2-yl)propanoate;

sodium (S)-3-(3-(1,6-dimethyl-4-oxido-2-oxo-1,2-dihydropyridin-3-yl)ureido)-3-(4-fluoro-2',6'-dimethylbiphenyl-3-yl)propanoate;

sodium (S)-3-(4-fluoro-2',6'-dimethylbiphenyl-3-yl)-3-(3-(1-methyl-4-oxido-2-oxo-1,2-dihydropyridin-3-yl)ureido)propanoate;

sodium (S)-3-(3-(1-methyl-4-oxido-2-oxo-1,2-dihydropyridin-3-yl)ureido)-3-(2',4,4'-trifluorobiphenyl-3-yl)propanoate;

sodium (S)-3-(3-(1,6-dimethyl-4-oxido-2-oxo-1,2-dihydropyridin-3-yl)ureido)-3-(2',4,4'-trifluorobiphenyl-3-yl)propanoate;

sodium (S)-3-(4-fluoro-3'-methoxybiphenyl-3-yl)-3-(3-(1-methyl-4-oxido-2-oxo-1,2-dihydropyridin-3-yl)ureido)propanoate;

sodium (S)-3-(4-fluoro-3'-(trifluoromethoxy)biphenyl-3-yl)-3-(3-(1-methyl-4-oxido-2-oxo-1,2-dihydropyridin-3-yl)ureido)propanoate;

sodium (S)-3-(3-(1,6-dimethyl-4-oxido-2-oxo-1,2-dihydropyridin-3-yl)ureido)-3-(4-fluoro-3'-(trifluoromethoxy)biphenyl-3-yl)propanoate;
sodium (S)-3-(4-methoxybiphenyl-3-yl)-3-(3-(1-methyl-4-oxido-2-oxo-1,2-dihydro pyridin-3-yl)ureido)propanoate;
sodium (S)-3-(3-(1,6-dimethyl-4-oxido-2-oxo-1,2-dihydropyridin-3-yl)ureido)-3-(2',5,6'-trimethylbiphenyl-3-yl)propanoate;
sodium (S)-3-(3-(1-methyl-4-oxido-2-oxo-1,2-dihydropyridin-3-yl)ureido)-3-(2'-methylbiphenyl-3-yl)propanoate;
sodium (S)-3-(3-(1,6-dimethyl-4-oxido-2-oxo-1,2-dihydropyridin-3-yl)ureido)-3-(2'-methylbiphenyl-3-yl)propanoate;
sodium (S)-3-(5-fluoro-2',6'-dimethylbiphenyl-3-yl)-3-(3-(1-methyl-4-oxido-2-oxo-1,2-dihydropyridin-3-yl)ureido)propanoate;
sodium (S)-3-(3-(1-methyl-4-oxido-2-oxo-1,2-dihydropyridin-3-yl)ureido)-3-(5-(3-(trifluoromethoxy)phenyl)thiophen-2-yl)propanoate;
sodium (S)-3-(4-methoxy-2',6'-dimethylbiphenyl-3-yl)-3-(3-(1-methyl-4-oxido-2-oxo-1,2-dihydropyridin-3-yl)ureido)propanoate;
sodium (S)-3-(3-(1,6-dimethyl-4-oxido-2-oxo-1,2-dihydropyridin-3-yl)ureido)-3-(4-fluoro-3'-methoxybiphenyl-3-yl)propanoate;
sodium (S)-3-(5-fluoro-3'-methoxybiphenyl-3-yl)-3-(3-(1-methyl-4-oxido-2-oxo-1,2-dihydropyridin-3-yl)ureido)propanoate;
sodium (S)-3-(5-fluoro-3'-methoxybiphenyl-3-yl)-3-(3-(4-hydroxy-1,6-dimethyl-2-oxo-1,2-dihydropyridin-3-yl)ureido)propanoate;
sodium (S)-3-(3-(1,6-dimethyl-4-oxido-2-oxo-1,2-dihydropyridin-3-yl)ureido)-3-(5-fluoro-3'-trifluoromethoxybiphenyl-3-yl)propanoate;
sodium (S)-3-(5-fluoro-3'-(trifluoromethoxy)biphenyl-3-yl)-3-(3-(1-methyl-4-oxido-2-oxo-1,2-dihydropyridin-3-yl)ureido)propanoate;
sodium (S)-3-(5-(3,5-dimethylisoxazol-4-yl)thiophen-2-yl)-3-(3-(1-methyl-4-oxido-2-oxo-1,2-dihydropyridin-3-yl)ureido)propanoate;
sodium (S)-3-(3-(1,6-dimethyl-4-oxido-2-oxo-1,2-dihydropyridin-3-yl)ureido)-3-(3-(3,5-dimethylisoxazol-4-yl)phenyl)propanoate;
sodium (S)-3-(3-(1,6-dimethyl-4-oxido-2-oxo-1,2-dihydropyridin-3-yl)ureido)-3-(2-fluorobiphenyl-3-yl)propanoate;
sodium (S)-3-(3-(1,6-dimethyl-4-oxido-2-oxo-1,2-dihydropyridin-3-yl)ureido)-3-(6-fluoro-2'-methylbiphenyl-3-yl)propanoate;
sodium (S)-3-(6-fluoro-2'-methylbiphenyl-3-yl)-3-(3-(1-methyl-4-oxido-2-oxo-1,2-dihydropyridin-3-yl)ureido)propanoate;
sodium (S)-3-(3-(1-methyl-4-oxido-2-oxo-1,2-dihydropyridin-3-yl)ureido)-3-(5-phenylthiophen-2-yl)propanoate;
sodium (S)-3-(5-(2,5-difluorophenyl)thiophen-2-yl)-3-(3-(1-methyl-4-oxido-2-oxo-1,2-dihydropyridin-3-yl)ureido)propanoate;
sodium (S)-3-(3-(1-methyl-4-oxido-2-oxo-1,2-dihydropyridin-3-yl)ureido)-3-(5-(trifluoro methoxy)biphenyl-3-yl)propanoate;
sodium (S)-3-(3-(1-methyl-4-oxido-2-oxo-1,2-dihydropyridin-3-yl)ureido)-3-(2'-methylbiphenyl-4-yl)propanoate;
sodium (S)-3-(5-methoxybiphenyl-3-yl)-3-(3-(7-oxido-5-oxo-1,2,3,5-tetrahydroindolizin-6-yl)ureido)propanoate;
sodium (S)-3-(3-(1-methyl-4-oxido-2-oxo-1,2-dihydropyridin-3-yl)ureido)-3-(5-(trifluoro methyl)biphenyl-3-yl)propanoate;
sodium (S)-3-(5-(3-chlorophenyl)thiophen-2-yl)-3-(3-(1-methyl-4-oxido-2-oxo-1,2-dihydropyridin-3-yl)ureido)propanoate;
sodium (S)-3-(5-(3-fluorophenyl)thiophen-2-yl)-3-(3-(1-methyl-4-oxido-2-oxo-1,2-dihydropyridin-3-yl)ureido)propanoate;
sodium (S)-3-(2',4'-difluorobiphenyl-4-yl)-3-(3-(1-methyl-4-oxido-2-oxo-1,2-dihydropyridin-3-yl)ureido)propanoate;
sodium (S)-3-(2',4'-difluorobiphenyl-4-yl)-3-(3-(1,6-dimethyl-4-oxido-2-oxo-1,2-dihydropyridin-3-yl)ureido)propanoate;
sodium (S)-3-(2',4'-difluorobiphenyl-4-yl)-3-(3-(1,5-dimethyl-4-oxido-2-oxo-1,2-di hydropyridin-3-yl)ureido)propanoate;
sodium (S)-3-(3-(1-methyl-4-oxido-2-oxo-1,2-dihydropyridin-3-yl)ureido)-3-(2'-methyl-6-(trifluoromethoxy)biphenyl-3-yl)propanoate;
sodium (S)-3-(3-(1-methyl-4-oxido-2-oxo-1,2-dihydropyridin-3-yl)ureido)-3-(6-(trifluoromethoxy)biphenyl-3-yl)propanoate;
sodium 3-(3'-acetylbiphenyl-3-yl)-3-(3-(1,5-dimethyl-4-oxido-2-oxo-1,2-dihydro pyridin-3-yl)ureido)propanoate;
sodium 3-(4'-acetylbiphenyl-3-yl)-3-(3-(1,5-dimethyl-4-oxido-2-oxo-1,2-dihydro pyridin-3-yl)ureido)propanoate;
sodium (S)-3-(3-(1,5-dimethyl-4-oxido-2-oxo-1,2-dihydropyridin-3-yl)ureido)-3-(4-phenyl thiophen-2-yl)propanoate;
sodium (S)-3-(3-(1,5-dimethyl-4-oxido-2-oxo-1,2-dihydropyridin-3-yl)ureido)-3-(5-phenyl thiophen-2-yl)propanoate;
sodium (S)-3-(2',4'-difluorobiphenyl-3-yl)-3-(3-(7-oxido-5-oxo-1,2,3,5-tetrahydroindolizin-6-yl)ureido)propanoate;
sodium (S)-3-(3-(1-methyl-4-oxido-2-oxo-1,2-dihydropyridin-3-yl)ureido)-3-(3-(thiazol-2-yl)phenyl)propanoate;
sodium (S)-3-(3-(1,6-dimethyl-4-oxido-2-oxo-1,2-dihydropyridin-3-yl)ureido)-3-(5-fluoromethyl-3'-(trifluoromethoxy)biphenyl-3-yl)propanoate;
sodium (S)-3-(3-(1,6-dimethyl-4-oxido-2-oxo-1,2-dihydropyridin-3-yl)ureido)-3-(2',4',5-trifluorobiphenyl-3-yl)propanoate;
sodium (S)-3-(3-(1-methyl-4-oxido-2-oxo-1,2-dihydropyridin-3-yl)ureido)-3-(2',4',5-trifluorobiphenyl-3-yl)propanoate;
sodium (S)-3-(3'-methoxy-6-(trifluoromethoxy)biphenyl-3-yl)-3-(3-(1-methyl-4-oxido-2-oxo-1,2-dihydropyridin-3-yl)ureido)propanoate;
sodium (S)-3-(3-(1,6-dimethyl-4-oxido-2-oxo-1,2-dihydropyridin-3-yl)ureido)-3-(3'-methoxy-6-(trifluoromethoxy)biphenyl-3-yl)propanoate;
sodium (S)-3-(2',6'-dimethylbiphenyl-4-yl)-3-(3-(1-methyl-4-oxido-2-oxo-1,2-dihydropyridin-3-yl)ureido)propanoate;
sodium (S)-3-(3-(1,6-dimethyl-4-oxido-2-oxo-1,2-dihydropyridin-3-yl)ureido)-3-(2'-methylbiphenyl-4-yl)propanoate;

sodium (S)-3-(3-(1,6-dimethyl-4-oxido-2-oxo-1,2-dihydropyridin-3-yl)ureido)-3-(2',6'-dimethylbiphenyl-4-yl)propanoate;

sodium (S)-3-(3-(1-methyl-4-oxido-2-oxo-1,2-dihydropyridin-3-yl)ureido)-3-(3-(pyridin-2-yl)phenyl)propanoate;

sodium (S)-3-3-(6-methoxypyridazin-3-yl)phenyl)-3-(3-(1-methyl-4-oxido-2-oxo-1,2-dihydropyridin-3-yl)ureido)propanoate;

sodium (S)-3-(3-(1-methyl-4-oxido-2-oxo-1,2-dihydropyridin-3-yl)ureido)-3-(5-phenylpyridin-3-yl)propanoate;

sodium (S)-3-(3-(1,6-dimethyl-4-oxido-2-oxo-1,2-dihydropyridin-3-yl)ureido)-3-(5-fluoro-2',6'-dimethylbiphenyl-3-yl)propanoate;

sodium (S)-3-(biphenyl-4-yl)-3-(3-(1,5-dimethyl-4-oxido-2-oxo-1,2-dihydropyridin-3-yl)ureido)propanoate;

sodium (S)-3-(3-(1-methyl-4-oxido-2-oxo-1,2-dihydropyridin-3-yl)ureido)-3-(3-(6'-methoxypyridin-2-yl)phenyl)propanoate;

sodium (S)-3-(3-(1,5-dimethyl-4-oxido-2-oxo-1,2-dihydropyridin-3-yl)ureido)-3-(4'-methoxybiphenyl-3-yl)propanoate;

sodium (S)-3-(3-(1H-imidazol-1-yl)phenyl)-3-(3-(1-methyl-4-oxido-2-oxo-1,2-dihydropyridin-3-yl)ureido)propanoate;

sodium (S)-3-(3-(4-hydroxy-1-methyl-2-oxo-1,2-dihydropyridin-3-yl)ureido)-3-(3-(pyrazin-2-yl)phenyl)propanoate, sodium 3-(3-bromophenyl)-3-(3-(4-hydroxy-1,5-dimethyl-2-oxo-1,2-dihydro pyridin-3-yl) ureido)propanoate, or sodium 3-(3-bromophenyl)-3-(3-(1-ethyl-4-hydroxy-5-methyl-2-oxo-1,2-dihydropyridin-3-yl)ureido)propanoate.

* * * * *